(12) United States Patent
Amberg et al.

(10) Patent No.: US 8,846,741 B2
(45) Date of Patent: Sep. 30, 2014

(54) N-SUBSTITUTED AMINOBENZOCYCLOHEPTENE, AMINOTETRALINE, AMINOINDANE AND PHENALKYLAMINE DERIVATIVES, PHARMACEUTICAL COMPOSITIONS CONTAINING THEM, AND THEIR USE IN THERAPY

(71) Applicants: AbbVie Deutschland GmbH & Co. KG, Wiesbaden (DE); AbbVie Inc., North Chicago, IL (US)

(72) Inventors: Wilhelm Amberg, Ludwigshafen (DE); Udo Lange, Ludwigshafen (DE); Frauke Pohlki, Ludwigshafen (DE); Ernesto Santandrea, Zofingen (CH); Charles Hutchins, Green Oaks, IL (US)

(73) Assignees: AbbVie Inc., North Chicago, IL (US); AbbVie Deutschland GmbH & Co. KG, Wiesbaden (DE)

( * ) Notice: Subject to any disclaimer, the term of this patent is extended or adjusted under 35 U.S.C. 154(b) by 0 days.

(21) Appl. No.: 13/680,488

(22) Filed: Nov. 19, 2012

(65) Prior Publication Data

US 2013/0131132 A1 May 23, 2013

Related U.S. Application Data

(60) Provisional application No. 61/597,887, filed on Feb. 13, 2012, provisional application No. 61/561,653, filed on Nov. 18, 2011.

(51) Int. Cl.
| | |
|---|---|
| *C07D 403/12* | (2006.01) |
| *C07D 305/08* | (2006.01) |
| *A61K 31/4178* | (2006.01) |
| *A61P 25/04* | (2006.01) |
| *A61P 25/18* | (2006.01) |
| *C07D 233/84* | (2006.01) |

(52) U.S. Cl.
USPC ........ 514/397; 514/407; 514/449; 548/312.1; 548/364.7; 549/511

(58) Field of Classification Search
USPC ......... 548/112, 115, 122, 454, 453, 576, 594, 548/950, 953
See application file for complete search history.

(56) References Cited

U.S. PATENT DOCUMENTS

| 4,927,838 A | 5/1990 | Guthrie et al. |
| 5,506,246 A | 4/1996 | Junge et al. |

(Continued)

FOREIGN PATENT DOCUMENTS

| DE | 10315570 A1 | 10/2004 |
| EP | 0091241 | 10/1983 |

(Continued)

OTHER PUBLICATIONS

Dohi T., et al., "Glycine Transporter Inhibitors as a Novel Drug Discovery Strategy for Neuropathic Pain," Pharmacology & Therapeutics, 2009, vol. 123 (1), pp. 54-79.

(Continued)

*Primary Examiner* — Michael Barker
*Assistant Examiner* — Amanda L Aguirre
(74) *Attorney, Agent, or Firm* — Lisa V. Mueller; Michael Best & Friedrich LLP

(57) ABSTRACT

The present invention relates to N-substituted aminobenzocycloheptene, aminotetraline, aminoindane and phenalkylamine derivatives of the formula (I), (II), (III) or (IV)

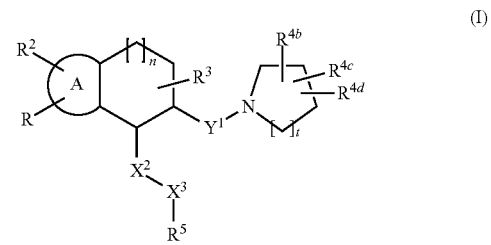

(I)

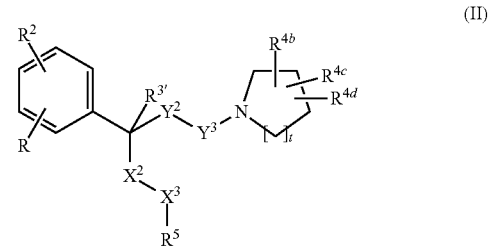

(II)

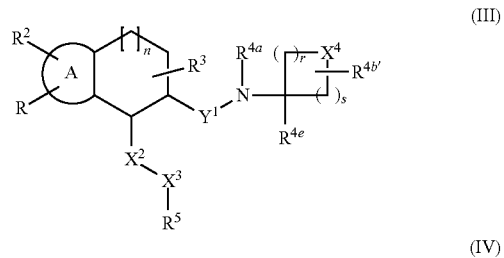

(III)

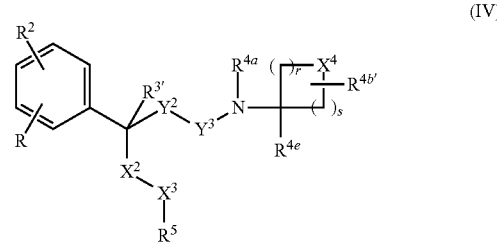

(IV)

or a physiologically tolerated salt thereof. The invention relates to pharmaceutical compositions comprising such N-substituted amino-benzocycloheptene, aminotetraline, aminoindane and phenalkylamine derivatives, and the use of such N-substituted aminobenzocycloheptene, aminotetraline, aminoindane and phenalkylamine derivatives for therapeutic purposes. The N-substituted aminobenzocycloheptene, aminotetraline, aminoindane and phenalkylamine derivatives are GlyT1 inhibitors.

19 Claims, No Drawings

(56) References Cited

U.S. PATENT DOCUMENTS

| | | |
|---|---|---|
| 5,519,034 A | 5/1996 | Kozlik et al. |
| 5,545,755 A | 8/1996 | Lin et al. |
| 6,057,357 A | 5/2000 | Horwell et al. |
| 6,331,636 B1 | 12/2001 | Romero et al. |
| 6,426,364 B1 | 7/2002 | Egle et al. |
| 7,189,850 B2 | 3/2007 | Ceccarelli et al. |
| 7,427,612 B2 | 9/2008 | Alberati-Giani et al. |
| 7,462,617 B2 | 12/2008 | Alberati-Giani et al. |
| 7,511,013 B2 | 3/2009 | Molino et al. |
| 7,514,068 B2 | 4/2009 | Tung |
| 7,521,421 B2 | 4/2009 | Naicker et al. |
| 7,528,131 B2 | 5/2009 | Persichetti et al. |
| 7,531,685 B2 | 5/2009 | Czarnik |
| 7,534,814 B2 | 5/2009 | Ascher et al. |
| 7,538,189 B2 | 5/2009 | Naicker et al. |
| 8,420,670 B2 | 4/2013 | Amberg et al. |
| 8,563,617 B2 | 10/2013 | Amberg et al. |
| 8,642,587 B2 | 2/2014 | Lange et al. |
| 8,653,100 B2 | 2/2014 | Amberg et al. |
| 2002/0169197 A1 | 11/2002 | Egle et al. |
| 2003/0083359 A1 | 5/2003 | Lee et al. |
| 2004/0026364 A1 | 2/2004 | Kihara |
| 2005/0124627 A1 | 6/2005 | Schadt et al. |
| 2005/0153963 A1 | 7/2005 | Dargazanli et al. |
| 2005/0153980 A1 | 7/2005 | Schadt et al. |
| 2005/0159450 A1 | 7/2005 | Dargazanli et al. |
| 2005/0267152 A1 | 12/2005 | Bloomfield et al. |
| 2006/0074105 A1 | 4/2006 | Ware et al. |
| 2006/0223802 A1 | 10/2006 | Dargazanli et al. |
| 2006/0223861 A1 | 10/2006 | Dargazanli et al. |
| 2006/0223885 A1 | 10/2006 | Dargazanli et al. |
| 2006/0223886 A1 | 10/2006 | Dargazanli et al. |
| 2007/0021408 A1 | 1/2007 | Molino et al. |
| 2007/0155753 A1 | 7/2007 | Ye et al. |
| 2007/0214087 A1 | 9/2007 | Kawaguchi et al. |
| 2008/0070941 A1 | 3/2008 | Dargazanli et al. |
| 2008/0119486 A1 | 5/2008 | Jolidon et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |
| 2012/0040947 A1 | 2/2012 | Pohlki et al. |
| 2012/0040948 A1 | 2/2012 | Pohlki et al. |
| 2012/0077796 A1 | 3/2012 | Pohlki et al. |
| 2012/0088790 A1 | 4/2012 | Pohlki et al. |
| 2012/0295881 A1 | 11/2012 | Lange et al. |
| 2012/0316153 A1 | 12/2012 | Amberg et al. |
| 2013/0035323 A1 | 2/2013 | Amberg et al. |
| 2013/0184238 A1 | 7/2013 | Amberg et al. |
| 2013/0203749 A1 | 8/2013 | Amberg et al. |
| 2013/0210880 A1 | 8/2013 | Amberg et al. |
| 2014/0031331 A1 | 1/2014 | Amberg et al. |

FOREIGN PATENT DOCUMENTS

| | | |
|---|---|---|
| EP | 0303961 A2 | 2/1989 |
| EP | 0420064 A2 | 4/1991 |
| EP | 0258755 B1 | 9/1991 |
| EP | 1199306 | 4/2002 |
| EP | 1254662 A2 | 11/2002 |
| EP | 1284257 B1 | 10/2005 |
| EP | 2246331 | 11/2010 |
| EP | 2246331 A1 | 11/2010 |
| WO | WO 81/03491 | 12/1981 |
| WO | 9015047 A1 | 12/1990 |
| WO | 9206967 A1 | 4/1992 |
| WO | WO 92/19234 | 11/1992 |
| WO | 9222533 A1 | 12/1992 |
| WO | 9313073 A1 | 7/1993 |
| WO | WO 95/07271 | 3/1995 |
| WO | WO 97/10223 | 3/1997 |
| WO | 9745115 A1 | 12/1997 |
| WO | 9804521 A1 | 2/1998 |
| WO | 9856757 A1 | 12/1998 |
| WO | 0007978 A1 | 2/2000 |
| WO | 0020376 A1 | 4/2000 |
| WO | 0109120 A1 | 2/2001 |
| WO | 02/076979 | 10/2002 |
| WO | 03031435 A1 | 4/2003 |
| WO | 03045924 A1 | 6/2003 |
| WO | 03053942 A1 | 7/2003 |
| WO | 03055478 A1 | 7/2003 |
| WO | WO 03/076420 | 9/2003 |
| WO | WO 03/087086 | 10/2003 |
| WO | WO 03/089411 | 10/2003 |
| WO | 03097586 A1 | 11/2003 |
| WO | 2004007468 A1 | 1/2004 |
| WO | 2004013100 A2 | 2/2004 |
| WO | WO 2004/013101 | 2/2004 |
| WO | 2004022528 A2 | 3/2004 |
| WO | 2004071445 A2 | 8/2004 |
| WO | 2004072034 A1 | 8/2004 |
| WO | 2004080968 A1 | 9/2004 |
| WO | 2004096761 A1 | 11/2004 |
| WO | 2004112787 A1 | 12/2004 |
| WO | 2004113280 A1 | 12/2004 |
| WO | 2004113301 A1 | 12/2004 |
| WO | WO 2004/110149 | 12/2004 |
| WO | 2005014563 A1 | 2/2005 |
| WO | 2005023260 A1 | 3/2005 |
| WO | 2005023261 A1 | 3/2005 |
| WO | WO 2005/037781 | 4/2005 |
| WO | WO 2005/037782 | 4/2005 |
| WO | WO 2005/037783 | 4/2005 |
| WO | WO 2005/037785 | 4/2005 |
| WO | WO 2005/037792 | 4/2005 |
| WO | 2005040166 A1 | 5/2005 |
| WO | 2005046601 A2 | 5/2005 |
| WO | 2005049023 A1 | 6/2005 |
| WO | 2005058317 A1 | 6/2005 |
| WO | 2005058882 A1 | 6/2005 |
| WO | 2005058885 A2 | 6/2005 |
| WO | WO 2005/099353 | 10/2005 |
| WO | 2005123681 A1 | 12/2005 |
| WO | WO 2006/008754 | 1/2006 |
| WO | WO 2006/034235 | 3/2006 |
| WO | 2006063709 A1 | 6/2006 |
| WO | 2006082001 A1 | 8/2006 |
| WO | WO 2006/102760 | 10/2006 |
| WO | 2006121767 A2 | 11/2006 |
| WO | WO 2007/143823 | 12/2007 |
| WO | 2008038053 A1 | 4/2008 |
| WO | WO 2008/038053 | 4/2008 |
| WO | WO 2008/148755 | 12/2008 |
| WO | WO 2009/024611 | 2/2009 |
| WO | 2009121872 A2 | 10/2009 |
| WO | 2010020548 A1 | 2/2010 |
| WO | WO 2010025856 A1 * | 3/2010 |
| WO | 2010092180 A1 | 8/2010 |
| WO | WO 2010/092181 | 8/2010 |
| WO | 2010138901 A1 | 12/2010 |
| WO | WO 2012/020130 | 2/2012 |
| WO | WO 2012/020131 | 2/2012 |
| WO | WO 2012/020133 | 2/2012 |
| WO | WO 2012/152915 | 11/2012 |

OTHER PUBLICATIONS

Erhunmwunse M.O., et al., "A Novel Rearrangement Reaction of Beta-diaxo-alpha-ketoacetals," Tetrahedron Letters, 2009, vol. 50, pp. 3568-3570.

Harsing L.G. Jr., et al., "Glycine Transporter Type-1 and its Inhibitors," Current Medicinal Chemistry, 2006, vol. 13 (9), pp. 1017-1044.

Hashimoto K., et al., "Glycine Transporter Inhibitors as Therapeutic Agents for Schizophrenia," Recent Patents on CNS Drug Discovery, 2006, vol. 1 (1), pp. 43-53.

(56) References Cited

OTHER PUBLICATIONS

Javitt D.C., "Glutamate as a Therapeutic Target in Psychiatric Disorders," Molecular Psychiatry, 2004, vol. 9 (11), pp. 984-997.
Jellimann C., et al., "Synthesis of Phenalene and Acenaphthene Derivatives as New Conformationally Restricted Ligands for Melatonin Receptors," Journal of Medicinal Chemistry, 2000, vol. 43 (22), pp. 4051-4062.
Jensen B.L., et al., "Total Synthesis of 4,5,7a,8-Tetrahydro-1,2-dimethoxyphenanthro[10,1-bc]-azepin-6(7H)-one: A Photochemical Approach," Journal of Heterocyclic Chemistry, 1986, vol. 23, pp. 343-347.
Jetter M.C., et al., "Heteroaryl Beta-tetralin Ureas as Novel Antagonists of Human TRPV1," Bioorganic & Medicinal Chemistry Letters, 2007, vol. 17 (22), pp. 6160-6163.
Lindsley C.W., et al., "Design, Synthesis, and in Vivo Efficacy of Glycine Transporter-1 (GlyT1) Inhibitors Derived from a Series of [4-phenyl-1-(propylsulfonyl)piperidin-4-yl]methyl Benzamides," ChemMedChem, 2006, vol. 1 (8), pp. 807-811.
Lindsley C.W., et al., "Progress in the Preparation and Testing of Glycine Transporter Type-1 (GlyT1) Inhibitors," Current Topics in Medicinal Chemistry, 2006, vol. 6 (17), pp. 1883-1896.
Lindsley C.W., et al., "Progress Towards Validating the NMDA Receptor Hypofunction Hypothesis of Schizophrenia," Current Topics in Medicinal Chemistry, 2006, vol. 6 (8), pp. 771-785.
Lowe J., et al., "A Novel, Non-substrate-based Series of Glycine Type 1 Transporter Inhibitors Derived from High-throughput Screening," Bioorganic & Medicinal Chemistry Letters, 2007, vol. 17 (6), pp. 1675-1678.
Mai K., et al., "A Fast N-Substituted Alpha-Aminonitrile Synthesis," Synthetic Communications, 1985, vol. 15 (2), pp. 157-163.
Nunez E., et al., "Differential Effects of the Tricyclic Antidepressant Amoxapine on Glycine Uptake Mediated by the Recombinant GLYT1 and GLYT2 Glycine Transporters," British Journal of Pharmacology, 2000, vol. 129 (1), pp. 200-206.
Papageorgiou C., et al., "163.Synthesis of Hydroxy-and Methoxy-Substituted Octahydrobenzo[g]isoquinolines as Potential Ligands for Serotonin Receptors," Helvetica Chimica Acta, 1989, vol. 72, pp. 1463-1470.
Reddy K.S., et al., "Synthesis of a 9-Fluorenone Derived Beta-Amino Alcohol Ligand Depicting High Catalytic Activity and Pronounced Non-Linear Stereochemical Effects," Synthesis, 2000, No. 1, pp. 165-176.
Reddy M.P., et al., "Applications of the Vilsmeier Reaction. 13. Vilsmeier Approach to Polycyclic Aromatic Hydrocarbons," Journal of Organic Chemistry, 1981, vol. 46, pp. 5371-5373.
Thompson H.W., et al., "Stereochemical Control of Reductions. 9. Haptophilicity Studies with 1,1-disubstituted 2-methyleneacenaphthenes," The Journal of Organic Chemistry, 2002, vol. 67 (9), pp. 2813-2825.
Ting P.C., et al., "The Synthesis of Substituted Bipiperidine Amide Compounds as CCR3 Antagonists," Bioorganic & Medicinal Chemistry Letters, 2005, vol. 15 (5), pp. 1375-1378.
Zhao Z., et al., "Synthesis and SAR of GlyT1 Inhibitors Derived from a Series of N-((4-(morpholine-4-carbonyl)-1-(propylsulfonyl)piperidin-4-yl)methyl)benzamides," Bioorganic & Medicinal Chemistry Letters, 2006, vol. 16 (23), pp. 5968-5972.
Ashby, E.C. et al., "Single electron transfer in reactions of alkyl halides with lithium thiolates," J. Org. Chem. (1985) 50(25):5184-5193.
Barbasiewicz, M. et al., "Intermolecular reactions of chlorohydrine anions: acetalization of carbonyl compounds under basic conditions," Org. Lett. (2006) 8(17):3745-3748.
Belliotti, T.R. et al., "Structure-activity relationships of pregabalin and analogues that target the alpha(2)-delta protein," J. Med. Chem. (2005) 48(7):2294-2307.
Bermejo, A. et al., "Syntheses and antitumor targeting G1 phase of the cell cycle of benzoyldihydroisoquinolines and related 1-substituted isoquinolines," J. Med. Chem. (2002) 45:5058-5068.
Beylot, M. et al., "In vivo studies of intrahepatic metabolic pathways," Diabetes Metabolism (1997) 23(3):251-257.
Bishop, D.C., "Analgetics based on the azetidine ring," Azetidine Analgetics (1968) 11:466-470.
Blagojevic, N. et al., "Role of heavy water in boron neutron capture therapy," Topics in Dosimetry and Treatment Planning for Neutron Capture Thearpy (1994) 125-134.
Blake, M.I. et al., "Studies with deuterated drugs," J. Pharm. Sci. (1975) 64(3):367-391.
Boulay, D. et al., "Characterization of SSR103800, a selective inhibitor of the glycine transporter-1 in models predictive of therapeutic activity in schizophrenia," Pharmacology, Biochemistry and Behavior (2008) 91:47-58.
Brickner, S.J. et al., "Synthesis and antibacterial activity of U-100592 and U-100766, two oxazolidinone antibacterial agents for the potential treatment of multidrug-resistant gram-positive bacterial infections," J. Med. Chem. (1996) 39(3):673-679.
Burn, D., "Alkylation with the vilsmeier reagent," Chem. And Industry (1973) 870-873.
Burns, N. Z. et al., "Total synthesis of haouamine A: the indeno-tetrahydropyridine core," Tetrahedron (2009) 65(33):6600-6610.
Butte, N. F. et al., "Measurement of milk intake: tracer-to-infant deuterium dilution method," Br. J. Nutrition (1991) 65:3-14.
Cheng, Y. et al., "Relationship between the inhibition constant (KI) and the concentration of inhibitor which causes 50 percent inhibition ($I_{50}$) of an enzymatic reaction," Biochem. Pharmacol. (1973) 22:3099-3108.
Cheung, F.K. et al., "The use of a [4+2] cycloadditional reaction for the preparation of a series of 'tethered' Ru(II)-diamine and aminoalcohol complexes," Org. & Biomol. Chem. (2007) 5(7):1093-1103.
Chrzanowska, M. et al., "Asymmetric synthesis of isoquinoline alkaloids," Chem. Rev. (2004) 104(7):3341-3370.
Clayden et al., Tetra. Lett. (2003) 44(15):3059-3062.
Clezy, P.S. et al., "Preparation of a deuterated analogue of tetrahydropapaveroline suitable for use as an internal standard for G.C./M.S. analysis of this alkaloid: retro pictet-spengler condensation," Australian J. Chem. (1998) 41:483-491.
Colandrea, V.J. et al., "Synthesis and regioselective alkylation of 1.6- and 1.7-naphthyridines," Tetra. Lett. (2000) 41:8053-8057.
Coward, W.A. et al., "New method for measuring milk intakes in breast-fed babies," The Lancet (1979) 13-14.
Czajka, D.M. et al., "Effect of deuterium oxide on the reproductive potential of mice," Annals of the New York Academy of Sciences (1960) 84:770-779.
Czajka, D.M. et al., "Physiological effects of deuterium on dogs," Am. J. Physiology (1961) 201(2):357-362.
Denkewalter, R.G. et al., Progress of Pharmaceutical Research, Drug Research (1966) 10:223-226.
Di, L. et al., "Optimization of a higher throughput microsomal stability screening assay for profiling drug discovery candidates," J. Biomol. Screening (2003) 8(4):453-462.
Duan, Z.C. et al., "Highly enantioselective Rh-catalyzed hydrogenation of beta gamma-unsaturated phosphonates with chiral ferrocene-based monophosphoramidite ligands," J. Org. Chem. (2009) 74(23):9191-9194.
Ferles, M. et al., "Reduction of 1-isoquinolyl-dimethylmethanol and 1-(1-isoquinolyl)cyclohexanon," Collection of Czechoslovak Chem. Comm. (1981) 46(1):262-265.
Fiedler, H.B., "Lexikon der hilfsstoffe fur pharmazie, Kosmetik und angrenzende Gebiete," (1996) 4th Edition, Table of Contents.
Foster, A.B. et al., "Deuterium isotope effects in the metabolism of drugs and xenobiotics: implications for drug design," Advances in Drug Research (1985) 14:2-36.
Fraser et al., Canadian Journal of Chemistry (1971) 49(5):800-802.
Grant & Hackh's Chemical Dictionary, 5th Edition (1987), p. 148.
Green, G.M. et al., "Polystyrene-supported benzenesulfonyl azide: a diazo transfer reagent that is both efficient and safe," J. Org. Chem. (2001) 66(7):2509-2511.
Greene, T.W. et al., in Protective Groups in Organic Synthesis, 2nd Edition, John Wiley & Sons, Inc., (1991) Table of Contents.
Greene, T.W. et al., in Protective Groups in Organic Synthesis, 3rd Edition, John Wiley & Sons, Inc., (1999) Preface, Table of Contents and Abbreviations.

(56) References Cited

OTHER PUBLICATIONS

Guillonneau, C. et al., "Synthesis of 9-O-substituted derivatives of 9-hydroxy-5, 6-dimethyl-6H-pyrido[4,3-b]carbazole-1-carboxylic acid (2-(dimethylamino)ethyl)amide and their 10- and 11-methyl analogues with improved antitumor activity," J. Med. Chem. (1999) 42(12):2191-2203.
Gupta, A. et al., "Simple and efficient synthesis of steroidal hybrids of estrogen and vitamin D3," Synthetic Comm. (2009) 39:61-69.
Hashimoto, K. "Glycerine transport inhibitors for the treatment of schizophrenia," The Open Medicinal Chemistry Journal (2010) 4:10-19.
Hashimoto, K. et al., "Phencyclidine-induced cognitive deficits in mice are improved by subsequent subchronic administration of the glycine transporter-1 inhibitor NFPS and D-serine," Eurp. Neuropsychopharmacology (2008) 18:414-421.
Hillier, M.C. et al., "A one-pot preparation of 1,3-disubstituted azetidines," J. Org. Chem. (2006) 71(20):7885-7887.
Ikunaka, M. et al., "The highly selective equatorial hydride delivery by biocatalysis: chemoenzymatic synthesis of trans-2-(4-propylcyclohexyl)-1,3-propanediol via cis-4-propylcyclohexanol," Organic Process Research and Development (2004) 8(3):389-395.
Jutz, C. et al., "The Vilsmeier-Haackarnold acylations. C-C bond-forming reactions of chloromethyleniminium ions," Adv. Org. Chem. (1976) 9(1):225-342.
Kaiser, C. et al., "6,7-dichloro-1-(3,4,5-trimethyoxygenzyl)-1,2,3,4-tetrahydroisoquinoline. A structurally novel beta-adrenergic receptor blocking agent," J. Med. Chem. (1986) 29(11):2381-2384.
Kato, S. et al., "Synthesis of deuterated mosapride citrate," J. Labelled Compounds and Radiopharmaceuticals (1995) 36(10):927-932.
King, F.D., editor "Bioisosteres, conformational restriction and pro-drugs—case history: an example of a conformational restriction approach," Medical Chemistry: Principles and Practice (1994), Chapter 14, 206-209.
Kinney, G.G. et al., "The glycerine transporter type 1 inhibitor N-[3-(4'-fluorophenyl)-3-(4'-phenylphenoxy) propyl] sarcosine potentiates NMDA receptor-mediated responses in vivo and produces an antipsychotic profile in rodent behavior," The Journal of Neurosci. (2003) 23(20):7586-7591.
Kocienski, P.J., Protective Groups, Georg Thieme Verlag Stuttgart, Germany, Table of Contents (1994).
Kreher, R.P., Hetarene II, Georg Thieme Verlag Stuttgart, Germany (1991) 583-726.
Kuhakarn, C. et al., "Synthesis of alkylated indolizidine alkaloids via pummerer mediated cyclization: synthesis of indolizidine 167B, 5-butylindolizidine and monomorine I," Tetrahedron (2008) 64(8):1663-1670.
Kushner et al., "Pharmacological uses and perspectives of heavy water and deuterated compounds," Canadian J. Physiol. Pharmacol. (1999) 77(2):79-88.
Lizondo, J. et al., "Linezolid: oxazolindinone antibacterial," Drugs of the Future (1996) 21(11):1116-1123.
Maclennan, A.H. et al., "Neonatal body water turnover: a putative index of perinatal morbidity," Amer. J. Obstetrics & Gynecology (1981) 139(8):948-952.
Mallesham, B. et al., "Highly efficient cul-catalyzed coupline of aryl bromides with oxazolidinones using Buchwald's protocol: a short route to linezolid and toloxatone," Org. Lett. (2003) 5(7):963-965.
McOmie, J.F.W., ed., Protective Groups in Organic Chemistry, Plenum Press (1973) Table of Contents.
Meek, J.S. et al., "Diels-Alder reactions of 9-substituted anthracenes.1 II. 9-cyanoanthracene," J. Amer. Chem. Soc. (1956) 78(20):5413-5416.
Memetzidis, G. et al., "Synthesis of aromatic chloroberbines," Heterocycles (1990) 31(2):341-351.
Mezler, M. et al., "Inhibitors of GlyT1 affect glycine transport via discrete binding sites," Mol. Pharmacol. (2008) 74(6):1705-1715.
Munson, P.J. et al., "Ligand: a versatile computerized approach for characterization of ligand-binding systems," Anal. Biochem. (1980) 107(1):220-239.

Obach, R.S., "Prediction of human clearance of twenty-nine drugs from hepatic microsomal intrinsic clearance data: an examination of in vitro half-life approach and nonspecific binding to microsomes," Drug Metabolism and Disposition (1999) 27(11):1350-1359.
Obach, R.S., "The prediction of human clearance from hepatic microsomal metabolism data," Curr. Opin. Drug Disc. & Development (2001) 4(1):36-44.
Paal, T.A. et al., "Lipase-catalyzed kinetic and dynamic kinetic resolution of 1,2,3,4-tetrahydroisoquinoline-1-carboxylic acid," Tetrahedron: asymmetry (2007) 18(12):1428-1433.
Pinard, E. et al., "Selective gly T1 inhibitors: discovery of [4-(3-fluoro-5-trifluoremethylpyridin-2-yl)piperazin-1-yl]-]-[5-methanesulfonyl-2-((S)-2,2,2-trifluoro-1-methylethoxy)phenyl)methanone (RG1678), a promising novel medicine to treat schizophrenia," J. Med. Chem. (2010) 53:4603-4614.
Pitts, M.R. et al., "Indium metal as a reducing agent in organic synthesis," J. Chem Soc. Perkin Transactions (2001) 1:955-977.
Pons, G. et al., "Stable isotopes labeling of drugs in pediatric clinical pharmacology," Pediatrics (1999) 104(32):633-639.
Prout, F.S. et al., "3-Benzyl-3-Methylpentanoic acid," Organic Syntheses, Coll. (1963) 4:93; (1955) 35:6.
Quirante, J. et al., "Synthesis of diazatricyclic core of magangamines from Cis-perhydroisoquinolines," J. Org. Chem. (2008) 73(7):768-771.
Ranu et al., "Indium (III) chloride-promoted rearrangement of epoxides: a selective synthesis of substituted benzylic aldehydes and ketones," J. Org. Chem. (1998) 8212-8216.
Reddy, M.P. et al., "Applications of the Vilsmeier reaction. 13. Vilsmeier approach to polycyclic aromatic hydrocarbons," J. Org. Chem. (1981) 46:5371-5373.
Reimann, E. et al., "A convenient synthesis of 1-benzyl-1,2,3,4-tetrahydroisoquinolines by combined Strecker/Bruylants reaction," Monatshefte fur Chemie/Chemical Monthly (2004) 135(10):1289-1295.
Rodewald, L.E. et al., "Deuterium oxide as a tracer for measurement of compliance in pediatric clinical drug trials," J. Pediatrics (1989) 114(5):885-891.
Schwarcz, H.P., "Use of stable isotopes to determine compliance," Controlled Clinical Trials (1984) 5(Supp 4):573-575.
Schwarz, J.B. et al., "Novel cyclopropyl beta-amino acid analogues of pregabalin and gabapentin that target the alpha2-delta protein," J. Med. Chem. (2005) 48(8):3026-3035.
Sharma, S.D. et al., "Phosphorous oxychloride (POCI3): a key molecule in organic synthesis," Indian J. Chem. (1998) 37B:965-978.
Sur, C. et al., "Glycine transporter 1 inhibitors and modulation of NMDA receptor-mediated excitatory neurotransmission," Curr. Drug Targets (2007) 8:643-649.
Taber, D.F. et al., "Enantioselective ring construction: synthesis of (+)-alpha-cuparenone," J. Amer. Chem. Soc. (1985) 107:196-199.
Tavares, F.X. et al., "Potent, selective, and orally efficacious antagonists of melanin-concentrating hormone receptor 1," J. Med. Chem. (2006) 49(24):7095-7107.
Thomson, J.F., "Physiological effects of D20 in mammals," Annals of the N.Y. Academy of Sci. (1960) 84:736-744.
Tsai, G. et al., "Gene knockout of glycine transporter 1: characterization of the behavioral phenotype," PNAS (2004) 101(22):8485-8490.
Vogel, S. et al., "Palladium-catalyzed intramolecular allylic alkylation of alpha-sulfinyl carbanions: a new asymmetric route to enantiopure gamma-lactams," Tetra. Lett. (2010) 51(11):1459-1461.
White, J.D. et al., "Catalyzed asymmetric diels-alder reaction of benzoquinone. Total synthesis of (−)-ibogamine," Org. Lett. (2000) 2(15):2373-2376.
Zhou, D. et al., "Studies toward the discovery of the next generation of antidepressants. Part 5: 3,4-dihydro-2H-benzo[1,4]oxazine derivatives with dual 5-HT1A receptor and serotonin transporter affinity," Bioorg. Med. Chem. Lett. (2006) 16(5):1338-1341.
United States Patent Office Notice of Allowance for U.S. Appl. No. 12/706,326 dated Jun. 11, 2013 (10 pages).
United States Patent Office Notice of Allowance for U.S. Appl. No. 12/706,326 dated Feb. 21, 2013 (9 pages).

(56) References Cited

OTHER PUBLICATIONS

United States Patent Office Action for U.S. Appl. No. 12/706,326 dated Sep. 21, 2012 (7 pages).
United States Patent Office Notice of Allowance for U.S. Appl. No. 12/666,629 dated Dec. 11, 2012 (5 pages).
United States Patent Office Action for U.S. Appl. No. 12/666,629 dated Jul. 5, 2012 (11 pages).
United States Patent Office Notice of Allowance for U.S. Appl. No. 12/706,321 dated Sep. 30, 2013 (10 pages).
United States Patent Office Action for U.S. Appl. No. 12/706,321 dated Mar. 27, 2012 (11 pages).
United States Patent Office Notice of Allowance for U.S. Appl. No. 12/933,326 dated Jan. 9, 2014 (2 pages).
United States Patent Office Notice of Allowance for U.S. Appl. No. 12/933,326 dated Dec. 9, 2013 (4 pages).
United States Patent Office Notice of Allowance for U.S. Appl. No. 12/933,326 dated Oct. 1, 2013 (8 pages).
United States Patent Office Notice of Allowance for U.S. Appl. No. 12/933,326 dated Jan. 11, 2013 (5 pages).
United States Patent Office Action for U.S. Appl. No. 12/933,326 dated Oct. 29, 2012 (6 pages).
United States Patent Office Notice of Allowance for U.S. Appl. No. 13/206,937 dated Feb. 21, 2014 (9 pages).
United States Patent Office Action for U.S. Appl. No. 13/206,937 dated Aug. 28, 2013 (6 pages).
United States Patent Office Action for U.S. Appl. No. 13/206,750 dated Feb. 19, 2014 (6 pages).
United States Patent Office Notice of Allowance for U.S. Appl. No. 13/207,030 dated Mar. 11, 2014 (9 pages).
United States Patent Office Notice of Allowance for U.S. Appl. No. 13/207,160 dated Mar. 17, 2014 (9 pages).
United States Patent Office Action for U.S. Appl. No. 13/566,051 dated Sep. 16, 2013 (15 pages).
International Search Report for Application No. PCT/EP2010/051903, mailed May 26, 2010.
International Search Report for Application No. PCT/EP2008/061007 dated Aug. 10, 2009 (6 pages).
International Search Report for Application No. PCT/EP2009/053800 dated Nov. 20, 2009 (6 pages).
International Search Report for Application No. PCT/EP2012/058760 dated Aug. 27, 2012 (4 pages).
International Search Report for Application No. PCT/EP2012/065294 dated Sep. 21, 2012 (4 pages).
Written Opinion for Application No. PCT/EP2010/051903, mailed Aug. 16, 2011.
Written Opinion for Application No. PCT/EP2008/061007 dated Aug. 10, 2009 (7 pages).
Written Opinion for Application No. PCT/EP2009/053800 dated Nov. 20, 2009 (7 pages).
Written Opinion for Application No. PCT/EP2012/058760 dated Aug. 27, 2012 (4 pages).
United States Patent Office Action for U.S. Appl. No. 13/546,434 dated Apr. 14, 2014 (12 pages).
United States Patent Office Action for U.S. Appl. No. 13/792,105 dated Apr. 16, 2014 (6 pages).
United States Patent Office Action for U.S. Appl. No. 13/789,967 dated Apr. 1, 2014 (11 pages).
United States Patent Office Action for U.S. Appl. No. 14/031,265 dated Apr. 15, 2014 (14 pages).
United States Patent Office Notice of Allowance for U.S. Appl. No. 13/207,030 dated May 13, 2015 (9 pages).
United States Patent Office Notice of Allowance for U.S. Appl. No. 13/206,937 dated May 15, 2014 (9 pages).
United States Patent Office Notice of Allowance for U.S. Appl. No. 13/207,160 dated Jun. 6, 2014 (9 pages).
United States Patent Office Notice of Allowance for U.S. Appl. No. 13/566,051 dated May 29, 2014 (8 pages).

* cited by examiner

N-SUBSTITUTED AMINOBENZOCYCLOHEPTENE, AMINOTETRALINE, AMINOINDANE AND PHENALKYLAMINE DERIVATIVES, PHARMACEUTICAL COMPOSITIONS CONTAINING THEM, AND THEIR USE IN THERAPY

CROSS-REFERENCE TO RELATED APPLICATIONS

This claims priority to U.S. Provisional Patent Application No. 61/597,887, filed on Feb. 13, 2012 and U.S. Provisional Patent Application No. 61/561,653, filed on Nov. 18, 2011, the contents of all of which are herein fully incorporated by reference.

BACKGROUND OF THE INVENTION

The present invention relates to N-substituted aminobenzocycloheptene, aminotetraline, aminoindane and phenalkylamine derivatives, pharmaceutical compositions comprising such N-substituted aminobenzocycloheptene, aminotetraline, aminoindane and phenalkylamine derivatives, and the use of such N-substituted aminobenzocycloheptene, aminotetraline, aminoindane and phenalkylamine derivatives for therapeutic purposes. The N-substituted aminobenzocycloheptene, aminotetraline, aminoindane and phenalkylamine derivatives are GlyT1 inhibitors.

Dysfunction of glutamatergic pathways has been implicated in a number of disease states in the human central nervous system (CNS) including but not limited to schizophrenia, cognitive deficits, dementia, Parkinson disease, Alzheimer disease and bipolar disorder. A large number of studies in animal models lend support to the NMDA hypofunction hypothesis of schizophrenia.

NMDA receptor function can be modulated by altering the availability of the co-agonist glycine. This approach has the critical advantage of maintaining activity-dependent activation of the NMDA receptor because an increase in the synaptic concentration of glycine will not produce an activation of NMDA receptors in the absence of glutamate. Since synaptic glutamate levels are tightly maintained by high affinity transport mechanisms, an increased activation of the glycine site will only enhance the NMDA component of activated synapses.

Two specific glycine transporters, GlyT1 and GlyT2 have been identified and shown to belong to the Na/Cl-dependent family of neurotransmitter transporters which includes taurine, gamma-aminobutyric acid (GABA), proline, monoamines and orphan transporters. GlyT1 and GlyT2 have been isolated from different species and shown to have only 50% identity at the amino acid level. They also have a different pattern of expression in mammalian central nervous system, with GlyT2 being expressed in spinal cord, brainstem and cerebellum and GlyT1 present in these regions as well as forebrain areas such as cortex, hippocampus, septum and thalamus. At the cellular level, GlyT2 has been reported to be expressed by glycinergic nerve endings in rat spinal cord whereas GlyT1 appears to be preferentially expressed by glial cells. These expression studies have led to the suggestion that GlyT2 is predominantly responsible for glycine uptake at glycinergic synapses whereas GlyT1 is involved in monitoring glycine concentration in the vicinity of NMDA receptor expressing synapses. Recent functional studies in rat have shown that blockade of GlyT1 with the potent inhibitor (N-[3-(4'-fluorophenyl)-3-(4'-phenylphenoxy)propyl])-sarcosine (NFPS) potentiates NMDA receptor activity and NMDA receptor-dependent long-term potentiation in rat.

Molecular cloning has further revealed the existence of three variants of GlyT1, termed GlyT-1a, GlyT-1b and GlyT-1c, each of which displays a unique distribution in the brain and peripheral tissues. The variants arise by differential splicing and exon usage, and differ in their N-terminal regions.

The physiological effects of GlyT1 in forebrain regions together with clinical reports showing the beneficial effects of GlyT1 inhibitor sarcosine in improving symptoms in schizophrenia patients suggest that selective GlyT1 inhibitors represent a new class of antipsychotic drugs.

Glycine transporter inhibitors are already known in the art, for example:

U.S. Pat. No. 6,426,364

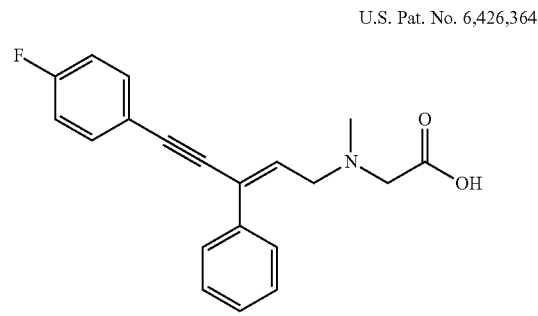

US 2002169197

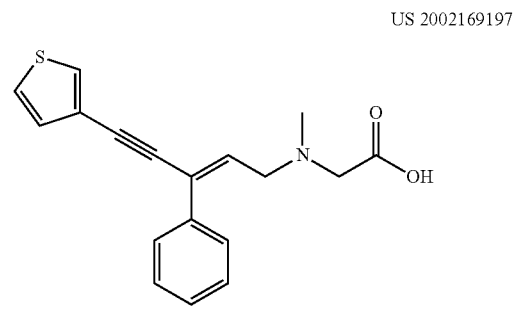

EP 1 284 257

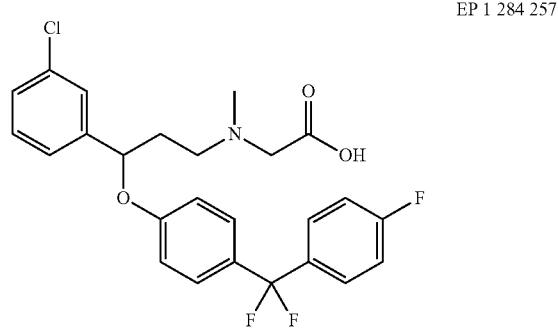

WO 2003053942

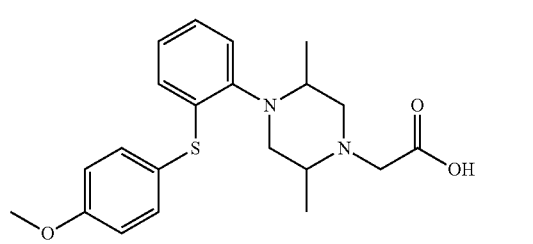

WO 2004096761
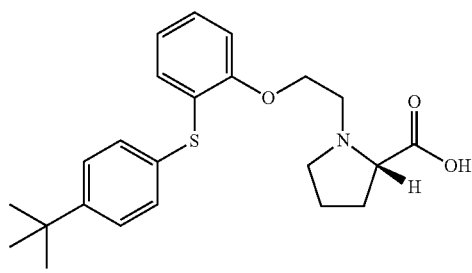
WO 2004113301
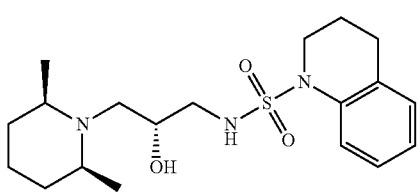
WO 2003031435
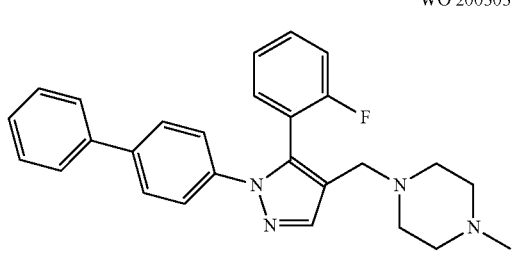
WO 2005049023
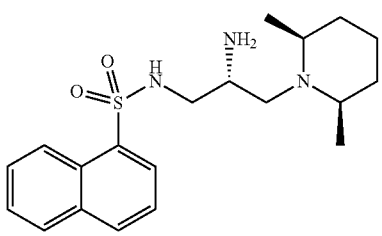
DE 10315570
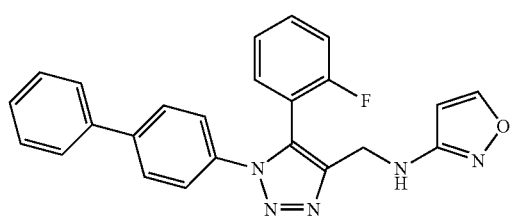
WO 2003089411
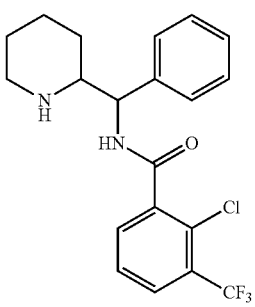
WO 2003055478
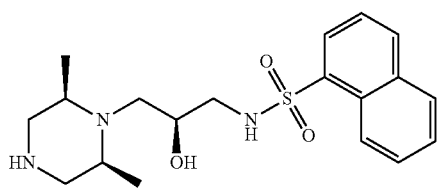
WO 2004013100
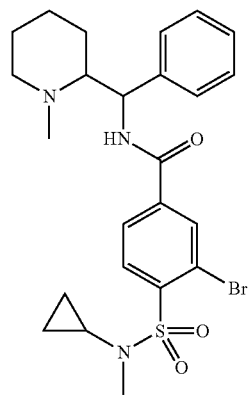
WO 2004113280
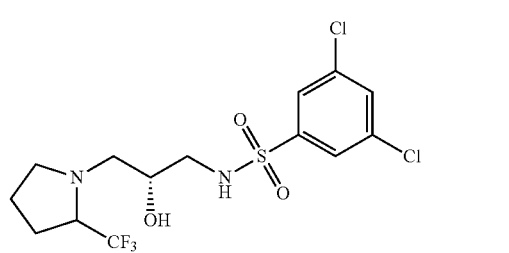
WO 2004112787
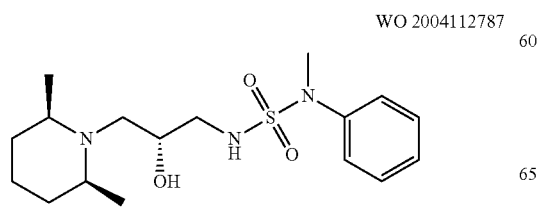
WO 2004013101
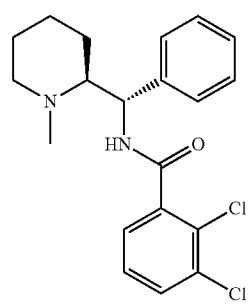

WO 2005037783
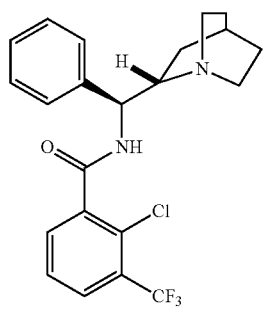
WO 2005037785
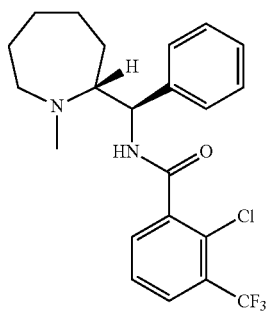
WO 2005037792
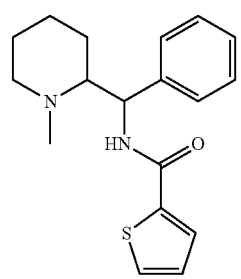
WO 2004072034
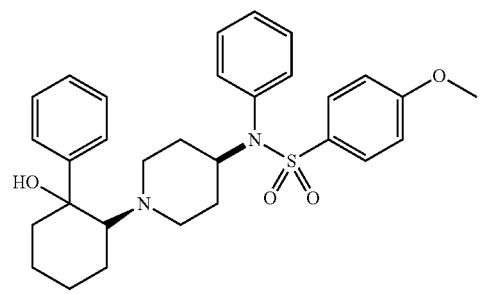
WO 2005037781
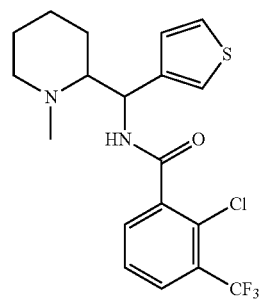
WO 2005014563
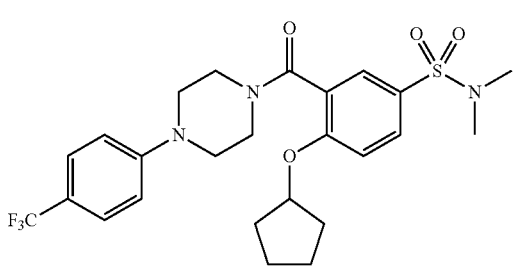
WO 2005037782
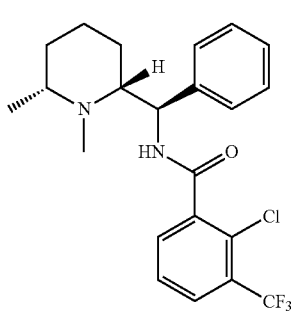
WO 2005023260
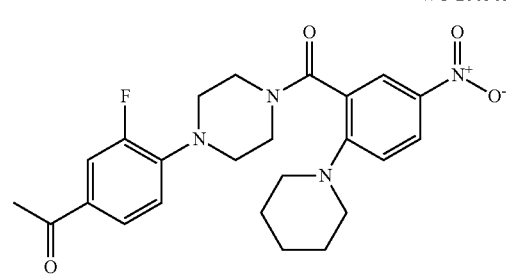
WO 2005037785
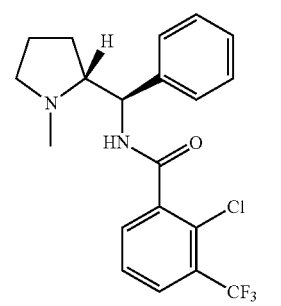
WO 2005023261
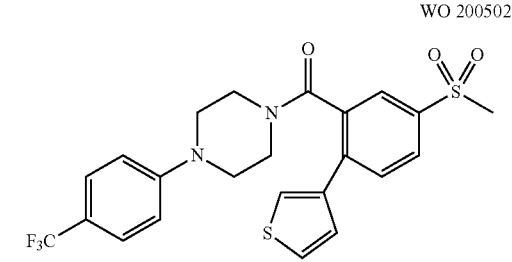

WO 2005040166

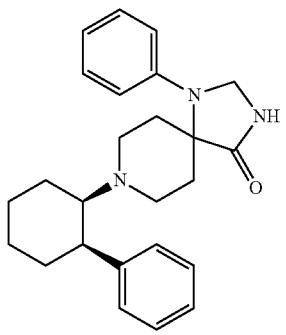

WO 2005046601

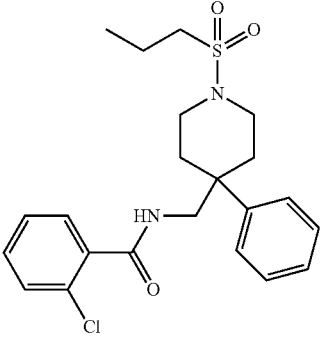

WO 2005058882

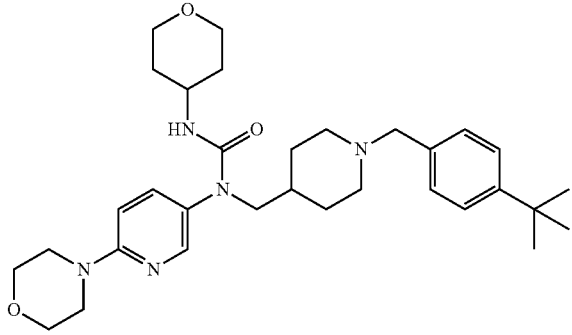

WO 2003087086

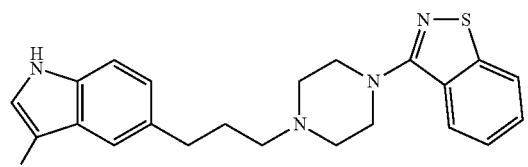

WO 2003076420

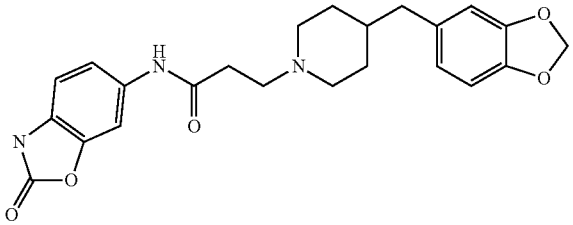

WO 2005058885

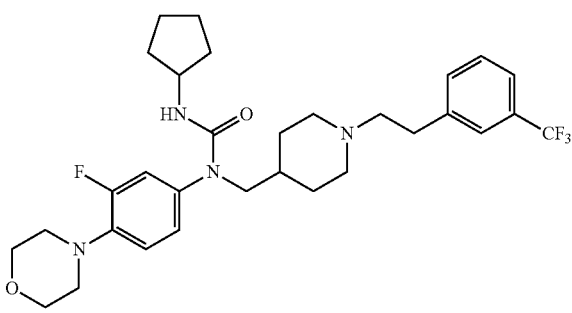

WO 2004022528

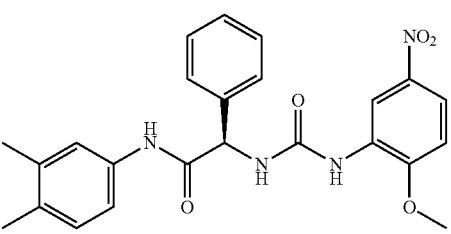

WO 2005058317

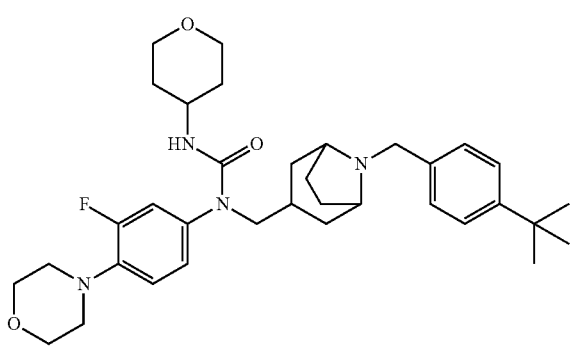

(see also Hashimoto K., Recent Patents on CNS Drug Discovery, 2006, 1, 43-53; Harsing L. G. et al., Current Medicinal Chemistry, 2006, 13, 1017-1044; Javitt D. C., Molecular Psychiatry (2004) 9, 984-997; Lindsley, C. W. et al., Current Topics in Medicinal Chemistry, 2006, 6, 771-785; Lindsley C. W. et al., Current Topics in Medicinal Chemistry, 2006, 6, 1883-1896).

It was one object of the present invention to provide further glycine transporter inhibitors.

SUMMARY OF THE INVENTION

The present invention relates to N-substituted aminobenzocycloheptene, aminotetraline, aminoindane and phenalkylamine derivatives of the formula (I), (II), (III) or (IV)

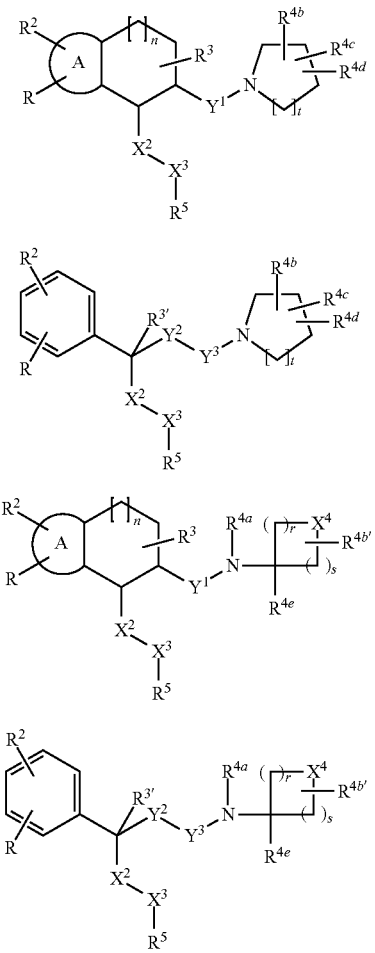

wherein

A is a 5- or 6-membered ring;

R is $R^1$—W-$A^1$-Q-Y-$A^2$-$X^1$—;

$R^1$ is hydrogen, alkyl, cycloalkylalkyl, halogenated alkyl, trialkylsilylalkyl, hydroxyalkyl, alkoxyalkyl, aminoalkyl, alkylaminoalkyl, dialkylaminoalkyl, alkylcarbonylaminoalkyl, alkyloxycarbonylaminoalkyl, alkylaminocarbonylaminoalkyl, dialkylaminocarbonylaminoalkyl, alkylsulfonylaminoalkyl, (optionally substituted arylalkyl)aminoalkyl, optionally substituted arylalkyl, optionally substituted heterocyclylalkyl, cycloalkyl, alkylcarbonyl, alkoxycarbonyl, halogenated alkoxycarbonyl, aryloxycarbonyl, aminocarbonyl, alkylaminocarbonyl, (halogenated alkyl)aminocarbonyl, arylaminocarbonyl, alkenyl, alkynyl, optionally substituted aryl, hydroxy, alkoxy, halogenated alkoxy, hydroxyalkoxy, alkoxyalkoxy, aminoalkoxy, alkylaminoalkoxy, dialkylaminoalkoxy, alkylcarbonylaminoalkoxy, arylcarbonylaminoalkoxy, alkoxycarbonylaminoalkoxy, arylalkoxy, alkylsulfonylaminoalkoxy, (halogenated alkyl)sulfonylaminoalkoxy, arylsulfonylaminoalkoxy, (arylalkyl)sulfonylaminoalkoxy, heterocyclylsulfonylaminoalkoxy, heterocyclylalkoxy, aryloxy, heterocyclyloxy, alkylthio, halogenated alkylthio, alkylamino, (halogenated alkyl)amino, dialkylamino, di-(halogenated alkyl)amino, alkylcarbonylamino, (halogenated alkyl)carbonylamino, arylcarbonylamino, alkylsulfonylamino, (halogenated alkyl)sulfonylamino, arylsulfonylamino or optionally substituted heterocyclyl;

W is —$NR^8$— or a bond;

$A^1$ is optionally substituted alkylene or a bond;

Q is —$S(O)_2$— or —C(O)—;

Y is —$NR^9$— or a bond;

$A^2$ is optionally substituted alkylene, alkylene-CO—, —CO-alkylene, alkylene-O-alkylene, alkylene-$NR^{10}$-alkylene, optionally substituted alkenylene, optionally substituted alkynylene, optionally substituted arylene, optionally substituted heteroarylene or a bond;

$X^1$ is —O—, —$NR^{11}$—, —S—, optionally substituted alkylene, optionally substituted alkenylen, optionally substituted alkynylene;

$R^2$ is hydrogen, halogen, alkyl, halogenated alkyl, hydroxyalkyl, —CN, alkenyl, alkynyl, optionally substituted aryl, hydroxy, alkoxy, halogenated alkoxy, alkoxycarbonyl, alkenyloxy, arylalkoxy, alkylcarbonyloxy, alkylthio, alkylsulfinyl, alkylsulfonyl, aminosulfonyl, amino, alkylamino, alkenylamino, nitro or optionally substituted heterocyclyl, or two radicals $R^2$ together with the ring atoms of A to which they are bound form a 5- or 6-membered ring;

$R^3$ is hydrogen, halogen, alkyl or alkoxy, or two radicals $R^3$ together with the carbon atom to which they are attached form a carbonyl group;

$R^{3'}$ is hydrogen or alkyl;

$Y^1$ is a bond or optionally substituted alkylene;

$Y^2$ is >$CR^{14a}R^{14b}$ or a bond;

$Y^3$ is >$CR^{15a}R^{15b}$ or a bond;

t is 0, 1, 2 or 3;

r is 1, 2 or 3;

s is 1, 2 or 3;

$R^{4a}$ is hydrogen, alkyl, cycloalkylalkyl, halogenated alkyl, hydroxyalkyl, alkoxyalkyl, aminoalkyl, $CH_2CN$, —CHO, alkylcarbonyl, (halogenated alkyl)carbonyl, arylcarbonyl, alkoxycarbonyl, aryloxycarbonyl, alkylaminocarbonyl, alkenyl, —C(=NH)$NH_2$, —C(=NH)NHCN, alkylsulfonyl, arylsulfonyl, amino, —NO or heterocyclyl;

$R^{4b}$ is hydrogen, halogen, alkyl, cycloalkylalkyl, halogenated alkyl, trialkylsilylalkyl, hydroxyalkyl, alkoxyalkyl, aminoalkyl, alkylaminoalkyl, dialkylaminoalkyl, alkylcarbonylaminoalkyl, alkyloxycarbonylaminoalkyl, alkylaminocarbonylaminoalkyl, dialkylaminocarbonylaminoalkyl, alkylsulfonylaminoalkyl, (optionally substituted arylalkyl)aminoalkyl, optionally substituted arylalkyl, optionally substituted heterocyclylalkyl, cycloalkyl, alkylcarbonyl, alkoxycarbonyl, halogenated alkoxycarbonyl, aryloxycarbonyl, aminocarbonyl, alkylaminocarbonyl, (halogenated alkyl)aminocarbonyl, arylaminocarbonyl, alkenyl, alkynyl, optionally substituted aryl, cyano, hydroxy, alkoxy, halogenated alkoxy, hydroxyalkoxy, alkoxyalkoxy, aminoalkoxy, alkylaminoalkoxy, dialkylaminoalkoxy, alkylcarbonylaminoalkoxy, arylcarbonylaminoalkoxy, alkoxycarbonylaminoalkoxy, arylalkoxy, alkylsulfonylaminoalkoxy, (halogenated alkyl)sulfonylaminoalkoxy, arylsulfonylaminoalkoxy, (arylalkyl)sulfonylaminoalkoxy, heterocyclylsulfonylaminoalkoxy, heterocyclylalkoxy, aryloxy, heterocyclyloxy, alkylthio, halogenated alkylthio, alkylamino, (halogenated alkyl)amino, dialkylamino, di(halogenated alkyl)amino, alkylcarbonylamino, (halogenated alkyl)carbonylamino, arylcarbonylamino, alkylsulfonylamino, (halogenated alkyl)sulfonylamino, arylsulfonylamino or optionally substituted heterocyclyl;

$R^{4c}$, $R^{4d}$ together are alkylene optionally substituted with 1, 2 or 3 substituents $R^{4f}$, wherein one —$CH_2$— of alkylene may be replaced by an oxygen atom or —$NR^{20}$—;

$R^{4f}$ is hydrogen, halogen, alkyl, cycloalkylalkyl, halogenated alkyl, trialkylsilylalkyl, hydroxyalkyl, alkoxyalkyl, aminoalkyl, alkylaminoalkyl, dialkylaminoalkyl, alkylcarbonylaminoalkyl, alkyloxycarbonylaminoalkyl, alkylaminocarbonylaminoalkyl, dialkylaminocarbonylaminoalkyl, alkylsulfonylaminoalkyl, (optionally substituted arylalkyl)aminoalkyl, optionally substituted arylalkyl, optionally substituted heterocyclylalkyl, cycloalkyl, alkylcarbonyl, alkoxycarbonyl, halogenated alkoxycarbonyl, aryloxycarbonyl, aminocarbonyl, alkylaminocarbonyl, (halogenated alkyl)aminocarbonyl, arylaminocarbonyl, alkenyl, alkynyl, optionally substituted aryl, cyano, hydroxy, alkoxy, halogenated alkoxy, hydroxyalkoxy, alkoxyalkoxy, aminoalkoxy, alkylaminoalkoxy, dialkylaminoalkoxy, alkylcarbonylaminoalkoxy, arylcarbonylaminoalkoxy, alkoxycarbonylaminoalkoxy, arylalkoxy, alkylsulfonylaminoalkoxy, (halogenated alkyl)sulfonylaminoalkoxy, arylsulfonylaminoalkoxy, (arylalkyl)sulfonylaminoalkoxy, heterocyclylsulfonylaminoalkoxy, heterocyclylalkoxy, aryloxy, heterocyclyloxy, alkylthio, halogenated alkylthio, alkylamino, (halogenated alkyl)amino, dialkylamino, di(halogenated alkyl)amino, alkylcarbonylamino, (halogenated alkyl)carbonylamino, arylcarbonylamino, alkylsulfonylamino, (halogenated alkyl)sulfonylamino, arylsulfonylamino or optionally substituted heterocyclyl;

$R^{4b'}$ is hydrogen, halogen, alkyl, cycloalkylalkyl, halogenated alkyl, trialkylsilylalkyl, hydroxyalkyl, alkoxyalkyl, aminoalkyl, alkylaminoalkyl, dialkylaminoalkyl, alkylcarbonylaminoalkyl, alkyloxycarbonylaminoalkyl, alkylaminocarbonylaminoalkyl, dialkylaminocarbonylaminoalkyl, alkylsulfonylaminoalkyl, (optionally substituted arylalkyl)aminoalkyl, optionally substituted arylalkyl, optionally substituted heterocyclylalkyl, cycloalkyl, alkylcarbonyl, alkoxycarbonyl, halogenated alkoxycarbonyl, aryloxycarbonyl, aminocarbonyl, alkylaminocarbonyl, (halogenated alkyl)aminocarbonyl, arylaminocarbonyl, alkenyl, alkynyl, optionally substituted aryl, cyano, hydroxy, alkoxy, halogenated alkoxy, hydroxyalkoxy, alkoxyalkoxy, aminoalkoxy, alkylaminoalkoxy, dialkylaminoalkoxy, alkylcarbonylaminoalkoxy, arylcarbonylaminoalkoxy, alkoxycarbonylaminoalkoxy, arylalkoxy, alkylsulfonylaminoalkoxy, (halogenated alkyl)sulfonylaminoalkoxy, arylsulfonylaminoalkoxy, (arylalkyl)sulfonylaminoalkoxy, heterocyclylsulfonylaminoalkoxy, heterocyclylalkoxy, aryloxy, heterocyclyloxy, alkylthio, halogenated alkylthio, alkylamino, (halogenated alkyl)amino, dialkylamino, di(halogenated alkyl)amino, alkylcarbonylamino, (halogenated alkyl)carbonylamino, arylcarbonylamino, alkylsulfonylamino, (halogenated alkyl)sulfonylamino, arylsulfonylamino or optionally substituted heterocyclyl;

$R^{4e}$ is hydrogen, halogen, alkyl, cycloalkylalkyl, halogenated alkyl, trialkylsilylalkyl, hydroxyalkyl, alkoxyalkyl, aminoalkyl, alkylaminoalkyl, dialkylaminoalkyl, alkylcarbonylaminoalkyl, alkyloxycarbonylaminoalkyl, alkylaminocarbonylaminoalkyl, dialkylaminocarbonylaminoalkyl, alkylsulfonylaminoalkyl, (optionally substituted arylalkyl)aminoalkyl, optionally substituted arylalkyl, optionally substituted heterocyclylalkyl, cycloalkyl, alkylcarbonyl, alkoxycarbonyl, halogenated alkoxycarbonyl, aryloxycarbonyl, aminocarbonyl, alkylaminocarbonyl, (halogenated alkyl)aminocarbonyl, arylaminocarbonyl, alkenyl, alkynyl, optionally substituted aryl, cyano, hydroxy, alkoxy, halogenated alkoxy, hydroxyalkoxy, alkoxyalkoxy, aminoalkoxy, alkylaminoalkoxy, dialkylaminoalkoxy, alkylcarbonylaminoalkoxy, arylcarbonylaminoalkoxy, alkoxycarbonylaminoalkoxy, arylalkoxy, alkylsulfonylaminoalkoxy, (halogenated alkyl)sulfonylaminoalkoxy, arylsulfonylaminoalkoxy, (arylalkyl)sulfonylaminoalkoxy, heterocyclylsulfonylaminoalkoxy, heterocyclylalkoxy, aryloxy, heterocyclyloxy, alkylthio, halogenated alkylthio, alkylamino, (halogenated alkyl)amino, dialkylamino, di(halogenated alkyl)amino, alkylcarbonylamino, (halogenated alkyl)carbonylamino, arylcarbonylamino, alkylsulfonylamino, (halogenated alkyl)sulfonylamino, arylsulfonylamino or optionally substituted heterocyclyl, provided that in formula (III) or (IV) at least one of $R^{4b'}$ and $R^{4e}$ is not hydrogen;

$X^2$ is —O—, —NR$^6$—, —S—, >CR$^{12a}$R$^{12b}$ or a bond;

$X^3$ is —O—, —NR$^7$—, —S—, >CR$^{13a}$R$^{13b}$ or a bond;

$X^4$ is —O—, —NR$^{21}$—, —S—, —S(O)—, —S(O)$_2$—, or a bond;

$R^5$ is optionally substituted aryl, optionally substituted cycloalkyl or optionally substituted heterocyclyl;

n is 0, 1 or 2;

$R^6$ is hydrogen, alkyl or cycloalkyl;

$R^7$ is hydrogen, alkyl or cycloalkyl;

$R^8$ is hydrogen, alkyl or cycloalkyl;

$R^9$ is hydrogen, alkyl, cycloalkyl, aminoalkyl, optionally substituted arylalkyl or heterocyclyl; or $R^9$, $R^1$ together are alkylene; or $R^9$ is alkylene that is bound to a carbon atom in $A^2$ and $A^2$ is alkylene or to a carbon atom in $X^1$ and $X^1$ is alkylene;

$R^{10}$ is hydrogen, alkyl, cycloalkyl or alkylsulfonyl;

$R^{11}$ is hydrogen, alkyl or cycloalkyl, or $R^9$, $R^{11}$ together are alkylene, $R^{12a}$ is hydrogen, optionally substituted alkyl, alkylaminoalkyl, dialkylaminoalkyl, heterocyclylalkyl, optionally substituted aryl or hydroxy;

$R^{12b}$ is hydrogen or alkyl, or $R^{12a}$, $R^{12b}$ together are carbonyl or optionally substituted alkylene, wherein one —CH$_2$— of alkylene may be replaced by an oxygen atom or —NR$^{16}$—;

$R^{13a}$ is hydrogen, optionally substituted alkyl, alkylaminoalkyl, dialkylaminoalkyl, heterocyclylalkyl, optionally substituted aryl or hydroxy;

$R^{13b}$ is hydrogen or alkyl, or $R^{13a}$, $R^{13b}$ together are carbonyl or optionally substituted alkylene, wherein one —CH$_2$— of alkylene may be replaced by an oxygen atom or —NR$^{17}$—;

$R^{14a}$ is hydrogen, optionally substituted alkyl, alkylaminoalkyl, dialkylaminoalkyl, heterocyclyl-$C_1$-$C_6$-alkyl, optionally substituted aryl or hydroxy;

$R^{14b}$ is hydrogen or alkyl, or $R^{14a}$, $R^{14b}$ together are carbonyl or optionally substituted alkylene, wherein one or two —CH$_2$— of alkylene may be replaced by an oxygen atom or —NR$^{18}$—;

$R^{15a}$ is hydrogen, optionally substituted alkyl, alkylaminoalkyl, dialkylaminoalkyl, heterocyclylalkyl, optionally substituted aryl or hydroxy;

$R^{15b}$ is hydrogen, alkyl or cycloalkyl, or $R^{15a}$, $R^{15b}$ together are carbonyl or optionally substituted alkylene, wherein one or two —CH$_2$— of alkylene may be replaced by an oxygen atom or —NR$^{19}$—;

$R^{16}$ is hydrogen, alkyl or cycloalkyl;

$R^{17}$ is hydrogen, alkyl or cycloalkyl;

$R^{18}$ is hydrogen, alkyl or cycloalkyl;
$R^{19}$ is hydrogen, alkyl or cycloalkyl;
$R^{20}$ is hydrogen, alkyl or cycloalkyl; and
$R^{21}$ is hydrogen, alkyl or cycloalkyl,
or a physiologically tolerated salt thereof.

Thus, the present invention relates to N-substituted aminobenzocycloheptene, aminotetraline, aminoindane and phenalkylamine derivatives having the formula (Ia), (IIa), (IIIa) or (IVa)

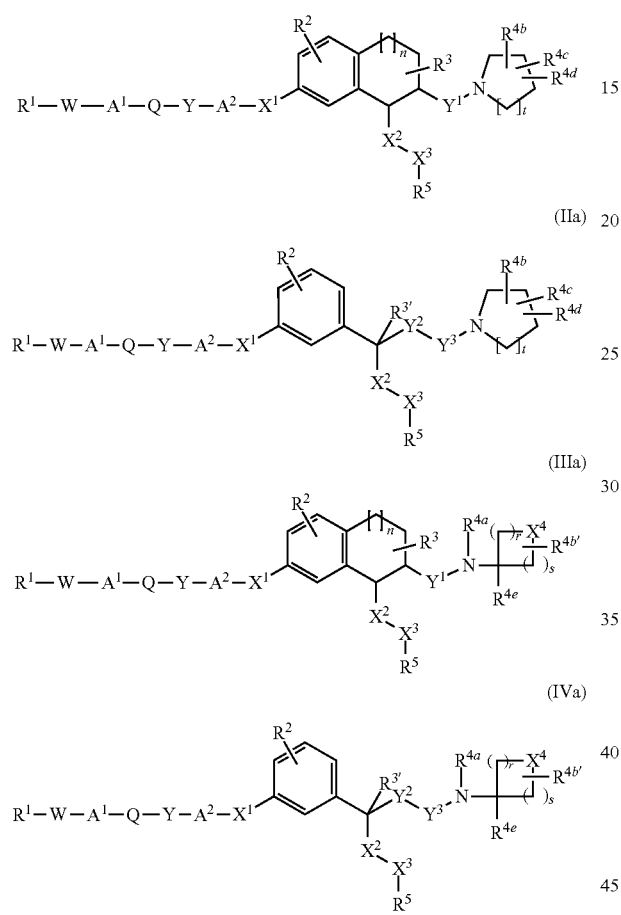

wherein $R^1$, W, $A^1$, Q, Y, $A^2$, $X^1$, $R^2$, $R^3$, $R^{3'}$, $Y^1$, $Y^2$, $Y^3$, r, s, t, $R^{4a}$, $R^{4b}$, $R^{4b'}$, $R^{4c}$, $R^{4d}$, $R^{4e}$, $X^2$, $X^3$, $X^4$, $R^5$, n are as defined herein.

Further, the present invention relates to N-substituted aminobenzocycloheptene, aminotetraline, aminoindane and phenalkylamine derivatives of formula (I), (II), (III) or (IV) wherein R is —CN, i.e. N-substituted aminobenzocycloheptene, aminotetraline, aminoindane and phenalkylamine derivatives having the formula (Ib), (IIb), (IIIb), or (IVb)

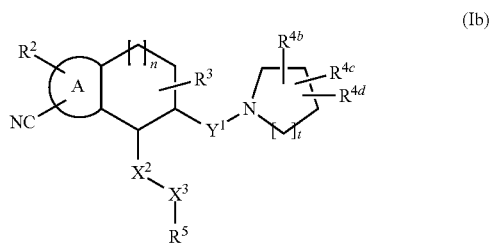

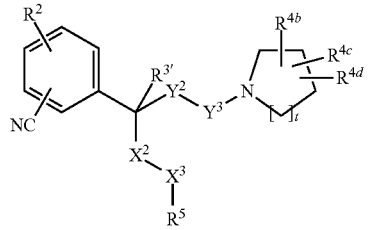

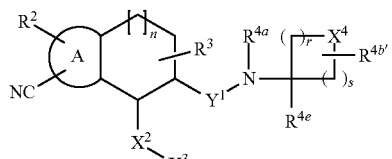

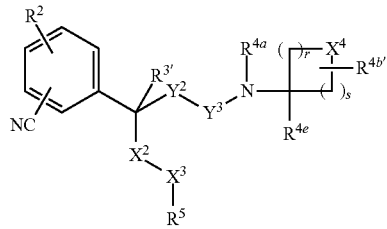

wherein A, $R^2$, $R^3$, $R^{3'}$, $Y^1$, $Y^2$, $Y^3$, r, s, t, $R^{4a}$, $R^{4b}$, $R^{4b'}$, $R^{4c}$, $R^{4d}$, $R^{4e}$, $X^2$, $X^3$, $X^4$, $R^5$, n are as defined herein.

Thus, the term aminobenzocycloheptene, aminotetraline and aminoindane derivative is used herein to denote in particular tetralines (n=1) and fused cyclohexanes (n=1) wherein the benzene ring is replaced by a 5- or 6-membered heterocyclic ring as well as homologous bicyclic compounds wherein n is 0 or 2 (benzocycloheptenes and fused cycloheptanes (n=2) or indanes and fused cyclopentanes (n=0)). The term phenalkylamine derivative is used herein to denote in particular phenethylamines ($Y^2$ is a bond and $Y^3$ is >$CR^{15a}R^{15b}$) and phenpropylamines ($Y^2$ is >$CR^{14a}R^{14b}$ and $Y^3$ and $Y^3$ is $CR^{15a}R^{15b}$).

Said compounds of formula (I), (II), (III) or (IV), i.e., the N-substituted aminobenzocycloheptene, aminotetraline and aminoindane derivatives of formula (I) or (III) as well as the phenalkylamine derivatives of formula (II) or (IV) and their physiologically tolerated salts, are glycine transporter inhibitors and thus useful as pharmaceuticals. The compounds of formula (I), (II), (III) or (IV) may exhibit favorable efflux properties which may lead to enhanced oral bioavailability and/or increased brain availability.

The present invention thus further relates to the compounds of formula (I), (II), (III) or (IV) for use in therapy.

The present invention also relates to pharmaceutical compositions which comprise a carrier and a compound of formula (I), (II), (III) or (IV).

In particular, said compounds, i.e., the N-substituted aminobenzocycloheptene, aminotetraline, aminoindane and phenalkylamine derivatives and their physiologically tolerated salts, are inhibitors of the glycine transporter GlyT1.

The present invention thus further relates to the compounds of formula (I), (II), (III) or (IV) for use in inhibiting the glycine transporter.

The present invention also relates to the use of the compounds of formula (I), (II), (III) or (IV) in the manufacture of a medicament for inhibiting the glycine transporter GlyT1 and corresponding methods of inhibiting the glycine transporter GlyT1.

Glycine transport inhibitors and in particular inhibitors of the glycine transporter GlyT1 are known to be useful in treating a variety of neurologic and psychiatric disorders.

The present invention thus further relates to the compounds of formula (I), (II), (III) or (IV) for use in treating a neurologic or psychiatric disorder.

The present invention further relates to the compounds of formula (I), (II), (III) or (IV) for use in treating pain.

The present invention also relates to the use of the compounds of formula (I), (II), (III) or (IV) in the manufacture of a medicament for treating a neurologic or psychiatric disorder and corresponding methods of treating said disorders. The present invention also relates to the use of the compounds of formula (I), (II), (III) or (IV) in the manufacture of a medicament for treating pain and corresponding methods of treating pain.

The present invention further relates to N-substituted aminobenzocycloheptene, aminotetraline and aminoindane derivatives of formula (V) or (VI)

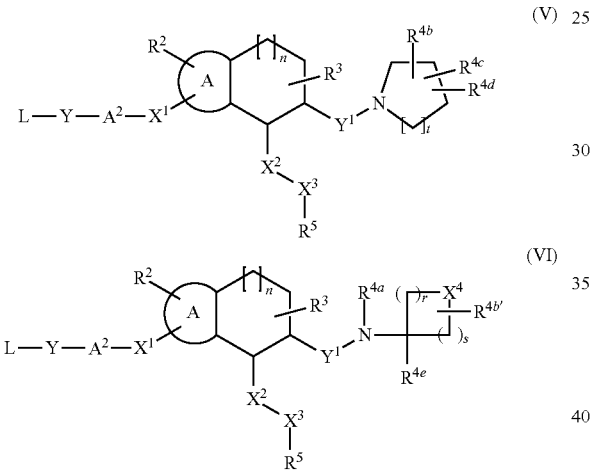

wherein L is an amino-protecting group, Y is $NR^9$, and A, $A^2$, $X^1$, $R^2$, $R^3$, $Y^1$, r, s, t, $R^{4a}$, $R^{4b}$, $R^{4b'}$, $R^{4c}$, $R^{4d}$, $R^{4e}$, $X^2$, $X^3$, $X^4$, $R^5$, n, $R^9$ are defined as above.

The N-substituted aminobenzocycloheptene, aminotetraline and aminoindane derivatives of formula (V) and (VI) are useful as intermediates in the preparation of GlyT1 inhibitors, in particular those of formula (I) and (III), respectively.

DETAILED DESCRIPTION OF THE INVENTION

Provided that the N-substituted aminobenzocycloheptene, aminotetraline, aminoindane and phenalkylamine derivatives of the formula (I), (II), (III), (IV), (V) or (VI) of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula (I), (II), (III), (IV), (V) or (VI) and/or of their salts.

According to one embodiment, an enantiomer of the compounds of formula (I) of the present invention has the following formula:

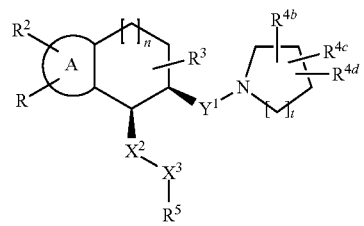

wherein A, R, $R^2$, $R^3$, $Y^1$, t, $R^{4b}$, $R^{4c}$, $R^{4d}$, $X^2$, $X^3$, $R^5$, n are as defined herein.

According to another embodiment, an enantiomer of the compounds of formula (I) of the present invention has the following formula:

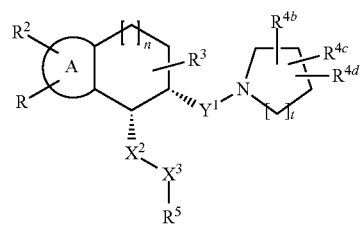

wherein A, R, $R^2$, $R^3$, $Y^1$, t, $R^{4b}$, $R^{4c}$, $R^{4d}$, $X^2$, $X^3$, $R^5$, n are as defined herein.

According to another embodiment, an enantiomer of the compounds of formula (I) of the present invention has the following formula:

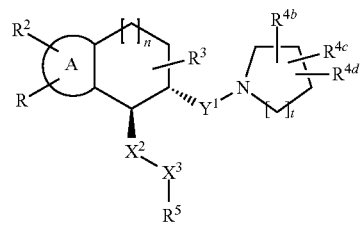

wherein A, R, $R^2$, $R^3$, $Y^1$, t, $R^{4b}$, $R^{4c}$, $R^{4d}$, $X^2$, $X^3$, $R^5$, n are as defined herein.

According to another embodiment, an enantiomer of the compounds of formula (I) of the present invention has the following formula:

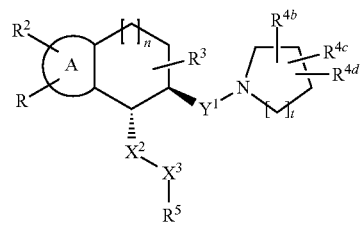

wherein A, R, $R^2$, $R^3$, $Y^1$, t, $R^{4b}$, $R^{4c}$, $R^{4d}$, $X^2$, $X^3$, $R^5$, n are as defined herein.

According to one embodiment, an enantiomer of the compounds of formula (II) of the present invention has the following formula:

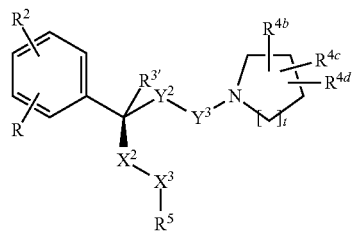

wherein R, R², R³', Y², Y³, t, R⁴ᵇ, R⁴ᶜ, R⁴ᵈ, X², X³, R⁵ are as defined herein.

According to another embodiment, an enantiomer of the compounds of formula (II) of the present invention has the following formula:

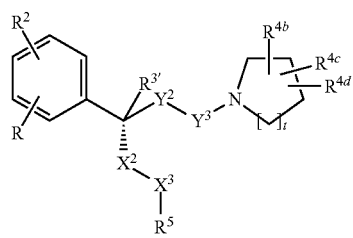

wherein R, R², R³', Y², Y³, t, R⁴ᵇ, R⁴ᶜ, R⁴ᵈ, X², X³, R⁵ are as defined herein.

According to one embodiment, an enantiomer of the compounds of formula (III) of the present invention has the following formula:

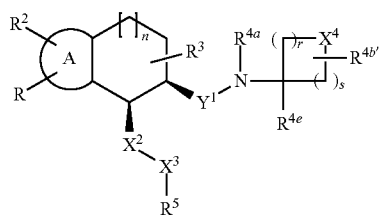

wherein A, R, R², R³, Y¹, r, s, R⁴ᵃ, R⁴ᵇ', R⁴ᵉ, X², X³, X⁴, R⁵, n are as defined herein.

According to another embodiment, an enantiomer of the compounds of formula (III) of the present invention has the following formula:

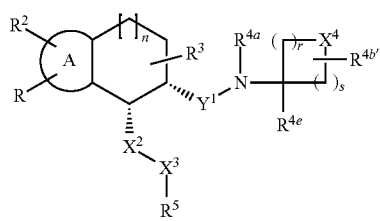

wherein A, R, R², R³, Y¹, r, s, R⁴ᵃ, R⁴ᵇ', R⁴ᵉ, X², X³, X⁴, R⁵, n are as defined herein.

According to another embodiment, an enantiomer of the compounds of formula (III) of the present invention has the following formula:

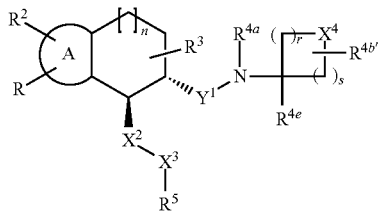

wherein A, R, R², R³, Y¹, r, s, R⁴ᵃ, R⁴ᵇ', R⁴ᵉ, X², X³, X⁴, R⁵, n are as defined herein.

According to another embodiment, an enantiomer of the compounds of formula (III) of the present invention has the following formula:

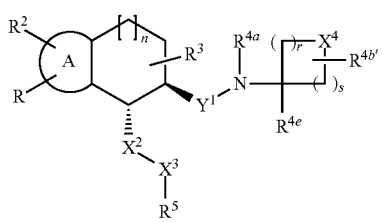

wherein A, R, R², R³, Y¹, r, s, R⁴ᵃ, R⁴ᵇ', R⁴ᵉ, X², X³, X⁴, R⁵, n are as defined herein.

According to one embodiment, an enantiomer of the compounds of formula (IV) of the present invention has the following formula:

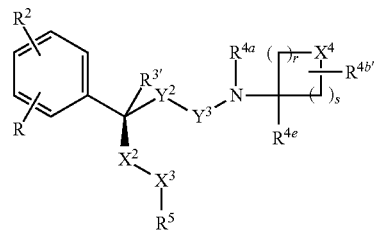

wherein R, R², R³', Y², Y³, r, s, R⁴ᵃ, R⁴ᵇ', R⁴ᵉ, X², X³, X⁴, R⁵ are as defined herein.

According to another embodiment, an enantiomer of the compounds of formula (IV) of the present invention has the following formula:

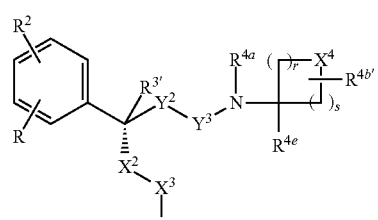

wherein R, R², R³', Y², Y³, r, s, R⁴ᵃ, R⁴ᵇ', R⁴ᵉ, X², X³, X⁴, R⁵ are as defined herein.

The physiologically tolerated salts of the tetraline and indane derivatives of the formula (I), (II), (III), (IV), (V) or (VI) are especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, cycloaliphatic sulfonic acids, such as S-(+)-10-camphor sulfonic acid, aromatic sulfonic acids, such as benzenesulfonic acid and toluenesulfonic acid, di- and tricarboxylic acids and hydroxycarboxylic acids having 2 to 10 carbon atoms, such as oxalic acid, malonic acid, maleic acid, fumaric acid, lactic acid, tartaric acid, citric acid, glycolic acid, adipic acid and benzoic acid. Other utilizable acids are described, e.g., in Fortschritte der Arzneimittelforschung [Advances in drug research], Volume 10, pages 224 ff., Birkhäuser Verlag, Basel and Stuttgart, 1966. The physiologically tolerated salts of the tetraline and indane derivatives also include salts of a physiologically tolerated anion with tetraline and indane derivatives wherein one or more than one nitrogen atom is quaternized, e.g. with an alkyl residue (e.g. methyl or ethyl).

The present invention moreover relates to compounds of formula (I), (II), (III), (IV), (V) or (VI) as defined herein, wherein at least one of the atoms has been replaced by its stable, non-radioactive isotope (e.g., hydrogen by deuterium, $^{12}C$ $^{13}C$, $^{14}N$ by $^{15}N$, $^{16}O$ by $^{18}O$) and preferably wherein at least one hydrogen atom has been replaced by a deuterium atom.

Of course, such compounds contain more of the respective isotope than this naturally occurs and thus is anyway present in the compounds (I), (II), (III), (IV), (V) or (VI).

Stable isotopes (e.g., deuterium, $^{13}C$, $^{15}N$, $^{18}O$) are nonradioactive isotopes which contain one or more additional neutron than the normally abundant isotope of the respective atom. Deuterated compounds have been used in pharmaceutical research to investigate the in vivo metabolic fate of the compounds by evaluation of the mechanism of action and metabolic pathway of the non-deuterated parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. *Labelled Comp. Radiopharmaceut.*, 36(10):927-932 (1995); Kushner et al., *Can. J. Physiol. Pharmacol.*, 77, 79-88 (1999).

Incorporation of a heavy atom particularly substitution of deuterium for hydrogen, can give rise to an isotope effect that could alter the pharmacokinetics of the drug. This effect is usually insignificant if the label is placed at a metabolically inert position of the molecule. Stable isotope labeling of a drug can alter its physico-chemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet. Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

The organic moieties mentioned in the above definitions of the variables are—like the term halogen—collective terms for individual listings of the individual group members. The prefix $C_n$-$C_m$ indicates in each case the possible number of carbon atoms in the group.

Unless indicated otherwise, the term "substituted" means that a radical is substituted with 1, 2 or 3, especially 1, substituent which are in particular selected from the group consisting of halogen, $C_1$-$C_4$-alkyl, hydroxy-$C_1$-$C_4$-alkyl, $C_3$-$C_{12}$-heterocyclyl-alkyl, $C_1$-$C_4$-alkoxy-$C_1$-$C_4$-alkyl, amino-$C_1$-$C_4$-alkyl, $C_1$-$C_4$-alkenyl, oxo (=O), OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—($C_1$-$C_6$-alkyl)$_2$, $SO_2N$—($C_1$-$C_6$-alkyl)$_2$, $NH_2$, NH—$C_1$-$C_6$-alkyl, N—($C_1$-$C_6$-alkyl)$_2$, NH—($C_1$-$C_4$-alkyl-$C_6$-$C_{12}$-aryl), NH—CO—$C_1$-$C_6$-alkyl, NH—$SO_2$—$C_1$-$C_6$-alkyl, $SO_2$—$C_1$-$C_6$-alkyl, $C_6$-$C_{12}$-aryl, O—$C_6$-$C_{12}$-aryl, O—$CH_2$—$C_6$-$C_{12}$-aryl, CONH—$C_6$-$C_{12}$-aryl, $SO_2NH$—$C_6$-$C_{12}$-aryl, CONH—$C_3$-$C_{12}$-heterocyclyl, $SO_2NH$—$C_3$-$C_{12}$-heterocyclyl, $SO_2$—$C_6$-$C_{12}$-aryl, NH—$SO_2$—$C_6$-$C_{12}$-aryl, NH—CO—$C_6$-$C_{12}$-aryl, NH—$SO_2$—$C_3$-$C_{12}$-heterocyclyl, NH—CO—$C_3$-$C_{12}$-heterocyclyl and $C_3$-$C_{12}$-heterocyclyl, wherein aryl and heterocyclyl in turn may be unsubstituted or substituted with 1, 2 or 3 substituents selected from the group consisting of halogen, $C_1$-$C_4$-alkyl, $C_1$-$C_4$-haloalkyl, $C_1$-$C_4$-alkoxy and $C_1$-$C_4$-haloalkoxy.

The term halogen denotes in each case fluorine, bromine, chlorine or iodine, in particular fluorine or chlorine.

$C_1$-$C_4$-Alkyl is a straight-chain or branched alkyl group having from 1 to 4 carbon atoms. Examples of an alkyl group are methyl, $C_2$-$C_4$-alkyl such as ethyl, n-propyl, iso-propyl, n-butyl, 2-butyl, iso-butyl or tert-butyl. $C_1$-$C_2$-Alkyl is methyl or ethyl, $C_1$-$C_3$-alkyl is additionally n-propyl or iso-propyl.

$C_1$-$C_6$-Alkyl is a straight-chain or branched alkyl group having from 1 to 6 carbon atoms. Examples include methyl, $C_2$-$C_4$-alkyl as mentioned herein and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Halogenated $C_1$-$C_4$-alkyl is a straight-chain or branched alkyl group having 1 to 4 carbon atoms, preferably 1 to 3 carbon atoms, more preferably 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethyl, dihalogenomethyl, trihalogenomethyl, (R)-1-halogenoethyl, (S)-1-halogenoethyl, 2-halogenoethyl, 1,1-dihalogenoethyl, 2,2-dihalogenoethyl, 2,2,2-trihalogenoethyl, (R)-1-halogenopropyl, (S)-1-halogenopropyl, 2-halogenopropyl, 3-halogenopropyl, 1,1-dihalogenopropyl, 2,2-dihalogenopropyl, 3,3-dihalogenopropyl, 3,3,3-trihalogenopropyl, (R)-2-halogeno-1-methylethyl, (S)-2-halogeno-1-methylethyl, (R)-2,2-dihalogeno-1-methylethyl, (S)-2,2-dihalogeno-1-methylethyl, (R)-1,2-dihalogeno-1-methylethyl, (S)-1,2-dihalogeno-1-methylethyl, (R)-2,2,2-trihalogeno-1-methylethyl, (S)-2,2,2-trihalogeno-1-methylethyl, 2-halogeno-1-(halogenomethyl)ethyl, 1-(dihalogenomethyl)-2,2-dihalogenoethyl, (R)-1-halogenobutyl, (S)-1-halogenobutyl, 2-halogenobutyl, 3-halogenobutyl, 4-halogenobutyl, 1,1-dihalogenobutyl, 2,2-dihalogenobutyl, 3,3-dihalogenobutyl, 4,4-dihalogenobutyl, 4,4,4-trihalogenobutyl, etc. Particular examples include the fluorinated $C_1$-$C_4$ alkyl groups as defined, such as trifluoromethyl.

$C_6$-$C_{12}$-Aryl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by $C_6$-$C_{12}$-aryl, such as in benzyl.

Hydroxy-$C_1$-$C_4$-alkyl is a straight-chain or branched alkyl group having 1 to 4 carbon atoms, preferably 1 to 3 carbon atoms, more preferably 1 or 2 carbon atoms, wherein one or two hydrogen atoms are replaced by one or two hydroxyl groups, such as in hydroxymethyl, (R)-1-hydroxyethyl, (S)-1-hydroxyethyl, 2-hydroxyethyl, (R)-1-hydroxypropyl, (S)-1-hydroxypropyl, 2-hydroxypropyl, 3-hydroxypropyl, (R)-2-hydroxy-1-methylethyl, (S)-2-hydroxy-1-methylethyl, 2-hydroxy-1-(hydroxymethyl)ethyl, (R)-1-hydroxybutyl, (S)-1-hydroxybutyl, 2-hydroxybutyl, 3-hydroxybutyl, 4-hydroxybutyl.

$C_1$-$C_6$-Alkoxy-$C_1$-$C_4$-alkyl is a straight-chain or branched alkyl group having 1 to 4 carbon atoms, preferably 1 to 3 carbon atoms, more preferably 1 or 2 carbon atoms, wherein one or two hydrogen atoms are replaced by one or two alkoxy groups having 1 to 6, preferably 1 to 4, in particular 1 or 2 carbon atoms, such as in methoxymethyl, (R)-1-methoxyethyl, (S)-1-methoxyethyl, 2-methoxyethyl, (R)-1-methoxypropyl, (S)-1-methoxypropyl, 2-methoxypropyl, 3-methoxypropyl, (R)-2-methoxy-1-methylethyl, (S)-2-methoxy-1-methylethyl, 2-methoxy-1-(methoxymethyl)ethyl, (R)-1-methoxybutyl, (S)-1-methoxybutyl, 2-methoxybutyl, 3-methoxybutyl, 4-methoxybutyl, ethoxymethyl, (R)-1-ethoxyethyl, (S)-1-ethoxyethyl, 2-ethoxyethyl, (R)-1-ethoxypropyl, (S)-1-ethoxypropyl, 2-ethoxypropyl, 3-ethoxypropyl, (R)-2-ethoxy-1-methylethyl, (S)-2-ethoxy-1-methylethyl, 2-ethoxy-1-(ethoxymethyl)ethyl, (R)-1-ethoxybutyl, (S)-1-ethoxybutyl, 2-ethoxybutyl, 3-ethoxybutyl, 4-ethoxybutyl.

Amino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by an amino group, such as in aminomethyl, 2-aminoethyl.

$C_1$-$C_6$-Alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylamino group, in particular by a $C_1$-$C_4$-alkylamino group, such as in methylaminomethyl, ethylaminomethyl, n-propylaminomethyl, iso-propylaminomethyl, n-butylaminomethyl, 2-butylaminomethyl, isobutylaminomethyl or tert-butylaminomethyl.

Di-$C_1$-$C_6$-Alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a di-$C_1$-$C_6$-Alkylamino group, in particular by a di-$C_1$-$C_4$-alkylamino group, such as in dimethylaminomethyl.

$C_1$-$C_6$-Alkylcarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylcarbonylamino group, in particular by a $C_1$-$C_4$-alkylcarbonylamino group, such as in methylcarbonylaminomethyl, ethylcarbonylaminomethyl, n-propylcarbonylaminomethyl, iso-propylcarbonylaminomethyl, n-butylcarbonylaminomethyl, 2-butylcarbonylaminomethyl, iso-butylcarbonylaminomethyl or tert-butylcarbonylaminomethyl.

$C_1$-$C_6$-Alkylaminocarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylaminocarbonylamino group, in particular by a $C_1$-$C_4$-alkylaminocarbonylamino group, such as in methylaminocarbonylaminomethyl, ethylaminocarbonylaminomethyl, n-propylaminocarbonylaminomethyl, iso-propylaminocarbonylaminomethyl, n-butylaminocarbonylaminomethyl, 2-butylaminocarbonylaminomethyl, isobutylaminocarbonylaminomethyl or tert-butylaminocarbonylaminomethyl.

Di-$C_1$-$C_6$-alkylaminocarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a di-$C_1$-$C_6$-alkylaminocarbonylamino group, in particular by a di-$C_1$-$C_4$-alkylaminocarbonylamino group, such as in dimethylaminocarbonylaminomethyl, dimethylaminocarbonylaminoethyl, dimethylaminocarbonylaminon-propyl.

$C_1$-$C_6$-Alkylsulfonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylsulfonylamino group, in particular by a $C_1$-$C_4$-alkylsulfonylamino group, such as in methylsulfonylaminomethyl, ethylsulfonylaminomethyl, n-propylsulfonylaminomethyl, isopropylsulfonylaminomethyl, n-butylsulfonylaminomethyl, 2-butylsulfonylaminomethyl, isobutylsulfonylaminomethyl or tert-butylsulfonylaminomethyl.

($C_6$-$C_{12}$-Aryl-$C_1$-$C_6$-alkyl)amino-$C_1$-$C_4$ alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a ($C_6$-$C_{12}$-aryl-$C_1$-$C_6$-alkyl)amino group, in particular a ($C_6$-$C_{12}$-aryl-$C_1$-$C_2$-alkyl) amino group, such as in benzylaminomethyl.

$C_3$-$C_{12}$-Heterocyclyl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by $C_3$-$C_{12}$-heterocyclyl, such as in N-pyrrolidinylmethyl, N-piperidinylmethyl, N-morpholinylmethyl.

$C_3$-$C_{12}$-Cycloalkyl is a cycloaliphatic radical having from 3 to 12 carbon atoms. In particular, 3 to 6 carbon atoms form the cyclic structure, such as cyclopropyl, cyclobutyl, cyclopentyl and cyclohexyl. The cyclic structure may be unsubstituted or may carry 1, 2, 3 or 4 $C_1$-$C_4$ alkyl radicals, preferably one or more methyl radicals.

Carbonyl is >C=O.

$C_1$-$C_6$-Alkylcarbonyl is a radical of the formula R—C(O)—, wherein R is an alkyl radical having from 1 to 6, preferably from 1 to 4, in particular 1 or 2 carbon atoms as defined herein. Examples include acetyl, propionyl, n-butyryl, 2-methylpropionyl, pivaloyl.

Halogenated $C_1$-$C_6$-alkylcarbonyl is $C_1$-$C_6$-alkylcarbonyl as defined herein, wherein at least one, e.g. 1, 2, 3, 4 or all of the hydrogen atoms are replaced by 1, 2, 3, 4 or a corresponding number of identical or different halogen atoms. Examples include fluoromethylcarbonyl, difluoromethylcarbonyl, trifluoromethylcarbonyl. Further examples are 1,1,1-trifluoroeth-2-ylcarbonyl, 1,1,1-trifluoroprop-3-ylcarbonyl.

$C_6$-$C_{12}$-Arylcarbonyl is a radical of the formula R—C(O)—, wherein R is an aryl radical having from 6 to 12 carbon atoms as defined herein. Examples include benzoyl.

$C_1$-$C_6$-Alkoxycarbonyl is a radical of the formula R—O—C(O)—, wherein R is an alkyl radical having from 1 to 6, preferably from 1 to 4, in particular 1 or 2 carbon atoms as defined herein. Examples include methoxycarbonyl and tert-butyloxycarbonyl.

Halogenated $C_1$-$C_6$-alkoxycarbonyl is a $C_1$-$C_6$-alkoxycarbonyl as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Aryloxycarbonyl is a radical of the formula R—O—C(O)—, wherein R is an aryl radical having from 6 to 12 carbon atoms as defined herein. Examples include phenoxycarbonyl.

Cyano is —C≡N.

Aminocarbonyl is $NH_2C(O)$—.

$C_1$-$C_6$-Alkylaminocarbonyl is a radical of the formula R—NH—C(O)—, wherein R is an alkyl radical having from 1 to 6, preferably from 1 to 4, in particular 1 or 2 carbon atoms as defined herein. Examples include methylaminocarbonyl.

(Halogenated $C_1$-$C_4$-alkyl)aminocarbonyl is a $C_1$-$C_4$-alkylaminocarbonyl as defined herein, wherein at least one, e.g. 1, 2, 3, 4 or all of the hydrogen atoms are replaced by 1, 2, 3, 4 or a corresponding number of identical or different hydrogen atoms.

$C_6$-$C_{12}$-Arylaminocarbonyl is a radical of the formula R—NH—C(O)—, wherein R is an aryl radical having from 6 to 12 carbon atoms as defined herein. Examples include phenylaminocarbonyl.

$C_2$-$C_6$-Alkenyl is a singly unsaturated hydrocarbon radical having 2, 3, 4, 5 or 6 carbon atoms, e.g. vinyl, allyl (2-propen-1-yl), 1-propen-1-yl, 2-propen-2-yl, methallyl(2-methylprop-2-en-1-yl) and the like. $C_3$-$C_5$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

$C_2$-$C_6$-Alkynyl is a singly unsaturated hydrocarbon radical having 2, 3, 4, 5 or 6 carbon atoms, e.g. ethynyl, 2-propyn-1-yl, 1-propyn-1-yl, 2-propyn-2-yl and the like. $C_3$-$C_5$-Alkynyl is, in particular, 2-propyn-1-yl, 2-butyn-1-yl, 3-butyn-1-yl, 2-pentyn-1-yl, 3-pentyn-1-yl, 4-pentyn-1-yl.

$C_1$-$C_4$-Alkylene is straight-chain or branched alkylene group having from 1 to 4 carbon atoms. Examples include methylene and ethylene. A further example is propylene.

$C_2$-$C_4$-Alkenylene is straight-chain or branched alkenylene group having from 2 to 4 carbon atoms.

$C_2$-$C_4$-Alkynylene is straight-chain or branched alkynylene group having from 2 to 4 carbon atoms. Examples include propynylene.

$C_6$-$C_{12}$-Aryl is a 6- to 12-membered, in particular 6- to 10-membered, aromatic cyclic radical. Examples include phenyl and naphthyl.

$C_3$-$C_{12}$-Arylene is an aryl diradical. Examples include phen-1,4-ylene and phen-1,3-ylene.

Hydroxy is —OH.

$C_1$-$C_6$-Alkoxy is a radical of the formula R—O—, wherein R is a straight-chain or branched alkyl group having from 1 to 6, in particular 1 to 4 carbon atoms. Examples include methoxy, ethoxy, n-propoxy, isopropoxy, n-butoxy, 2-butoxy, isobutoxy(2-methylpropoxy), tert.-butoxy pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Halogenated $C_1$-$C_6$-alkoxy is a straight-chain or branched alkoxy group having from 1 to 6, preferably from 1 to 4, in particular 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethoxy, dihalogenomethoxy, trihalogenomethoxy, (R)-1-halogenoethoxy, (S)-1-halogenoethoxy, 2-halogenoethoxy, 1,1-dihalogenoethoxy, 2,2-dihalogenoethoxy, 2,2,2-trihalogenoethoxy, (R)-1-halogenopropoxy, (S)-1-halogenopropoxy, 2-halogenopropoxy, 3-halogenopropoxy, 1,1-dihalogenopropoxy, 2,2-dihalogenopropoxy, 3,3-dihalogenopropoxy, 3,3,3-trihalogenopropoxy, (R)-2-halogeno-1-methylethoxy, (S)-2-halogeno-1-methylethoxy, (R)-2,2-dihalogeno-1-methylethoxy, (S)-2,2-dihalogeno-1-methylethoxy, (R)-1,2-dihalogeno-1-methylethoxy, (S)-1,2-dihalogeno-1-methylethoxy, (R)-2,2,2-trihalogeno-1-methylethoxy, (S)-2,2,2-trihalogeno-1-methylethoxy, 2-halogeno-1-(halogenomethyl)ethoxy, 1-(dihalogenomethyl)-2,2-dihalogenoethoxy, (R)-1-halogenobutoxy, (S)-1-halogenobutoxy, 2-halogenobutoxy, 3-halogenobutoxy, 4-halogenobutoxy, 1,1-dihalogenobutoxy, 2,2-dihalogenobutoxy, 3,3-dihalogenobutoxy, 4,4-dihalogenobutoxy, 4,4,4-trihalogenobutoxy, etc. Particular examples include the fluorinated $C_1$-$C_4$ alkoxy groups as defined, such as trifluoromethoxy.

$C_1$-$C_6$-Hydroxyalkoxy is an alkoxy radical having from 1 to 6, preferably from 1 to 4 carbon atoms as defined herein, wherein one or two hydrogen atoms are replaced by hydroxy. Examples include 2-hydroxyethoxy, 3-hydroxypropoxy, 2-hydroxypropoxy, 1-methyl-2-hydroxyethoxy and the like.

$C_1$-$C_6$-Alkoxy-$C_1$-$C_4$-alkoxy is an alkoxy radical having from 1 to 4 carbon atoms, preferably 1 or 2 carbon atoms as defined herein, wherein one or two hydrogen atoms are replaced by one or two alkoxy radicals having from 1 to 6, preferably from 1 to 4 carbon atoms as defined herein. Examples include methoxymethoxy, 2-methoxyethoxy, 1-methoxyethoxy, 3-methoxypropoxy, 2-methoxypropoxy, 1-methyl-1-methoxyethoxy, ethoxymethoxy, 2-ethoxyethoxy, 1-ethoxyethoxy, 3-ethoxypropoxy, 2-ethoxypropoxy, 1-methyl-1-ethoxyethoxy and the like.

Amino-$C_1$-$C_4$-alkoxy is an alkoxy radical having from 1 to 4, preferably 1 or 2 carbon atoms as defined herein, wherein one hydrogen atom is replaced by an amino group. Examples include 2-aminoethoxy.

$C_1$-$C_6$-Alkylamino-$C_1$-$C_4$-alkoxy is an alkoxy radical having from 1 to 4, preferably 1 or 2 carbon atoms as defined herein, wherein one hydrogen atom is replaced by an alkylamino group having from 1 to 6, preferably from 1 to 4 carbon atoms as defined herein. Examples include methylaminomethoxy, ethylaminomethoxy, n-propylaminomethoxy, isopropylaminomethoxy, n-butylaminomethoxy, 2-butylaminomethoxy, isobutylaminomethoxy, tert-butylaminomethoxy, 2-(methylamino)ethoxy, 2-(ethylamino)ethoxy, 2-(n-propylamino)ethoxy, 2-(iso-propylamino)ethoxy, 2-(n-butylamino)ethoxy, 2-(2-butylamino)ethoxy, 2-(iso-butylamino)ethoxy, 2-(tert-butylamino)ethoxy.

Di-$C_1$-$C_6$-alkylamino-$C_1$-$C_4$-alkoxy is an alkoxy radical having from 1 to 4, preferably 1 or 2 carbon atoms as defined herein, wherein one hydrogen atom is replaced by a dialkylamino group having from 1 to 6, preferably from 1 to 4 carbon atoms as defined herein. Examples include dimethylaminomethoxy, diethylaminomethoxy, N-methyl-N-ethylamino)ethoxy, 2-(dimethylamino)ethoxy, 2-(diethylamino)ethoxy, 2-(N-methyl-N-ethylamino)ethoxy.

$C_1$-$C_6$-Alkylcarbonylamino-$C_1$-$C_4$-alkoxy is an alkoxy radical having from 1 to 4, preferably 1 or 2 carbon atoms as defined herein, wherein one hydrogen atom is replaced by an alkylcarbonylamino group wherein the alkyl group has from 1 to 6, preferably from 1 to 4 carbon atoms as defined herein. Examples include methylcarbonylaminomethoxy, ethylcarbonylaminomethoxy, n-propylcarbonylaminomethoxy, isopropylcarbonylaminomethoxy, n-butylcarbonylaminomethoxy, 2-butylcarbonylaminomethoxy, isobutylcarbonylaminomethoxy, tert-butylcarbonylaminomethoxy, 2-(methylcarbonylamino)ethoxy, 2-(ethylcarbonylamino)ethoxy, 2-(n-propylcarbonylamino)ethoxy, 2-(iso-propylcarbonylamino)ethoxy, 2-(n-butylcarbonylamino)ethoxy, 2-(2-butylcarbonylamino)ethoxy, 2-(iso-butylcarbonylamino)ethoxy, 2-(tert-butylcarbonylamino)ethoxy.

$C_6$-$C_{12}$-Arylcarbonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylcarbonylamino group as defined herein. Examples include 2-(benzoylamino)ethoxy.

$C_1$-$C_6$-Alkoxycarbonylamino-$C_1$-$C_4$-alkoxy is an alkoxy radical having from 1 to 4, preferably 1 or 2 carbon atoms as defined herein, wherein one hydrogen atom is replaced by an alkoxycarbonylamino group wherein the alkoxy group has from 1 to 6, preferably from 1 to 4 carbon atoms as defined herein. Examples include methoxycarbonylaminomethoxy, ethoxycarbonylaminomethoxy, n-propoxycarbonylaminomethoxy, isopropoxycarbonylaminomethoxy, n-butoxycarbonylaminomethoxy, 2-butoxycarbonylaminomethoxy, iso-butoxycarbonylaminomethoxy, tertbutoxycarbonylaminomethoxy, 2-(methoxycarbonylamino)ethoxy, 2-(ethoxycarbonylamino)ethoxy, 2-(n-propoxycarbonylamino)ethoxy, 2-(iso-propoxycarbonylamino)ethoxy, 2-(n-butoxycarbonylamino)ethoxy, 2-(2-butoxycarbonylamino)ethoxy, 2-(isobutoxycarbonylamino)ethoxy, 2-(tert-butoxycarbonylamino)ethoxy.

$C_2$-$C_6$-Alkenyloxy is a radical of the formula R—O—, wherein R is a straight-chain or branched alkenyl group having from 2 to 6, in particular 2 to 4 carbon atoms. Examples include vinyloxy, allyloxy(2-propen-1-yloxy), 1-propen-1- yloxy, 2-propen-2-yloxy, methallyloxy(2-methylprop-2-en-1-yloxy) and the like. $C_3$-$C_5$-Alkenyloxy is, in particular, allyloxy, 1-methylprop-2-en-1-yloxy, 2-buten-1-yloxy, 3-buten-1-yloxy, methallyloxy, 2-penten-1-yloxy, 3-penten-1-yloxy, 4-penten-1-yloxy, 1-methylbut-2-en-1-yloxy or 2-ethylprop-2-en-1-yloxy.

$C_6$-$C_{12}$-Aryl-$C_1$-$C_4$-alkoxy is an alkoxy radical having from 1 to 4, preferably 1 or 2 carbon atoms as defined herein, wherein one hydrogen atom is replaced by a $C_6$-$C_{12}$-aryl group as defined herein. Examples include benzyloxy.

$C_1$-$C_6$-Alkylsulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein. Examples include 2-(methylsulfonylamino)ethoxy, 2-(ethylsulfonylamino)ethoxy, 2-[(2-methylpropyl)sulfonylamino]ethoxy.

(Halogenated $C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein, wherein the alkyl group is halogenated. Examples include 2-(trifluoromethylsulfonylamino)ethoxy.

$C_6$-$C_{12}$-Arylsulfonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylsulfonylamino group as defined herein. Examples include 2-(phenylsulfonylamino)ethoxy, 2-(naphthylsulfonylamino)ethoxy.

($C_6$-$C_{12}$-Aryl-$C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by a ($C_6$-$C_{12}$-aryl-$C_1$-$C_6$-alkyl)sulfonylamino group, preferably by a ($C_6$-$C_{12}$-aryl-$C_1$-$C_2$-alkyl)sulfonylamino group. Examples include 2-(benzylsulfonylamino)ethoxy.

$C_3$-$C_{12}$-Heterocyclylsulfonylamino-$C_1$-$C_4$-alkoxy is an alkoxy radical having from 1 to 4, preferably 1 or 2 carbon atoms as defined herein, wherein one hydrogen atom is replaced by a $C_3$-$C_{12}$-heterocyclylsulfonylamino group as defined herein. Examples include 2-(pyridin-3-yl-sulfonylamino)ethoxy.

$C_3$-$C_{12}$-Heterocyclyl-$C_1$-$C_4$-alkoxy is an alkoxy radical having from 1 to 4, preferably 1 or 2 carbon atoms as defined herein, wherein one hydrogen atom is replaced by a $C_3$-$C_{12}$-heterocyclyl group as defined herein. Examples include 2-(N-pyrrolidinyl)ethoxy, 2-(N-morpholinyl)ethoxy and 2-(N-imidazolyl)ethoxy.

$C_1$-$C_2$-Alkylenedioxo is a radical of the formula —O—R—O—, wherein R is a straight-chain or branched alkylene group having from 1 or 2 carbon atoms as defined herein. Examples include methylenedioxo.

$C_6$-$C_{12}$-Aryloxy is a radical of the formula R—O—, wherein R is an aryl group having from 6 to 12, in particular 6 carbon atoms as defined herein. Examples include phenoxy.

$C_3$-$C_{12}$-Heterocyclyloxy is a radical of the formula R—O—, wherein R is a $C_3$-$C_{12}$-heterocyclyl group having from 3 to 12, in particular from 3 to 7 carbon atoms as defined herein. Examples include pyridin-2-yloxy.

$C_1$-$C_6$-Alkylthio is a radical of the formula R—S—, wherein R is an alkyl radical having from 1 to 6, preferably from 1 to 4 carbon atoms as defined herein. Examples include methylthio, ethylthio, propylthio, butylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropyl and 1-ethyl-2-methylpropyl.

Halogenated $C_1$-$C_6$-alkylthio is a radical of the formula R—S—, wherein R is a halogenated alkyl radical having from 1 to 6, preferably from 1 to 4 carbon atoms as defined herein. Examples include halogenomethylthio, dihalogenomethylthio, trihalogenomethylthio, (R)-1-halogenoethylthio, (S)-1-halogenoethylthio, 2-halogenoethylthio, 1,1-dihalogenoethylthio, 2,2-dihalogenoethylthio, 2,2,2-trihalogenoethylthio, (R)-1-halogenopropylthio, (S)-1-halogenopropylthio, 2-halogenopropylthio, 3-halogenopropylthio, 1,1-dihalogenopropylthio, 2,2-dihalogenopropylthio, 3,3-dihalogenopropylthio, 3,3,3-trihalogenopropylthio, (R)-2-halogeno-1-methylethylthio, (S)-2-halogeno-1-methylethylthio, (R)-2,2-dihalogeno-1-methylethylthio, (S)-2,2-dihalogeno-1-methylethylthio, (R)-1,2-dihalogeno-1-methylethylthio, (S)-1,2-dihalogeno-1-methylethylthio, (R)-2,2,2-trihalogeno-1-methylethylthio, (S)-2,2,2-trihalogeno-1-methylethylthio, 2-halogeno-1-(halogenomethyl)ethylthio, 1-(dihalogenomethyl)-2,2-dihalogenoethylthio, (R)-1-halogenobutylthio, (S)-1-halogenobutylthio, 2-halogenobutylthio, 3-halogenobutylthio, 4-halogenobutylthio, 1,1-dihalogenobutylthio, 2,2-dihalogenobutylthio, 3,3-dihalogenobutylthio, 4,4-dihalogenobutylthio, 4,4,4-trihalogenobutylthio, etc. Particular examples include the fluorinated $C_1$-$C_4$ alkylthio groups as defined, such as trifluoromethylthio.

$C_1$-$C_6$-Alkylsulfinyl is a radical of the formula R—S(O)—, wherein R is an alkyl radical having from 1 to 6, preferably from 1 to 4 carbon atoms as defined herein. Examples include methylsulfinyl, ethylsulfinyl, propylsulfinyl, butylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, hexylsulfinyl, 1,1-dimethylpropylsulfinyl, 1,2-dimethylpropylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropyl and 1-ethyl-2-methylpropyl.

$C_1$-$C_6$-Alkylsulfonyl is a radical of the formula R—S(O)$_2$—, wherein R is an alkyl radical having from 1 to 6, preferably from 1 to 4 carbon atoms as defined herein. Examples include methylsulfonyl, ethylsulfonyl, propylsulfonyl, butylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropyl and 1-ethyl-2-methylpropyl.

(Halogenated $C_1$-$C_6$-alkyl)sulfonyl is a $C_1$-$C_6$-alkylsulfonyl as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylsulfonyl is a radical of the formula R—S(O)$_2$—, wherein R is an aryl radical having from 6 to 12 carbon atoms as defined herein. Examples include phenylsulfonyl.

($C_6$-$C_{12}$-Aryl-$C_1$-$C_4$-alkyl)sulfonyl is a radical of the formula R—S(O)$_2$—, wherein R is a $C_6$-$C_{12}$-aryl-$C_1$-$C_4$-alkyl radical, in particular a $C_6$-$C_{12}$-aryl-$C_1$-$C_2$-alkyl radical as defined herein. Examples include benzylsulfonyl.

$C_3$-$C_{12}$-Heterocyclylsulfonyl is a radical of the formula R—S(O)$_2$—, wherein R is $C_3$-$C_{12}$-heterocyclyl as defined herein.

Aminosulfonyl is NH$_2$—S(O)$_2$—.

$C_1$-$C_6$-Alkylaminosulfonyl is a radical of the formula R—NH—S(O)$_2$— wherein R is an alkyl radical having from 1 to 6, preferably from 1 to 4 carbon atoms as defined herein. Examples include methylaminosulfonyl, ethylaminosulfonyl, n-propylaminosulfonyl, isopropylaminosulfonyl, n-butylaminosulfonyl, 2-butylaminosulfonyl, iso-butylaminosulfonyl, tert-butylaminosulfonyl.

Di-$C_1$-$C_6$-alkylaminosulfonyl is a radical of the formula RR'N—S(O)$_2$— wherein R and R' are independently of each other an alkyl radical having from 1 to 6, preferably from 1 to 4 carbon atoms as defined herein. Examples include dimethylaminosulfonyl, diethylaminosulfonyl, N-methyl-N-ethylaminosulfonyl.

$C_6$-$C_{12}$-Arylaminosulfonyl is a radical of the formula R—NH—S(O)$_2$— wherein R is an aryl radical having from 6 to 12, preferably 6 carbon atoms as defined herein.

Amino is NH$_2$.

$C_1$-$C_6$-Alkylamino is a radical of the formula R—NH— wherein R is an alkyl radical having from 1 to 6, in particular from 1 to 4 carbon atoms as defined herein. Examples include methylamino, ethylamino, n-propylamino, iso-propylamino, n-butylamino, 2-butylamino, iso-butylamino, tert-butylamino.

(Halogenated $C_1$-$C_6$-alkyl)amino is a $C_1$-$C_6$-alkylamino as defined herein, wherein at least one, e.g. 1, 2, 3, 4 or all of the hydrogen atoms are replaced by 1, 2, 3, 4 or a corresponding number of identical or different halogen atoms.

Di-$C_1$-$C_6$-alkylamino is a radical of the formula RR'N— wherein R and R' are independently of each other an alkyl radical having from 1 to 6, in particular from 1 to 4 carbon atoms as defined herein. Examples include dimethylamino, diethylamino, N-methyl-N-ethylamino.

Di-(halogenated $C_1$-$C_6$-alkyl)amino is a di-$C_1$-$C_6$-alkylamino as defined herein, wherein at least one, e.g. 1, 2, 3, 4 or all of the hydrogen atoms are replaced by 1, 2, 3, 4 or a corresponding number of identical or different halogen atoms.

$C_1$-$C_6$-Alkylcarbonylamino is a radical of the formula R—C(O)—NH—, wherein R is an alkyl radical having from 1 to 6, in particular from 1 to 4 carbon atoms as defined herein. Examples include acetamido(methylcarbonylamino), propionamido, n-butyramido, 2-methylpropionamido(isopropylcarbonylamino), 2,2-dimethylpropionamido and the like.

(Halogenated $C_1$-$C_6$-alkyl)carbonylamino is a $C_1$-$C_6$-alkylcarbonylamino as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylcarbonylamino is a radical of the formula R—C(O)—NH—, wherein R is an aryl radical having from 6 to 12 carbon atoms as defined herein. Examples include phenylcarbonylamino.

$C_2$-$C_6$-Alkenylamino is a radical of the formula R—NH—, wherein R is a straight-chain or branched alkenyl group having from 2 to 6, in particular 2 to 4 carbon atoms. Examples include vinylamino, allylamino(2-propen-1-ylamino), 1-propen-1-ylamino, 2-propen-2-ylamino, methallylamino(2-methylprop-2-en-1-ylamino) and the like. $C_3$-$C_5$-Alkenylamino is, in particular, allylamino, 1-methylprop-2-en-1-ylamino, 2-buten-1-ylamino, 3-buten-1-ylamino, methallylamino, 2-penten-1-ylamino, 3-penten-1-ylamino, 4-penten-1-ylamino, 1-methylbut-2-en-1-ylamino or 2-ethylprop-2-en-1-ylamino.

$C_1$-$C_6$-Alkylsulfonylamino is a radical of the formula R—S(O)$_2$—NH—, wherein R is an alkyl radical having from 1 to 6, in particular from 1 to 4 carbon atoms as defined herein. Examples include methylsulfonylamino, ethylsulfonylamino, n-propylsulfonylamino, isopropylsulfonylamino, n-butylsulfonylamino, 2-butylsulfonylamino, iso-butylsulfonylamino, tert-butylsulfonylamino.

(Halogenated $C_1$-$C_6$ alkyl)sulfonylamino is a $C_1$-$C_6$-alkylsulfonylamino as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylsulfonylamino is a radical of the formula R—S(O)$_2$—NH—, wherein R is an aryl radical having from 6 to 12 carbon atoms as defined herein. Examples include phenylsulfonylamino.

Nitro is —NO$_2$.

$C_3$-$C_{12}$-Heterocyclyl is a 3- to 12-membered heterocyclic radical including a saturated heterocyclic radical, which generally has 3, 4, 5, 6, or 7 ring forming atoms (ring members), an unsaturated non-aromatic heterocyclic radical, which generally has 5, 6 or 7 ring forming atoms, and a heteroaromatic radical (hetaryl), which generally has 5, 6 or 7 ring forming atoms. The heterocyclic radicals may be bound via a carbon atom (C-bound) or a nitrogen atom (N-bound). Preferred heterocyclic radicals comprise 1 nitrogen atom as ring member atom and optionally 1, 2 or 3 further heteroatoms as ring members, which are selected, independently of each other from O, S and N. Likewise preferred heterocyclic radicals comprise 1 heteroatom as ring member, which is selected from O, S and N, and optionally 1, 2 or 3 further nitrogen atoms as ring members.

Examples of $C_3$-$C_{12}$-heterocyclyl include:
C- or N-bound 3-4-membered, saturated rings, such as
2-oxiranyl, 2-oxetanyl, 3-oxetanyl, 2-aziridinyl, 3-thiethanyl, 1-azetidinyl, 2-azetidinyl, 3-azetidinyl;
C-bound, 5-membered, saturated rings, such as
tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydro-pyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;
C-bound, 6-membered, saturated rings, such as
tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4- oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;

N-bound, 5-membered, saturated rings, such as tetrahydropyrrol-1-yl(pyrrolidin-1-yl), tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl;

N-bound, 6-membered, saturated rings, such as piperidin-1-yl, hexahydropyrimidin-1-yl, hexahydropyrazin-1-yl(piperazin-1-yl), hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl(morpholin-1-yl), tetrahydro-1,2-oxazin-2-yl;

C-bound, 5-membered, partially unsaturated rings, such as 2,3-dihydrofuran-2-yl, 2,3-dihydrofuran-3-yl, 2,5-dihydrofuran-2-yl, 2,5-di-hydrofuran-3-yl, 4,5-dihydrofuran-2-yl, 4,5-dihydrofuran-3-yl, 2,3-dihydro-thien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydro-oxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl;

C-bound, 6-membered, partially unsaturated rings, such as 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydro-pyridin-3-yl, 1,2-dihydropyridin-4-yl, 1,2-dihydropyridin-5-yl, 1,2-dihydro-pyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydro-pyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydro-pyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4- thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

N-bound, 5-membered, partially unsaturated rings, such as 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl;

N-bound, 6-membered, partially unsaturated rings, such as 1,2,3,4-tetrahydropyridin-1-yl, 1,2,5,6-tetrahydropyridin-1-yl, 1,4-dihydro-pyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

C-bound, 5-membered, heteroaromatic rings, such as 2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl;

C-bound, 6-membered, heteroaromatic rings, such as pyridin-2-yl, pyridin-3-yl, pyridin-4-yl (4-pyridyl), pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl;

N-bound, 5-membered, heteroaromatic rings, such as pyrrol-1-yl, pyrazol-1-yl, imidazol-1-yl, 1,2,3-triazol-1-yl, 1,2,4-triazol-1-yl, tetrazol-1-yl.

Heterocyclyl also includes bicyclic heterocycles, which comprise one of the described 5- or 6-membered heterocyclic rings and a further anellated, saturated or unsaturated or aromatic carbocycle, such as a benzene, cyclohexane, cyclohexene or cyclohexadiene ring, or a further anellated 5- or 6-membered heterocyclic ring, this heterocyclic ring being saturated or unsaturated or aromatic. These include quinolinyl, isoquinolinyl, indolyl, indolizinyl, isoindolyl, indazolyl, benzofuryl, benzthienyl, benzo[b]thiazolyl, benzoxazolyl, benzthiazolyl and benzimidazolyl. Examples of 5- or 6-membered heteroaromatic compounds comprising an anellated cycloalkenyl ring include dihydroindolyl, dihydroindolizinyl, dihydroisoindolyl, dihydrochinolinyl, dihydroisoquinolinyl, chromenyl and chromanyl.

$C_3$-$C_{12}$-Heteroarylene is a heteroaryl diradical. Examples include pyrid-2,5-ylene and pyrid-2,4-ylene.

With respect to the compounds' capability of inhibiting glycine transporter 1, the variables A, R, $R^1$, W, $A^1$, Q, Y, $A^2$, $X^1$, $R^2$, $R^3$, $R^{3'}$, $Y^1$, $Y^2$, $Y^3$ r, s, t, $R^{4a}$, $R^{4b}$, $R^{4b'}$, $R^{4c}$, $R^{4d}$, $R^{4e}$, $X^2$, $X^3$, $X^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, n preferably have the following meanings which, when taken alone or in combination, represent particular embodiments of the compounds of the formula (I), (II), (III), (IV), (V) or (VI) or any other formula disclosed herein.

In said formula (I), (III), (V) or (VI), there may be one or more than one substituent R, $R^2$, $R^3$ and/or $R^{4b}/R^{4b'}$. More particularly, there may be up to 3 substituents $R^2$, up to 6 substituents $R^3$ and up to 3 substituents $R^{4b}/R^{4b'}$. Preferably there is one substituent R, 1, 2 or 3 substituents $R^2$, and/or 1, 2 or 3 substituents $R^{4b}/R^{4b'}$. Formulae (I) and (III) may thus be depicted as follows:

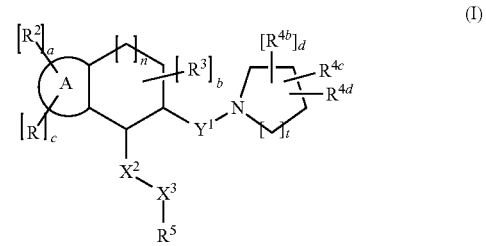

(I)

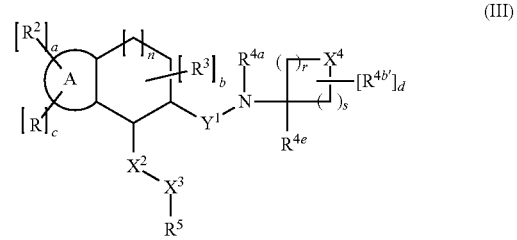

(III)

wherein a is 1, 2 or 3, b is 1, 2, 3, 4, 5 or 6, c is 1, and d is 1, 2, or 3. If there is more than one radical $R^2$, these may be the same or different radicals. If there is more than one radical $R^3$, these may be the same or different radicals. If there is more than one radical $R^{4b}/R^{4b'}$, these may be the same or different radicals.

In said formula (II) or (IV), there may be one or more than one substituent R, $R^2$ and/or $R^{4b}/R^{4b'}$. More particularly, there may be up to 4 substituents $R^2$. Preferably there is one substituent R, 1, 2, 3 or 4 substituents $R^2$, and/or 1, 2 or 3 substituents $R^{4b}/R^{4b'}$. Formulae (II) and (IV) may thus be depicted as follows:

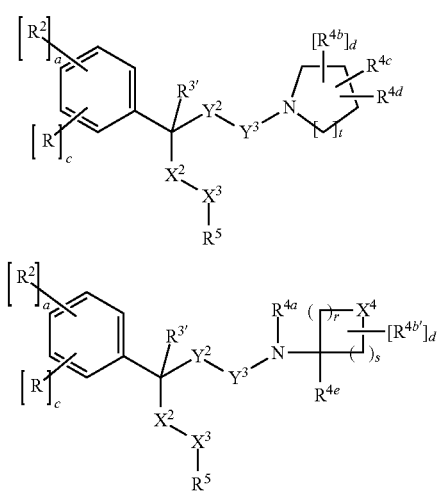

(II)

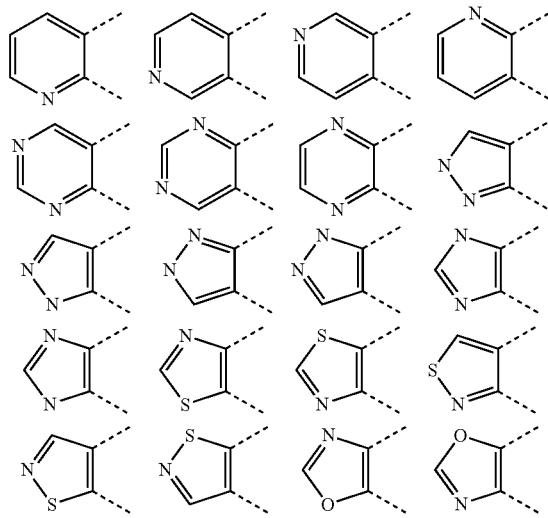

wherein a is 1, 2, 3 or 4, c is 1, and d is 1, 2, or 3. If there is more than one radical $R^2$, these may be the same or different radicals. If there is more than one radical $R^{4b}/R^{4b'}$, these may be the same or different radicals.

A is a 5- or 6-membered ring which includes two carbon atoms from the cyclopentane, cyclohexane or cycloheptane moiety to which A is fused. A may be a homocyclic or heterocyclic ring. The ring may be saturated, unsaturated non-aromatic or aromatic. According to a particular embodiment, A is a benzene ring. As a heterocyclic ring, A may include 1, 2 or 3 heteroatoms as ring member atoms, which are selected, independently of each other from N, S and O. Preferred heterocyclic rings comprise 1 nitrogen atom as ring member atom and optionally 1 or 2 further heteroatoms as ring members, which are selected, independently of each other from O, S and N. Likewise preferred heterocyclic rings comprise 1 heteroatom as ring member atom, which is selected from O, S and N, and optionally 1 or 2 further nitrogen atoms as ring member atoms. According to a particular embodiment, A is a heterocyclic ring selected from the group consisting of the following 5- or 6-membered heterocyclic rings:

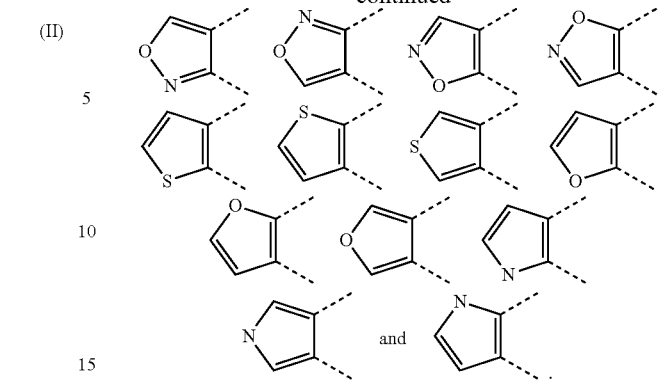

In said formulae, hydrogen atoms are not depicted. This is meant to illustrate that the free valency of a carbon or nitrogen atom may be either bound to a hydrogen atom, to R or to $R^2$. Accordingly, R and $R^2$ may be C- or N-bound at any position of ring A.

The skilled person will appreciate that some of the rings depicted above may be represented with a different structure, e.g. with hydrogen atoms having other positions than those shown above, for instance as given in the following structures:

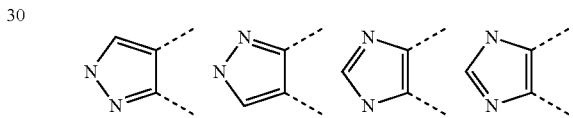

Preferably, A is a heterocyclic ring selected from the group consisting of the following 5- or 6-membered heterocyclic rings:

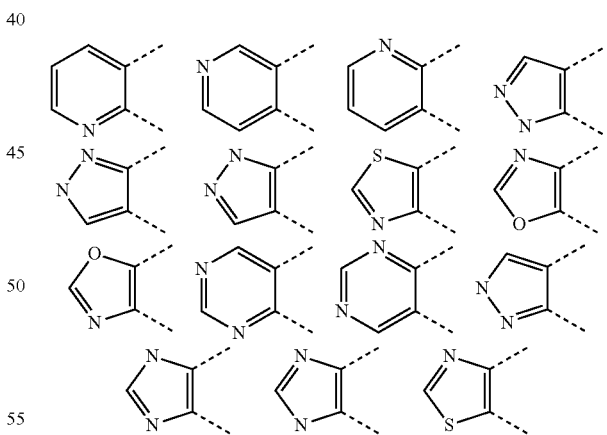

According to a further particular embodiment, A is a heterocyclic ring selected from the group consisting of the following 5- or 6-membered heterocyclic rings:

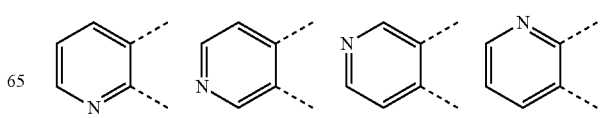

-continued

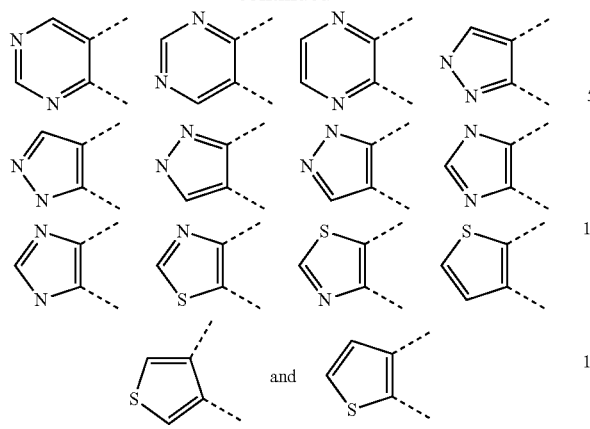

According to a preferred embodiment, A is a heterocyclic ring selected from the group consisting of the following 5- or 6-membered heterocyclic rings:

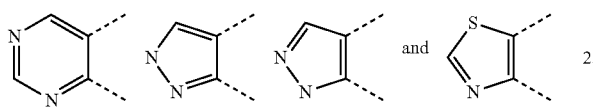

If ring A is a 5-membered heterocyclic ring it is preferred that R is bound to $G^1$ or $G^2$, in particular $G^2$:

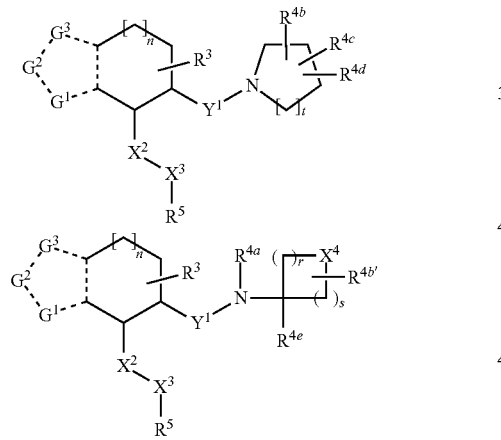

In said formula, $G^1$, $G^2$ and $G^3$ independently are —CH=, —CH$_2$—, —N=, —NH—, S or O, at least one of $G^1$, $G^2$ and $G^3$ is —CH= or —CH$_2$—, the dotted line represents a single or a double bond and $R^3$, $Y^1$, r, s, t, $R^{4a}$, $R^{4b}$, $R^{4b'}$, $R^{4c}$, $R^{4d}$, $R^{4e}$, $X^2$, $X^3$, $X^4$, $R^5$, n are as defined herein.

If ring A is 6-membered heterocyclic ring it is preferred that R is bound to $G^1$ or $G^2$, in particular $G^2$:

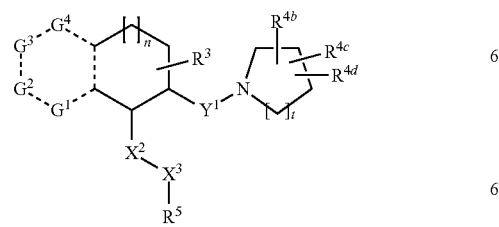

-continued

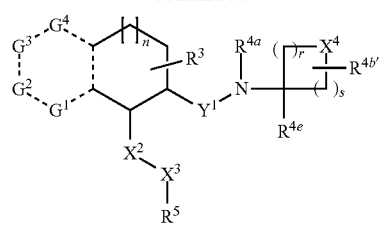

In said formula, $G^1$, $G^2$, $G^3$ and $G^4$ independently are —CH=, —CH$_2$—, —N=, —NH—, S or O, at least one of $G^1$, $G^2$, $G^3$ and $G^4$ is —CH= or —CH$_2$—, the dotted line represents a single or a double bond and $R^3$, $Y^1$, r, s, t, $R^{4a}$, $R^{4b}$, $R^{4b'}$, $R^{4c}$, $R^{4d}$, $R^{4e}$, $X^2$, $X^3$, $X^4$, $R^5$, n are as defined herein.

Heterocyclic compounds having the following partial structures are preferred:

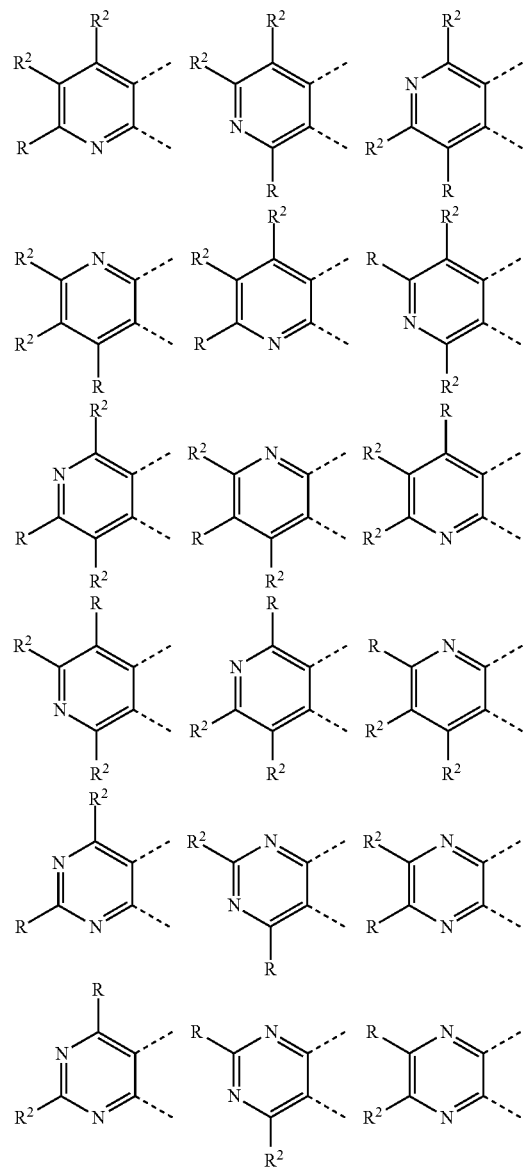

-continued

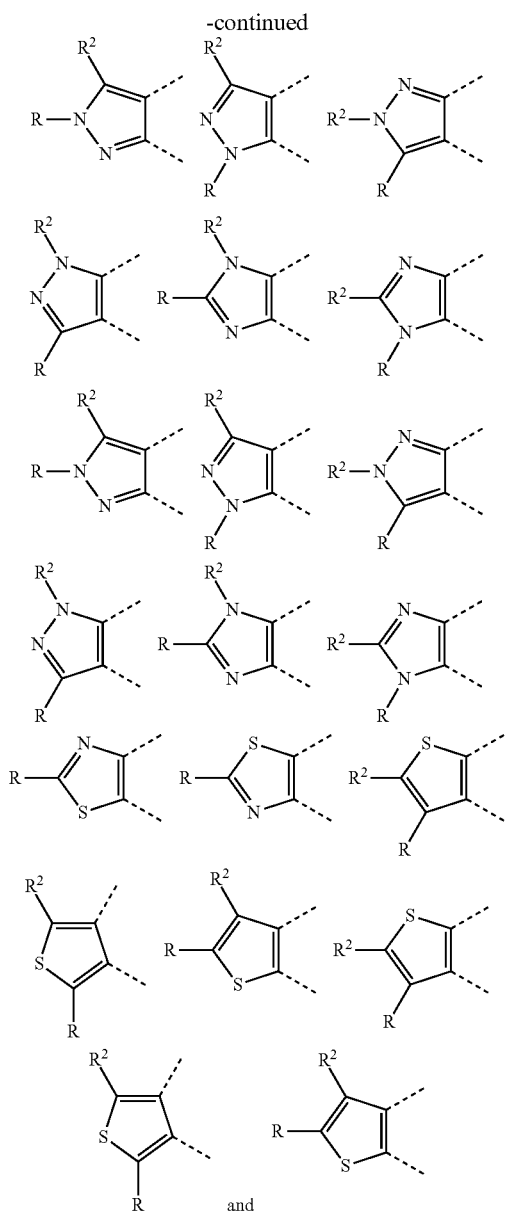

Heterocyclic compounds having the following partial structures are particularly preferred:

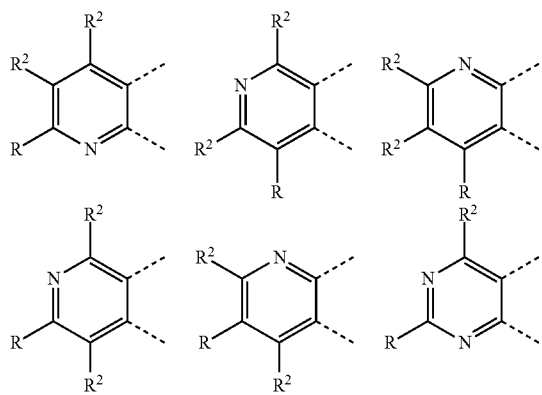

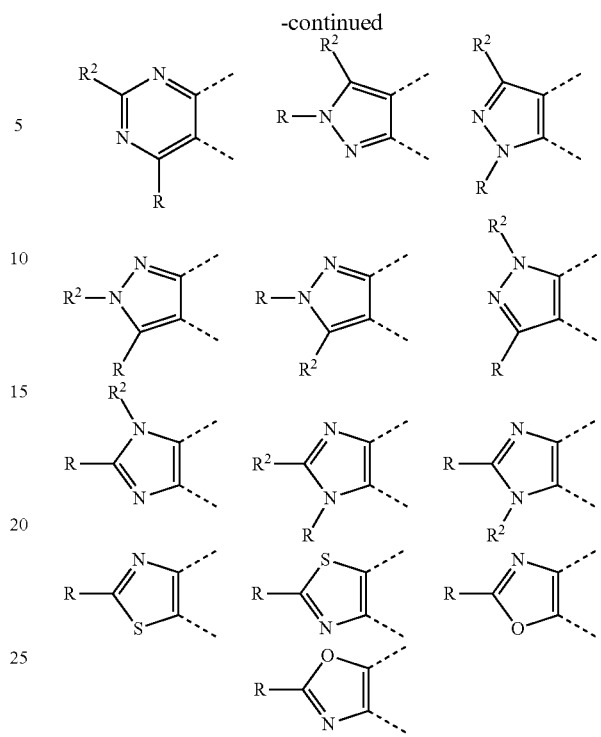

In said formulae, R and $R^2$ are as defined herein. If there is more than one radical $R^2$, these may be the same or different radicals.

According to a particular embodiment, the partial structures depicted above are fused with a cyclohexane moiety (i.e., n is 1). The same applies to the preferred and particular embodiments disclosed for ring A.

According to one embodiment, R is cyano.

Preferably, R is $R^1$—W-$A^1$-Q-Y-$A^2$-$X^1$— and A, $R^1$, W, $A^1$, Q, Y, $A^2$, $X^1$, $R^2$, $R^3$, $R^{3'}$, $Y^1$, $Y^2$, $Y^3$, r, s, t, $R^{4a}$, $R^{4b}$, $R^{4b'}$, $R^{4c}$, $R^{4d}$, $R^{4e}$, $X^2$, $X^3$, $X^4$, $R^5$, n are as defined herein.

$R^1$ is hydrogen, $C_1$-$C_6$-alkyl (e.g. methyl, ethyl, n-propyl, isopropyl, n-butyl, sec-butyl or n-pentyl), $C_3$-$C_{12}$-cycloalkyl-$C_1$-$C_4$-alkyl (e.g. cyclopropylmethyl, cyclopentylmethyl or cyclohexylmethyl), halogenated $C_1$-$C_6$-alkyl (e.g. 3-fluoro-prop-1-yl, 3-chloroprop-1-yl or 3,3,3-trifluoroprop-1-yl), tri-($C_1$-$C_4$-alkyl)-silyl-$C_1$-$C_4$-alkyl (e.g. trimethylsilylethyl), hydroxy-$C_1$-$C_4$-alkyl, $C_1$-$C_6$-alkoxy-$C_1$-$C_4$-alkyl (e.g. ethoxyethyl), amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkylcarbonylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $C_3$-$C_{12}$-heterocyclyl-$C_1$-$C_4$-alkyl, $C_3$-$C_{12}$-cycloalkyl (e.g. cyclopropyl or cyclobutyl), $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl (e.g. prop-1,2-en-1-yl), $C_2$-$C_6$-alkynyl, optionally substituted $C_6$-$C_{12}$-aryl (e.g. phenyl, 2-methylphenyl), hydroxy, $C_1$-$C_6$-alkoxy (e.g. tert-butyloxy), halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-

$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $C_3$-$C_{12}$-heterocyclylsulfonylamino-$C_1$-$C_4$-alkoxy, $C_3$-$C_{12}$-heterocyclyl-$C_1$-$C_4$-alkoxy, $C_6$-$C_{12}$-aryloxy, $C_3$-$C_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkyl)amino, di-$C_1$-$C_6$-alkylamino (e.g. dimethylamino), di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $C_3$-$C_{12}$-heterocyclyl (e.g. 3-pyridyl, 2-thienyl, 4-methyl-2-thienyl, 5-methyl-2-thienyl, 5-chloro-2-thienyl, 2,5-dimethyl-3-thienyl, 1,2-diazol-4-yl, 1-methyl-1,2-diazol-4-yl, 1-ethyl-1,2-diazol-4-yl, 1-difluormethyl-1,2-diazol-4-yl, 2-methyl-1,3-diazol-4-yl, 1-methyl-1,3-diazol-4-yl, 2-methyl-1,3-thiazol-5-yl, 2,4-dimethyl-1,3-thiazol-5-yl, 3-pyrrolidinyl, 1-methyl-pyrrol-3-yl, 2-pyridyl, 1-methyl-1,2-diazol-3-yl, 1-methyl-3-trifluoromethyl-1,2-diazol-4-yl, 1,2-dimethyl-1,3-diazol-4-yl, 5-methylisoxazol-3-yl or 1-methyl-1,2,4-triazol-3-yl).

Preferably, $R^1$ is $C_1$-$C_6$-alkyl (e.g. methyl, ethyl, n-propyl, isopropyl, sec-butyl, n-butyl or n-pentyl), $C_3$-$C_{12}$-cycloalkyl-$C_1$-$C_4$-alkyl (e.g. cyclopropylmethyl, cyclopentylmethyl or cyclohexylmethyl), halogenated $C_1$-$C_6$-alkyl (e.g. 3-fluoroprop-1-yl, 3-chloroprop-1-yl or 3,3,3-trifluoroprop-1-yl), tri-($C_1$-$C_4$-alkyl)-silyl-$C_1$-$C_4$-alkyl (e.g. trimethylsilylethyl), $C_1$-$C_6$-alkoxy-$C_1$-$C_4$-alkyl (e.g. ethoxyethyl), amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, $C_6$-$C_{12}$-aryl-$C_1$-$C_4$-alkyl, $C_3$-$C_{12}$-cycloalkyl (e.g. cyclopropyl or cyclobutyl), $C_2$-$C_6$-alkenyl (e.g. prop-1,2-en-1-yl), optionally substituted $C_6$-$C_{12}$-aryl (e.g. phenyl), hydroxy, $C_1$-$C_6$-alkylamino, (halogenated $C_1$-$C_6$-alkyl)amino, di-$C_1$-$C_6$-alkylamino or optionally substituted $C_3$-$C_{12}$-heterocyclyl (e.g. 3-pyridyl, 2-thienyl, 4-methyl-2-thienyl, 5-methyl-2-thienyl, 5-chloro-2-thienyl, 2,5-dimethyl-3-thienyl, 1,2-diazol-4-yl, 1-methyl-1,2-diazol-4-yl, 1-ethyl-1,2-diazol-4-yl, 1-difluormethyl-1,2-diazol-4-yl, 2-methyl-1,3-diazol-4-yl, 1-methyl-1,3-diazol-4-yl, 2-methyl-1,3-thiazol-5-yl, 2,4-dimethyl-1,3-thiazol-5-yl or 3-pyrrolidinyl).

In particular, $R^1$ is $C_1$-$C_6$-alkyl (e.g. n-propyl), $C_3$-$C_{12}$-cycloalkyl-$C_1$-$C_4$-alkyl (e.g. cyclopropylmethyl), $C_3$-$C_{12}$-cycloalkyl (e.g. cyclobutyl), or optionally substituted $C_3$-$C_{12}$-heterocyclyl (e.g. 3-pyridyl, 1-methyl-1,2-diazol-4-yl, 1-methyl-1,3-diazol-4-yl, 3-oxetanyl, 1-methylpyrrol-3-yl).

In connection with $R^1$, substituted $C_6$-$C_{12}$-aryl in particular includes $C_6$-$C_{12}$-aryl, such as phenyl or naphthyl, substituted with 1, 2 or 3 substituents selected from the group consisting of halogen, $C_1$-$C_4$-alkyl, $C_1$-$C_4$-haloalkyl, cyano, $C_1$-$C_4$-alkoxy, $C_1$-$C_4$-haloalkoxy, amino, $C_1$-$C_4$-alkylamino, $C_1$-$C_4$-dialkylamino, morpholino and piperidinyl. The same applies to substituted $C_6$-$C_{12}$-aryl in substituted $C_6$-$C_{12}$-aryl-$C_1$-$C_4$-alkyl.

In connection with $R^1$, substituted $C_3$-$C_{12}$-heterocyclyl in particular includes $C_3$-$C_{12}$-heterocyclyl, such as pyridyl, thienyl, diazolyl, quinolinyl, piperidinyl, piperazinyl or morpholinyl, pyrrolyl, isoxazolyl and triazolyl being further examples of such $C_3$-$C_{12}$-heterocyclyl, substituted with 1, 2 or 3 substituents selected from the group consisting of halogen, $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g., morpholino or piperidinyl). The same applies to substituted $C_3$-$C_{12}$-heteroaryl in substituted $C_3$-$C_{12}$-heteroaryl-$C_1$-$C_4$-alkyl.

According to one embodiment, W is —$NR^8$— and Y is a bond. According to an alternative embodiment, W is a bond and Y is —$NR^9$—. According to a further alternative embodiment, W is a bond and Y is a bond, especially if $R^1$ is a nitrogen-bound radical, e.g. nitrogen-bound heterocyclyl such as piperazinyl or morpholinyl.

According to one embodiment, Q is —$S(O)_2$—. According to an alternative embodiment, Q is —$C(O)$—.

According to a particular embodiment, —W-$A^1$-Q-Y— is —W-$A^1$-$S(O)_2$—$NR^9$—, —$NR^8$—$S(O)_2$—, -$A^1$-$S(O)_2$— or —$S(O)_2$—. According to a further particular embodiment, —W-$A^1$-Q-Y— is —W-$A^1$-CO—$NR^9$— or —$NR^8$—CO—.

$A^1$ is optionally substituted $C_1$-$C_4$-alkylene or a bond. In connection with $A^1$, substituted $C_1$-$C_4$-alkylene in particular includes $C_1$-$C_4$-alkylene substituted with 1, 2 or 3 substituents selected from the group consisting of halogen, $C_1$-$C_4$-alkyl and cyano. Preferably, $A^1$ is a bond. If $A^1$ is $C_1$-$C_4$-alkylene, W is preferably —$NR^8$—.

$A^2$ is optionally substituted $C_1$-$C_4$-alkylene (e.g. 1,2-ethylene or 1,3-propylene), $C_1$-$C_4$-alkylene-CO—, —CO—$C_1$-$C_4$-alkylene, $C_1$-$C_4$-alkylene-O—$C_1$-$C_4$-alkylene, $C_1$-$C_4$-alkylene-$NR^{10}$—$C_1$-$C_4$-alkylene, optionally substituted $C_6$-$C_{12}$-arylene, optionally substituted $C_6$-$C_{12}$-heteroarylene or a bond. Additionally, $A^2$ may be optionally substituted $C_2$-$C_4$-alkenylen or optionally substituted $C_2$-$C_4$-alkynylene. Preferably, $A^2$ is optionally substituted $C_1$-$C_4$-alkylene (e.g. 1,2-ethylene or 1,3-propylene). More preferably, $A^2$ is $C_1$-$C_4$-alkylene (e.g. 1,2-ethylene). Alternatively, it is preferred that $A^2$ is optionally substituted $C_6$-$C_{12}$-arylene, in particular $C_6$-$C_{12}$-arylene selected from the group consisting of phen-1,4-ylene and phen-1,3-ylene, or optionally substituted $C_6$-$C_{12}$-heteroarylene, in particular $C_6$-$C_{12}$-heteroarylene selected from the group consisting of pyrid-2,5-ylene and pyrid-2,4-ylene. If $A^2$ is a bond, $X^1$ is preferably optionally substituted $C_1$-$C_4$-alkylene. Alternatively, if $A^2$ is a bond, $X^1$ is in particular optionally substituted $C_2$-$C_4$-alkenylene or optionally substituted $C_2$-$C_4$-alkynylene.

In connection with $A^2$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl and cyano.

In connection with $A^2$, substituted $C_2$-$C_4$-alkenylene or substituted $C_2$-$C_4$-alkynylene in particular includes $C_2$-$C_4$-alkenylene or $C_2$-$C_4$-alkynylene substituted with 1, 2 or 3 substituents selected from the group consisting of halogen, $C_1$-$C_4$-alkyl, $C_1$-$C_4$-haloalkyl and cyano.

In connection with $A^2$, substituted $C_6$-$C_{12}$-arylene in particular includes $C_6$-$C_{12}$-arylene substituted with 1, 2 or 3 substituents selected from the group consisting of $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g., morpholino or piperidinyl).

In connection with $A^2$, substituted $C_6$-$C_{12}$-heteroarylene in particular includes $C_6$-$C_{12}$-heteroarylene substituted with 1, 2 or 3 substituents selected from the group consisting of $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g, morpholino or piperidinyl).

$X^1$ is —O—, —$NR^{11}$—, —S— or optionally substituted $C_1$-$C_4$-alkylene (e.g. —$CH_2$—, 1,2-ethylene and 1,3-propylene). In connection with $X^1$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl and cyano. Additionally, $X^1$ may be optionally substituted $C_2$-$C_4$-alkenylen or optionally substituted $C_2$-$C_4$-alkynylene (e.g. propynylene). In connection with $X^1$, substituted $C_2$-$C_4$-alkenylene or substituted $C_2$-$C_4$-alkynylene in particular includes $C_2$-$C_4$-alkenylene or $C_2$-$C_4$-alkynylene substituted with 1, 2 or 3 substituents selected from the group consisting of halogen, $C_1$-$C_4$-alkyl, $C_1$-$C_4$-haloalkyl and cyano. Preferably, $X^1$ is —O—, —$NR^{11}$, or —S—. More preferably, $X^1$ is —O—. Alternatively, it is preferred if $X^1$ is optionally substituted $C_1$-$C_4$-alkylene (e.g. —$CH_2$— or 1,2-ethylene).

According to a particular embodiment, $A^2$ is a bond and $X^1$ is optionally substituted $C_1$-$C_4$-alkylene, optionally substituted $C_2$-$C_4$-alkenylene or optionally substituted $C_2$-$C_4$-alkynylene.

According to a particular embodiment, $R^1$—W-$A^1$-Q-Y-$A^2$-$X^1$— is $R^1$—$S(O)_2$—NH-$A^2$-$X^1$—, $R^1$—NH—$S(O)_2$-$A^2$-$X^1$—, $R^1$—C(O)—NH-$A^2$-$X^1$— or $R^1$—NH—C(O)-$A^2$-$X^1$—.

According to a particular embodiment, the structural element —Y-$A^2$-$X^1$— comprises at least 2, 3 or 4 atoms in the main chain. According to further particular embodiments the structural element —Y-$A^2$-$X^1$— has up to 4, 5 or 6 atoms in the main chain, such as 2 to 6, 2 to 5 or 2 to 4 atoms in the main chain, especially 2, 3 or 4 atoms in the main chain.

According to a further particular embodiment, —Y-$A^2$-$X^1$— is —$C_1$-$C_4$-alkylene-O— or —$NR^9$—$C_1$-$C_4$-alkylene-O—, with —Y-$A^2$-$X^1$— preferably having 2 to 6, 3 to 5 and especially 4 atoms in the main chain. Particular examples of —Y-$A^2$-$X^1$— include —$(CH_2)_3$—O— and —$NR^9$—$(CH_2)_2$—O—. In this particular embodiment, $R^9$ is as defined herein and preferably $R^9$ is hydrogen, $C_1$-$C_6$-alkyl (e.g. methyl or ethyl) or $C_3$-$C_{12}$-cycloalkyl (e.g. cyclopropyl), or $R^9$ is $C_1$-$C_4$-alkylene that is bound to a carbon atom in $A^2$ which is $C_1$-$C_4$-alkylene.

According to a further particular embodiment, —Y-$A^2$-$X^1$— is —$NR^9$—$C_1$-$C_4$-alkylene- (e.g. —NH—$CH_2$—, —NH—$(CH_2)_2$— or —NH—$(CH_2)_3$—), with —Y-$A^2$-$X^1$— preferably having 2 to 6, 2 to 5, 2 to 4 and especially 2, 3 or 4 atoms in the main chain. In this particular embodiment, $R^9$ is as defined herein and preferably $R^9$ is hydrogen, $C_1$-$C_6$-alkyl (e.g. methyl or ethyl) or $C_3$-$C_{12}$-cycloalkyl (e.g. cyclopropyl); or $R^9$ is $C_1$-$C_4$-alkylene that is bound to a carbon atom in $X^1$ which is $C_1$-$C_4$-alkylene.

According to a further particular embodiment, —Y-$A^2$-$X^1$—is —$NR^9$—$C_2$-$C_4$-alkenylene- or —$NR^9$—$C_2$-$C_4$-alkynylene- (e.g. —NH—$CH_2$—C≡C—), with —Y-$A^2$-$X^1$— preferably having 2 to 6, 3 to 5 and especially 4 atoms in the main chain. In this particular embodiment, $R^9$ is as defined herein and preferably is $R^9$ is hydrogen, $C_1$-$C_6$-alkyl (e.g. methyl or ethyl) or $C_3$-$C_{12}$-cycloalkyl (e.g. cyclopropyl or cyclobutyl). If A is a heterocyclic ring, this embodiment of —Y-$A^2$-$X^1$— is particularly suitable.

According to a further particular embodiment, —Y-$A^2$-$X^1$— is —$C_1$-$C_4$-alkylene- (e.g. —$(CH_2)_2$—), with —Y-$A^2$-$X^1$— preferably having 2 to 6, 2 to 5, 2 to 4 and especially 2 atoms in the main chain. If A is a heterocyclic ring, this embodiment of —Y-$A^2$-$X^1$— is particularly suitable.

According to a further particular embodiment, the structural motif —Y-$A^2$-$X^1$ as disclosed herein is bound to Q being —$S(O)_2$— or —C(O)—. Particular examples for this embodiment include compounds of the invention wherein R is $R^1$—$S(O)_2$—Y-$A^2$-$X^1$ or $R^1$—C(O)—Y-$A^2$-$X^1$.

The radical R and in particular the radical $R^1$—W-$A^1$-Q-Y-$A^2$-$X^1$— may, in principle, be bound to the 5-, 6-, 7- or 8-position of the bicyclic skeleton of the compounds of the invention (type I and III formulae) or to the corresponding positions of the monocyclic skeleton of the compounds of the invention (type II and IV formulae):

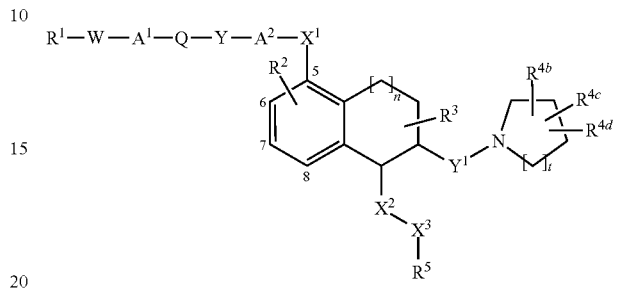

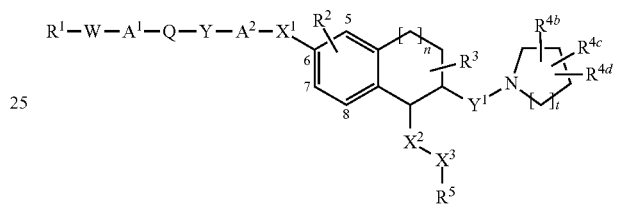

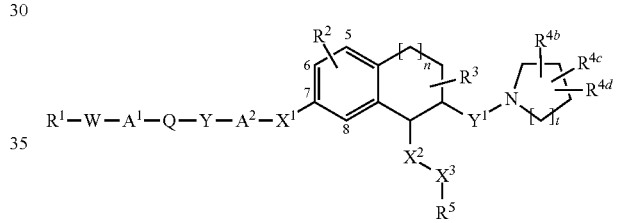

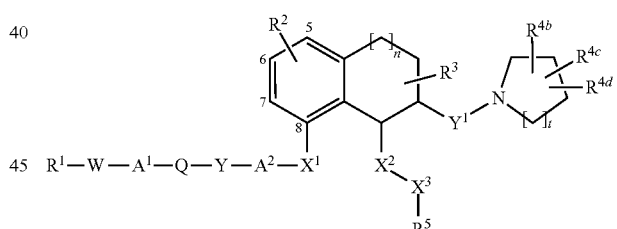

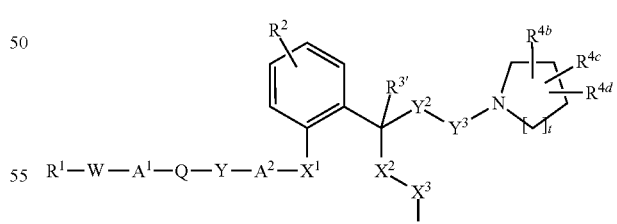

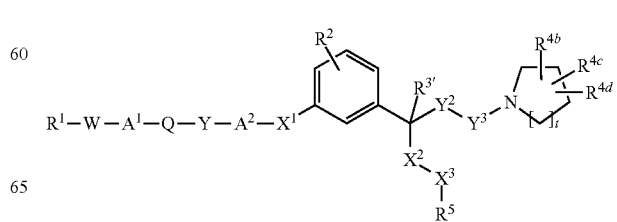

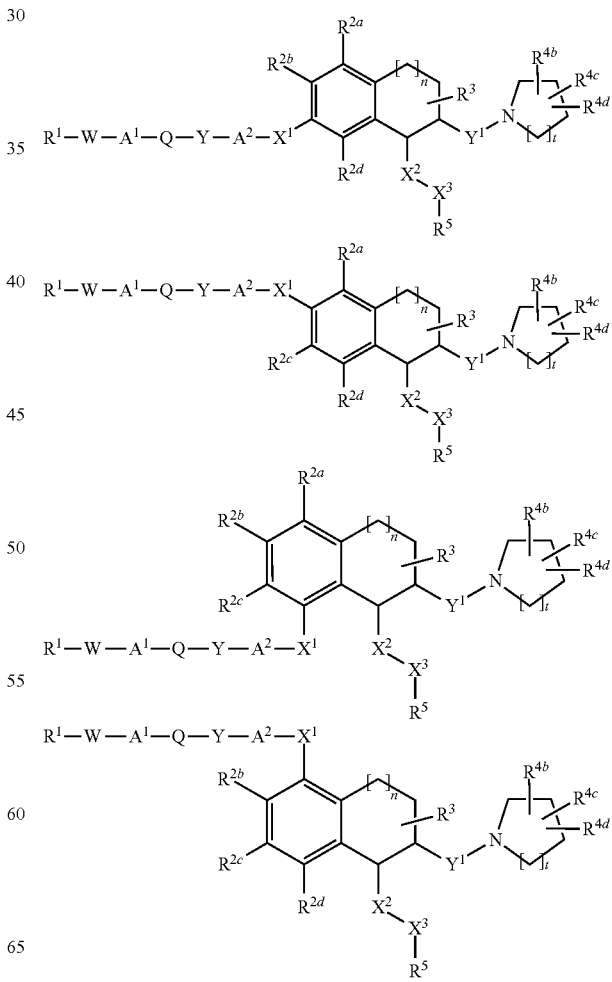

Further particular examples include compounds of the above formulae wherein the radical $R^1$—W-$A^1$-Q-Y-$A^2$-$X^1$— is replaced by the radical —CN.

According to a first aspect, aminobenzocycloheptene, aminotetraline and aminoindane derivatives of the invention having the radical $R^1$—W-$A^1$-Q-Y-$A^2$-$X^1$— (or the radical —CN) in the 5-, 6-, 7-position are preferred.

Particularly preferred are aminobenzocycloheptene, aminotetraline and aminoindane derivatives of the invention having the radical $R^1$—W-$A^1$-Q-Y-$A^2$-$X^1$— (or the radical —CN) in the 7-position.

According to a second aspect, phenalkylamine derivatives having the radical $R^1$—W-$A^1$-Q-Y-$A^2$-$X^1$— (or the radical —CN) in the meta-position (with respect to the alkylamine moiety) are particularly preferred.

In addition to the radical $R^1$—W-$A^1$-Q-Y-$A^2$-$X^1$— (or the radical —CN), the compounds of the invention may have one or more than one further substituent bound to the ring A or to the benzene ring. In these positions, the skeleton of the compounds of the invention may thus be substituted with one or more than one radical $R^2$. If there is more than one radical $R^2$, these may be the same or different radicals. In particular, in 5-, 6-, 7- and/or 8-position, the skeleton of the aminobenzocycloheptene, aminotetraline and aminoindane derivatives of the invention may be substituted with one or more than one radical $R^2$. The compounds of the invention may therefore be represented by one of the following formulae:

In said formulae, $R^1$, W, $A^1$, Q, Y, $A^2$, $X^1$, $R^2$, $R^3$, $R^{3'}$, $Y^1$, $Y^2$, $Y^3$, r, s, t, $R^{4a}$, $R^{4b}$, $R^{4b'}$, $R^{4c}$, $R^{4d}$, $R^{4e}$, $X^2$, $X^3$, $X^4$, $R^5$, n are as defined herein.

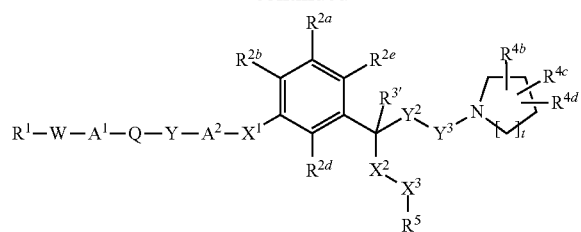
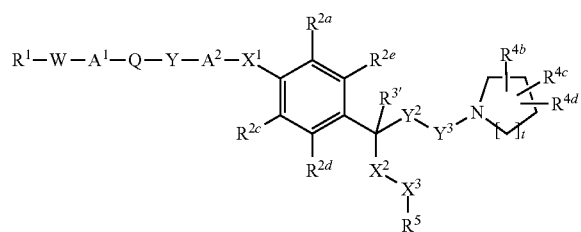
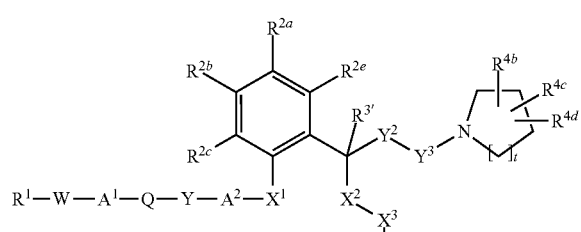
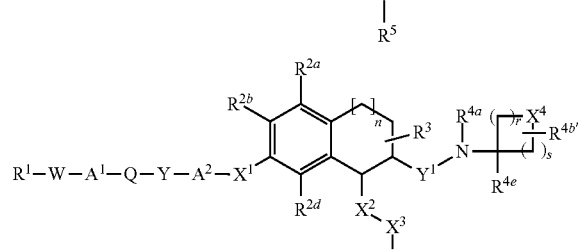
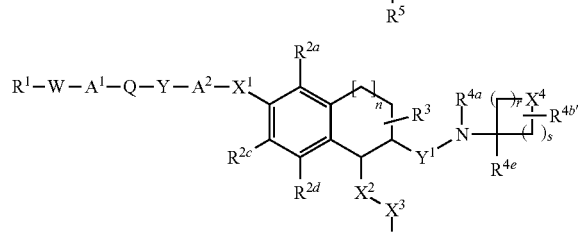
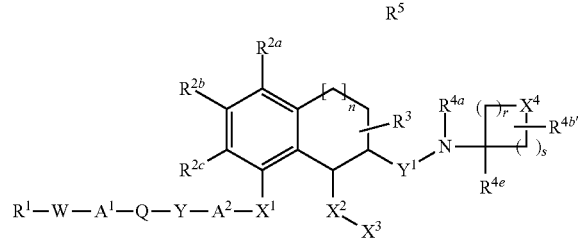
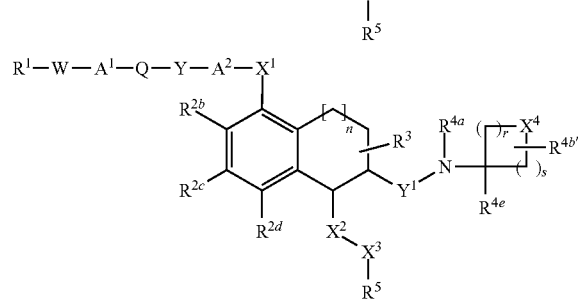
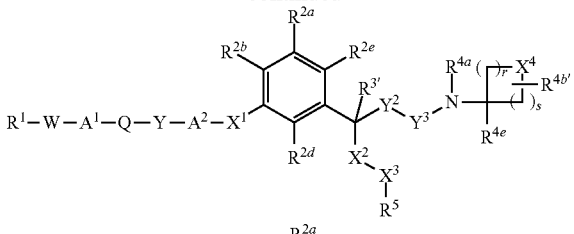
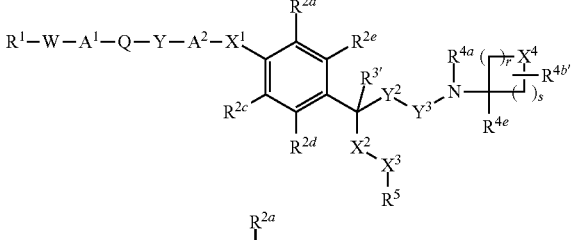
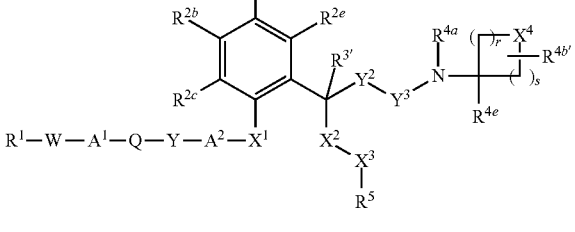

or by corresponding formulae wherein the radical $R^1$—W-$A^1$-Q-Y-$A^2$-$X^1$— is replaced by the radical —CN, wherein $R^{2a}$, $R^{2b}$, $R^{2c}$, $R^{2d}$, $R^{2e}$ independently have one of the meanings given for $R^2$, and $R^1$, W, $A^1$, Q, Y, $A^2$, $X^1$, $R^2$, $R^3$, $R^{3'}$, $Y^1$, $Y^2$, $Y^3$, r, s, t, $R^{4a}$, $R^{4b}$, $R^{4b'}$, $R^{4c}$, $R^{4d}$, $R^{4e}$, $X^2$, $X^3$, $X^4$, $R^5$, n are as defined herein.

$R^2$ is hydrogen, halogen (e.g. fluorine), $C_1$-$C_6$-alkyl, halogenated $C_1$-$C_4$-alkyl, hydroxy-$C_1$-$C_4$-alkyl, —CN, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-alkoxycarbonyl, $C_2$-$C_6$-alkenyloxy, $C_6$-$C_{12}$-aryl-$C_1$-$C_4$-alkoxy, $C_1$-$C_6$-alkylcarbonyloxy, $C_1$-$C_6$-alkylthio, $C_1$-$C_6$-alkylsulfinyl, $C_1$-$C_6$-alkylsulfonyl, aminosulfonyl, amino, $C_1$-$C_6$-alkylamino, $C_2$-$C_6$-alkenylamino, nitro or optionally substituted $C_3$-$C_{12}$-heterocyclyl, or two radicals $R^2$ together with the ring atoms to which they are bound form a 5- or 6 membered ring.

An optionally substituted 5- or 6-membered ring that is formed by two radicals $R^2$ together with the ring atoms of A to which they are bound is, for instance, a benzene ring.

In connection with $R^2$, substituted $C_6$-$C_{12}$-aryl in particular includes $C_6$-$C_{12}$-aryl, such as phenyl, substituted with 1, 2 or 3 substituents selected from the group consisting of halogen and $C_1$-$C_4$-alkyl, $C_1$-$C_4$-haloalkyl, cyano, $C_1$-$C_4$-alkoxy and $C_1$-$C_4$-haloalkoxy.

In connection with $R^2$, substituted $C_3$-$C_{12}$-heterocyclyl in particular includes $C_3$-$C_{12}$-heterocyclyl, such as morpholinyl, pyrrolidinyl and piperidinyl, substituted with 1, 2 or 3 substituents selected from the group consisting of halogen, $C_1$-$C_4$-alkyl, $C_1$-$C_4$-haloalkyl, cyano, $C_1$-$C_4$-alkoxy and $C_1$-$C_4$-haloalkoxy.

Preferably, $R^2$ is hydrogen, halogen (e.g. fluorine), —CN or $C_1$-$C_6$-alkoxy, or $R^2$ is hydrogen, halogen (e.g. fluorine) or $C_1$-$C_6$-alkoxy. In particular, $R^2$ is hydrogen, —CN or halogen (e.g. fluorine), or $R^2$ is hydrogen or halogen (e.g. fluorine).

According to a particular embodiment, the compounds of the invention have one of the following formulae:

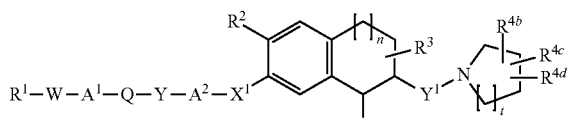

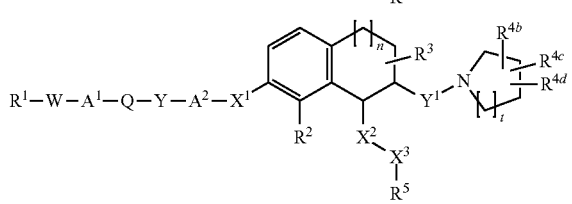

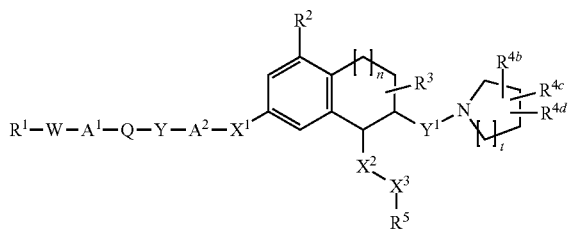

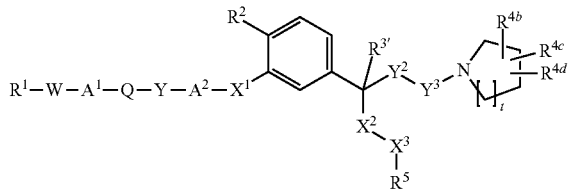

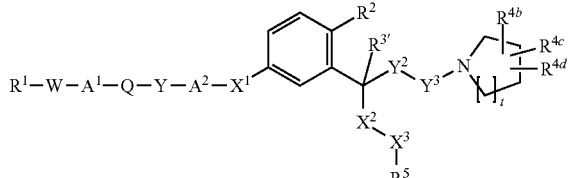

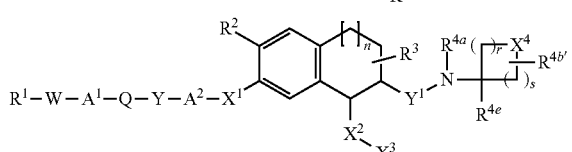

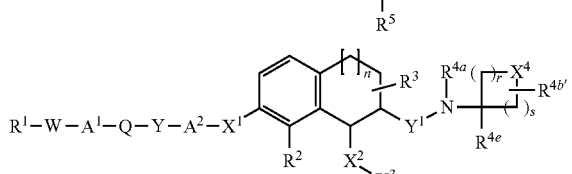

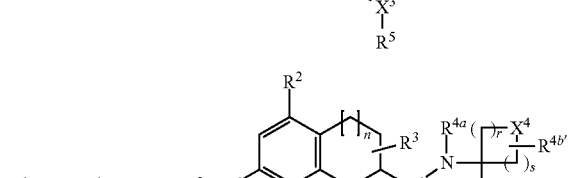

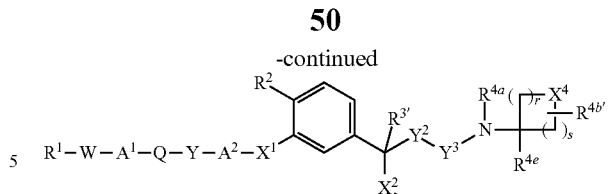

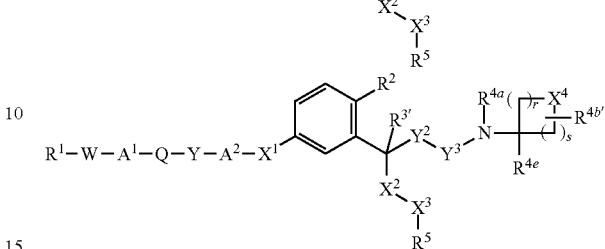

or by corresponding formulae wherein the radical $R^1$—W-$A^1$-Q-Y-$A^2$-$X^1$— is replaced by the radical —CN, wherein $R^1$, W, $A^1$, Q, Y, $A^2$, $R^2$, $R^3$, $R^{3'}$, $Y^1$, $Y^2$, $Y^3$, r, s, t, $R^{4a}$, $R^{4b}$, $R^{4b'}$, $R^{4c}$, $R^{4d}$, $R^{4e}$, $X^2$, $X^3$, $X^4$, $R^5$, n are as defined herein.

In 1-, 2-, 3- and/or 4-position, the aminobenzocycloheptene, aminotetraline and aminoindane derivatives of the invention may be substituted with one or more than one radical $R^3$. If there is more than one radical $R^3$, these may be the same or different radicals. The compounds of the invention may therefore be represented by the following formula:

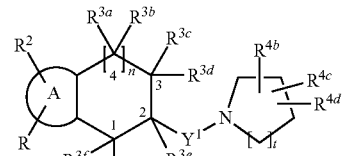

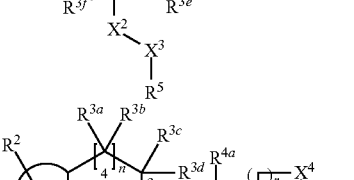

wherein $R^{3a}$, $R^{3b}$, $R^{3c}$, $R^{3d}$, $R^{3e}$, $R^{3f}$ independently have one of the meanings given for $R^3$, and A, R, $R^2$, $R^3$, $Y^1$, r, s, t, $R^{4a}$, $R^{4b}$, $R^{4b'}$, $R^{4c}$, $R^{4d}$, $R^{4e}$, $X^2$, $X^3$, $X^4$, $R^5$, n are as defined herein.

According to a particular embodiment, the compounds of the invention have one of the following formulae:

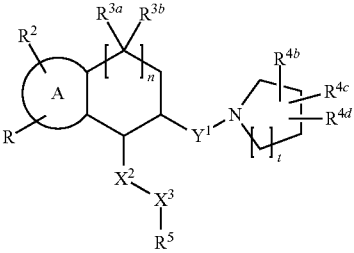

-continued

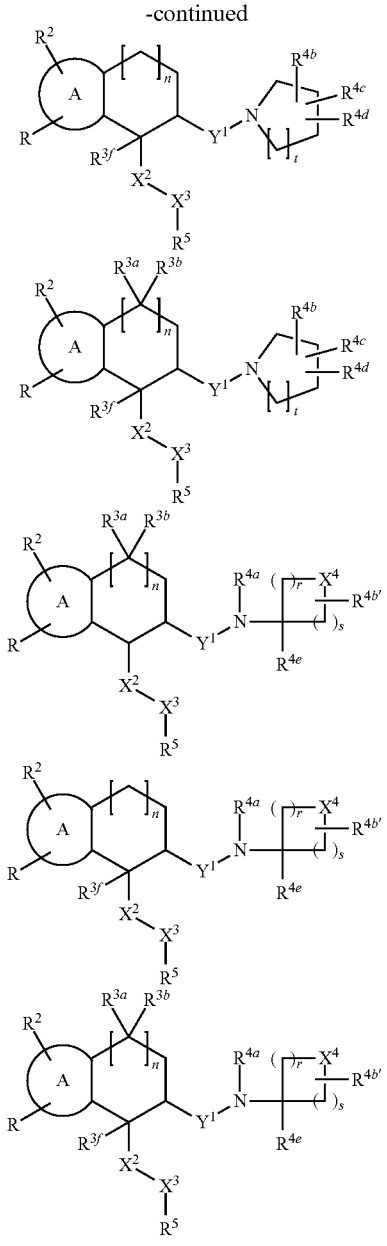

wherein $R^{3a}$, $R^{3b}$, $R^{3f}$ independently have the meaning of $R^3$ and A, R, $R^2$, $R^3$, $Y^1$, r, s, t, $R^{4a}$, $R^{4b}$, $R^{4b'}$, $R^{4c}$, $R^{4d}$, $R^{4e}$, $X^2$, $X^3$, $X^4$, $R^5$, n are as defined herein.

$R^3$ is hydrogen, halogen, $C_1$-$C_6$-alkyl, $C_1$-$C_6$-alkoxy, or two radicals $R^3$ together with the carbon atom to which they are attached form a carbonyl group.

Preferably, $R^3$ is hydrogen or $C_1$-$C_6$-alkyl. In particular, $R^3$ is hydrogen.

$R^{3'}$ is hydrogen or $C_1$-$C_6$-alkoxy.

In particular, $R^3$ is hydrogen.

$Y^1$ is a bond or optionally substituted $C_1$-$C_4$-alkylene (e.g. methylene or 1,2-ethylene). Preferably, $Y^1$ is a bond. In connection with $Y^1$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl, $C_3$-$C_{12}$-cycloalkyl and cyano. In particular, $Y^1$ is $C_1$-$C_4$-alkylene (e.g. methylene or 1,2-ethylene).

$Y^2$ is a bond or $>CR^{14a}R^{14b}$. According to one embodiment, $Y^2$ is a bond.

$Y^3$ is $>CR^{15a}R^{15b}$ or a bond.

Thus, according to one embodiment —$Y^2$—$Y^3$— is $>CR^{15a}R^{15b}$ and according to another embodiment —$Y^2$—$Y^3$— is a bond.

$R^{14a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxyl.

$R^{14b}$ is hydrogen or $C_1$-$C_6$-alkyl.

Alternatively, $R^{14a}$, together are carbonyl or optionally substituted $C_1$-$C_6$-alkylene, wherein one or two —$CH_2$— of $C_1$-$C_6$-alkylene may be replaced by an oxygen atom or —$NR^{18}$—

$R^{15a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxyl.

$R^{15b}$ is hydrogen or $C_1$-$C_6$-alkyl.

According to a particular embodiment, $R^{15a}$ is hydrogen and $R^{15b}$ is hydrogen.

Alternatively, $R^{15a}$, $R^{15b}$ together are carbonyl or optionally substituted $C_1$-$C_6$-alkylene, wherein one or two —$CH_2$— of $C_1$-$C_6$-alkylene may be replaced by an oxygen atom or —$NR^{19}$—

The index t is 0, 1, 2 or 3. According to a particular embodiment, t is 1.

$R^{4b}$ is hydrogen, halogen, $C_1$-$C_6$-alkyl, $C_3$-$C_{12}$-cycloalkyl-$C_1$-$C_4$-alkyl, halogenated $C_1$-$C_6$-alkyl, tri-($C_1$-$C_4$-alkyl)-silyl-$C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkylcarbonylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $C_3$-$C_{12}$-heterocyclyl-$C_1$-$C_4$-alkyl, $C_3$-$C_{12}$-cycloalkyl, $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl, $C_2$-$C_6$-alkynyl, optionally substituted $C_6$-$C_{12}$-aryl, cyano, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $C_3$-$C_{12}$-heterocyclylsulfonylamino-$C_1$-$C_4$-alkoxy, $C_3$-$C_{12}$-heterocyclyl-$C_1$-$C_4$-alkoxy, $C_6$-$C_{12}$-aryloxy, $C_3$-$C_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $C_3$-$C_{12}$-heterocyclyl Preferably, $R^{4b}$ is hydrogen, halogen; $C_1$-$C_6$-alkyl, $C_3$-$C_{12}$-cycloalkyl-$C_1$-$C_4$-alkyl, halogenated $C_1$-$C_6$-alkyl, hydroxy-$C_1$-$C_4$-alkyl, $C_1$-$C_6$-alkoxy-$C_1$-$C_4$-alkyl, optionally substituted $C_6$-$C_{12}$-aryl-$C_1$-$C_4$-alkyl, $C_2$-$C_6$-alkenyl, $C_2$-$C_6$-alkynyl, optionally substituted $C_6$-$C_{12}$-aryl, cyano, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, $C_6$-$C_{12}$-aryl-$C_1$-$C_4$-alkoxy, $C_3$-$C_{12}$-heterocyclyloxy or optionally substituted $C_3$-$C_{12}$-heterocyclyl.

More preferably, $R^{4b}$ is hydrogen, halogen; $C_1$-$C_6$-alkyl, $C_3$-$C_6$-cycloalkyl-$C_1$-$C_4$-alkyl, halogenated $C_1$-$C_6$-alkyl, hydroxy-$C_1$-$C_4$-alkyl, $C_1$-$C_6$-alkoxy-$C_1$-$C_4$-alkyl, optionally substituted $C_6$-aryl-$C_1$-$C_4$-alkyl, optionally substituted $C_6$-aryl, cyano, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy or $C_6$-aryl-$C_1$-$C_4$-alkoxy.

In particular, $R^{4b}$ is hydrogen.

$R^{4c}$, $R^{4d}$ together are $C_1$-$C_6$-alkylene optionally substituted with 1, 2 or 3 substituents $R^{4f}$, wherein one —CH$_2$— of $C_1$-$C_6$-alkylene may be replaced by an oxygen atom or —NR$^{20}$—.

In connection with $R^{4c}$ and $R^{4d}$, substituted $C_1$-$C_5$-alkylene in particular includes $C_1$-$C_4$-alkylene optionally substituted with 1, 2 or 3 substituents ($R^{41}$) selected from the group consisting of hydrogen, halogen; $C_1$-$C_6$-alkyl, $C_3$-$C_{12}$-cycloalkyl-$C_1$-$C_4$-alkyl, halogenated $C_1$-$C_6$-alkyl, hydroxy-$C_1$-$C_4$-alkyl, $C_1$-$C_6$-alkoxy-$C_1$-$C_4$-alkyl, optionally substituted $C_6$-$C_{12}$-aryl-$C_1$-$C_4$-alkyl, $C_2$-$C_6$-alkenyl, $C_2$-$C_6$-alkynyl, optionally substituted $C_6$-$C_{12}$-aryl, cyano, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, $C_6$-$C_{12}$-aryl-$C_1$-$C_4$-alkoxy, $C_3$-$C_{12}$-heterocyclyloxy or optionally substituted $C_3$-$C_{12}$-heterocyclyl, and more preferably hydrogen, halogen; $C_1$-$C_6$-alkyl, $C_3$-$C_6$-cycloalkyl-$C_1$-$C_4$-alkyl, halogenated $C_1$-$C_6$-alkyl, hydroxy-$C_1$-$C_4$-alkyl, $C_1$-$C_6$-alkoxy-$C_1$-$C_4$-alkyl, optionally substituted $C_6$-aryl-$C_1$-$C_4$-alkyl, optionally substituted $C_6$-aryl, cyano, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy or $C_6$-aryl-$C_1$-$C_4$-alkoxy.

In particular, $R^{4c}$, $R^{4d}$ together with the carbon atom or the carbon atoms to which they are bound form a 3-, 4-, 5- or 6-membered ring, for example a ring comprised by the formula:

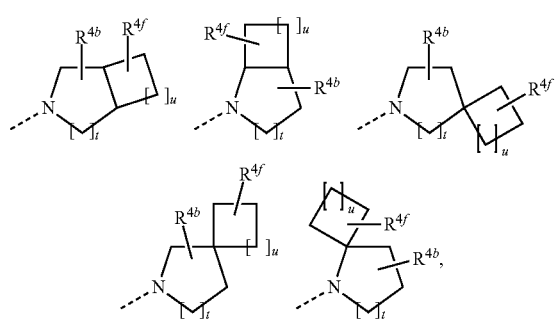

wherein t is defined as herein and u is 0, 1, 2, or 3, and $R^{4b}$ and $R^{4f}$ are as defined herein. Particular combinations of u and t include t=1 and u=0.

In said formulae, there may be one or more than one radical $R^{4b}$ and/or $R^{4f}$. More particularly, there may be up to 3 radicals $R^{4b}$ and/or be up to 3 radicals $R^{4f}$. Preferably there is one radical $R^{4b}$ and/or one radical $R^{4f}$. Said formulae may thus also be depicted as follows:

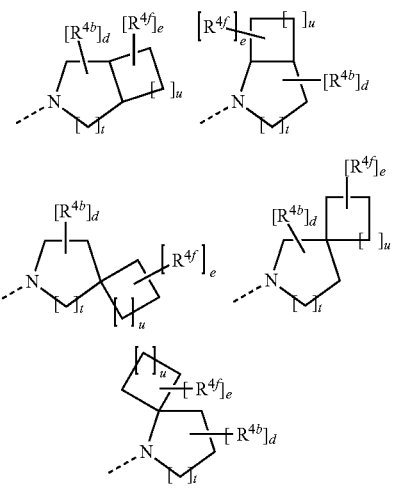

In said formulae, d is 1, 2 or 3 and e is 1, 2, or 3. If there is more than one radical $R^{4b}$, these may be the same or different radicals. If there is more than one radical $R^{4f}$, these may be the same or different radicals.

The following examples of bicyclic moieties illustrate particular combinations of t, u and $R^{4b}$, $R^{4f}$ in the compounds of the present invention:

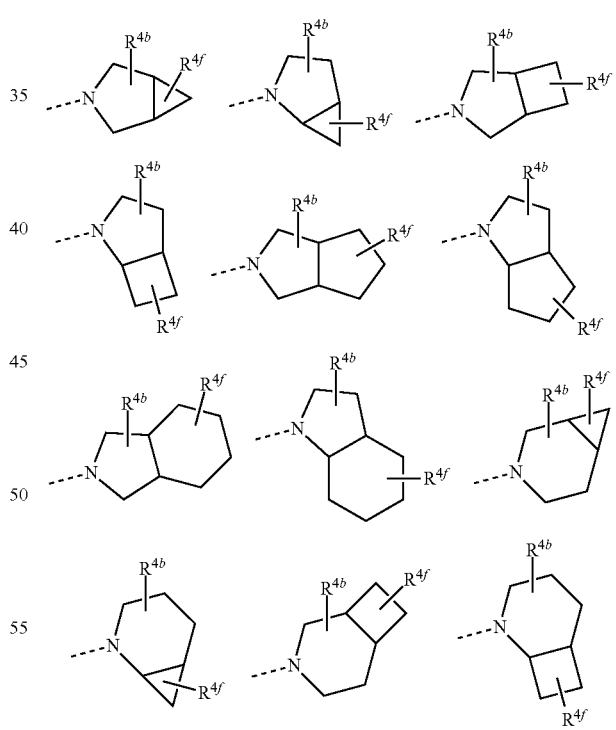

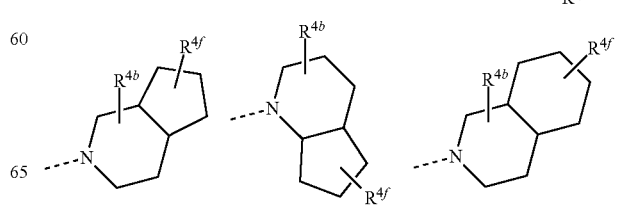

-continued

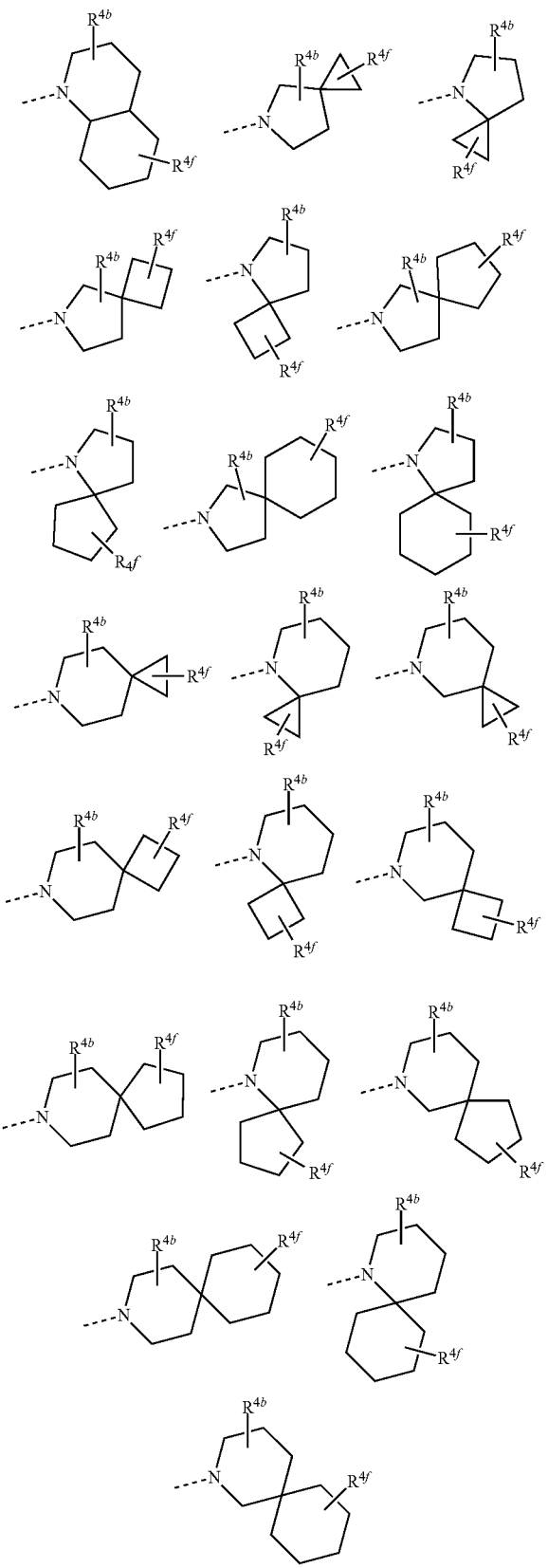

wherein $R^{4b}$, $R^{4f}$ are as defined herein and in particular are both hydrogen.

Compounds of the invention having the following bicyclic moiety:

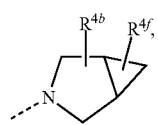

wherein $R^{4b}$, $R^{4f}$ are as defined herein and in particular are both hydrogen, are particularly preferred.

The index r is 1, 2 or 3. According to a particular embodiment, r is 1 or 2.

The index s is 1, 2 or 3. According to a particular embodiment, s is 1 or 2.

Particular combinations of r and s include moieties wherein r is 1 and s is 1, or r is 1 and s is 2.

$X^4$ is —O—, —$NR^{21}$—S—, —S(O)—, —S(O)$_2$—, or a bond.

Preferable, $X^4$ is —O— or a bond.

Particular combinations of r, s and $X^4$ include moieties where r is 1, s is 1 and $X^4$ is —O— (oxetanyl); r is 1, s is 1 and $X^4$ is a bond (cyclopropyl); or r is 1, s is 2 and $X^4$ is a bond (cyclobutyl).

$R^{4a}$ is hydrogen, $C_1$-$C_6$-alkyl (e.g. methyl, ethyl), halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $CH_2CN$, —CHO, $C_1$-$C_4$-alkylcarbonyl, (halogenated $C_1$-$C_4$-alkyl)carbonyl, $C_6$-$C_{12}$-arylcarbonyl, $C_1$-$C_4$-alkoxycarbonyl, $C_6$-$C_{12}$-aryloxycarbonyl, $C_1$-$C_6$-alkylaminocarbonyl, $C_2$-$C_6$-alkenyl, —C(=NH)NH$_2$, —C(=NH)NHCN, $C_1$-$C_6$-alkylsulfonyl, $C_6$-$C_{12}$-arylsulfonyl, amino, —NO or $C_3$-$C_{12}$-heterocyclyl.

Preferably, $R^{4a}$ is hydrogen, $C_1$-$C_6$-alkyl (e.g. methyl). In particular, $R^{4a}$ is hydrogen.

$R^{4b'}$ is hydrogen, halogen, $C_1$-$C_6$-alkyl, $C_3$-$C_{12}$-cycloalkyl-$C_1$-$C_4$-alkyl, halogenated $C_1$-$C_6$-alkyl, tri-($C_1$-$C_4$-alkyl)-silyl-$C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkylcarbonylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $C_3$-$C_{12}$-heterocyclyl-$C_1$-$C_4$-alkyl, $C_3$-$C_{12}$-cycloalkyl, $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl, $C_2$-$C_6$-alkynyl, optionally substituted $C_6$-$C_{12}$-aryl, cyano; hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $C_3$-$C_{12}$-heterocyclylsulfonylamino-$C_1$-$C_4$-alkoxy, $C_3$-$C_{12}$-heterocyclyl-$C_1$-$C_4$-alkoxy, $C_6$-$C_{12}$-aryloxy, $C_3$-$C_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkylamino, di-$C_1$-$C_6$-alkylamino, di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $C_3$-$C_{12}$-heterocyclyl.

Preferably, $R^{4b'}$ is hydrogen, halogen; $C_1$-$C_6$-alkyl, $C_3$-$C_{12}$-cycloalkyl-$C_1$-$C_4$-alkyl, halogenated $C_1$-$C_6$-alkyl, hydroxy-$C_1$-$C_4$-alkyl, $C_1$-$C_6$-alkoxy-$C_1$-$C_4$-alkyl, optionally substituted $C_6$-$C_{12}$-aryl-$C_1$-$C_4$-alkyl, $C_2$-$C_6$-alkenyl, $C_2$-$C_6$-alkynyl, optionally substituted $C_6$-$C_{12}$-aryl, cyano, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, $C_6$-$C_{12}$-aryl-$C_1$-$C_4$-alkoxy, $C_3$-$C_{12}$-heterocyclyloxy or optionally substituted $C_3$-$C_{12}$-heterocyclyl.

More preferably, $R^{4b'}$ is hydrogen, halogen; $C_1$-$C_6$-alkyl, $C_3$-$C_6$-cycloalkyl-$C_1$-$C_4$-alkyl, halogenated $C_1$-$C_6$-alkyl, hydroxy-$C_1$-$C_4$-alkyl, $C_1$-$C_6$-alkoxy-$C_1$-$C_4$-alkyl, optionally substituted $C_6$-aryl-$C_1$-$C_4$-alkyl, optionally substituted $C_6$-aryl, cyano, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy or $C_6$-aryl-$C_1$-$C_4$-alkoxy.

$R^{4e}$ is hydrogen, halogen, $C_1$-$C_6$-alkyl, $C_3$-$C_{12}$-cycloalkyl-$C_1$-$C_4$-alkyl, halogenated $C_1$-$C_6$-alkyl, tri-($C_1$-$C_4$-alkyl)-silyl-$C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkylcarbonylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $C_3$-$C_{12}$-heterocyclyl-$C_1$-$C_4$-alkyl, $C_3$-$C_{12}$-cycloalkyl, $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl, $C_2$-$C_6$-alkynyl, optionally substituted $C_6$-$C_{12}$-aryl, cyano, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $C_3$-$C_{12}$-heterocyclylsulfonylamino-$C_1$-$C_4$-alkoxy, $C_3$-$C_{12}$-heterocyclyl-$C_1$-$C_4$-alkoxy, $C_6$-$C_{12}$-aryloxy, $C_3$-$C_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkylamino, di-$C_1$-$C_6$-alkylamino, di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $C_3$-$C_{12}$-heterocyclyl.

In formula (III) or (IV), at least one of $R^{4b'}$ and $R^{4e}$ is not hydrogen, i.e. the ring structure of the moiety

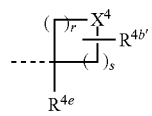

carries at least one substituent. According to a particular embodiment, $R^{4e}$ is not hydrogen.

Preferably, $R^{4e}$ is hydrogen, halogen; $C_1$-$C_6$-alkyl, $C_3$-$C_{12}$-cycloalkyl-$C_1$-$C_4$-alkyl, halogenated $C_1$-$C_6$-alkyl, hydroxy-$C_1$-$C_4$-alkyl, $C_1$-$C_6$-alkoxy-$C_1$-$C_4$-alkyl, optionally substituted $C_6$-$C_{12}$-aryl-$C_1$-$C_4$-alkyl, $C_2$-$C_6$-alkenyl, $C_2$-$C_6$-alkynyl, optionally substituted $C_6$-$C_{12}$-aryl, cyano or optionally substituted $C_3$-$C_{12}$-heterocyclyl.

More preferably, $R^{4e}$ is hydrogen, halogen; $C_1$-$C_6$-alkyl, $C_3$-$C_6$-cycloalkyl-$C_1$-$C_4$-alkyl, halogenated $C_1$-$C_6$-alkyl, hydroxy-$C_1$-$C_4$-alkyl, $C_1$-$C_6$-alkoxy-$C_1$-$C_4$-alkyl, optionally substituted $C_6$-aryl-$C_1$-$C_4$-alkyl, optionally substituted $C_6$-aryl, cyano or $C_6$-aryl-$C_1$-$C_4$-alkoxy.

It is in particular preferred if $R^{4e}$ is an electron withdrawing group.

$X^2$ is —O—, —$NR^6$—, —S—, >$CR^{12a}R^{12b}$ or a bond. Preferably, $X^2$ is >$CR^{12a}R^{12b}$.

$X^3$ is —O—, —S—, >$CR^{13a}R^{13b}$ or a bond. Preferably, $X^3$ is a bond.

Thus, it is preferred if $X^2$ is >$CR^{12a}R^{12b}$ and $X^3$ is a bond.

$R^{12a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy. Preferably, $R^{12a}$ is hydrogen or $C_1$-$C_6$-alkyl.

$R^{13a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy. Preferably, $R^{13a}$ is hydrogen or $C_1$-$C_6$-alkyl.

In connection with $R^{12a}$ and $R^{13a}$, substituted $C_1$-$C_6$-alkyl in particular includes $C_1$-$C_6$-alkyl substituted with 1, 2 or 3 substituents selected from the group consisting of halogen, hydroxy, $C_1$-$C_4$-alkoxy and amino.

In connection with $R^{12a}$ and $R^{13a}$, substituted $C_6$-$C_{12}$-aryl in particular includes $C_6$-$C_{12}$-aryl, such as phenyl, substituted with 1, 2 or 3 substituents selected from the group consisting of $C_1$-$C_4$-alkyl, $C_1$-$C_4$-haloalkyl, cyano, $C_1$-$C_4$-alkoxy and $C_1$-$C_4$-haloalkoxy.

$R^{12b}$ is hydrogen or $C_1$-$C_6$-alkyl. According to a particular embodiment, $R^{12b}$ is hydrogen.

$R^{13b}$ is hydrogen or $C_1$-$C_6$-alkyl. According to a particular embodiment, $R^{13b}$ is hydrogen.

Alternatively, $R^{12a}$ and $R^{12b}$, or $R^{13a}$ and $R^{13b}$, together are together are carbonyl or, preferably, optionally substituted $C_1$-$C_4$-alkylene (e.g. 1,3-propylene), wherein one —$CH_2$— of $C_1$-$C_4$-alkylene may be replaced by an oxygen atom or —$NR^{16}$— or $NR^{17}$.

In connection with $R^{12a}$ and $R^{12b}$, or $R^{13a}$ and $R^{13b}$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl, cyano, $C_1$-$C_4$-alkoxy and $C_1$-$C_4$-haloalkoxy.

According to a particular embodiment, $R^{12a}$ is $C_1$-$C_6$-alkyl and $R^{12b}$ is hydrogen or $C_1$-$C_6$-alkyl, or $R^{13a}$ is $C_1$-$C_6$-alkyl and $R^{13b}$ is hydrogen or $C_1$-$C_6$-alkyl.

According to a further particular embodiment, $R^{12a}$ is hydrogen and $R^{12b}$ is hydrogen, or $R^{13a}$ is hydrogen and $R^{13b}$ is hydrogen.

According to a further particular embodiment, $R^{12a}$ and $R^{12b}$ together are optionally substituted 1,3-propylene, or $R^{13a}$ and $R^{13b}$ together are optionally substituted 1,3-propylene.

$R^5$ is optionally substituted $C_6$-$C_{12}$-aryl (e.g. phenyl, 2-fluorophenyl, 2-chlorophenyl, 3-fluorophenyl, 3-chlorophenyl; 3-cyanophenyl, 3-methylphenyl, 3-trifluoromethylphenyl, 3-methoxyphenyl, 4-fluorophenyl, 4-chlorophenyl, 4-methoxyphenyl, 3,4-difluorophenyl, 3,5-difluorophenyl, 3-fluoro-5-chlorophenyl, 3-chloro-4-fluorophenyl, 2,4-dichlorophenyl or 3,4-dichlorophenyl), optionally substituted $C_3$-$C_{12}$-cycloalkyl (e.g. cyclohexyl) or optionally substituted $C_3$-$C_{12}$-heterocyclyl.

In connection with $R^5$, substituted $C_3$-$C_{12}$-cycloalkyl in particular includes $C_3$-$C_{12}$-cycloalkyl, such as cyclopropyl or cyclohexyl, substituted with 1, 2 or 3 substituents selected from the group consisting of halogen, optionally substituted $C_1$-$C_6$-alkyl, halogenated $C_1$-$C_6$-alkyl, CN, hydroxy, $C_1$-$C_6$-alkoxy, halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^5$, substituted $C_6$-$C_{12}$-aryl in particular includes $C_6$-$C_{12}$-aryl, such as phenyl, substituted with 1, 2 or 3 substituents selected from the group consisting of halogen (e.g. F, Cl, Br), optionally substituted $C_1$-$C_6$-alkyl (e.g. methyl), halogenated $C_1$-$C_6$-alkyl (e.g. trifluoromethyl), CN, hydroxy, $C_1$-$C_6$-alkoxy (e.g. methoxy), halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^5$, substituted $C_3$-$C_{12}$-heterocyclyl in particular includes $C_3$-$C_{12}$-heterocyclyl substituted with 1, 2 or 3 substituents selected from the group consisting of halogen, optionally substituted $C_1$-$C_6$-alkyl, halogenated $C_1$-$C_6$-alkyl, CN, hydroxy, $C_1$-$C_6$-alkoxy, halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^5$, $C_3$-$C_{12}$-heterocyclyl in particular is $C_3$-$C_{12}$-heteroaryl.

Preferably, $R^5$ is optionally substituted $C_6$-$C_{12}$-aryl, in particular as in the compounds of the formula:

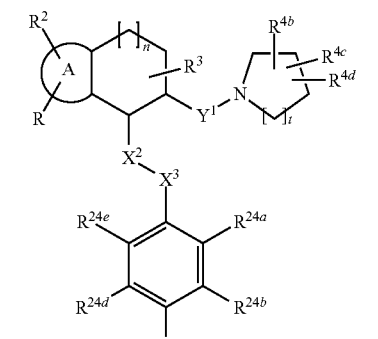

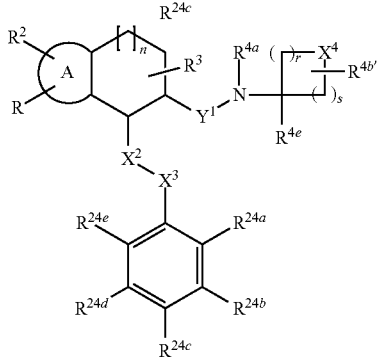

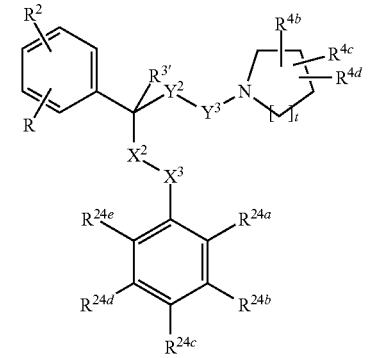

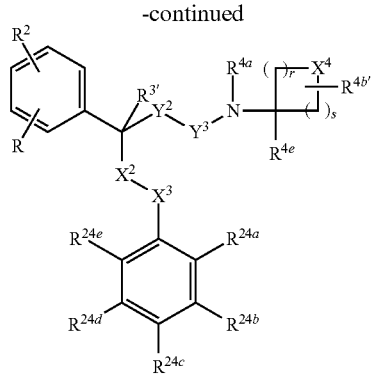

wherein A, R, $R^2$, $R^3$, $R^{3'}$, $Y^1$, $Y^2$, $Y^3$, r, s, t, $R^{4a}$, $R^{4b}$, $R^{4b'}$, $R^{4c}$, $R^{4d}$, $R^{4e}$, $X^2$, $X^3$, $X^4$, n are as defined herein, and
$R^{24a}$, $R^{24b}$, $R^{24c}$, $R^{24d}$, $R^{24e}$ independently are hydrogen, halogen (e.g. F, Cl or Br), optionally substituted $C_1$-$C_6$-alkyl (e.g. methyl), halogenated $C_1$-$C_6$-alkyl (e.g. trifluoromethyl), CN, hydroxy, $C_1$-$C_6$-alkoxy (e.g. methoxy), amino, $C_1$-$C_6$-alkylamino, di-$C_1$-$C_6$-alkylamino or $C_3$-$C_{12}$-heterocyclyl.

It is also preferred if $R^5$ is optionally substituted $C_6$-$C_{12}$-heteroaryl, in particular as in the compounds of the formula:

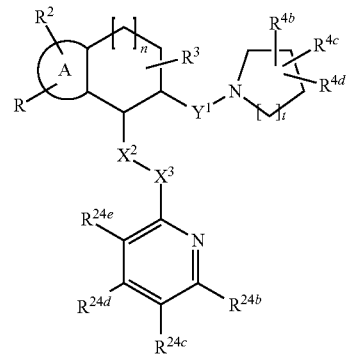

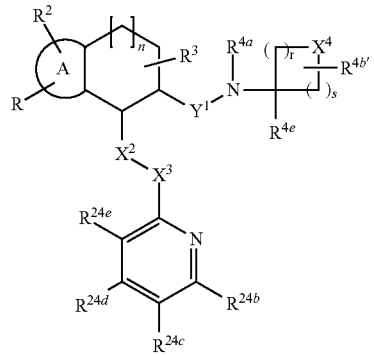

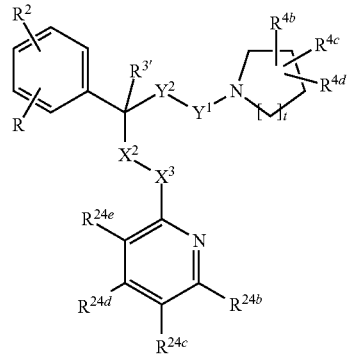

-continued

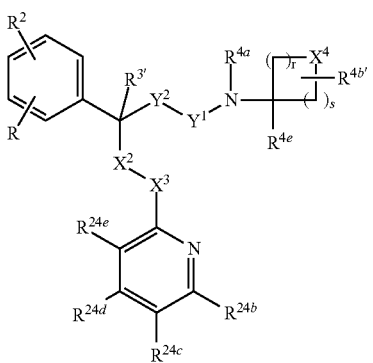

wherein A, R, R$^2$, R$^3$, R$^{3'}$, Y$^1$, Y$^2$, Y$^3$, r, s, t, R$^{4a}$, R$^{4b}$, R$^{4b'}$, R$^{4c}$, R$^{4d}$, R$^{4e}$, X$^2$, X$^3$, X$^4$, n are as defined herein, and R$^{24b}$, R$^{24c}$, R$^{24d}$, R$^{24e}$ independently are hydrogen, halogen (e.g. F, Cl or Br), optionally substituted C$_1$-C$_6$-alkyl (e.g. methyl), halogenated C$_1$-C$_6$-alkyl (e.g. trifluoromethyl), CN, hydroxy, C$_1$-C$_6$-alkoxy (e.g. methoxy), amino, C$_1$-C$_6$-alkylamino, di-C$_1$-C$_6$-alkylamino or C$_3$-C$_{12}$-heterocyclyl.

According to a particular embodiment, the invention relates to compounds of the formula:

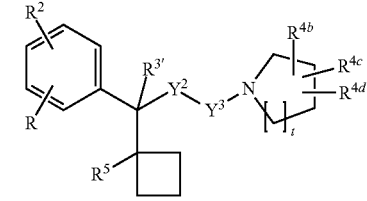
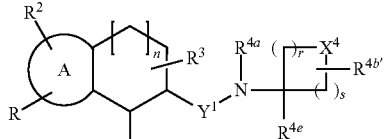
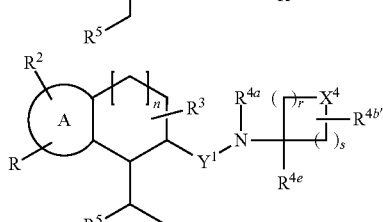
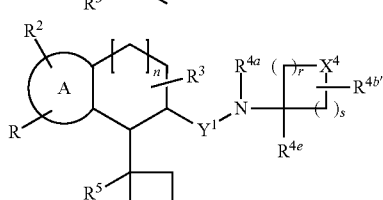
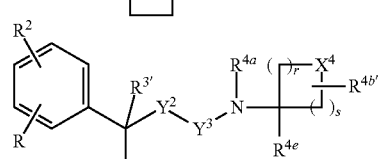
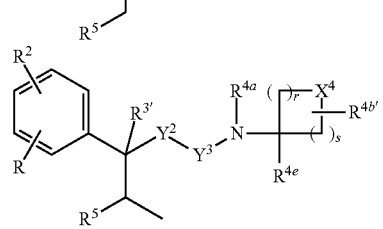
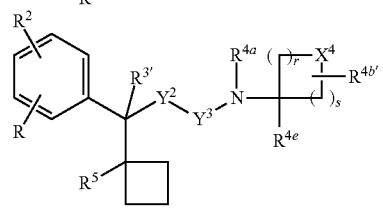

wherein A, R, R$^2$, R$^3$, R$^{3'}$, Y$^1$, Y$^2$, Y$^3$, r, s, t, R$^{4a}$, R$^{4b}$, R$^{4b'}$, R$^{4c}$, R$^{4d}$, R$^{4e}$, X$^4$, n are as defined herein, R$^5$ preferably being optionally substituted aryl and in particular optionally substituted phenyl as disclosed herein.

In connection with R$^5$ or R$^{24a}$, R$^{24b}$, R$^{24c}$, R$^{24d}$, R$^{24e}$, substituted C$_1$-C$_6$-alkyl in particular includes C$_1$-C$_6$-alkyl, especially C$_1$-C$_4$-alkyl, substituted with 1, 2 or 3 substituents selected from the group consisting of hydroxy, C$_1$-C$_6$-alkoxy, amino, C$_1$-C$_6$-alkylamino, di-C$_1$-C$_6$-alkylamino and C$_3$-C$_{12}$-heterocyclyl (e.g. morpholinyl or piperidinyl).

According to a particular embodiment, R$^{24a}$, R$^{24b}$, R$^{24d}$, R$^{24e}$ are hydrogen and R$^{24c}$ is different from hydrogen (para-mono-substitution).

According to a further particular embodiment, $R^{24a}$, $R^{24c}$, $R^{24d}$, $R^{24e}$ are hydrogen and $R^{24b}$ is different from hydrogen (meta-mono-substitution).

In connection with $R^{24a}$, $R^{24b}$, $R^{24c}$, $R^{24d}$, $R^{24e}$, $C_3$-$C_{12}$-heterocyclyl in particular includes morpholinyl, imidazolyl and pyrazolyl.

The index n is 0, 1 or 2. According to a particular embodiment, n is 1. According to another particular embodiment, n is 0.

$R^6$ is hydrogen, $C_1$-$C_6$-alkyl or $C_3$-$C_{12}$-cycloalkyl. Preferably, $R^6$ is hydrogen.

$R^7$ is hydrogen, $C_1$-$C_6$-alkyl or $C_3$-$C_{12}$-cycloalkyl. Preferably, $R^7$ is hydrogen.

$R^8$ is hydrogen, $C_1$-$C_6$-alkyl or $C_3$-$C_{12}$-cycloalkyl. Preferably, $R^8$ is hydrogen.

$R^9$ is hydrogen, $C_1$-$C_6$-alkyl (e.g. methyl or ethyl), $C_3$-$C_{12}$-cycloalkyl (e.g. cyclopropyl), amino-$C_1$-$C_6$-alkyl, optionally substituted $C_6$-$C_{12}$-aryl-$C_1$-$C_4$-alkyl or $C_3$-$C_{12}$-heterocyclyl (e.g. 3-azetidinyl). Preferably, $R^9$ is hydrogen or $C_1$-$C_6$-alkyl (e.g. methyl or ethyl).

According to a particular embodiment, $R^9$ and $R^1$ together are $C_1$-$C_4$-alkylene (e.g. 1, 3-1,2-ethylene or propylene) so as that $R^9$ and $R^1$ together with the atom in Q to which $R^1$ is bound and the nitrogen atom to which $R^9$ is bound form an heterocyclic ring having, in particular, 4, 5 or 6 ring member atoms (including the nitrogen atom and Q). With W and $A^1$ both being a bond, such a ring may be represented by the following partial structure:

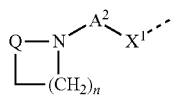

wherein $A^2$, $X^1$, Q are as defined herein (e.g. $S(O)_2$) and n is 0, 1, 2, 3 or 4.

According to a further particular embodiment, $R^9$ is $C_1$-$C_4$-alkylene (e.g. methylene or 1,3-propylene) that is bound to a carbon atom in $A^2$ and $A^2$ is $C_1$-$C_4$-alkylene so that $R^9$ and at least part of $A^2$ together with the nitrogen atom to which $R^9$ is bound form an N-containing heterocyclic ring having, in particular, 4, 5, 6 or 7 ring member atoms (including the nitrogen atom). Such a ring may be represented by the following partial structure:

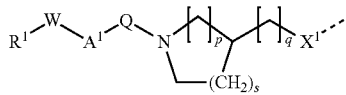

wherein $R^1$, W, $A^1$, Q and $X^1$ are as defined herein, p is 1 or 2, s is 0, 1 or 2 and q is 0, 1 or 2. In this particular embodiment, $X^1$ preferably is —O—. Particular combinations of p, s and q include p=1, s=0, q=1; and p=1, s=0, q=0. Alternatively, p is 0, s is 3 and q is 1, with $X^1$ preferably being —O—.

According to a further particular embodiment, $R^9$ is $C_1$-$C_4$-alkylene (e.g. methylene or 1,3-propylene) that is bound to a carbon atom in $X^1$ and $X^1$ is $C_1$-$C_4$-alkylene (e.g. 1,2-ethylene) so that $R^9$ and at least part of $X^1$ together with the nitrogen atom to which $R^9$ is bound form an N-containing heterocyclic ring having, in particular, 4, 5, 6 or 7 ring member atoms (including the nitrogen atom). With $A^2$ being a bond, such a ring may be represented by the following partial structure:

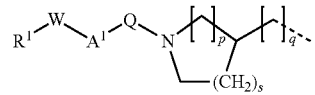

wherein $R^1$, W, $A^1$ and Q are as defined herein, p is 1 or 2, s is 0, 1 or 2 and q is 0, 1 or 2. Particular combinations of p, s and q include p=1, s=0, q=0.

$R^{10}$ is hydrogen, $C_1$-$C_6$-alkyl, $C_3$-$C_{12}$-cycloalkyl or $C_1$-$C_6$-alkylsulfonyl. Preferably, $R^{10}$ is hydrogen.

$R^{11}$ is hydrogen, $C_1$-$C_6$-alkyl or $C_3$-$C_{12}$-cycloalkyl. Preferably, $R^{11}$ is hydrogen.

Alternatively, $R^9$, $R^{11}$ together are $C_1$-$C_4$-alkylene (e.g. ethylene).

$R^{14}$ is hydrogen, $C_1$-$C_6$-alkyl or $C_3$-$C_{12}$-cycloalkyl. Preferably, $R^{14}$ is hydrogen.

$R^{15}$ is hydrogen, $C_1$-$C_6$-alkyl or $C_3$-$C_{12}$-cycloalkyl. Preferably, $R^{15}$ is hydrogen.

$R^{16}$ is hydrogen, $C_1$-$C_6$-alkyl or $C_3$-$C_{12}$-cycloalkyl. Preferably, $R^{16}$ is hydrogen.

$R^{17}$ is hydrogen, $C_1$-$C_6$-alkyl or $C_3$-$C_{12}$-cycloalkyl. Preferably, $R^{17}$ is hydrogen.

$R^{18}$ is hydrogen, $C_1$-$C_6$-alkyl or $C_3$-$C_{12}$-cycloalkyl. Preferably, $R^{18}$ is hydrogen.

$R^{19}$ is hydrogen, $C_1$-$C_6$-alkyl or $C_3$-$C_{12}$-cycloalkyl. Preferably, $R^{19}$ is hydrogen.

$R^{20}$ is hydrogen, $C_1$-$C_6$-alkyl or $C_3$-$C_{12}$-cycloalkyl. Preferably, $R^{20}$ is hydrogen.

$R^{21}$ is hydrogen, $C_1$-$C_6$-alkyl or $C_3$-$C_{12}$-cycloalkyl. Preferably, $R^{21}$ is hydrogen.

Particular embodiments of compounds of the invention result if

A is a benzene ring or a ring selected from the group consisting of the following 5- or 6-membered heterocyclic rings:

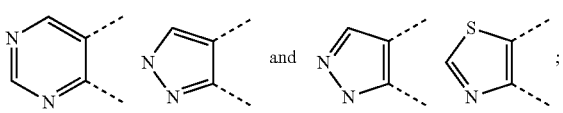

R is $R^1$—W-$A^1$-Q-Y-$A^2$-$X^1$—;

$R^1$ is $C_1$-$C_6$-alkyl (e.g. methyl, ethyl, n-propyl, isopropyl, n-butyl, sec-butyl, n-pentyl), $C_3$-$C_{12}$-cycloalkyl-$C_1$-$C_4$-alkyl (e.g. cyclopropylmethyl, cyclopentylmethyl, cyclohexylmethyl), halogenated $C_1$-$C_6$-alkyl (e.g. 3-fluoroprop-1-yl, 3-chloroprop-1-yl, 3,3,3-trifluoroprop-1-yl), tri-($C_1$-$C_4$-alkyl)-silyl-$C_1$-$C_4$-alkyl (e.g. trimethylsilylethyl), $C_1$-$C_6$-alkoxy-$C_1$-$C_4$-alkyl (e.g. ethoxyethyl), $C_3$-$C_{12}$-cycloalkyl (e.g. cyclopropyl, cyclobutyl, cyclohexyl), $C_2$-$C_6$-alkenyl (e.g. prop-1,2-en-1-yl), optionally substituted $C_6$-$C_{12}$-aryl (e.g. phenyl, 2-methylphenyl), or optionally substituted $C_3$-$C_{12}$-heterocyclyl (e.g. 1-methyl-pyrrol-3-yl, 2-pyridyl, 3-pyridyl, 4-pyridyl, 2-thienyl, 4-methyl-2-thienyl, 5-methyl-2-thienyl, 5-chloro-2-thienyl, 2,5-dimethyl-3-thienyl, 1,2-diazol-4-yl, 1-methyl-1,2-diazol-3-yl, 1-methyl-1,2-diazol-4-yl, 1-ethyl-1,2-diazol-4-yl, 1-difluormethyl-1,2-diazol-4-yl, 1-methyl-3-trifluoromethyl-1,2-diazol-4-yl, 2-methyl-1,3-diazol-4-yl, 1-methyl-1,3-diazol-4-yl, 1,2-dimethyl-1,3-diazol-4-yl, 5-methylisoxazol-3-yl, 2-methyl-1,3-thiazol-5-yl, 2,4-dimethyl-1,3-thiazol-5-yl, 1-methyl-1,2,4-triazol-3-yl, 3-pyrrolidinyl);

W is a bond;
A$^1$ is a bond;
Q is —S(O)$_2$— or —C(O)—;
Y is —NR$^9$— or a bond;
A$^2$ is C$_1$-C$_4$-alkylene (e.g. methylene, 1,2-ethylene, 1,3-propylene) or a bond;
X$^1$ is —O— or optionally substituted C$_1$-C$_4$-alkylene (e.g. methylene, 1,2-ethylene, 1,3-propylene) or C$_2$-C$_4$-alkynylene (e.g. prop-1,2-yn-1,3-ylene);
R$^2$ is hydrogen, halogen (e.g. fluorine) or cyano;
R$^3$ is hydrogen or halogen (e.g. fluorine), in particular hydrogen;
R$^{3'}$ is hydrogen;
Y$^1$ is a bond or optionally substituted C$_1$-C$_4$-alkylene (e.g. methylene, 1,2-ethylene);
Y$^2$ is a bond;
Y$^3$ is >CR$^{15a}$R$^{15b}$ or a bond;
t is as defined herein and in particular represents 1;
r is as defined herein and in particular represents 1;
s is as defined herein and in particular represents 1;
R$^{4a}$ is as defined herein and in particular represents hydrogen;
R$^{4b}$ is as defined herein and in particular represents hydrogen;
R$^{4c}$, R$^{4d}$
are as defined herein and in particular represent together optionally substituted C$_1$-C$_5$-alkylene (e.g. methylene);
R$^{4f}$ is as defined herein and in particular represents hydrogen;
R$^{4b'}$ is as defined herein and in particular represents hydrogen;
R$^{4e}$ is as defined herein and in particular represents cyano, provided that in formula (III) or (IV) at least one of R$^{4b}$ and R$^{4e}$ is not hydrogen;
X$^2$ is >CR$^{12a}$R$^{12b}$;
X$^3$ is a bond;
X$^4$ is —O—;
R$^5$ is optionally substituted phenyl (e.g. phenyl, 2-fluorophenyl, 2-chlorophenyl, 3-fluorophenyl, 3-chlorophenyl, 3-cyanophenyl, 3-methylphenyl, 3-trifluoromethylphenyl, 3-methoxyphenyl, 4-fluorophenyl, 4-chlorophenyl, 4-methoxyphenyl, 3,4-difluorophenyl, 3,5-difluorophenyl, 3-fluoro-5-chlorophenyl, 3-chloro-4-fluorophenyl, 3,4-dichlorophenyl, 2,4-dichlorophenyl) or optionally substituted C$_3$-C$_{12}$-cycloalkyl (e.g. cyclohexyl)
n is 0 or 1;
R$^9$ is hydrogen, C$_1$-C$_6$-alkyl (e.g. methyl, ethyl) or C$_3$-C$_{12}$-cycloalkyl (e.g. cyclopropyl), or
R$^9$, R$^1$
together are C$_1$-C$_4$-alkylene (e.g. 1,3-propylene); or
R$^9$ is C$_1$-C$_4$-alkylene (e.g. methylene, 1,3-propylene) that is bound to a carbon atom in A$^2$ and A$^2$ is C$_1$-C$_4$-alkylene (e.g. 1,2-ethylene, 1,3-propylene) or to a carbon atom in X$^1$ and X$^1$ is C$_1$-C$_4$-alkylene (e.g. 1,2-ethylene);
R$^{12a}$ is hydrogen; and
R$^{12b}$ is hydrogen, or
R$^{12a}$, R$^{12b}$
together are optionally substituted C$_1$-C$_4$-alkylene (e.g. 1,3-propylene);
R$^{15a}$ is hydrogen; and
R$^{15b}$ is hydrogen; or
R$^{15a}$, R$^{15b}$
together are carbonyl.
Further particular embodiments of compounds of the invention result if
A is a benzene ring;
R is R$^1$—W-A$^1$-Q-Y-A$^2$-X$^1$—;
R$^1$ is C$_1$-C$_6$-alkyl (e.g. ethyl or n-propyl), C$_3$-C$_{12}$-cycloalkyl-C$_1$-C$_4$-alkyl (e.g. cyclopropylmethyl), C$_3$-C$_{12}$-cycloalkyl (e.g. cyclobutyl), or optionally substituted C$_3$-C$_{12}$-heterocyclyl (e.g. 1-methyl-1,2-diazol-4-yl, 1-methyl-1,3-diazol-4-yl);
W is a bond;
A$^1$ is a bond;
Q is —S(O)$_2$—;
Y is —NR$^9$—;
A$^2$ is C$_1$-C$_4$-alkylene (e.g. 1,2-ethylene) or a bond;
X$^1$ is —O— or optionally substituted C$_1$-C$_4$-alkylene (e.g. methylene);
R$^2$ is hydrogen or cyano;
R$^3$ is hydrogen;
R$^{3'}$ is hydrogen;
Y$^1$ is a bond;
Y$^2$ is a bond;
Y$^3$ is a bond;
t is 1;
r is 1;
s is 1;
R$^{4a}$ is hydrogen;
R$^{4b}$ is hydrogen;
R$^{4c}$, R$^{4d}$
together are optionally substituted C$_1$-C$_5$-alkylene (e.g. methylene);
R$^{4f}$ is hydrogen;
R$^{4b'}$ is hydrogen;
R$^{4e}$ is cyano;
X$^2$ is >CR$^{12a}$R$^{12b}$;
X$^3$ is a bond;
X$^4$ is —O—;
R$^5$ is optionally substituted phenyl (e.g. phenyl, 2-fluorophenyl);
n is 1;
R$^9$ is hydrogen;
R$^{12a}$ is hydrogen; and
R$^{12b}$ is hydrogen.

Further particular compounds of the present invention are the individual phenalkylamine derivatives of the formula (Id) as listed in the following tables 1 to 24 and physiologically tolerated salts thereof:

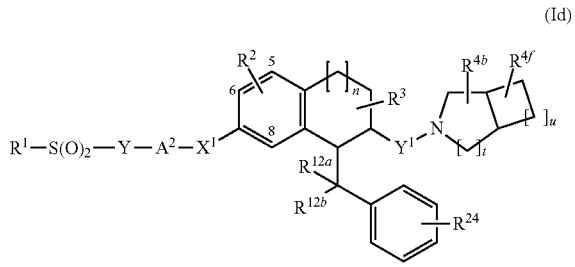

(Id)

Table 1

Compounds of the formula (Id) wherein —Y$^1$— is as defined herein and in particular represents a bond, —CH$_2$— or —(CH$_2$)$_2$—, n is 0 or 1, R$^2$ is hydrogen, R$^{3'}$ is hydrogen, R$^{24}$ is hydrogen and the combination of R$^1$, >CR$^{12a}$R$^{12b}$, t, u, R$^{4b}$, R$^{4f}$ for a compound in each case corresponds to one line of Table A (A-1 to A-80).

Table 2

Compounds of the formula (Id) wherein —Y$^1$— is as defined herein and in particular represents a bond, —CH$_2$— or —(CH$_2$)$_2$—, n is 0 or 1, R$^2$ is hydrogen, R$^{3'}$ is hydrogen, R$^{24}$ is 3-F and the combination of R$^1$, >CR$^{12a}$R$^{2b}$, t, u, R$^{4b}$, R$^{4f}$ for a compound in each case corresponds to one line of Table A (A-1 to A-80).

Table 3
Compounds of the formula (Id) wherein —$Y^1$— is as defined herein and in particular represents a bond, —$CH_2$— or —$(CH_2)_2$—, n is 0 or 1, $R^2$ is hydrogen, $R^{3'}$ is hydrogen, $R^{24}$ is 3-Cl and the combination of $R^1$, >$CR^{12a}R^{12b}$, t, u, $R^{4b}$, $R^{4f}$ for a compound in each case corresponds to one line of Table A (A-1 to A-80).

Table 4
Compounds of the formula (Id) wherein —$Y^1$— is as defined herein and in particular represents a bond, —$CH_2$— or —$(CH_2)_2$—, n is 0 or 1, $R^2$ is hydrogen, $R^{3'}$ is hydrogen, $R^{24}$ is 3-$CF_3$ and the combination of $R^1$, >$CR^{12a}R^{2b}$, t, u, $R^{4b}$, $R^{4f}$ for a compound in each case corresponds to one line of Table A (A-1 to A-80).

Table 5
Compounds of the formula (Id) wherein —$Y^1$— is as defined herein and in particular represents a bond, —$CH_2$— or —$(CH_2)_2$—, n is 0 or 1, $R^2$ is hydrogen, $R^{3'}$ is hydrogen, $R^{24}$ is 2-F and the combination of $R^1$, >$CR^{12a}R^{2b}$, t, u, $R^{4b}$, $R^{4f}$ for a compound in each case corresponds to one line of Table A (A-1 to A-80).

Table 6
Compounds of the formula (Id) wherein —$Y^1$— is as defined herein and in particular represents a bond, —$CH_2$— or —$(CH_2)_2$—, n is 0 or 1, $R^2$ is hydrogen, $R^{3'}$ is hydrogen, $R^{24}$ is 2-Cl and the combination of $R^1$, >$CR^{12a}R^{2b}$, t, u, $R^{4b}$, $R^{4f}$ for a compound in each case corresponds to one line of Table A (A-1 to A-80).

Table 7
Compounds of the formula (Id) wherein —$Y^1$— is as defined herein and in particular represents a bond, —$CH_2$— or —$(CH_2)_2$—, n is 0 or 1, $R^2$ is 5-F, $R^{3'}$ is hydrogen, $R^{24}$ is hydrogen and the combination of $R^1$, —Y-$A^2$-$X^1$—, >$CR^{12a}R^{12b}$, t, u, $R^{4b}$, $R^{4f}$ for a compound in each case corresponds to one line of Table A (A-1 to A-80).

Table 8
Compounds of the formula (Id) wherein —$Y^1$— is as defined herein and in particular represents a bond, —$CH_2$— or —$(CH_2)_2$—, n is 0 or 1, $R^2$ is 5-F, $R^{3'}$ is hydrogen, $R^{24}$ is 3-F and the combination of $R^1$, —Y-$A^2$-$X^1$—, >$CR^{12a}R^{12b}$, t, u, $R^{4b}$, $R^{4f}$ for a compound in each case corresponds to one line of Table A (A-1 to A-80).

Table 9
Compounds of the formula (Id) wherein —$Y^1$— is as defined herein and in particular represents a bond, —$CH_2$— or —$(CH_2)_2$—, n is 0 or 1, $R^2$ is 5-F, $R^{3'}$ is hydrogen, $R^{24}$ is 3-Cl and the combination of $R^1$, —Y-$A^2$-$X^1$—, >$CR^{12a}R^{12b}$, t, u, $R^{4b}$, $R^{4f}$ for a compound in each case corresponds to one line of Table A (A-1 to A-80).

Table 10
Compounds of the formula (Id) wherein —$Y^1$— is as defined herein and in particular represents a bond, —$CH_2$— or —$(CH_2)_2$—, n is 0 or 1, $R^2$ is 5-F, $R^{3'}$ is hydrogen, $R^{24}$ is 3-$CF_3$ and the combination of $R^1$, —Y-$A^2$-$X^1$—, >$CR^{12a}R^{12b}$, t, u, $R^{4b}$, $R^{4f}$ for a compound in each case corresponds to one line of Table A (A-1 to A-80).

Table 11
Compounds of the formula (Id) wherein —$Y^1$— is as defined herein and in particular represents a bond, —$CH_2$— or —$(CH_2)_2$—, n is 0 or 1, $R^2$ is 5-F, $R^{3'}$ is hydrogen, $R^{24}$ is 2-F and the combination of $R^1$, —Y-$A^2$-$X^1$—, >$CR^{12a}R^{12b}$, t, u, $R^{4b}$, $R^{4f}$ for a compound in each case corresponds to one line of Table A (A-1 to A-80).

Table 12
Compounds of the formula (Id) wherein —$Y^1$— is as defined herein and in particular represents a bond, —$CH_2$— or —$(CH_2)_2$—, n is 0 or 1, $R^2$ is 5-F, $R^{3'}$ is hydrogen, $R^{24}$ is 2-Cl and the combination of $R^1$, —Y-$A^2$-$X^1$—, >$CR^{12a}R^{12b}$, t, u, $R^{4b}$, $R^{4f}$ for a compound in each case corresponds to one line of Table A (A-1 to A-80).

Table 13
Compounds of the formula (Id) wherein —$Y^1$— is as defined herein and in particular represents a bond, —$CH_2$— or —$(CH_2)_2$—, n is 0 or 1, $R^2$ is 6-F, $R^{3'}$ is hydrogen, $R^{24}$ is hydrogen and the combination of $R^1$, >$CR^{12a}R^{12}$, t, u, $R^{4b}$, $R^{4f}$ for a compound in each case corresponds to one line of Table A (A-1 to A-80).

Table 14
Compounds of the formula (Id) wherein —$Y^1$— is as defined herein and in particular represents a bond, —$CH_2$— or —$(CH_2)_2$—, n is 0 or 1, $R^2$ is 6-F, $R^{3'}$ is hydrogen, $R^{24}$ is 3-F and the combination of $R^1$, —Y-$A^2$-$X^1$—, >$CR^{12a}R^{12b}$, t, u, $R^{4b}$, $R^{4f}$ for a compound in each case corresponds to one line of Table A (A-1 to A-80).

Table 15
Compounds of the formula (Id) wherein —$Y^1$— is as defined herein and in particular represents a bond, —$CH_2$— or —$(CH_2)_2$—, n is 0 or 1, $R^2$ is 6-F, $R^{3'}$ is hydrogen, $R^{24}$ is 3-Cl and the combination of $R^1$, —Y-$A^2$-$X^1$—, >$CR^{12a}R^{12b}$, t, u, $R^{4b}$, $R^{4f}$ for a compound in each case corresponds to one line of Table A (A-1 to A-80).

Table 16
Compounds of the formula (Id) wherein —$Y^1$— is as defined herein and in particular represents a bond, —$CH_2$— or —$(CH_2)_2$—, n is 0 or 1, $R^2$ is 6-F, $R^{3'}$ is hydrogen, $R^{24}$ is 3-$CF_3$ and the combination of $R^1$, —Y-$A^2$-$X^1$—, >$CR^{12a}R^{12b}$, t, u, $R^{4b}$, $R^{4f}$ for a compound in each case corresponds to one line of Table A (A-1 to A-80).

Table 17
Compounds of the formula (Id) wherein —$Y^1$— is as defined herein and in particular represents a bond, —$CH_2$— or —$(CH_2)_2$—, n is 0 or 1, $R^2$ is 6-F, $R^{3'}$ is hydrogen, $R^{24}$ is 2-F and the combination of $R^1$, —Y-$A^2$-$X^1$—, >$CR^{12a}R^{12b}$, t, u, $R^{4b}$, $R^{4f}$ for a compound in each case corresponds to one line of Table A (A-1 to A-80).

Table 18
Compounds of the formula (Id) wherein —$Y^1$— is as defined herein and in particular represents a bond, —$CH_2$— or —$(CH_2)_2$—, n is 0 or 1, $R^2$ is 6-F, $R^{3'}$ is hydrogen, $R^{24}$ is 2-Cl and the combination of $R^1$, —Y-$A^2$-$X^1$—, >$CR^{12a}R^{12b}$, t, u, $R^{4b}$, $R^{4f}$ for a compound in each case corresponds to one line of Table A (A-1 to A-80).

Table 19
Compounds of the formula (Id) wherein —$Y^1$— is as defined herein and in particular represents a bond, —$CH_2$— or —$(CH_2)_2$—, n is 0 or 1, $R^2$ is 8-F, $R^{3'}$ is hydrogen, $R^{24}$ is hydrogen and the combination of $R^1$, >$CR^{12a}R^{12b}$, t, u, $R^{4b}$, $R^{4f}$ for a compound in each case corresponds to one line of Table A (A-1 to A-80).

Table 20
Compounds of the formula (Id) wherein —$Y^1$— is as defined herein and in particular represents a bond, —$CH_2$— or —$(CH_2)_2$—, n is 0 or 1, $R^2$ is 8-F, $R^{3'}$ is hydrogen, $R^{24}$ is 3-F and the combination of $R^1$, —Y-$A^2$-$X^1$—, >$CR^{12a}R^{12b}$, t, u, $R^{4b}$, $R^{4f}$ for a compound in each case corresponds to one line of Table A (A-1 to A-80).

Table 21
Compounds of the formula (Id) wherein —$Y^1$— is as defined herein and in particular represents a bond, —$CH_2$— or —$(CH_2)_2$—, n is 0 or 1, $R^2$ is 8-F, $R^{3'}$ is hydrogen, $R^{24}$ is 3-Cl and the combination of $R^1$, —Y-$A^2$-$X^1$—, >$CR^{12a}R^{12b}$, t, u, $R^{4b}$, $R^{4f}$ for a compound in each case corresponds to one line of Table A (A-1 to A-80).

Table 22

Compounds of the formula (Id) wherein —$Y^1$— is as defined herein and in particular represents a bond, —$CH_2$— or —$(CH_2)_2$—, n is 0 or 1, $R^2$ is 8-F, $R^{3'}$ is hydrogen, $R^{24}$ is 3-$CF_3$ and the combination of $R^1$, —Y-$A^2$-$X^1$—, >$CR^{12a}R^{12b}$, t, u, $R^{4b}$, $R^{4f}$ for a compound in each case corresponds to one line of Table A (A-1 to A-80).

Table 23

Compounds of the formula (Id) wherein —$Y^1$— is as defined herein and in particular represents a bond, —$CH_2$— or —$(CH_2)_2$—, n is 0 or 1, $R^2$ is 8-F, $R^{3'}$ is hydrogen, $R^{24}$ is 2-F and the combination of $R^1$, —Y-$A^2$-$X^1$—, >$CR^{12a}R^{12b}$, t, u, $R^{4b}$, $R^{4f}$ for a compound in each case corresponds to one line of Table A (A-1 to A-80).

Table 24

Compounds of the formula (Id) wherein —$Y^1$— is as defined herein and in particular represents a bond, —$CH_2$— or —$(CH_2)_2$—, n is 0 or 1, $R^2$ is 8-F, $R^{3'}$ is hydrogen, $R^{24}$ is 2-Cl and the combination of $R^1$, —Y-$A^2$-$X^1$—, >$CR^{12a}R^{12b}$, t, u, $R^{4b}$, $R^{4f}$ for a compound in each case corresponds to one line of Table A (A-1 to A-80).

| | $R^1$ | —Y—$A^2$—$X^1$— | >$CR^{12a}R^{12b}$ | t | u | $R^{4b}$; $R^{4f}$ |
|---|---|---|---|---|---|---|
| A-1. | 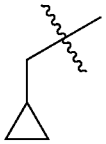 | —NH—$(CH_2)_2$—O— | —$CH_2$— | 1 | 0 | H; H |
| A-2. | 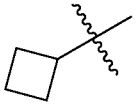 [SMILES: *C1CCC1] | —NH—$(CH_2)_2$—O— | —$CH_2$— | 1 | 0 | H; H |
| A-3. |  | —NH—$(CH_2)_2$—O— | —$CH_2$— | 1 | 0 | H; H |
| A-4. | 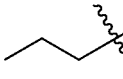 | —NH—$(CH_2)_2$—O— | —$CH_2$— | 1 | 0 | H; H |
| A-5. | 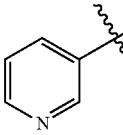 | —NH—$(CH_2)_2$—O— | —$CH_2$— | 1 | 0 | H; H |
| A-6. | 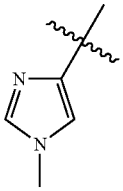 [SMILES: *c1cn(C)cn1] | —NH—$(CH_2)_2$—O— | —$CH_2$— | 1 | 0 | H; H |
| A-7. | 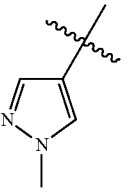 | —NH—$(CH_2)_2$—O— | —$CH_2$— | 1 | 0 | H; H |
| A-8. | 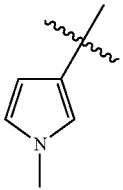 [SMILES: *c1ccn(C)c1] | —NH—$(CH_2)_2$—O— | —$CH_2$— | 1 | 0 | H; H |

-continued
| | R$^1$ | —Y—A$^2$—X$^1$— | >CR$^{12a}$R$^{12b}$ | t | u | R$^{4b}$; R$^{4f}$ |
|---|---|---|---|---|---|---|
| A-9. | 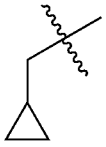 | —NH—(CH$_2$)$_2$— | —CH$_2$— | 1 | 0 | H; H |
| A-10 | 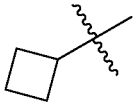 [SMILES: *C1CCC1] | —NH—(CH$_2$)$_2$— | —CH$_2$— | 1 | 0 | H; H |
| A-11 |  | —NH—(CH$_2$)$_2$— | —CH$_2$— | 1 | 0 | H; H |
| A-12 | 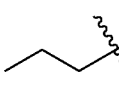 | —NH—(CH$_2$)$_2$— | —CH$_2$— | 1 | 0 | H; H |
| A-13 | 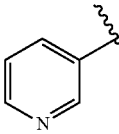 | —NH—(CH$_2$)$_2$— | —CH$_2$— | 1 | 0 | H; H |
| A-14 | 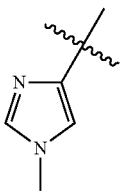 | —NH—(CH$_2$)$_2$— | —CH$_2$— | 1 | 0 | H; H |
| A-15 | 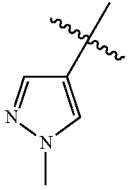 | —NH—(CH$_2$)$_2$— | —CH$_2$— | 1 | 0 | H; H |
| A-16 | 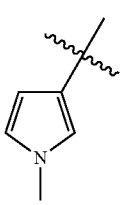 [SMILES: *c1ccn(C)c1] | —NH—(CH$_2$)$_2$— | —CH$_2$— | 1 | 0 | H; H |
| A-17 | 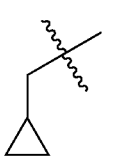 | —NH—CH$_2$— | —CH$_2$— | 1 | 0 | H; H |
| A-18 | 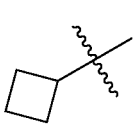 [SMILES: *C1CCC1] | —NH—CH$_2$— | —CH$_2$— | 1 | 0 | H; H |

-continued
| | R¹ | —Y—A²—X¹— | >CR¹²ᵃR¹²ᵇ | t | u | R⁴ᵇ; R⁴ᶠ |
|---|---|---|---|---|---|---|
| A-19 | 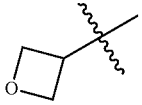 [SMILES: *C1COC1] | —NH—CH₂— | —CH₂— | 1 | 0 | H; H |
| A-20 | 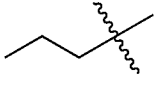 [SMILES: *CCC] | —NH—CH₂— | —CH₂— | 1 | 0 | H; H |
| A-21 | 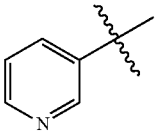 [SMILES: *c1cccnc1] | —NH—CH₂— | —CH₂— | 1 | 0 | H; H |
| A-22 | 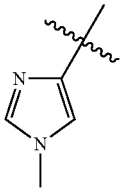 | —NH—CH₂— | —CH₂— | 1 | 0 | H; H |
| A-23 | 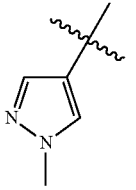 | —NH—CH₂— | —CH₂— | 1 | 0 | H; H |
| A-24 | 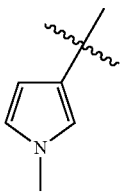 [SMILES: *c1ccn(C)c1] | —NH—CH₂— | —CH₂— | 1 | 0 | H; H |
| A-25 | 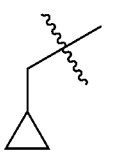 | 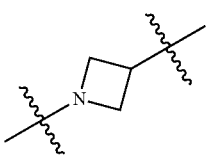 [SMILES: *C1CN(*)C1] | —CH₂— | 1 | 0 | H; H |
| A-26 | 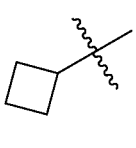 | 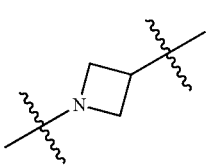 [SMILES: *C1CN(*)C1] | —CH₂— | 1 | 0 | H; H |
| A-27 | 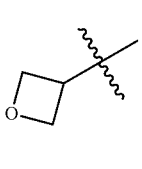 [SMILES: *C1COC1] | 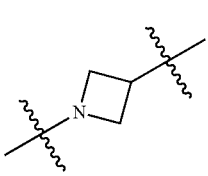 [SMILES: *C1CN(*)C1] | —CH₂— | 1 | 0 | H; H |

-continued

| | R¹ | —Y—A²—X¹— | >CR¹²ᵃR¹²ᵇ | t | u | R⁴ᵇ; R⁴ᶠ |
|---|---|---|---|---|---|---|
| A-28 | (propyl) | (azetidine) | —CH₂— | 1 | 0 | H; H |
| A-29 | (pyridin-3-yl) | (azetidine) | —CH₂— | 1 | 0 | H; H |
| A-30 | (1-methylimidazol-4-yl) | (azetidine) | —CH₂— | 1 | 0 | H; H |
| A-31 | (1-methylpyrazol-4-yl) | (azetidine) | —CH₂— | 1 | 0 | H; H |
| A-32 | (1-methylpyrrol-3-yl) | (azetidine) | —CH₂— | 1 | 0 | H; H |
| A-33 | (cyclopropylmethyl) | —(CH₂)₂— | —CH₂— | 1 | 0 | H; H |
| A-34 | (cyclobutyl) | —(CH₂)₂— | —CH₂— | 1 | 0 | H; H |
| A-35 | (oxetan-3-yl) | —(CH₂)₂— | —CH₂— | 1 | 0 | H; H |
| A-36 | (propyl) | —(CH₂)₂— | —CH₂— | 1 | 0 | H; H |
| A-37 | (pyridin-3-yl) | —(CH₂)₂— | —CH₂— | 1 | 0 | H; H |

-continued
| R¹ | —Y—A²—X¹— | >CR$^{12a}$R$^{12b}$ | t | u | R$^{4b}$; R$^{4f}$ |
|---|---|---|---|---|---|
| A-38 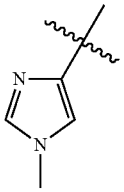 [SMILES: *c1cn(C)cn1] | —(CH$_2$)$_2$— | —CH$_2$— | 1 | 0 | H; H |
| A-39 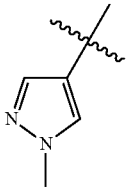 [SMILES: *c1cnn(C)c1] | —(CH$_2$)$_2$— | —CH$_2$— | 1 | 0 | H; H |
| A-40 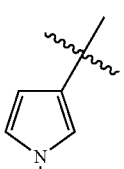 | —(CH$_2$)$_2$— | —CH$_2$— | 1 | 0 | H; H |
| A-41 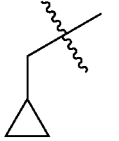 | —NH—(CH$_2$)$_2$—O— | 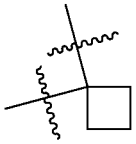 [SMILES: *C1(*)CCC1] | 1 | 0 | H; H |
| A-42 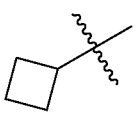 | —NH—(CH$_2$)$_2$—O— |  | 1 | 0 | H; H |
| A-43 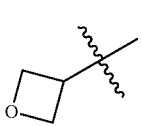 [SMILES: *C1COC1] | —NH—(CH$_2$)$_2$—O— |  | 1 | 0 | H; H |
| A-44 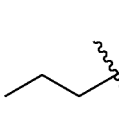 | —NH—(CH$_2$)$_2$—O— | 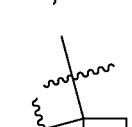 | 1 | 0 | H; H |
| A-45 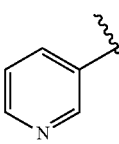 | —NH—(CH$_2$)$_2$—O— |  | 1 | 0 | H; H |
| A-46 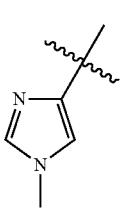 [SMILES: *c1cn(C)cn1] | —NH—(CH$_2$)$_2$—O— |  | 1 | 0 | H; H |

-continued
| | R¹ | —Y—A²—X¹— | >CR¹²ᵃR¹²ᵇ | t | u | R⁴ᵇ; R⁴ᶠ |
|---|---|---|---|---|---|---|
| A-47 | 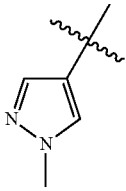 | —NH—(CH₂)₂—O— | 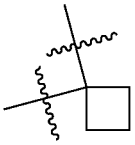 [SMILES: *C1(*)CCC1] | 1 | 0 | H; H |
| A-48 | 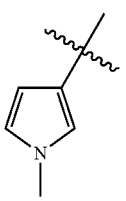 [SMILES: *c1ccn(C)c1] | —NH—(CH₂)₂—O— | 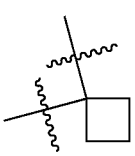 [SMILES: *C1(*)CCC1] | 1 | 0 | H; H |
| A-49 | 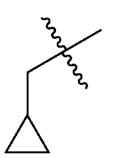 | —NH—(CH₂)₂— | 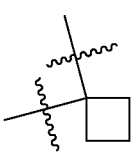 [SMILES: *C1(*)CCC1] | 1 | 0 | H; H |
| A-50 | 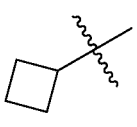 [SMILES: *C1CCC1] | —NH—(CH₂)₂— | 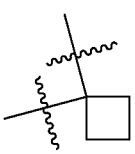 [SMILES: *C1(*)CCC1] | 1 | 0 | H; H |
| A-51 | 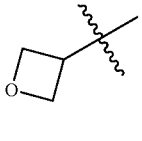 [SMILES: *C1COC1] | —NH—(CH₂)₂— | 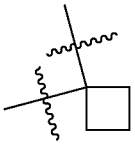 [SMILES: *C1(*)CCC1] | 1 | 0 | H; H |
| A-52 | 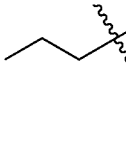 | —NH—(CH₂)₂— | 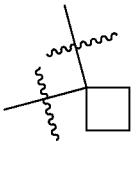 [SMILES: *C1(*)CCC1] | 1 | 0 | H; H |
| A-53 | 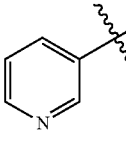 | —NH—(CH₂)₂— | 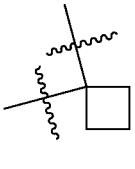 [SMILES: *C1(*)CCC1] | 1 | 0 | H; H |
| A-54 | 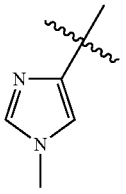 [SMILES: *c1cn(C)cn1] | —NH—(CH₂)₂— | 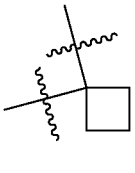 [SMILES: *C1(*)CCC1] | 1 | 0 | H; H |
| A-55 | 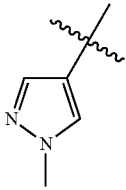 | —NH—(CH₂)₂— | 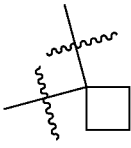 | 1 | 0 | H; H |

-continued
| | R¹ | —Y—A²—X¹— | >CR$^{12a}$R$^{12b}$ | t | u | R$^{4b}$; R$^{4f}$ |
|---|---|---|---|---|---|---|
| A-56 | 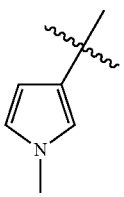 [SMILES: *c1ccn(C)c1] | —NH—(CH$_2$)$_2$— | 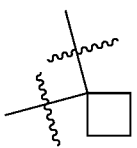 [SMILES: *C1(*)CCC1] | 1 | 0 | H; H |
| A-57 | 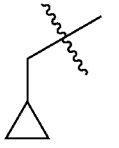 | —NH—CH$_2$— | 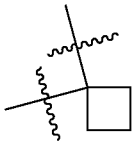 | 1 | 0 | H; H |
| A-58 | 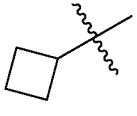 [SMILES: *C1CCC1] | —NH—CH$_2$— | 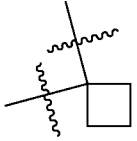 [SMILES: *C1(*)CCC1] | 1 | 0 | H; H |
| A-59 | 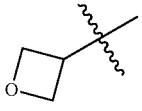 [SMILES: *C1COC1] | —NH—CH$_2$— | 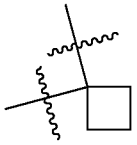 [SMILES: *C1(*)CCC1] | 1 | 0 | H; H |
| A-60 | 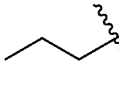 | —NH—CH$_2$— | 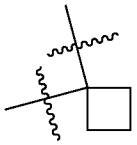 [SMILES: *C1(*)CCC1] | 1 | 0 | H; H |
| A-61 | 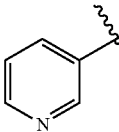 | —NH—CH$_2$— | 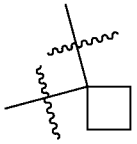 [SMILES: *C1(*)CCC1] | 1 | 0 | H; H |
| A-62 | 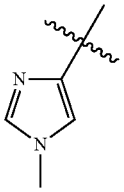 | —NH—CH$_2$— | 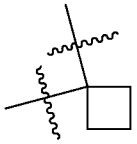 [SMILES: *C1(*)CCC1] | 1 | 0 | H; H |
| A-63 | 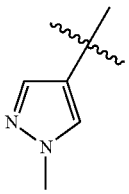 | —NH—CH$_2$— | 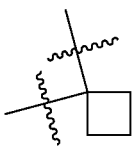 [SMILES: *C1(*)CCC1] | 1 | 0 | H; H |
| A-64 | 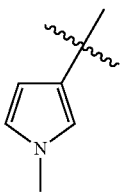 [SMILES: *c1ccn(C)c1] | —NH—CH$_2$— | 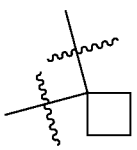 [SMILES: *C1(*)CCC1] | 1 | 0 | H; H |

-continued
| | R¹ | —Y—A²—X¹— | >CR$^{12a}$R$^{12b}$ | t | u | R$^{4b}$; R$^{4f}$ |
|---|---|---|---|---|---|---|
| A-65 | 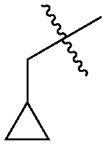 | 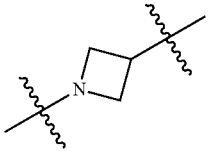 [SMILES: *C1CN(*)C1] | 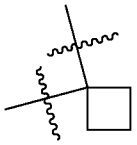 [SMILES: *C1(*)CCC1] | 1 | 0 | H; H |
| A-66 | 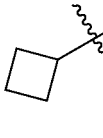 | 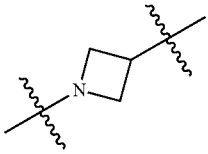 [SMILES: *C1CN(*)C1] | 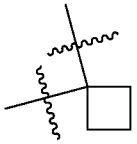 [SMILES: *C1(*)CCC1] | 1 | 0 | H; H |
| A-67 | 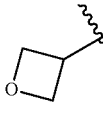 | 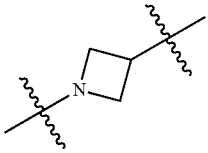 [SMILES: *C1CN(*)C1] | 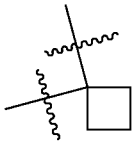 [SMILES: *C1(*)CCC1] | 1 | 0 | H; H |
| A-68 | 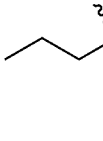 | 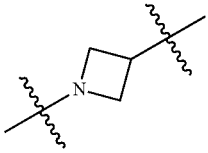 [SMILES: *C1CN(*)C1] | 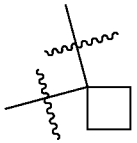 [SMILES: *C1(*)CCC1] | 1 | 0 | H; H |
| A-69 | 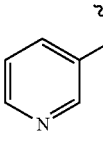 | 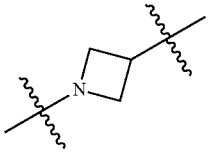 [SMILES: *C1CN(*)C1] | 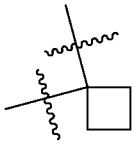 [SMILES: *C1(*)CCC1] | 1 | 0 | H; H |
| A-70 | 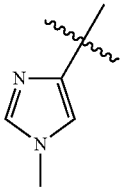 [SMILES: *c1cn(C)cn1] | 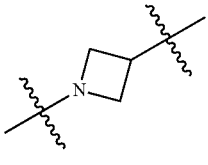 [SMILES: *C1CN(*)C1] | 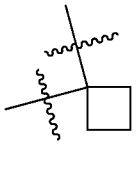 [SMILES: *C1(*)CCC1] | 1 | 0 | H; H |
| A-71 | 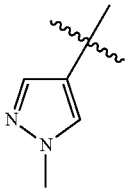 | 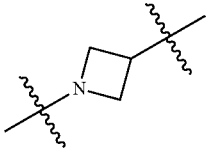 [SMILES: *C1CN(*)C1] | 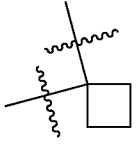 [SMILES: *C1(*)CCC1] | 1 | 0 | H; H |
| A-72 |  | 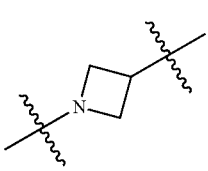 [SMILES: *C1CN(*)C1] | 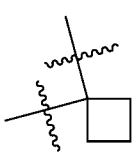 [SMILES: *C1(*)CCC1] | 1 | 0 | H; H |

-continued
| | R¹ | —Y—A²—X¹— | >CR^{12a}R^{12b} | t | u | R^{4b}; R^{4f} |
|---|---|---|---|---|---|---|
| A-73 | 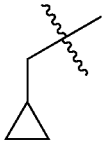 | —(CH₂)₂— | 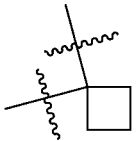 [SMILES: *C1(*)CCC1] | 1 | 0 | H; H |
| A-74 | 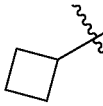 | —(CH₂)₂— |  | 1 | 0 | H; H |
| A-75 | 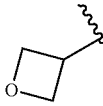 | —(CH₂)₂— |  | 1 | 0 | H; H |
| A-76 | 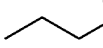 | —(CH₂)₂— | 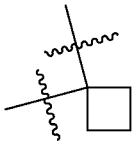 [SMILES: *C1(*)CCC1] | 1 | 0 | H; H |
| A-77 | 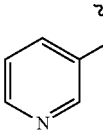 | —(CH₂)₂— | 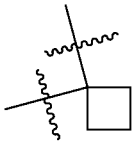 [SMILES: *C1(*)CCC1] | 1 | 0 | H; H |
| A-78 | 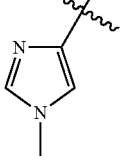 | —(CH₂)₂— | 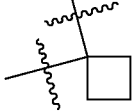 | 1 | 0 | H; H |
| A-79 | 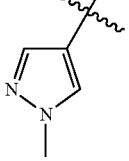 | —(CH₂)₂— | 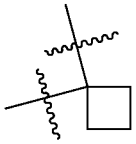 [SMILES: *C1(*)CCC1] | 1 | 0 | H; H |
| A-80 | 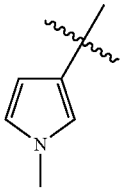 [SMILES: *c1ccn(C)c1] | —(CH₂)₂— |  | 1 | 0 | H; H |

Further particular compounds of the present invention are the individual phenalkylamine derivatives of the formula (Id) as listed in the following tables 25 to 48 and physiologically tolerated salts thereof:

$$R^1-S(O)_2-Y-A^2-X^1 \cdots \text{(IId)}$$

(structure with $R^2$, $R^4$, $R^{3'}$, $R^{4b}$, $R^{4f}$, $Y^2$, $Y^1$, $R^{12a}$, $R^{12b}$, $R^{24}$)

Table 25
Compounds of the formula (Id) wherein —$Y^2$—$Y^3$— is as defined herein and in particular represents a —$CH_2$—, —C(O)— or a bond, $R^2$ is hydrogen, $R^{3'}$ is hydrogen, $R^{24}$ is hydrogen and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 26
Compounds of the formula (Id) wherein —$Y^2$—$Y^3$— is as defined herein and in particular represents —$CH_2$—, —C(O)— or a bond, $R^2$ is hydrogen, $R^{3'}$ is hydrogen, $R^{24}$ is 3-F and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 27
Compounds of the formula (Id) wherein —$Y^2$—$Y^3$— is as defined herein and in particular represents —$CH_2$—, —C(O)— or a bond, $R^2$ is hydrogen, $R^{3'}$ is hydrogen, $R^{24}$ is 3-Cl and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 28
Compounds of the formula (Id) wherein —$Y^2$—$Y^3$— is as defined herein and in particular represents —$CH_2$—, —C(O)— or a bond, $R^2$ is hydrogen, $R^{3'}$ is hydrogen, $R^{24}$ is 3-$CF_3$ and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 29
Compounds of the formula (Id) wherein —$Y^2$—$Y^3$— is as defined herein and in particular represents —$CH_2$—, —C(O)— or a bond, $R^2$ is hydrogen, $R^{3'}$ is hydrogen, $R^{24}$ is 2-F and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 30
Compounds of the formula (Id) wherein —$Y^2$—$Y^3$— is as defined herein and in particular represents —$CH_2$—, —C(O)— or a bond, $R^2$ is hydrogen, $R^{3'}$ is hydrogen, $R^{24}$ is 2-Cl and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 31
Compounds of the formula (Id) wherein —$Y^2$—$Y^3$— is as defined herein and in particular represents —$CH_2$—, —C(O)— or a bond, $R^2$ is 2-F, $R^{3'}$ is hydrogen, $R^{24}$ is hydrogen and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 32
Compounds of the formula (Id) wherein —$Y^2$—$Y^3$— is as defined herein and in particular represents —$CH_2$—, —C(O)— or a bond, $R^2$ is 2-F, $R^{3'}$ is hydrogen, $R^{24}$ is 3-F and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 33
Compounds of the formula (Id) wherein —$Y^2$—$Y^3$— is as defined herein and in particular represents —$CH_2$—, —C(O)— or a bond, $R^2$ is 2-F, $R^{3'}$ is hydrogen, $R^{24}$ is 3-Cl and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 34
Compounds of the formula (Id) wherein —$Y^2$—$Y^3$— is as defined herein and in particular represents —$CH_2$—, —C(O)— or a bond, $R^2$ is 2-F, $R^{3'}$ is hydrogen, $R^{24}$ is 3-$CF_3$ and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 35
Compounds of the formula (Id) wherein —$Y^2$—$Y^3$— is as defined herein and in particular represents —$CH_2$—, —C(O)— or a bond, $R^2$ is 2-F, $R^{3'}$ is hydrogen, $R^{24}$ is 2-F and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 36
Compounds of the formula (Id) wherein —$Y^2$—$Y^3$— is as defined herein and in particular represents —$CH_2$—, —C(O)— or a bond, $R^2$ is 2-F, $R^{3'}$ is hydrogen, $R^{24}$ is 2-Cl and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 37
Compounds of the formula (Id) wherein —$Y^2$—$Y^3$— is as defined herein and in particular represents —$CH_2$—, —C(O)— or a bond, $R^2$ is 4-F, $R^{3'}$ is hydrogen, $R^{24}$ is hydrogen and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 38
Compounds of the formula (Id) wherein —$Y^2$—$Y^3$— is as defined herein and in particular represents —$CH_2$—, —C(O)— or a bond, $R^2$ is 4-F, $R^{3'}$ is hydrogen, $R^{24}$ is 3-F and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 39
Compounds of the formula (Id) wherein —$Y^2$—$Y^3$— is as defined herein and in particular represents —$CH_2$—, —C(O)— or a bond, $R^2$ is 4-F, $R^{3'}$ is hydrogen, $R^{24}$ is 3-Cl and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 40
Compounds of the formula (Id) wherein —$Y^2$—$Y^3$— is as defined herein and in particular represents —$CH_2$—, —C(O)— or a bond, $R^2$ is 4-F, $R^{3'}$ is hydrogen, $R^{24}$ is 3-$CF_3$ and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 41
Compounds of the formula (Id) wherein —$Y^2$—$Y^3$— is as defined herein and in particular represents —$CH_2$—, —C(O)— or a bond, $R^2$ is 4-F, $R^{3'}$ is hydrogen, $R^{24}$ is 2-F and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 42

Compounds of the formula (Id) wherein —$Y^2$—$Y^3$— is as defined herein and in particular represents —$CH_2$—, —C(O)— or a bond, $R^2$ is 4-F, $R^{3'}$ is hydrogen, $R^{24}$ is 2-Cl and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 43

Compounds of the formula (Id) wherein —$Y^2$—$Y^3$— is as defined herein and in particular represents —$CH_2$—, —C(O)— or a bond, $R^2$ is 4-Cl, $R^{3'}$ is hydrogen, $R^{24}$ is hydrogen and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 44

Compounds of the formula (Id) wherein —$Y^2$—$Y^3$— is as defined herein and in particular represents —$CH_2$—, —C(O)— or a bond, $R^2$ is 4-Cl, $R^{3'}$ is hydrogen, $R^{24}$ is 3-F and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 45

Compounds of the formula (Id) wherein —$Y^2$—$Y^3$— is as defined herein and in particular represents —$CH_2$—, —C(O)— or a bond, $R^2$ is 4-Cl, $R^{3'}$ is hydrogen, $R^{24}$ is 3-Cl and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 46

Compounds of the formula (Id) wherein —$Y^2$—$Y^3$— is as defined herein and in particular represents —$CH_2$—, —C(O)— or a bond, $R^2$ is 4-Cl, $R^{3'}$ is hydrogen, $R^{24}$ is 3-$CF_3$ and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 47

Compounds of the formula (Id) wherein —$Y^2$—$Y^3$— is as defined herein and in particular represents —$CH_2$—, —C(O)— or a bond, $R^2$ is 4-Cl, $R^{3'}$ is hydrogen, $R^{24}$ is 2-F and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

Table 48

Compounds of the formula (Id) wherein —$Y^2$—$Y^3$— is as defined herein and in particular represents —$CH_2$—, —C(O)— or a bond, $R^2$ is 4-Cl, $R^{3'}$ is hydrogen, $R^{24}$ is 2-Cl and the combination of $R^1$, —Y-$A^2$-$X^1$—, >$CR^{12a}R^{12b}$, t, u, $R^{4b}$, $R^{4f}$ for a compound in each case corresponds to one line of Table A (A-81 to A-160).

|  | $R^1$ | —Y—$A^2$—$X^1$— | >$CR^{12a}R^{12b}$ | t | u | $R^{4b}$; $R^{4f}$ |
|---|---|---|---|---|---|---|
| A-81. | cyclopropylmethyl | —NH—$(CH_2)_2$—O— | —$CH_2$— | 1 | 0 | H; H |
| A-82. | cyclobutyl | —NH—$(CH_2)_2$—O— | —$CH_2$— | 1 | 0 | H; H |
| A-83. | oxetan-3-yl | —NH—$(CH_2)_2$—O— | —$CH_2$— | 1 | 0 | H; H |
| A-84. | sec-butyl | —NH—$(CH_2)_2$—O— | —$CH_2$— | 1 | 0 | H; H |
| A-85. | pyridin-3-yl | —NH—$(CH_2)_2$—O— | —$CH_2$— | 1 | 0 | H; H |
| A-86. | 1-methyl-1H-imidazol-4-yl | —NH—$(CH_2)_2$—O— | —$CH_2$— | 1 | 0 | H; H |

-continued
| | R¹ | —Y—A²—X¹— | >CR$^{12a}$R$^{12b}$ | t | u | R$^{4b}$; R$^{4f}$ |
|---|---|---|---|---|---|---|
| A-87. | 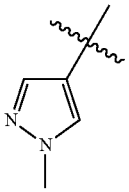 | —NH—(CH$_2$)$_2$—O— | —CH$_2$— | 1 | 0 | H; H |
| A-88. | 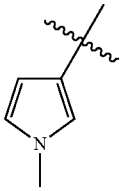 [SMILES: *c1ccn(C)c1] | —NH—(CH$_2$)$_2$—O— | —CH$_2$— | 1 | 0 | H; H |
| A-89. | 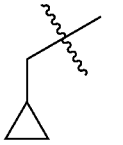 | —NH—(CH$_2$)$_2$— | —CH$_2$— | 1 | 0 | H; H |
| A-90. | 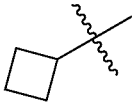 [SMILES: *C1CCC1] | —NH—(CH$_2$)$_2$— | —CH$_2$— | 1 | 0 | H; H |
| A-91. | 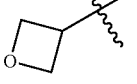 | —NH—(CH$_2$)$_2$— | —CH$_2$— | 1 | 0 | H; H |
| A-92. | 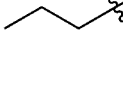 | —NH—(CH$_2$)$_2$— | —CH$_2$— | 1 | 0 | H; H |
| A-93. | 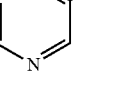 | —NH—(CH$_2$)$_2$— | —CH$_2$— | 1 | 0 | H; H |
| A-94. | 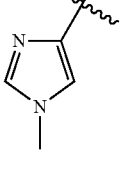 | —NH—(CH$_2$)$_2$— | —CH$_2$— | 1 | 0 | H; H |
| A-95. | 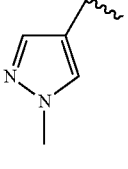 | —NH—(CH$_2$)$_2$— | —CH$_2$— | 1 | 0 | H; H |

-continued
| | R¹ | —Y—A²—X¹— | >CR$^{12a}$R$^{12b}$ | t | u | R$^{4b}$; R$^{4f}$ |
|---|---|---|---|---|---|---|
| A-96. | 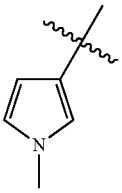 [SMILES: *c1ccn(C)c1] | —NH—(CH$_2$)$_2$— | —CH$_2$— | 1 | 0 | H; H |
| A-97. | 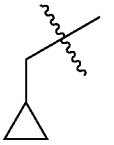 | —NH—CH$_2$— | —CH$_2$— | 1 | 0 | H; H |
| A-98. | 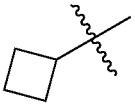 [SMILES: *C1CCC1] | —NH—CH$_2$— | —CH$_2$— | 1 | 0 | H; H |
| A-99. | 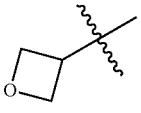 [SMILES: *C1COC1] | —NH—CH$_2$— | —CH$_2$— | 1 | 0 | H; H |
| A-100. | 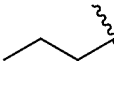 | —NH—CH$_2$— | —CH$_2$— | 1 | 0 | H; H |
| A-101. | 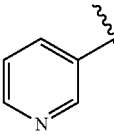 | —NH—CH$_2$— | —CH$_2$— | 1 | 0 | H; H |
| A-102. | 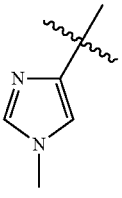 [SMILES: *c1cn(C)cn1] | —NH—CH$_2$— | —CH$_2$— | 1 | 0 | H; H |
| A-103. | 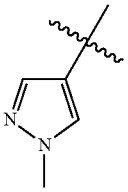 | —NH—CH$_2$— | —CH$_2$— | 1 | 0 | H; H |
| A-104. | 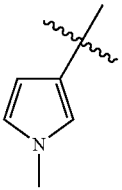 [SMILES: *c1ccn(C)c1] | —NH—CH$_2$— | —CH$_2$— | 1 | 0 | H; H |

-continued

| | R¹ | —Y—A²—X¹— | >CR¹²ᵃR¹²ᵇ | t | u | R⁴ᵇ; R⁴ᶠ |
|---|---|---|---|---|---|---|
| A-105. | cyclopropylmethyl | azetidinyl (N-linked) | —CH₂— | 1 | 0 | H; H |
| A-106. | cyclobutyl | azetidinyl (N-linked) | —CH₂— | 1 | 0 | H; H |
| A-107. | oxetanyl | azetidinyl (N-linked) | —CH₂— | 1 | 0 | H; H |
| A-108. | sec-butyl | azetidinyl (N-linked) | —CH₂— | 1 | 0 | H; H |
| A-109. | pyridin-3-yl | azetidinyl (N-linked) | —CH₂— | 1 | 0 | H; H |
| A-110. | 1-methyl-1H-imidazol-4-yl | azetidinyl (N-linked) | —CH₂— | 1 | 0 | H; H |
| A-111. | 1-methyl-1H-pyrazol-4-yl | azetidinyl (N-linked) | —CH₂— | 1 | 0 | H; H |
| A-112. | 1-methyl-1H-pyrrol-3-yl | azetidinyl (N-linked) | —CH₂— | 1 | 0 | H; H |
| A-113. | cyclopropylmethyl | —(CH₂)₂— | —CH₂— | 1 | 0 | H; H |

-continued
| | R¹ | —Y—A²—X¹— | >CR¹²ᵃR¹²ᵇ | t | u | R⁴ᵇ; R⁴ᶠ |
|---|---|---|---|---|---|---|
| A-114. |  | —(CH₂)₂— | —CH₂— | 1 | 0 | H; H |
| A-115. |  | —(CH₂)₂— | —CH₂— | 1 | 0 | H; H |
| A-116. | 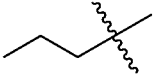 [SMILES: *CCC] | —(CH₂)₂— | —CH₂— | 1 | 0 | H; H |
| A-117. | 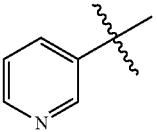 [SMILES: *c1cccnc1] | —(CH₂)₂— | —CH₂— | 1 | 0 | H; H |
| A-118. |  | —(CH₂)₂— | —CH₂— | 1 | 0 | H; H |
| A-119. | 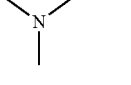 | —(CH₂)₂— | —CH₂— | 1 | 0 | H; H |
| A-120. |  | —(CH₂)₂— | —CH₂— | 1 | 0 | H; H |
| A-121. |  | —NH—(CH₂)₂—O— |  | 1 | 0 | H; H |
| A-122. |  | —NH—(CH₂)₂—O— | 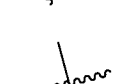 | 1 | 0 | H; H |
| A-123. |  | —NH—(CH₂)₂—O— | 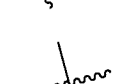 | 1 | 0 | H; H |

-continued
| | R¹ | —Y—A²—X¹— | >CR$^{12a}$R$^{12b}$ | t | u | R$^{4b}$; R$^{4f}$ |
|---|---|---|---|---|---|---|
| A-124. | 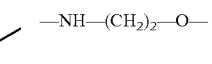 | —NH—(CH$_2$)$_2$—O— | 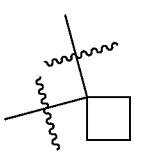 [SMILES: *C1(*)CCC1] | 1 | 0 | H; H |
| A-125. | 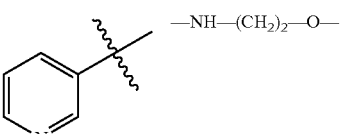 | —NH—(CH$_2$)$_2$—O— | 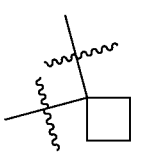 [SMILES: *C1(*)CCC1] | 1 | 0 | H; H |
| A-126. | 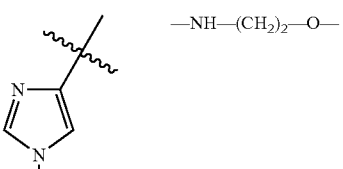 | —NH—(CH$_2$)$_2$—O— | 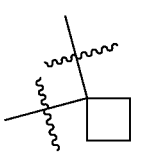 [SMILES: *C1(*)CCC1] | 1 | 0 | H; H |
| A-127. | 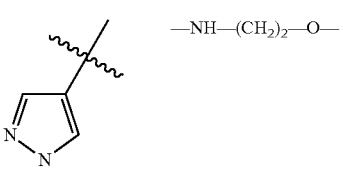 | —NH—(CH$_2$)$_2$—O— | 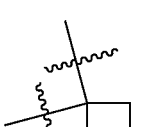 | 1 | 0 | H; H |
| A-128. | 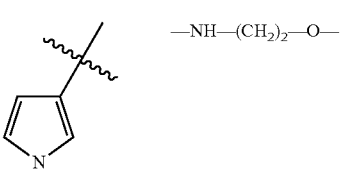 | —NH—(CH$_2$)$_2$—O— | 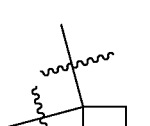 | 1 | 0 | H; H |
| A-129. | 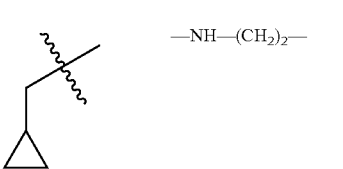 | —NH—(CH$_2$)$_2$— | 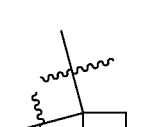 | 1 | 0 | H; H |
| A-130. | 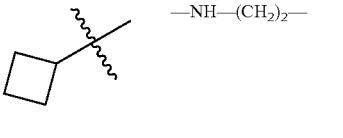 | —NH—(CH$_2$)$_2$— | 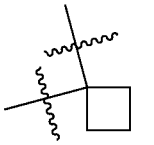 [SMILES: *C1(*)CCC1] | 1 | 0 | H; H |
| A-131. | 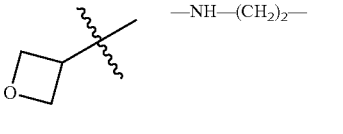 | —NH—(CH$_2$)$_2$— | 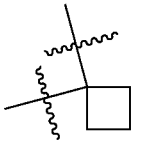 [SMILES: *C1(*)CCC1] | 1 | 0 | H; H |
| A-132. | 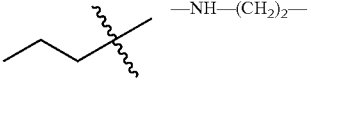 | —NH—(CH$_2$)$_2$— | 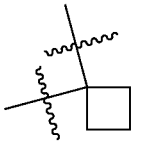 [SMILES: *C1(*)CCC1] | 1 | 0 | H; H |

-continued
| R¹ | —Y—A²—X¹— | >CR¹²ᵃR¹²ᵇ | t | u | R⁴ᵇ; R⁴ᶠ |
|---|---|---|---|---|---|
| A-133. 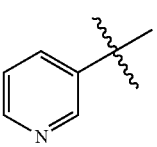 [SMILES: *c1cccnc1] | —NH—(CH₂)₂— | 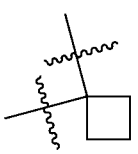 [SMILES: *C1(*)CCC1] | 1 | 0 | H; H |
| A-134. 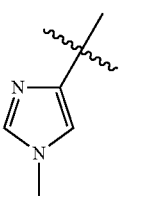 [SMILES: *c1cn(C)cn1] | —NH—(CH₂)₂— | 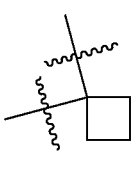 [SMILES: *C1(*)CCC1] | 1 | 0 | H; H |
| A-135. 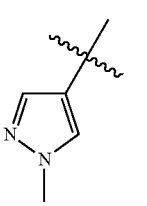 | —NH—(CH₂)₂— | 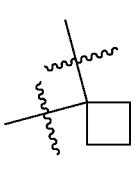 [SMILES: *C1(*)CCC1] | 1 | 0 | H; H |
| A-136. 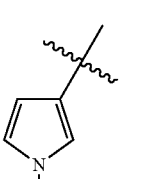 | —NH—(CH₂)₂— | 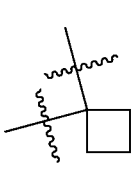 [SMILES: *C1(*)CCC1] | 1 | 0 | H; H |
| A-137. 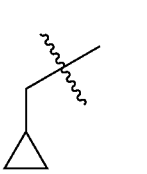 [SMILES: *CC1CC1] | —NH—CH₂— | 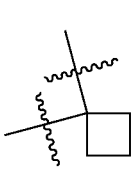 [SMILES: *C1(*)CCC1] | 1 | 0 | H; H |
| A-138. 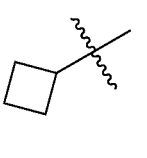 [SMILES: *C1CCC1] | —NH—CH₂— | 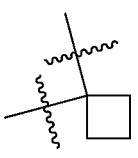 [SMILES: *C1(*)CCC1] | 1 | 0 | H; H |
| A-139. 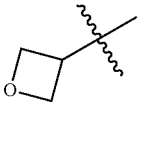 [SMILES: *C1COC1] | —NH—CH₂— | 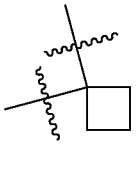 [SMILES: *C1(*)CCC1] | 1 | 0 | H; H |
| A-140. 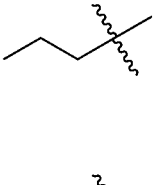 | —NH—CH₂— | 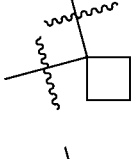 | 1 | 0 | H; H |
| A-141. 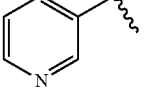 | —NH—CH₂— | 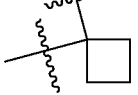 | 1 | 0 | H; H |

-continued

| | R¹ | —Y—A²—X¹— | >CR$^{12a}$R$^{12b}$ | t | u | R$^{4b}$; R$^{4f}$ |
|---|---|---|---|---|---|---|
| A-142. | (1-methylimidazol-4-yl) | —NH—CH$_2$— | (cyclobutyl) | 1 | 0 | H; H |
| A-143. | (1-methylpyrazol-4-yl) | —NH—CH$_2$— | (cyclobutyl) | 1 | 0 | H; H |
| A-144. | (1-methylpyrrol-3-yl) | —NH—CH$_2$— | (cyclobutyl) | 1 | 0 | H; H |
| A-145. | (cyclopropylmethyl) | (azetidin-3-yl) | (cyclobutyl) | 1 | 0 | H; H |
| A-146. | (cyclobutyl) | (azetidin-3-yl) | (cyclobutyl) | 1 | 0 | H; H |
| A-147. | (oxetan-3-yl) | (azetidin-3-yl) | (cyclobutyl) | 1 | 0 | H; H |
| A-148. | (propyl) | (azetidin-3-yl) | (cyclobutyl) | 1 | 0 | H; H |
| A-149. | (pyridin-3-yl) | (azetidin-3-yl) | (cyclobutyl) | 1 | 0 | H; H |

-continued

| | R¹ | —Y—A²—X¹— | >CR¹²ᵃR¹²ᵇ | t | u | R⁴ᵇ; R⁴ᶠ |
|---|---|---|---|---|---|---|
| A-150. | (1-methylimidazol-4-yl) | azetidin-3-yl (N-linked) | cyclobutyl | 1 | 0 | H; H |
| A-151. | (1-methylpyrazol-4-yl) | azetidin-3-yl (N-linked) | cyclobutyl | 1 | 0 | H; H |
| A-152. | (1-methylpyrrol-3-yl) | azetidin-3-yl (N-linked) | cyclobutyl | 1 | 0 | H; H |
| A-153. | cyclopropylmethyl | —(CH₂)₂— | cyclobutyl | 1 | 0 | H; H |
| A-154. | cyclobutyl | —(CH₂)₂— | cyclobutyl | 1 | 0 | H; H |
| A-155. | oxetan-3-yl | —(CH₂)₂— | cyclobutyl | 1 | 0 | H; H |
| A-156. | n-propyl | —(CH₂)₂— | cyclobutyl | 1 | 0 | H; H |
| A-157. | pyridin-3-yl | —(CH₂)₂— | cyclobutyl | 1 | 0 | H; H |
| A-158. | (1-methylimidazol-4-yl) | —(CH₂)₂— | cyclobutyl | 1 | 0 | H; H |

-continued

| R¹ | —Y—A²—X¹— | >CR$^{12a}$R$^{12b}$ | t | u | R$^{4b}$; R$^{4f}$ |
|---|---|---|---|---|---|
| A-159. 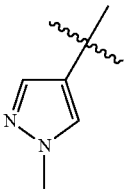 | —(CH$_2$)$_2$— | 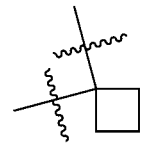 [SMILES: *C1(*)CCC1] | 1 | 0 | H; H |
| A-160. 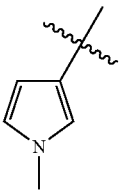 [SMILES: *c1ccn(C)c1] | —(CH$_2$)$_2$— | 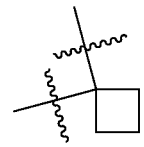 [SMILES: *C1(*)CCC1] | 1 | 0 | H; H |

Still further particular compounds of the present invention are the compounds disclosed in preparation examples and physiologically tolerated salts thereof. These include for each preparation example the exemplified compound as well as the corresponding free base and any other physiologically tolerated salts of the free base (if the exemplified compound is a salt), or any physiologically tolerated salt of the free base (if the exemplified compound is a free base). These further include enantiomers, diastereomers, tautomers and any other isomeric forms of said compounds, be they explicitly or implicitly disclosed.

The compounds of the formula (I), (II), (III) or (IV) can be prepared by analogy to methods which are well known in the art. Suitable methods for the preparation of compounds of formula (I), (II), (III) or (IV) are outlined in the following schemes.

Aminotetralines can be prepared by analogy to methods which are well known in the art. Suitable methods for the preparation of aminotetralines of formula (I) and (III) is outlined in the following schemes.

The process depicted in scheme 1 is useful for obtaining aminotetralines, wherein X¹ is —O— or —S—.

Scheme 1:

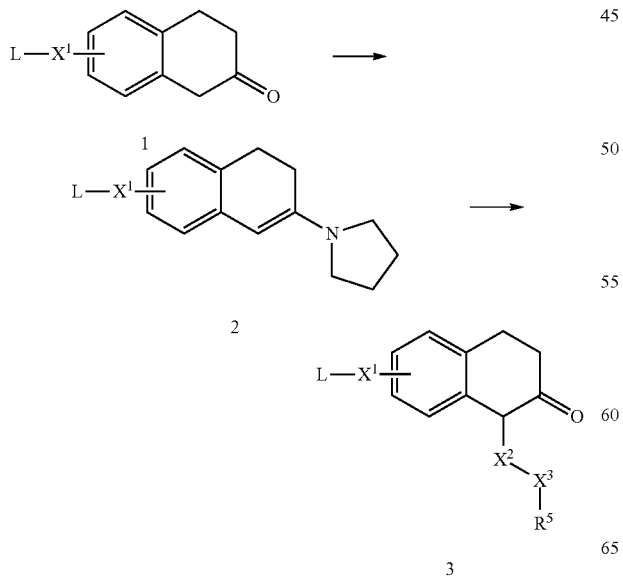

As shown in scheme 1, the compound of general formula 1 readily undergoes enamine alkylation to give the compound of general formula 3.

In scheme 1, the variables X², X³, R⁵ are as defined herein and L a suitable protecting group (e.g. L=Me). The process depicted in scheme 1 is also useful for obtaining aminotetralines, wherein X¹ is optionally substituted alkylene. In this case, L is a group that represents, or can be converted into, the desired side chain R¹—W-A¹-Q-Y-A²-.

Alternatively, compounds of formula 3 can be prepared as described in scheme 2.

Scheme 2:

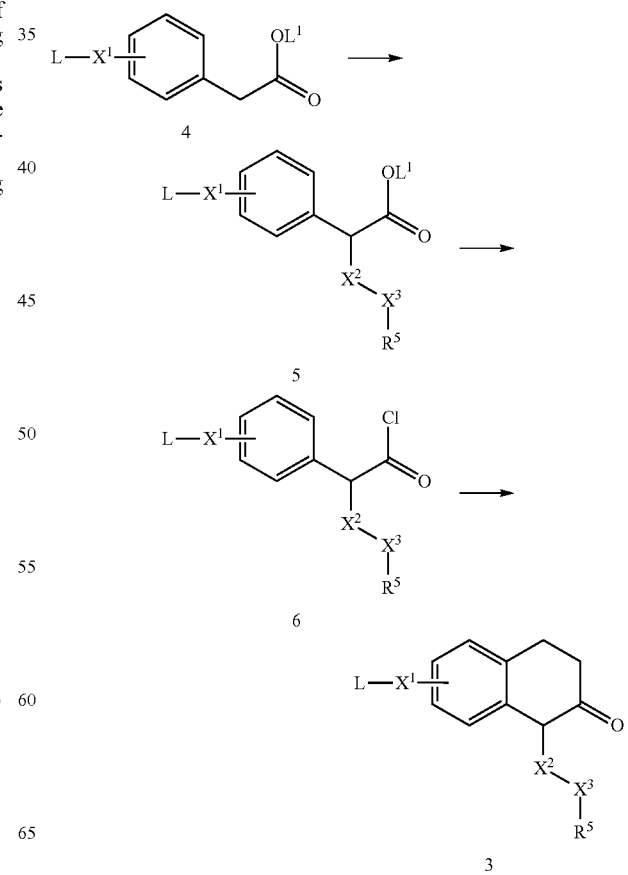

As shown in scheme 2, the compound of general formula 4 readily undergoes alkylation to give the compound of general formula 5. Conversion to the acid chloride and subsequent ring closure with ethylene in the presence of a Lewis acid (e.g. AlCl$_3$) affords compound 3 (e.g. J. Het. Chem., 23 (2), 343, 1986 and Bioorg. Med. Chem. Lett., 17 (22), 6160, 2007) The variables $X^2$, $X^3$, $R^5$ are as defined herein and L, $L^1$ are suitable protecting groups (e.g. L, $L^1$=Me). Compounds 3 can be further converted to compounds of the general formula (I).

The process depicted in scheme 3 is useful for obtaining aminotetralines, wherein $X^1$ is —O— or —S—, $A^2$ is optionally substituted alkylene, Y is —NR$^9$—, and Q is —S(O)$_2$.

Scheme 3:

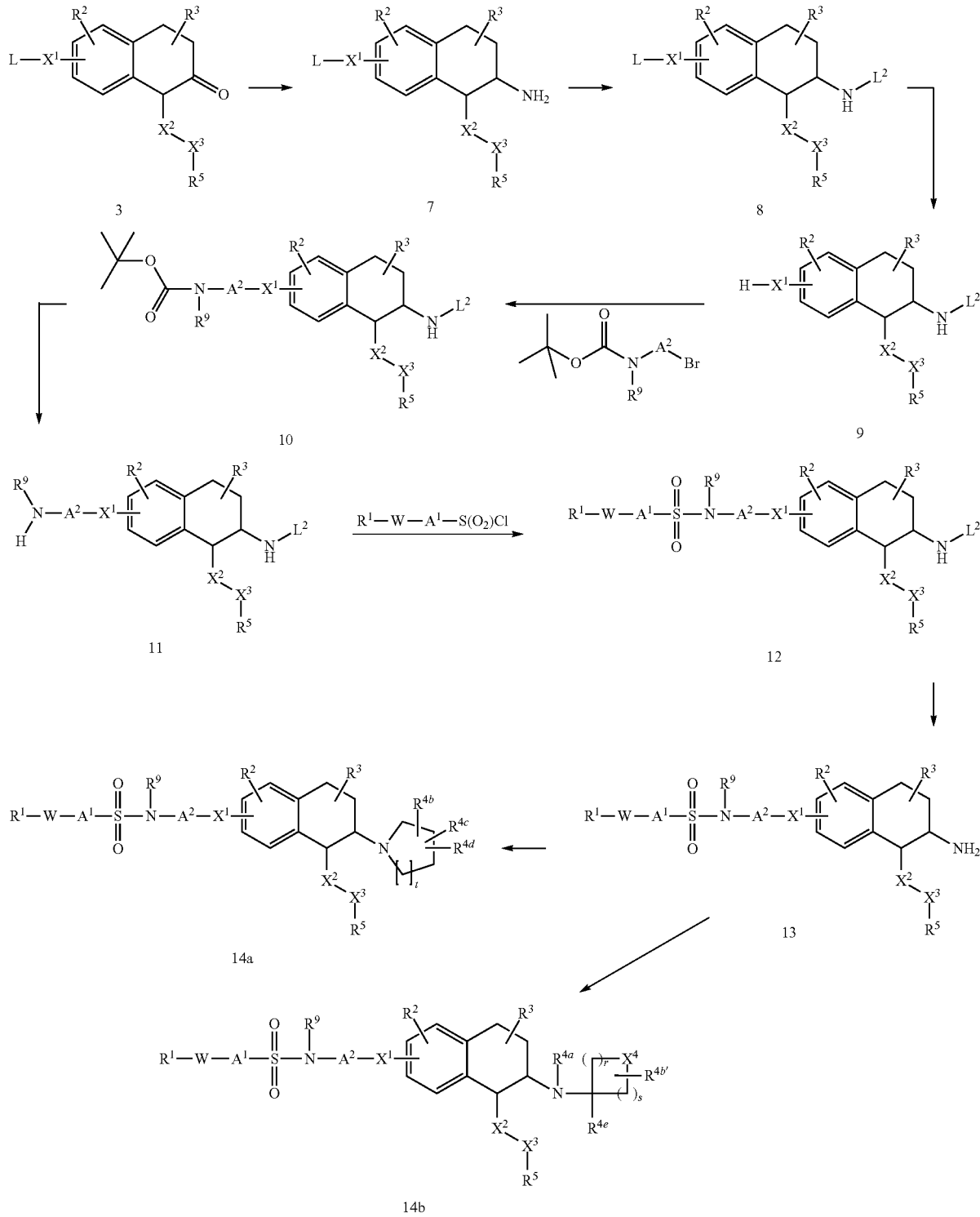

In scheme 3, the variables $R^1$, W, $A^1$, $R^2$, $R^3$, $R^{4a}$, $R^{4b}$, $R^{4b'}$, $R^{4c}$, $R^{4d}$, $R^{4e}$, $R^5$, $R^9$, $X^2$, $X^3$, $X^4$, r, s, t are as defined herein and L, $L^2$ are a suitable protecting groups (e.g. $L^2$=COOEt).
The process depicted in scheme 4 is useful for obtaining aminotetralines, wherein $X^1$ is methylene, $A^2$ is a bond, Y is —$NR^9$—, and Q is —$S(O)_2$.
Scheme 4:
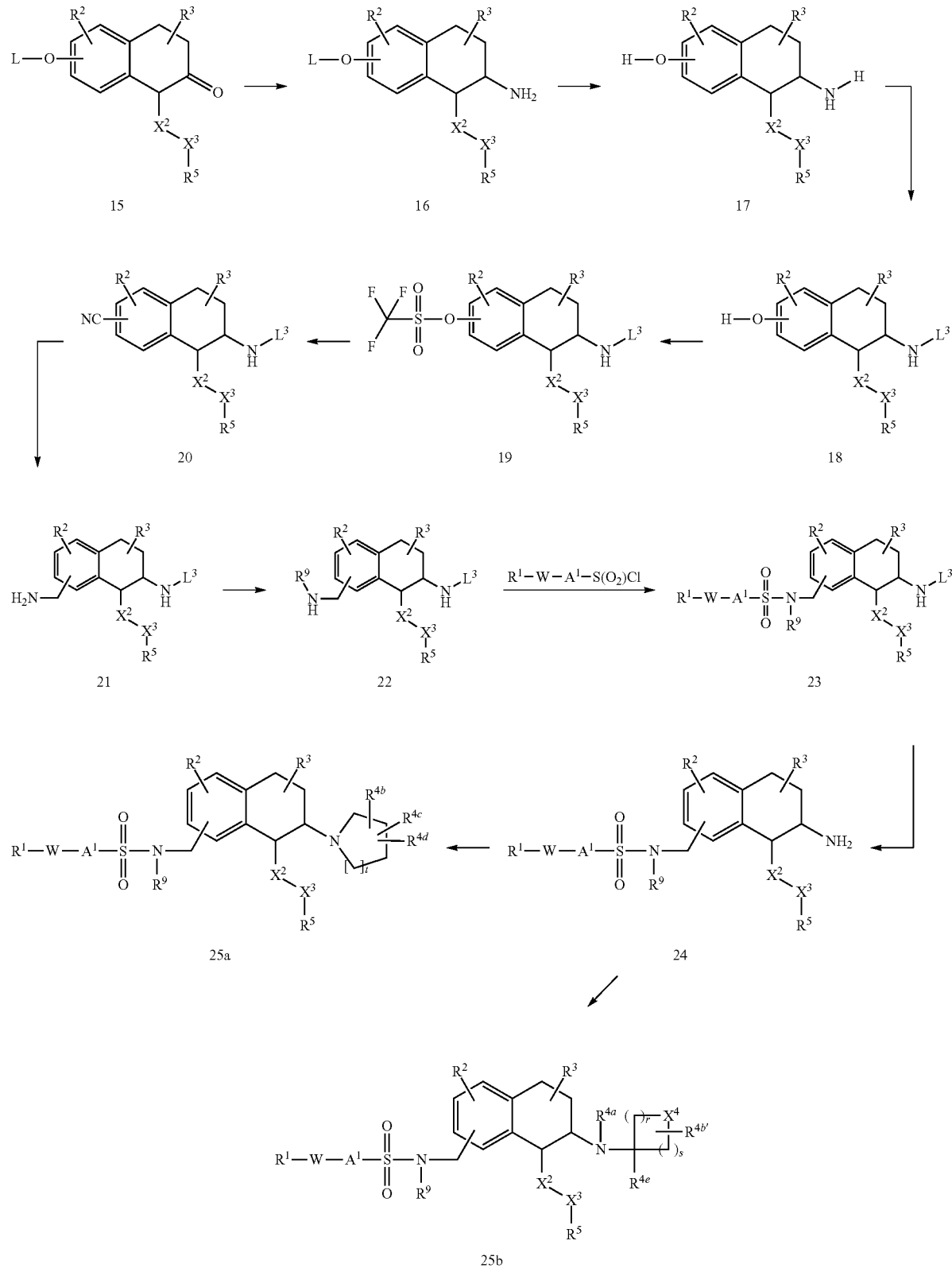

Alternatively to triflate 19, the corresponding bromide or iodide can be used to prepare compound 20.

In scheme 4, the variables $R^1$, W, $A^1$, $R^2$, $R^3$, $R^{4a}$, $R^{4b}$, $R^{4b'}$, $R^{4d}$, $R^{4e}$, $R^5$, $R^9$, $X^2$, $X^3$, $X^4$, r, s, t are as defined herein, and L, $L^3$ are suitable protecting groups (e.g. $L^3$=COOtBu).

The process depicted in scheme 5 is useful for obtaining aminotetralines, wherein $X^1$ is optionally substituted alkylene, $A^2$ is optionally substituted alkylene or a bond, Y is —$NR^9$—, and Q is —$S(O)_2$.

Instead of the trifluoroborate 66, the corresponding 9-borabicyclo[3.3.1]non-9-yl derivative can be used to prepare compound 26.

In scheme 5, the variables $R^1$, W, $A^1$, $R^2$, $R^3$, $R^{4a}$, $R^{4b}$, $R^{4b'}$, $R^{4c}$, $R^{4d}$, $R^{4e}$, $R^5$, $R^9$, $X^2$, $X^3$, $X^4$, r, s, t are as defined herein, and $L^3$ is a suitable protecting group (e.g. $L^3$=COOEt).

The process depicted in scheme 6 is useful for obtaining aminotetralines, wherein $X^1$ is —$NR^{11}$—, $A^2$ is optionally substituted alkylene, Y is —$NR^9$—, and Q is —$S(O)_2$.

Scheme 5:

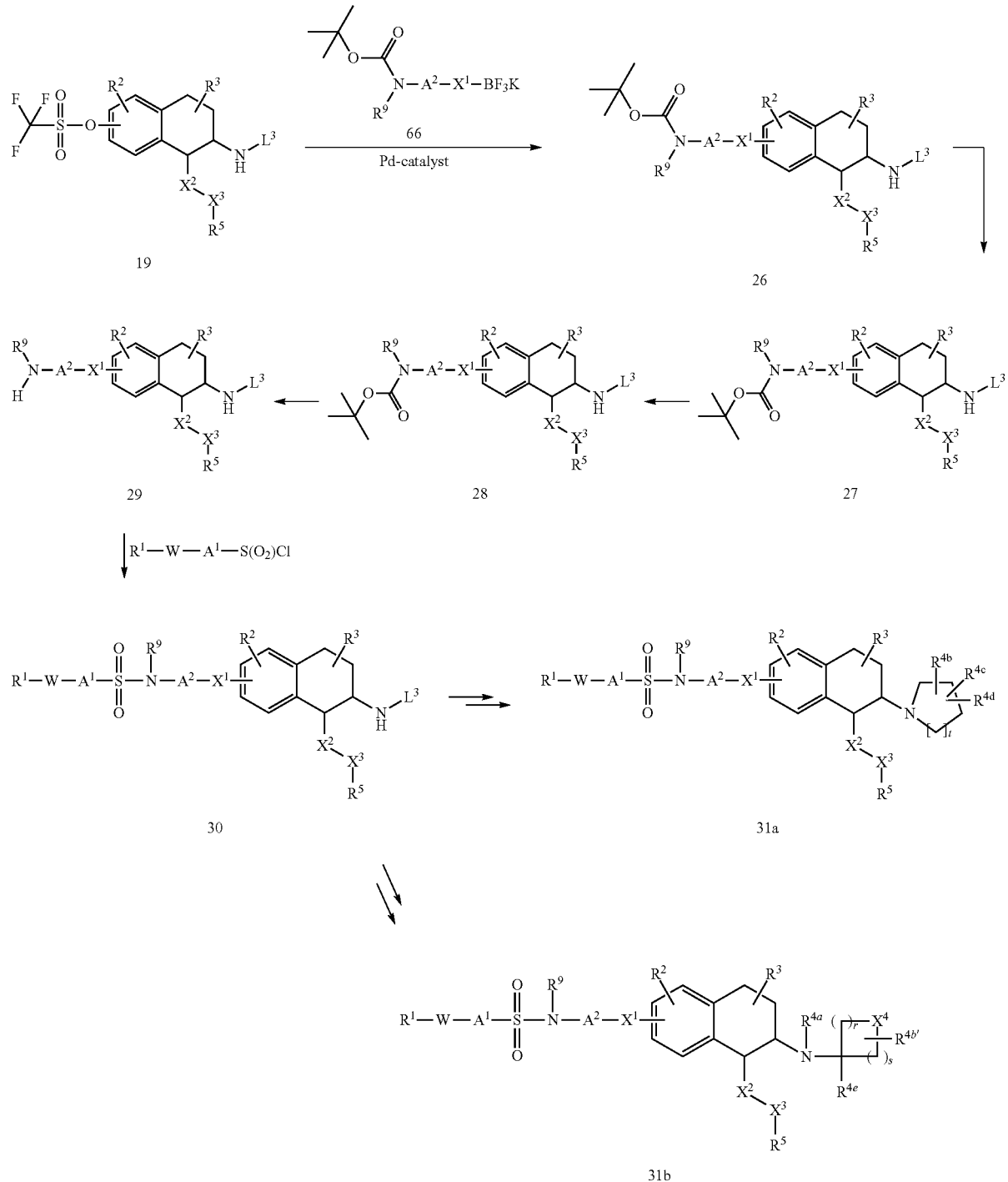

Scheme 6:

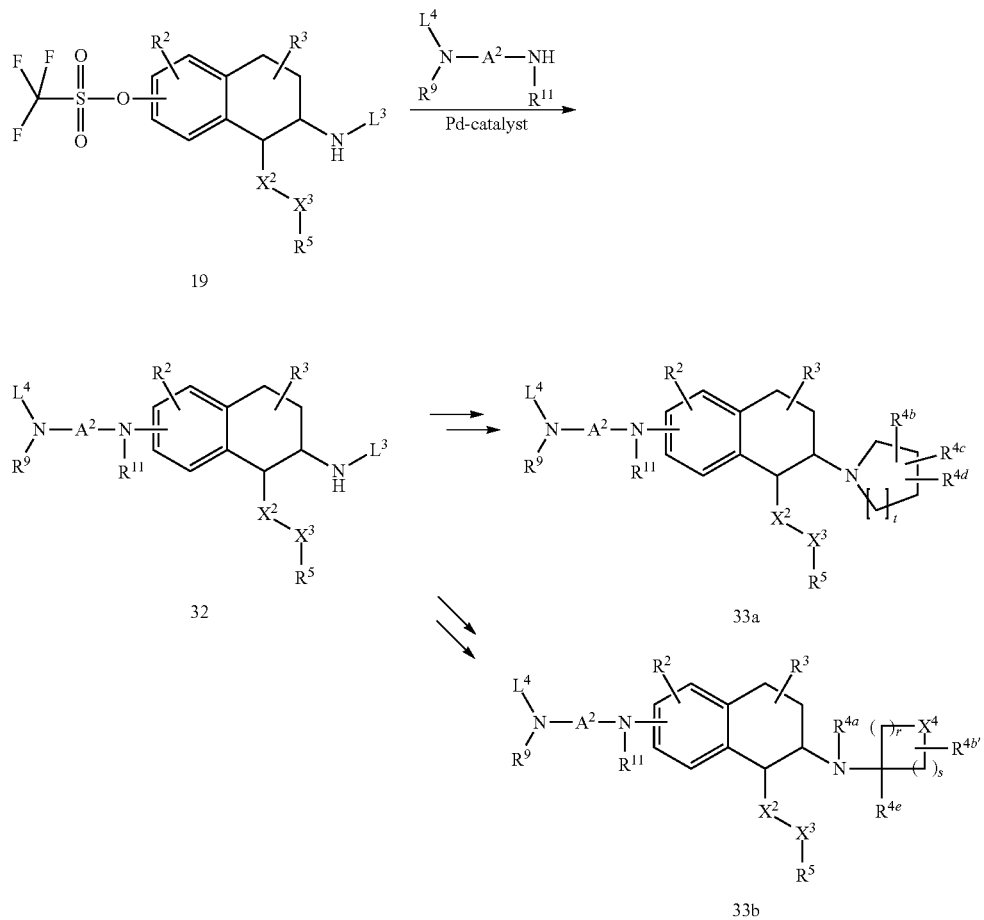

In scheme 6, the variables $R^2$, $R^3$, $R^{4a}$, $R^{4b}$, $R^{4b'}$, $R^{4c}$, $R^{4d}$, $R^{4e}$, $R^5$, $R^9$, $R^{11}$, $X^2$, $X^3$, $X^4$, r, s, t are as defined herein, and $L^3$, $L^4$ are suitable protecting groups.

The process depicted in the following schemes is useful for obtaining compounds of the general formula (I) in which A is a heterocycle.

Scheme 7:

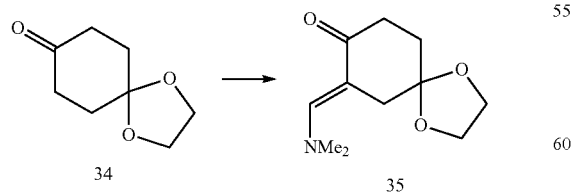

As shown in scheme 7, the compound of general formula 34 readily undergoes condensation with dimethylformamide dimethyl acetal to give the compound of general formula 35.

Scheme 8:

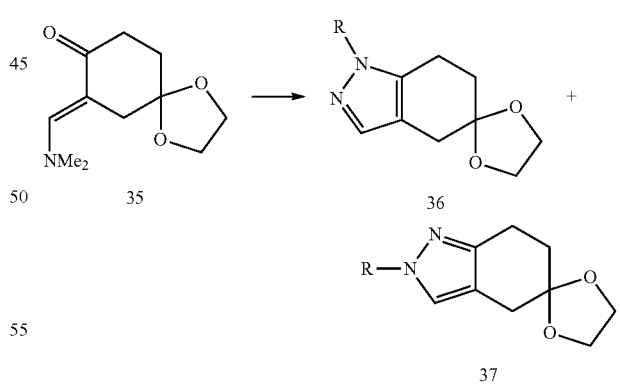

As shown in the above scheme 8, the intermediate of general formula 35 reacts with various nucleophiles of general formula $H_2N$—NH—R in an alcoholic solvent preferably methanol or ethanol at a temperature of about 20° to 80° C. to obtain the compounds of general formulae 36 and 37. In case of monosubstituted hydrazines regioisomeric products are formed. Compounds 36 and 37 can be transformed to compounds of the general formula (I) as depicted in Scheme 9.

In scheme 8, the variable R is as defined herein.

Scheme 9:

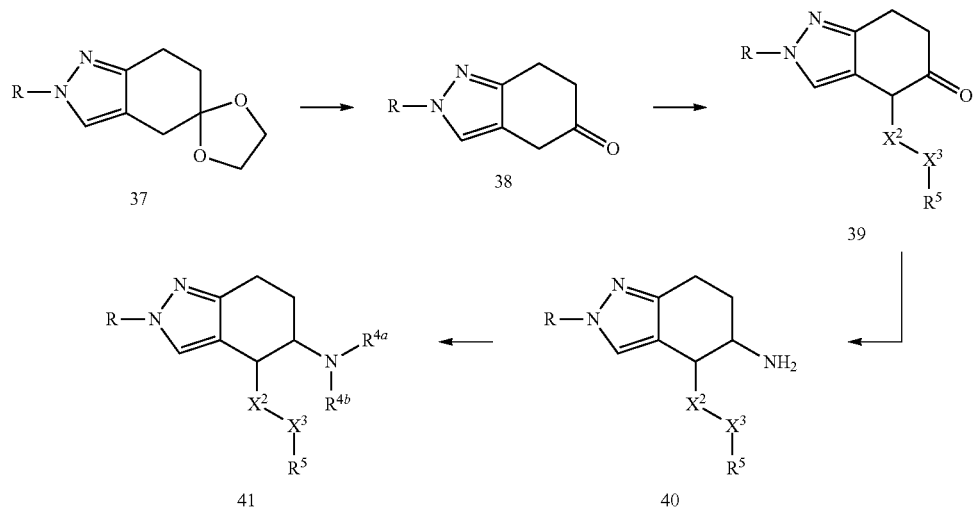

Alkylation of 38 can proceed via an enamine as described in scheme 1, or via an enolate. Reductive amination of 39 leads to 40. Alkylation or acylation of 40 affords 41. In scheme 9, the variables R, $R^{4a}$, $R^{4b}$, $R^5$, $X^2$, $X^3$ are as defined herein.

Scheme 10:

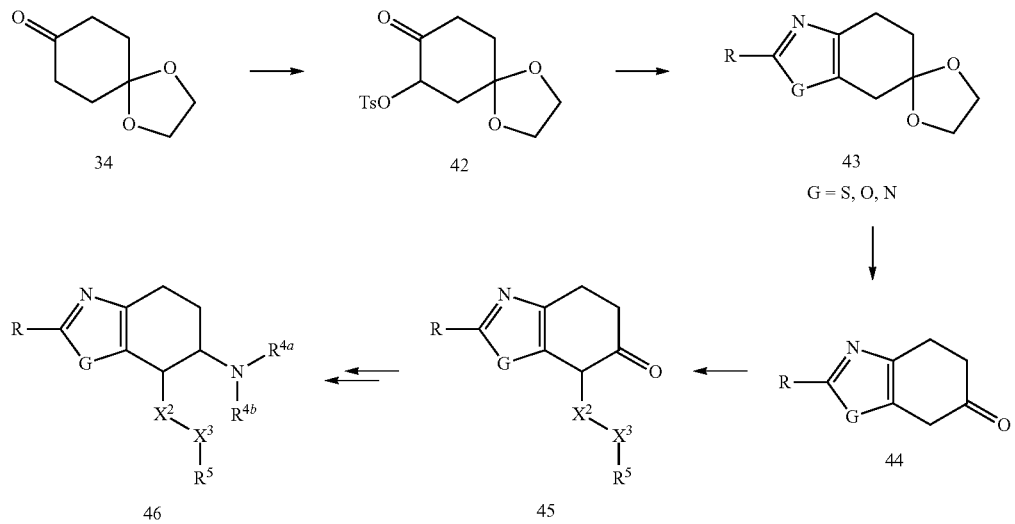

G = S, O, N

As shown in scheme 10, the reaction of compound of general formula 34 with hydroxyl(tosyloxy)iodobenzene gives the compound of formula 42. Reaction of compound of general formula 42 with 1,3-nucleophiles under appropriate conditions yield the compound of general formula 43. Further transformation to compounds of general formula 46 occurs as described in Scheme 9.

In scheme 10, the variables R, $R^{4a}$, $R^{4b}$, $R^5$, $X^2$, $X^3$ are as defined herein.

Scheme 11:

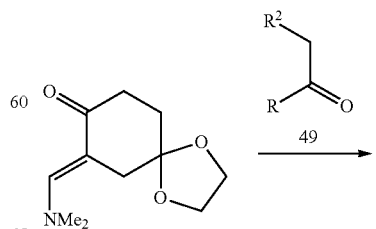

119

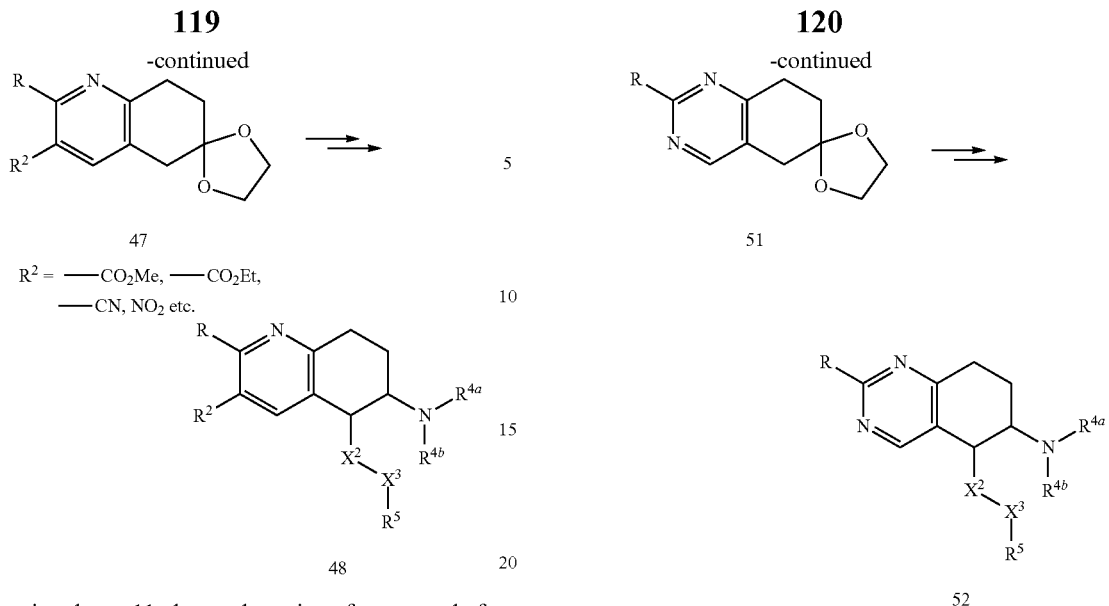

As shown in scheme 11, the condensation of compound of general formula 35 with reagent of general formula 49 and ammonia acetate in refluxing acetic acid give compound of general formula 47, which can be further transformed to compounds of general formula 48.

In scheme 11, the variables R, $R^{4a}$, $R^{4b}$, $R^5$, $X^2$, $X^3$ are as defined herein.

Scheme 12:

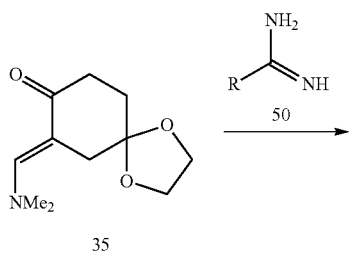

120

As shown in scheme 12, the cyclocondensation of intermediate of general formula 35 with the 1,3-nucleophiles of general formula 50 in the presence of suitable organic or inorganic bases such as KOH, NaOH, $NaHCO_3$, sodium ethoxide, sodium methoxide, triethyl amine and diisopropyl ethyl amine in an alcoholic solvent, preferably ethanol or methanol, at a temperature of about 20° to 80° C. yield the compound of general formula 51, which can be transformed further to give compounds of general formula 52.

In scheme 12, the variables R, $R^{4a}$, $R^{4b}$, $R^5$, $X^2$, $X^3$ are as defined herein.

Scheme 13:

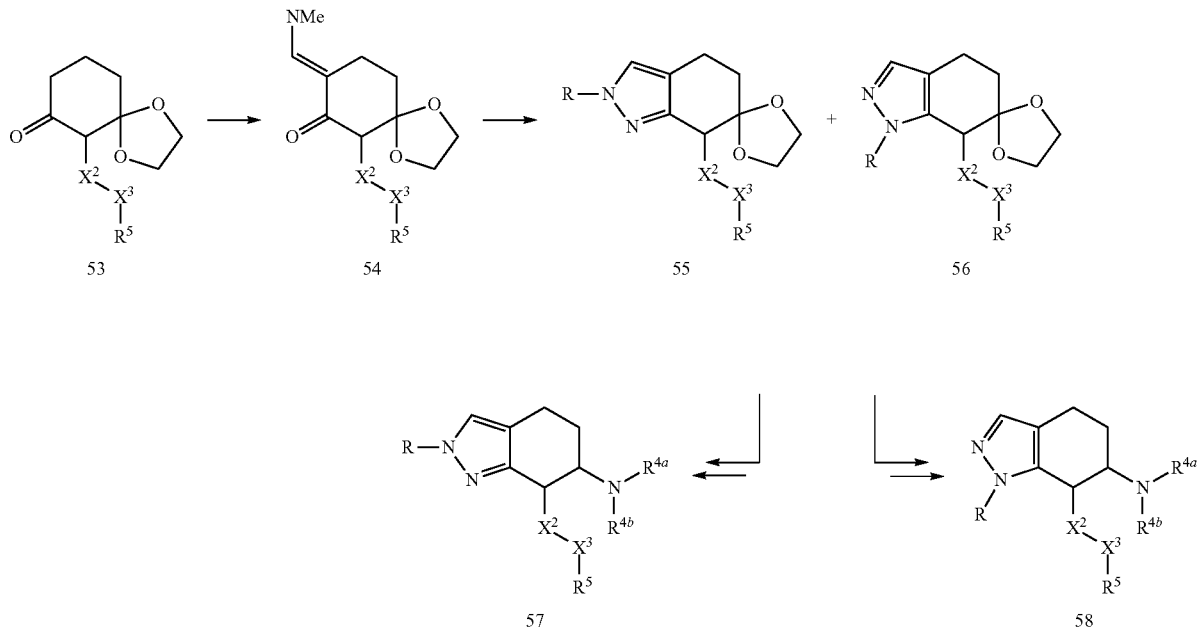

As shown in scheme 13, the intermediate of general formula 53 readily can undergo condensation with dimethylformamide dimethyl acetal to give the compound of general formula 54, which reacts with various nucleophiles of general formula H$_2$N—NH—R in an alcoholic solvent, preferably methanol or ethanol, at a temperature of about 20° to 80° C. to afford the compound of general formula 55 and 56. Compounds 55 and 56 can be transformed to compounds of the general formula (I) as depicted in the previous schemes.

In scheme 13, the variables R, R$^{4a}$, R$^{4b}$, R$^5$, X$^2$, X$^3$ are as defined herein.

Scheme 14:

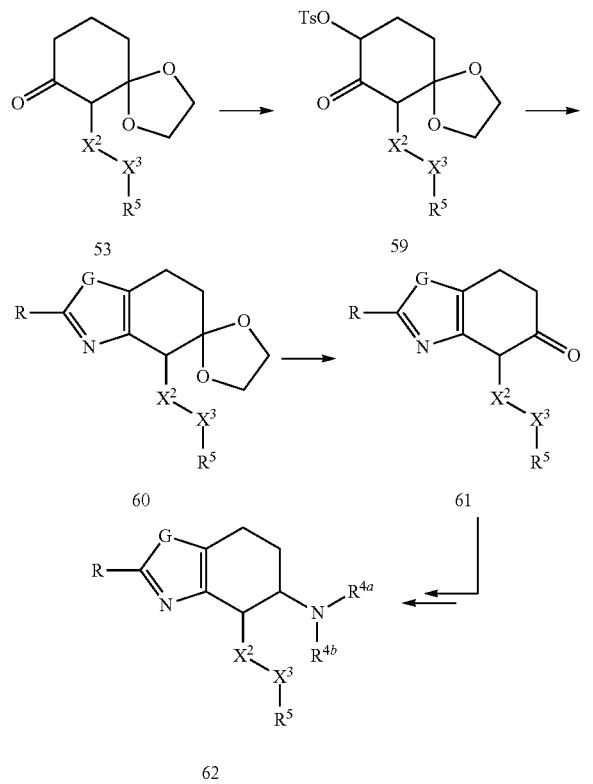

As shown in scheme 14, the reaction of compound of general formula 53 with hydroxyl(tosyloxy)iodobenzene gives the compound of formula 59, which reacts with 1,3-nucleophiles under appropriate conditions to yield the compound of general formula 60. Further transformation to compounds of general formula 62 occurs as described in the previous schemes.

In scheme 14, the variables G, R, R$^{4a}$, R$^{4b}$, R$^5$, X$^2$, X$^3$ are as defined herein.

Scheme 15:

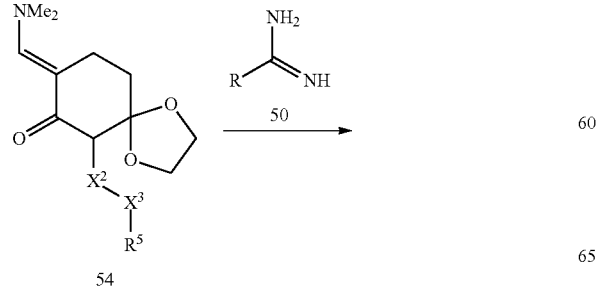

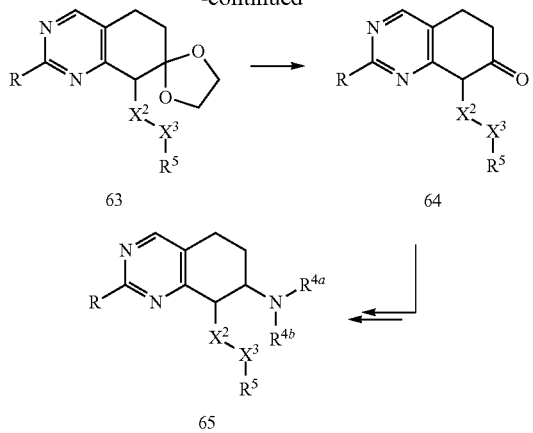

As shown in scheme 15, the cyclocondensation of intermediate of general formula 54 with the 1,3-nucleophiles of general formula 50 in the presence of suitable organic or inorganic bases such as KOH, NaOH, NaHCO$_3$, sodium ethoxide, sodium methoxide, triethyl amine and diisopropyl ethyl amine in an alcoholic solvent, preferably ethanol or methanol, at a temperature of about 20° to 80° C. yields the compound of general formula 63, which can be transformed further to give compounds of general formula 65 as described in the previous schemes.

In scheme 15, the variables R, R$^{4a}$, R$^{4b}$, R$^5$, X$^2$, X$^3$ are as defined herein.

Aminoindanes can be prepared by analogy to methods which are well known in the art. Suitable methods for the preparation of aminoindanes of formula (I) and (III) is outlined in the following schemes.

Scheme 16:

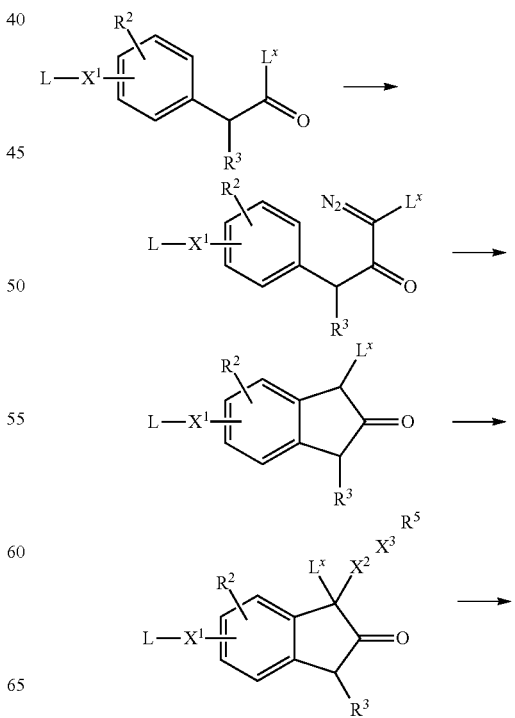

123
-continued

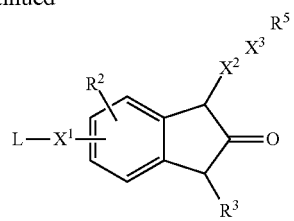

3

124

Scheme 16 depicts the general synthesis of indanones 3 using transition metal-catalyzed C,C-bond formation to synthesize the indanone from a diazoprecursor. Lx is an ester moiety. The side chain containing $X^2$, $X^3$ and $R^5$ can be introduced by an alkylation of the 1,3-dicarboyl intermediate. Saponification of the ester moiety and decarboxylation can yield indanone 3.

In scheme 16, the variables $R^2$, $R^3$, $R^5$, $X^1$, $X^2$, $X^3$, $L^x$ are as defined herein, and L is a suitable protecting group.

Scheme 17:

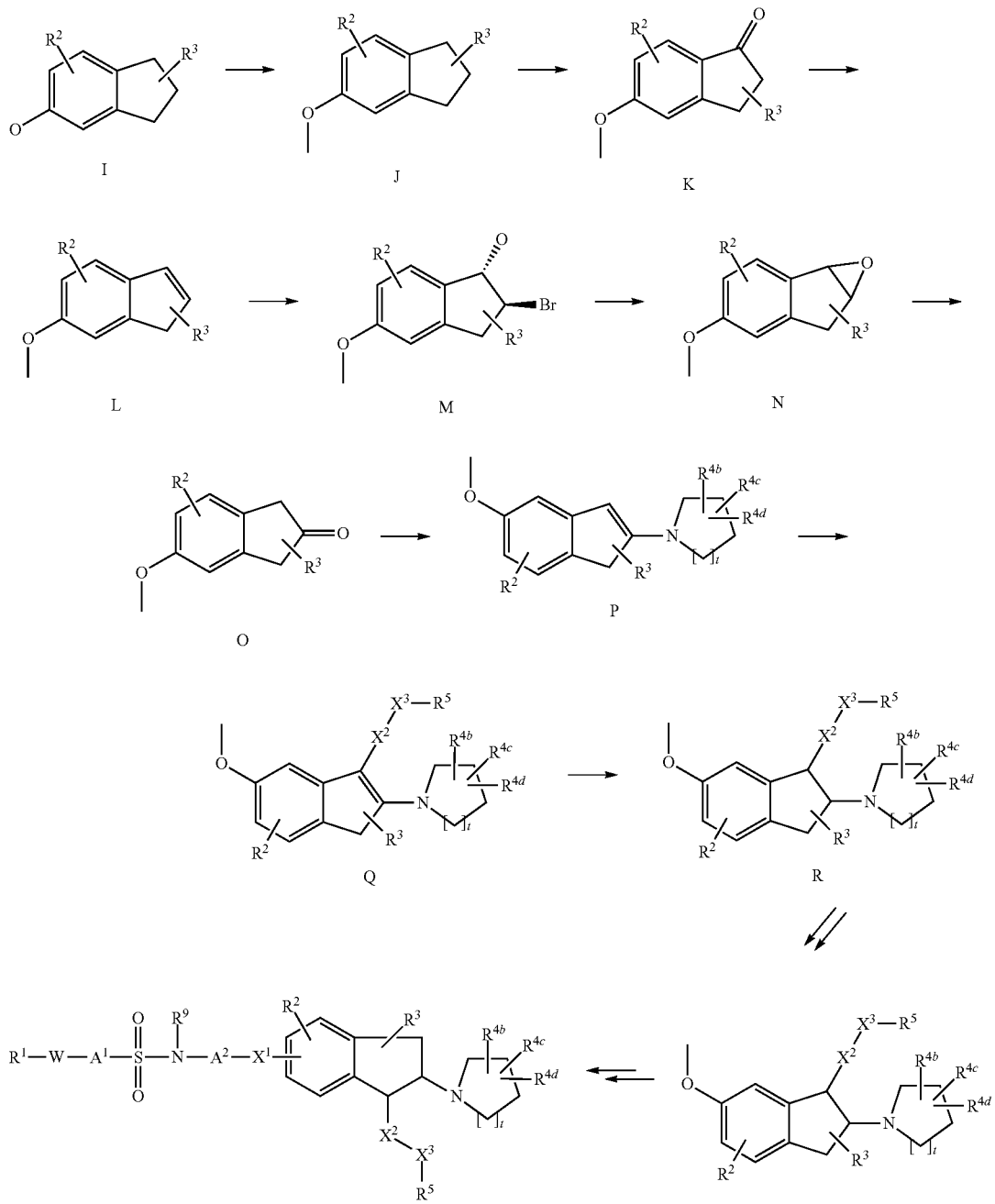

In scheme 17, the variables $R^1$, W, $A^1$, $A^2$, $X^1$, $R^2$, $R^3$, $R^{4b}$, $R^{4c}$, $R^{4d}$, $R^5$, $R^9$, $X^2$, $X^3$, t are as defined herein.

The process depicted in scheme 18 is useful for obtaining aminoindanes, wherein $X^1$ is —O— or —S—, $A^2$ is optionally substituted alkylene, Y is —$NR^9$—, and Q is —$S(O)_2$.

In scheme 18, the variables $R^1$, W, $A^1$, $A^2 R^2$, $R^3$, $R^{4a}$, $R^{4b}$, $R^{4b'}$, $R^{4c}$, $R^{4d}$, $R^{4e}$, $R^5$, $R^9$, $X^2$, $X^3$, $X^4$, r, s, t are as defined herein and L, $L^2$ are suitable protecting groups (e.g. $L^2$=COOEt).

The process depicted in scheme 18a is useful for obtaining indanes, wherein $X^1$ is —O— or —S—.

Scheme 18:

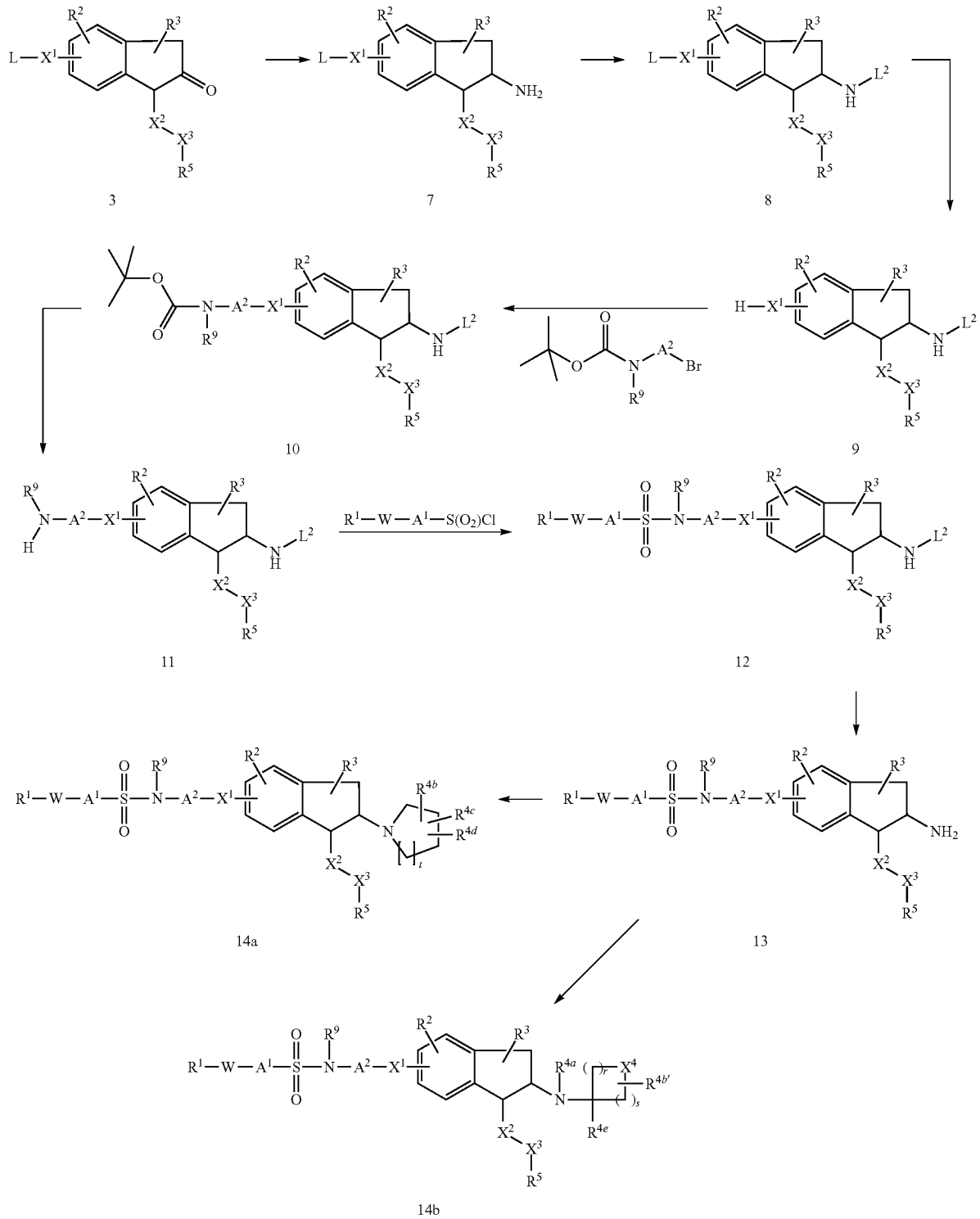

Scheme 18a:

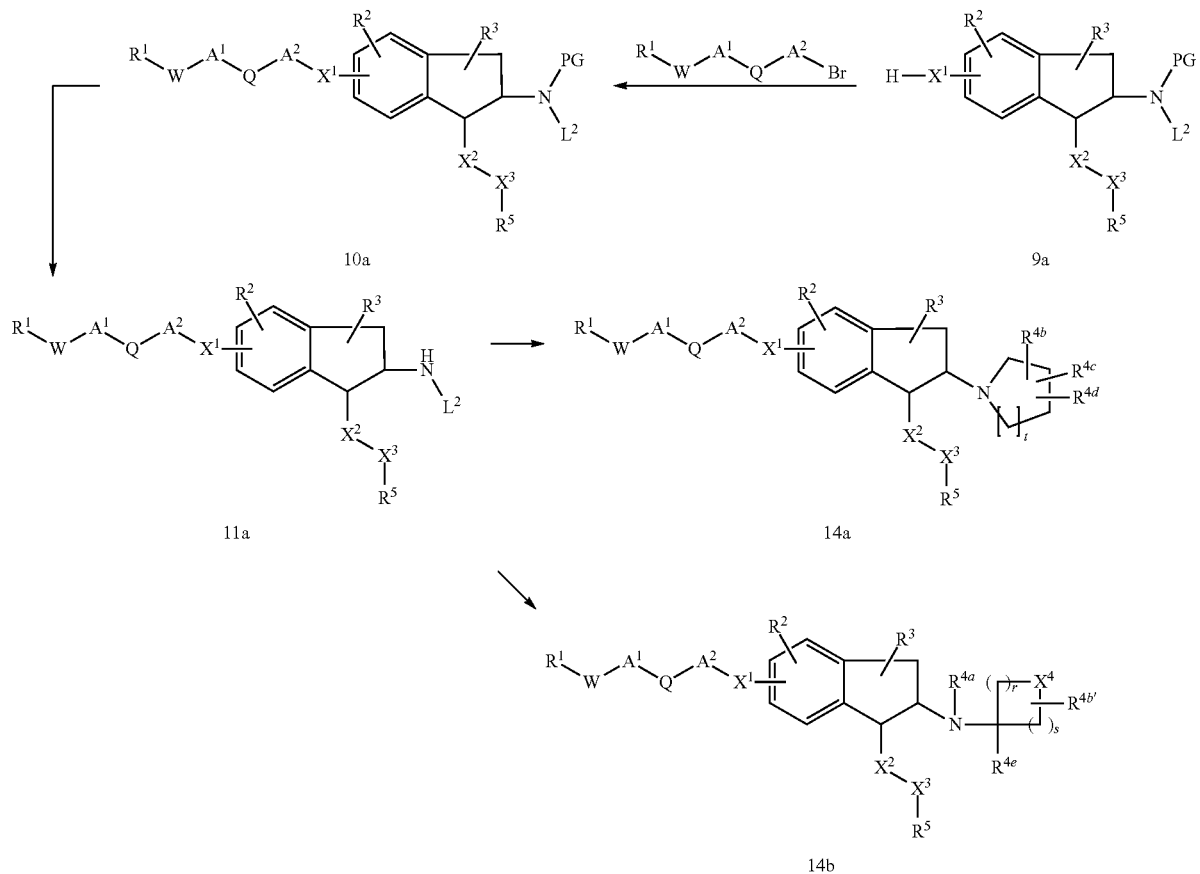

In scheme 18a, the variables $R^1$, W, Q, $A^1$, $A^2$, $R^2$, $R^3$, $R^{4a}$, $R^{4b}$, $R^{4b'}$, $R^{4c}$, $R^{4d}$, $R^{4e}$, $R^5$, $X^2$, $X^3$, $X^4$, r, s, t are as defined herein and PG, $L^2$ are suitable protecting groups. One example for compound $R^1$—W-$A^1$-Q-$A^2$-Br could be $CH_3$—$SO_2$—$CH_2$—$CH_2$—Br.

Further protocols for the synthesis of compounds wherein W is $NR^8$ are described in WO2009/121872.

The process depicted in scheme 19 is useful for obtaining aminoindanes, wherein $X^1$ is methylene, $A^2$ is a bond, Y is —$NR^9$—, and Q is —$S(O)_2$.

Scheme 19:

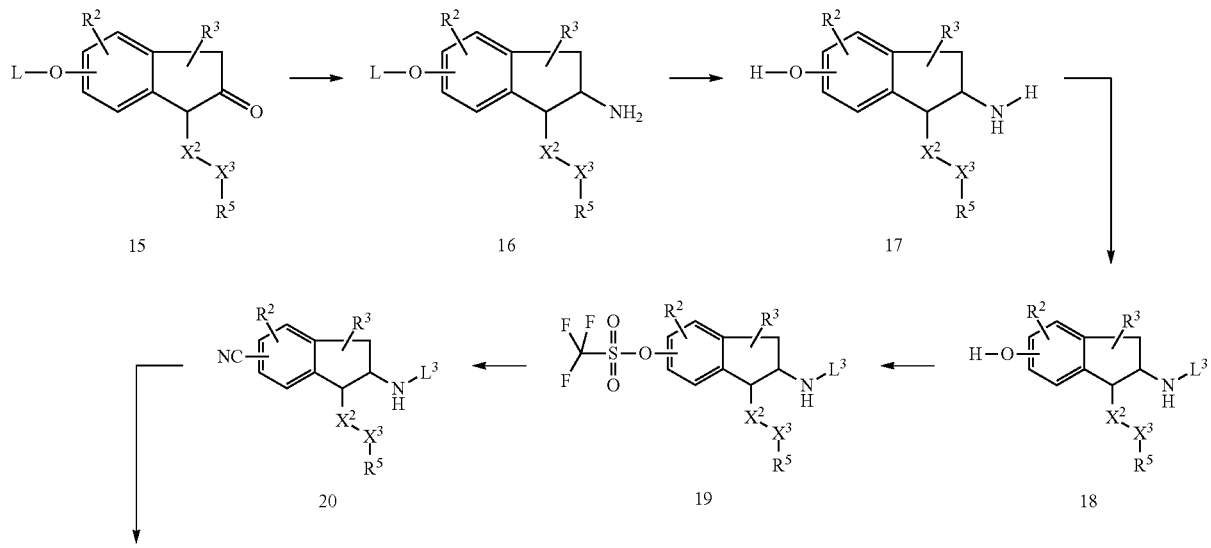

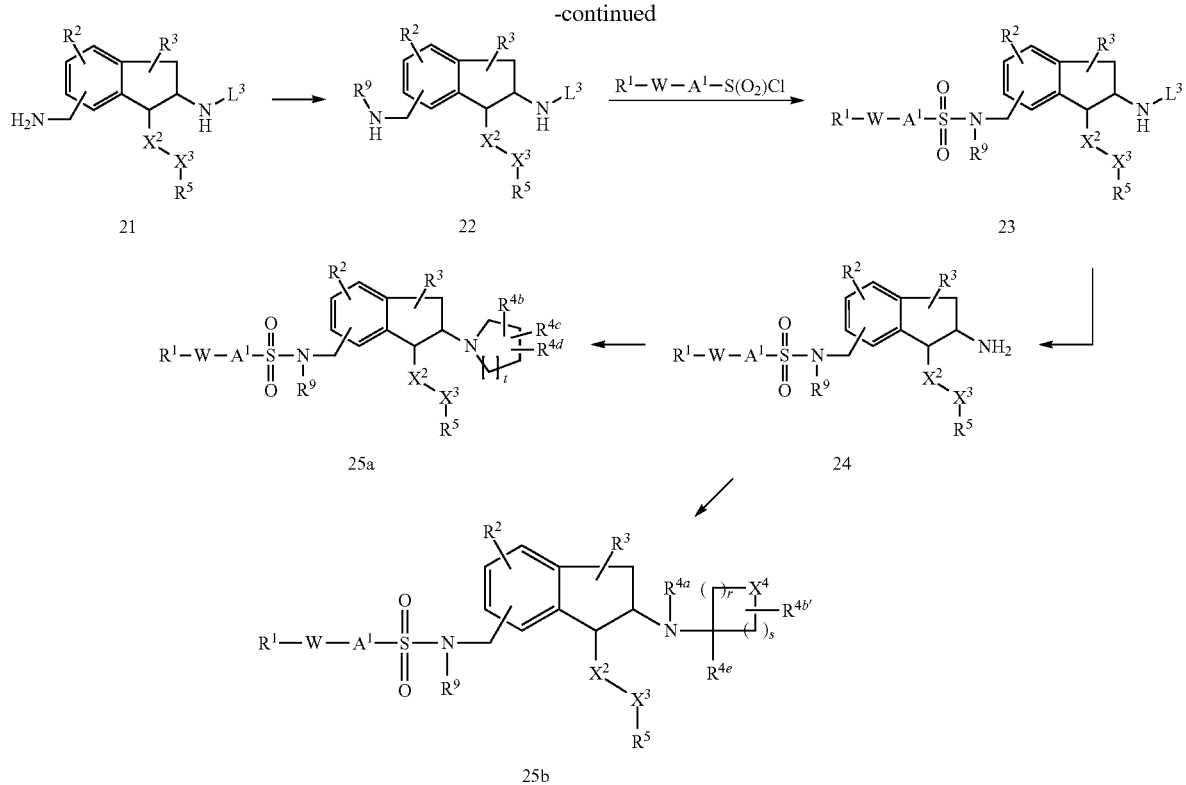

Alternatively to triflate 19, the corresponding bromide or iodide can be used to prepare compound 20.

In scheme 19, the variables $R^1$, W, $A^1$, $R^2$, $R^3$, $R^{4a}$, $R^{4b}$, $R^{4b'}$, $R^{4c}$, $R^{4d}$, $R^{4e}$, $R^5$, $R^9$, $X^2$, $X^3$, $X^4$, r, s, t are as defined herein, and L, $L^3$ are suitable protecting groups (e.g. $L^3$=COO$^t$-Bu).

The process depicted in scheme 20 is useful for obtaining aminoindanes, wherein $X^1$ is optionally substituted alkylene, $A^2$ is optionally substituted alkylene or a bond, Y is —$NR^9$—, and Q is —$S(O)_2$.

Scheme 20:

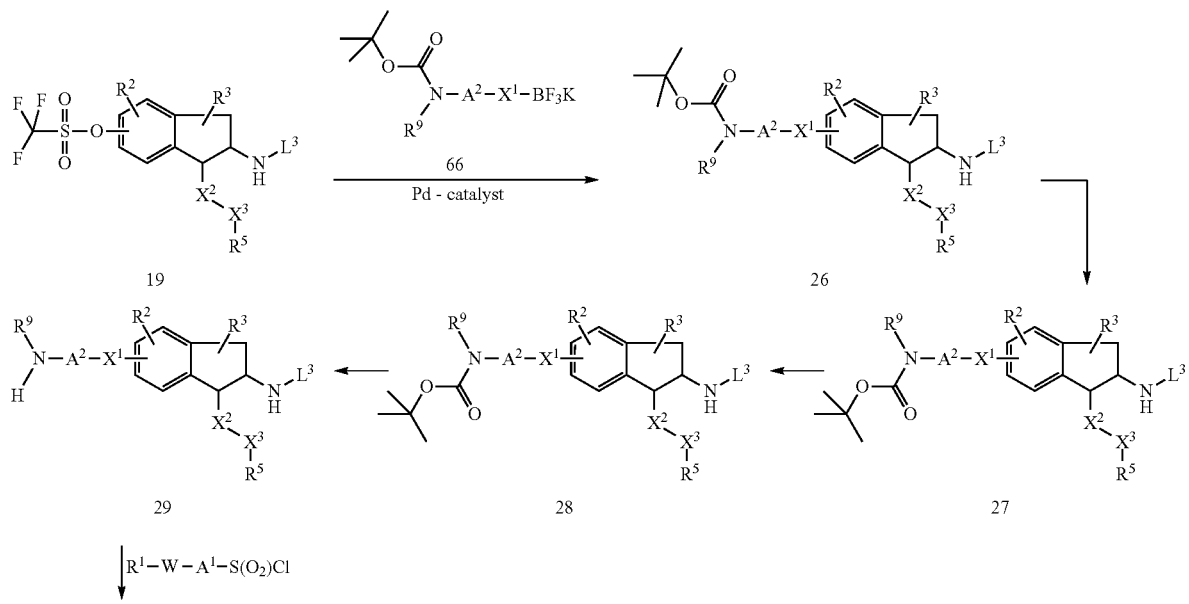

131

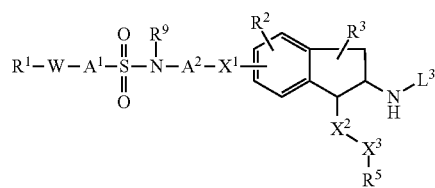

30

-continued

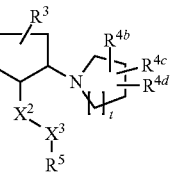

31a

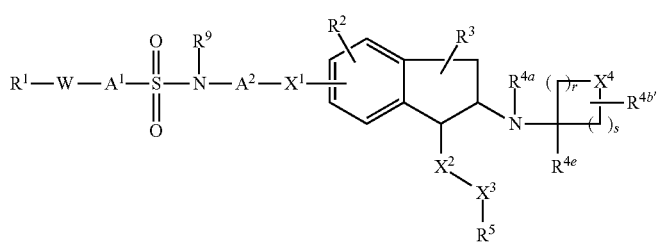

31b

Instead of the trifluoroborate 66, the corresponding 9-borabicyclo[3.3.1]non-9-yl derivative can be used to prepare compound 26.

In scheme 20, the variables $R^1$, W, $A^1$, $R^2$, $R^3$, $R^{4a}$, $R^{4b}$, $R^{4b'}$, $R^{4c}$, $R^{4d}$, $R^{4e}$, $R^5$, $R^9$, $X^2$, $X^3$, $X^4$, r, s, t are as defined herein, and $L^3$ is a suitable protecting group (e.g. $L^3$=COOEt).

The process depicted in scheme 21 is useful for obtaining aminoindanes, wherein $X^1$ is —$NR^{11}$—, $A^2$ is optionally substituted alkylene, Y is —$NR^9$—, and Q is —$S(O)_2$.

Scheme 21:

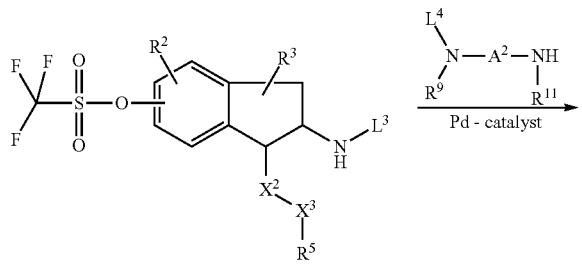

19

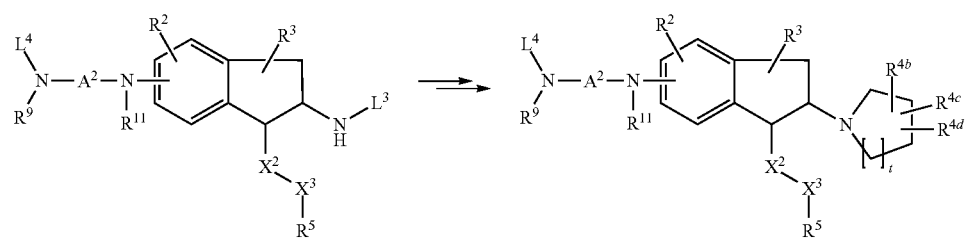

32                                               14a

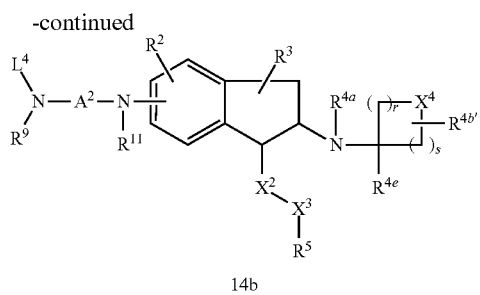
14b
In scheme 21, the variables $R^1$, W, $A^1$, $R^2$, $R^3$, $R^{4a}$, $R^{4b}$, $R^{4b'}$, $R^{4c}$, $R^{4d}$, $R^{4e}$, $R^5$, $R^9$, $R^{11}$, $X^2$, $X^3$, $X^4$, r, s, t are as defined herein, and $L^3$, $L^4$ are suitable protecting groups.
The process depicted in scheme 22 is also useful for obtaining the aminoindanes of the invention.
Scheme 22:
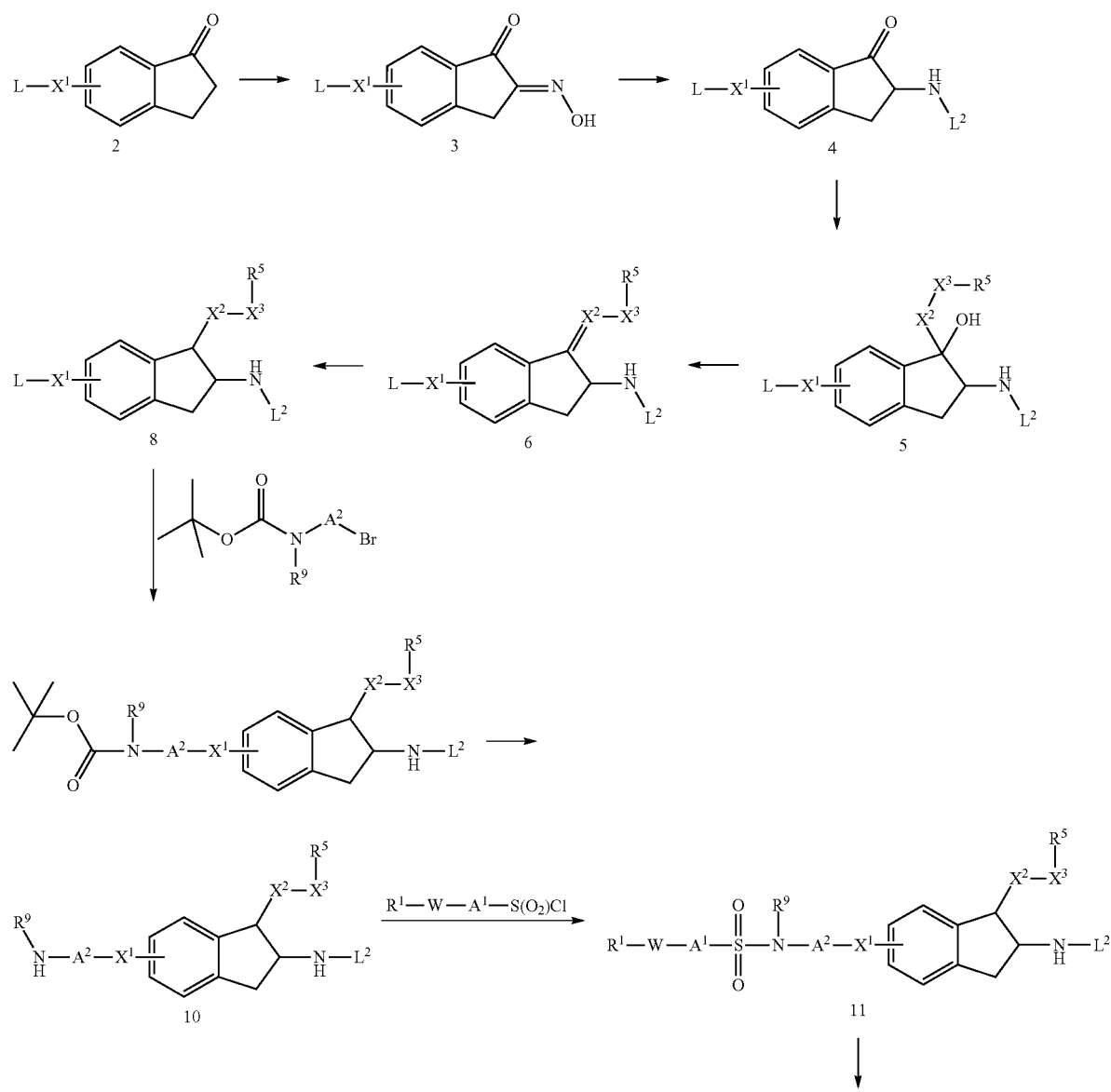

-continued

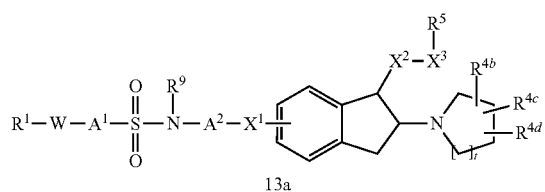

13a

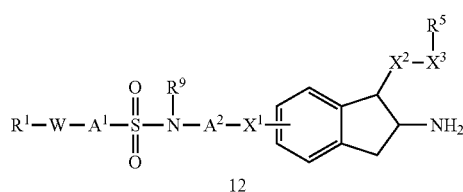

12

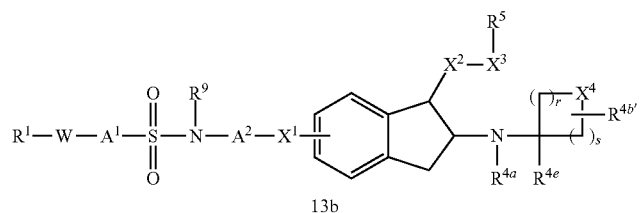

13b

1-Indanones 2 can be converted to the corresponding oximes 3 using a base followed by reaction with alkyl nitrites (e.g. isoamyl nitrite). Reduction of 3 (e.g. catalytic hydrogenation with palladium on barium sulfate) followed by protection of the amino group (e.g. using ethyl chloroformate and base) affords the N-protected alpha amino ketones 4. 1,2-Addition of a suitable nucleophile (e.g. Grignard reagent) followed by elimination (e.g. treatment with methane sulfonic acid) gives the intermediate 6. Reduction of 6 (e.g. catalytic hydrogenation using palladium on charcoal) yields 2-amino indane 8. Deprotection of $X^1$ (e.g. with boron tribromide when $L-X^1$ is methoxy) followed by alkylation using a suitably substituted bromide gives intermediate 9. Cleavage of the BOC-protection group (e.g. with hydrochloric acid) followed by reaction with a functionalized sulfonyl chloride gives sulfonamide 11. Removal of the protection group $L^2$ (e.g. using sodium hydroxide when $NH-L^2$ is a carbamate) gives 2-amino indanes 12. These can be further functionalized (e.g. acylation followed by reduction) to give N-substituted 2-amino indanes 13.

In scheme 22, the variables $R^1$, W, $A^1$, $A^2$, $R^2$, $R^3$, $R^{4a}$, $R^{4b}$, $R^{4b'}$, $R^{4c}$, $R^{4d}$, $R^{4e}$, $R^5$, $R^9$, $X^1$, $X^2$, $X^3$, $X^4$, r, s, t are as defined herein, and L, $L^2$ are suitable protecting groups.

The acid addition salts of the aminoindane derivatives of formula (I) are prepared in a customary manner by mixing the free base with a corresponding acid, optionally in solution in an organic solvent, for example a lower alcohol, such as methanol, ethanol or propanol, an ether, such as methyl tert-butyl ether or diisopropyl ether, a ketone, such as acetone or methyl ethyl ketone, an ester, such as ethyl acetate or a halogenated alkane, such as dichloromethane.

Phenalkylamines can be prepared by analogy to methods which are well known in the art. Suitable methods for the preparation of compounds of formula (II) and (IV) are outlined in the following schemes.

The process depicted in scheme 23 is useful for obtaining phenalkylamines, wherein $X^1$ is —O— or —S—, and $Y^1$ is a bond.

Scheme 23:

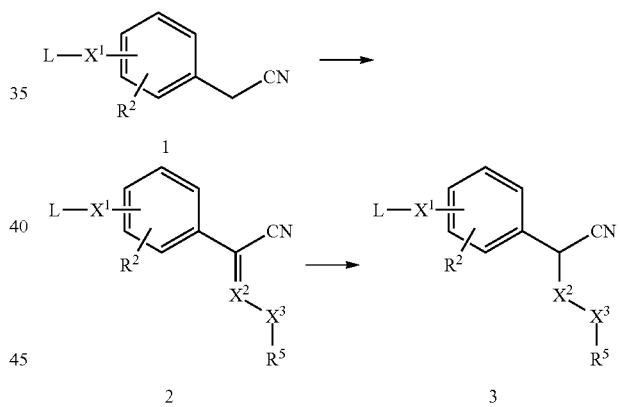

As shown in scheme 23, the compound of general formula 1 readily undergoes condensation with an aldehyde to give the compound of general formula 2. Subsequent hydrogenation (e.g. with $NaBH_4$) affords compound 3. Alternatively compounds of general formula 1 readily undergo alkylation in the presence of a strong base (e.g. LDA=lithium diisopropylamide) to give directly compounds of general formula 3. In this case the benzylic position can carry $R^3$ as additional substituent.

In scheme 23, the variables $X^2$, $X^3$, $R^2$, $R^5$ are as defined herein and L is a suitable protecting group (e.g. L=Me). Compounds 3 can be further converted to compounds of the general formula (I) as shown in scheme 24. Alternatively L is a group that represents, or can be converted into, the desired side chain $R^1$—W-$A^1$-Q-Y-$A^2$-.

Scheme 24:
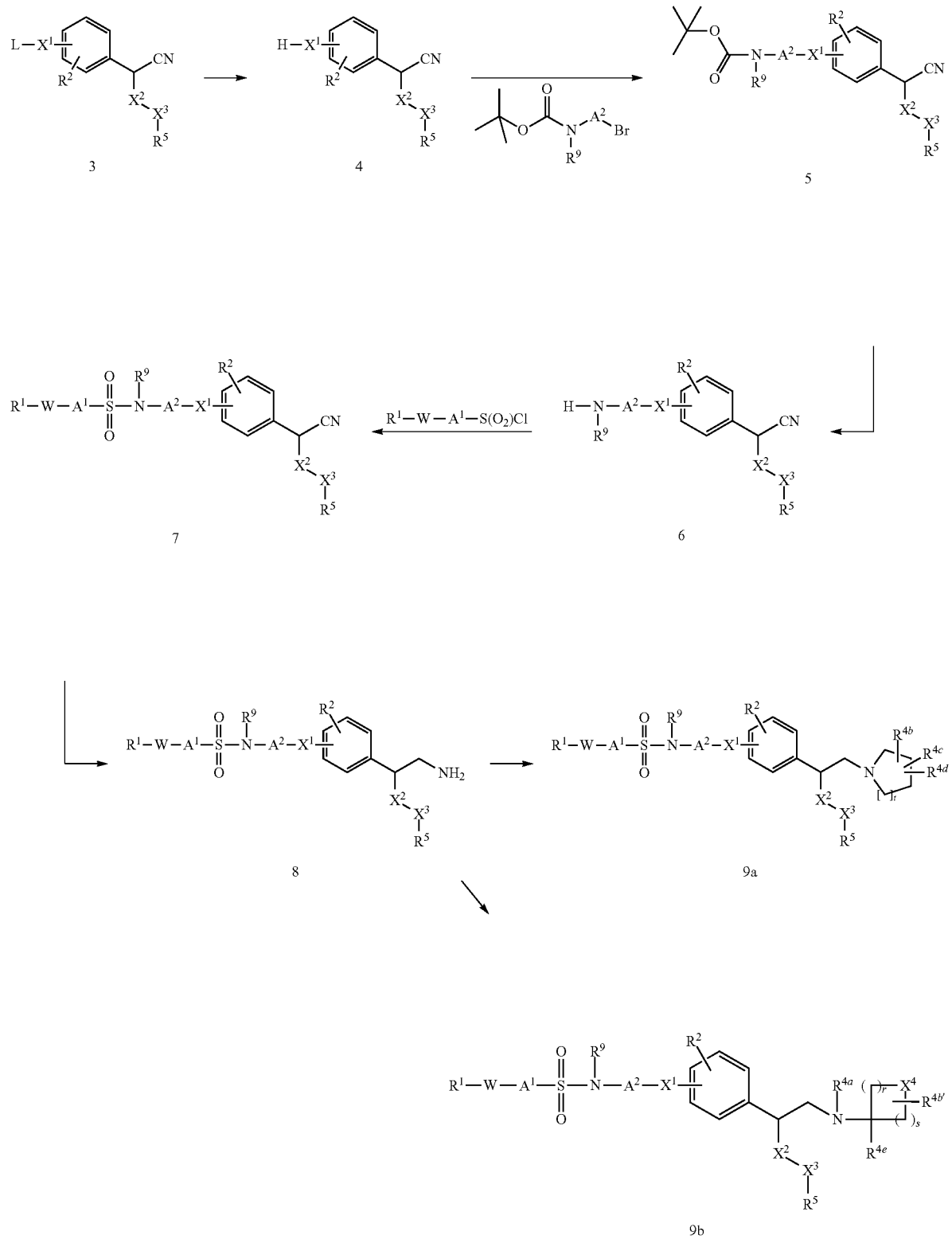
In scheme 24, the variables $R^1$, W, $A^1$, $A^2$, $R^2$, $R^{4a}$, $R^{4b}$, $R^{4b'}$, $R^{4c}$, $R^{4d}$, $R^{4e}$, $R^5$, $R^9$, $X^1$, $X^2$, $X^3$, $X^4$, r, s, t are as defined herein, and L is a suitable protecting group.
The process depicted in scheme 25 is useful for obtaining phenalkylamines, wherein $X^1$ is methylene, $A^2$ is a bond, Y is —$NR^9$—, and Q is —$S(O)_2$.

Scheme 25:
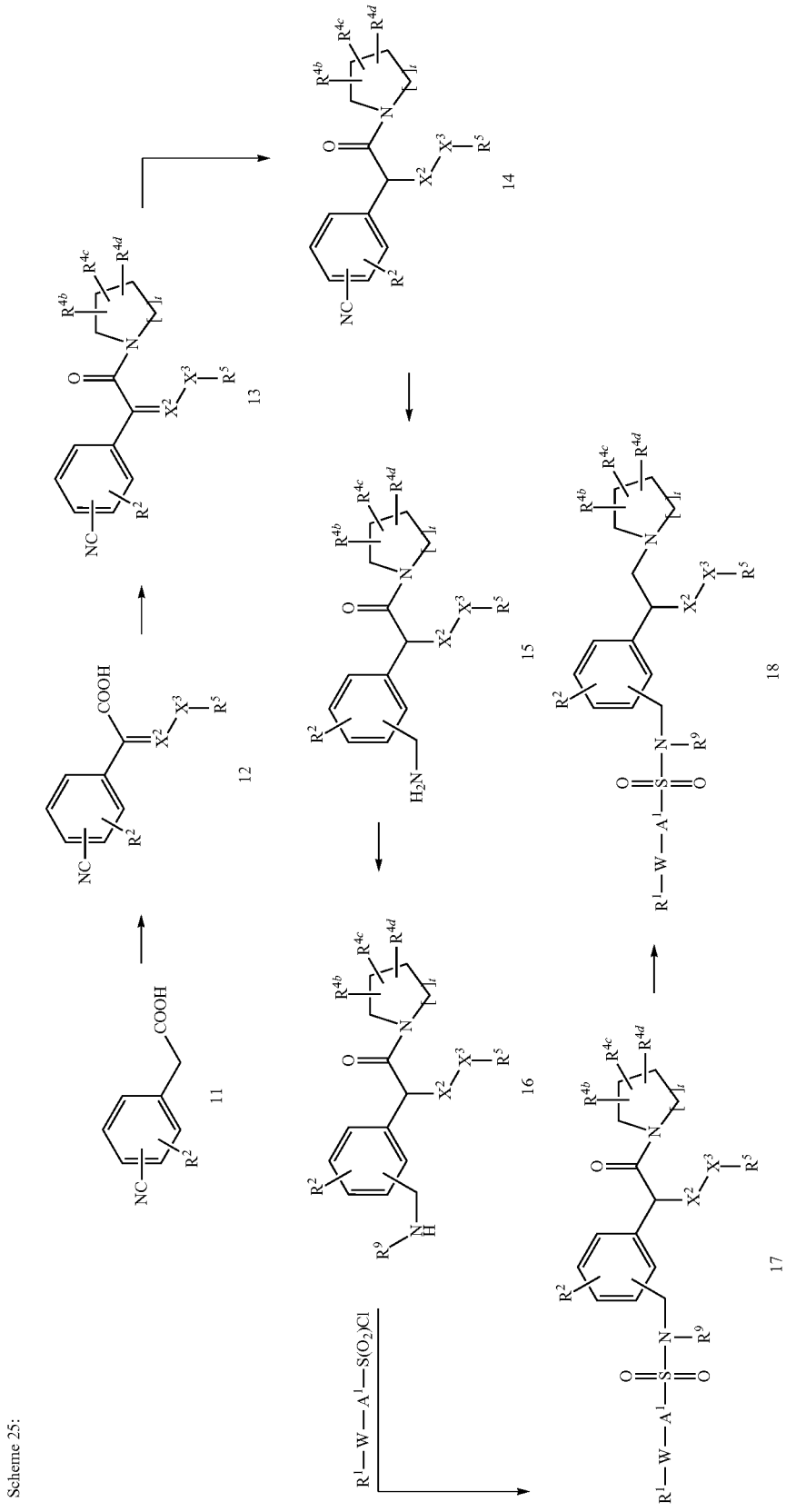

In scheme 25, the variables $R^1$, W, $A^1$, $R^2$, $R^{4b}$, $R^{4c}$, $R^{4d}$, $R^5$, $R^9$, $X^2$, $X^3$, t are as defined herein.

The process depicted in scheme 26 is useful for obtaining phenalkylamines, wherein $X^1$ is optionally substituted alkylene, $A^2$ is optionally substituted alkylene or a bond, Y is —$NR^9$— and Q is —$S(O)_2$.

Scheme 26:

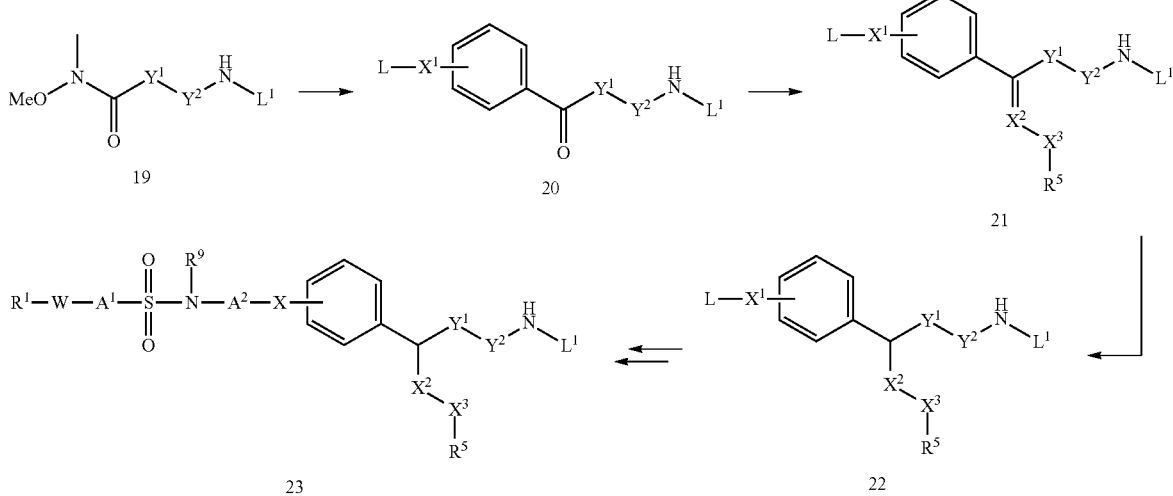

The Weinreb-amide of a suitable protected alpha or beta amino acid (19) undergoes transformation to compound 20 together with a metallo organic reagent (e.g. Grignard reagent). Synthesis of compound 21 could proceed by a Wittig reagent or by a metallo organic reagent (Grignard reagent). Subsequent hydrogenation leads to 22 which is further transformed to the final compound 23 as described in scheme 24.

In scheme 26, the variables $R^1$, W, $A^1$, $R^5$, $R^9$, $Y^1$, $Y^2$, $X^2$, $X^3$ are as defined herein, and L, $L^1$ are suitable protecting groups.

The process depicted in scheme 27 is useful for obtaining phenalkylamines, wherein $X^1$ is —$NR^{11}$—, $A^2$ is optionally substituted alkylene, Y is —$NR^9$—, and Q is —$S(O)_2$.

Scheme 27:

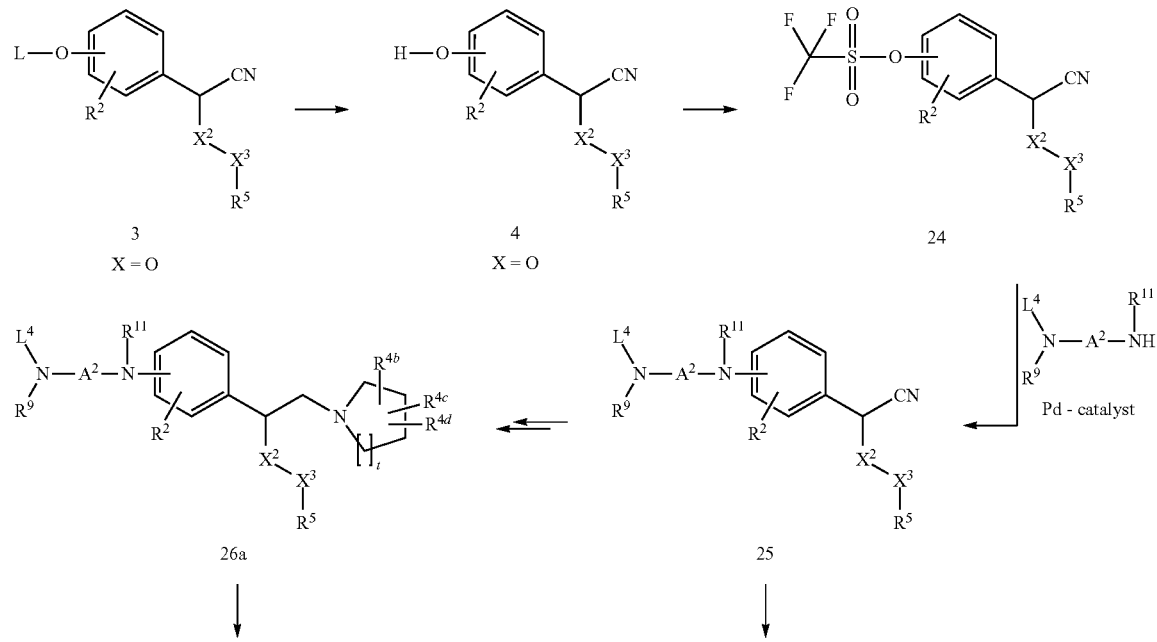

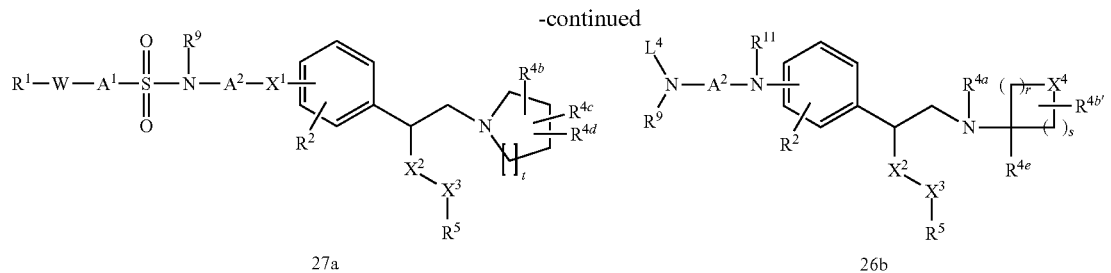

27a

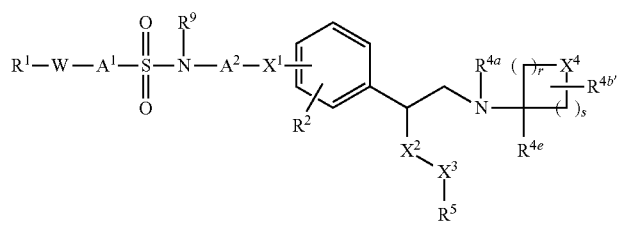

27b

In scheme 27, the variables $R^1$, W, $A^1$, $R^2$, $R^{4a}$, $R^{4b}$, $R^{4b'}$, $R^{4c}$, $R^{4d}$, $R^{4e}$, $R^5$, $R^9$, $R^{11}$, $X^2$, $X^3$, $X^4$, r, s, t are as defined herein, and L, $L^4$ are suitable protecting groups.

The process depicted in scheme 28 is useful for obtaining phenalkylamines, wherein $Y^1$, $Y^2$ is a bond.

Scheme 28:

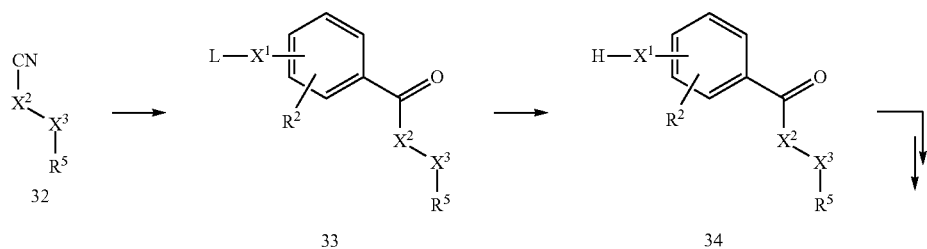

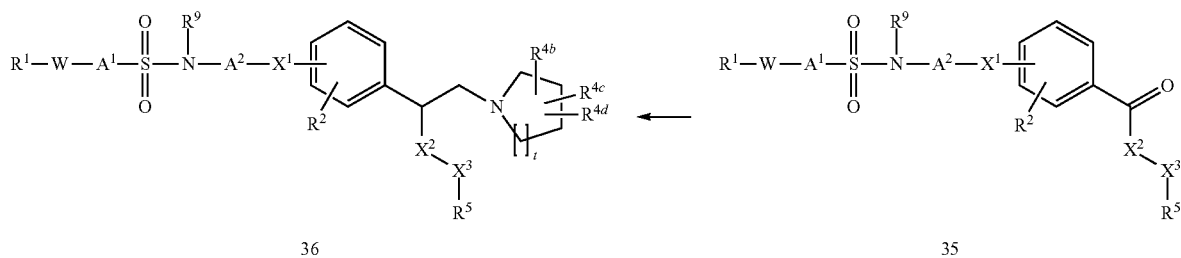

In scheme 28 the variables W, $A^1$, $A^2$, $R^1$, $R^2$, $R^{4b}$, $R^{4c}$, $R^{4d}$, $R^5$, $R^9$, $X^1$, $X^2$, $X^3$, t are as defined herein, and L is a suitable protecting group (e.g. L=benzyl).

The process depicted in scheme 29 is useful for obtaining phenalkylamines, wherein $X^1$ is —O— or —S—, and Y is a bond.

Scheme 29:

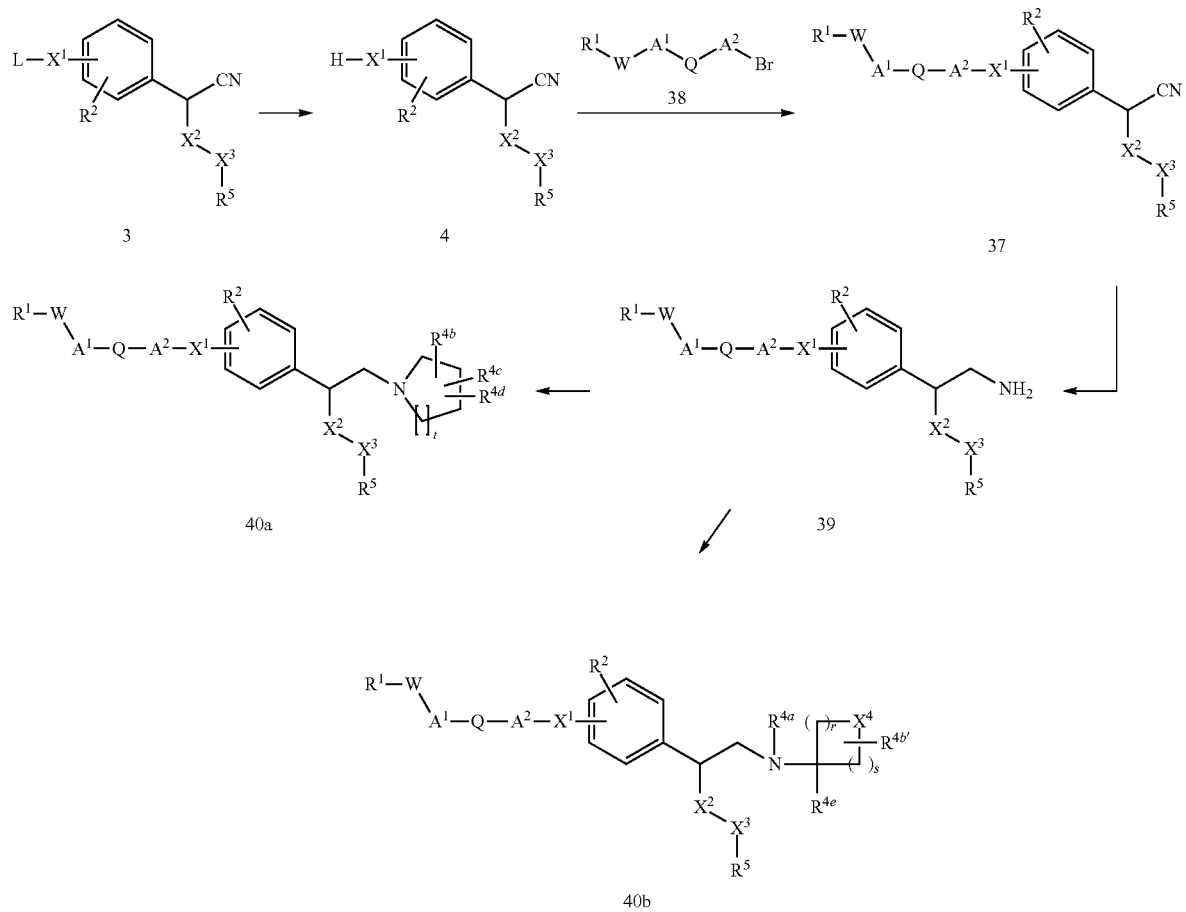

In scheme 29, the variables $A^1$, $A^2$, W, Q, $R^1$, $R^2$, $R^{4a}$, $R^{4b}$, $R^{4b'}$, $R^{4c}$, $R^{4d}$, $R^{4e}$, $R^5$, $X^2$, $X^3$, $X^4$, r, s, t are as defined herein, and L is a suitable protecting group. One example for compound 38 could be $CH_3$—$SO_2$—$CH_2$—$CH_2$—Br.

Further protocols for the synthesis of compounds in which Y is a bond and W is $NR^8$ are described in WO 2009/121872.

Further suitable methods for the preparation of compounds of formula (I) and (III) are outlined in the following schemes.

Scheme 30:

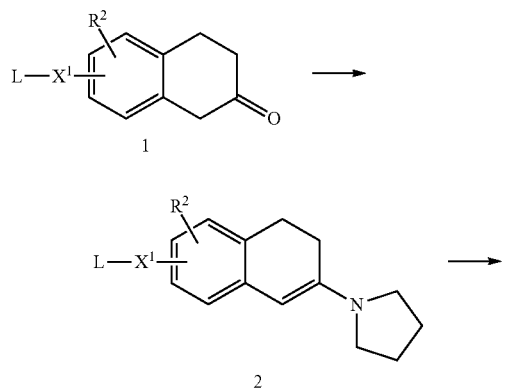

-continued

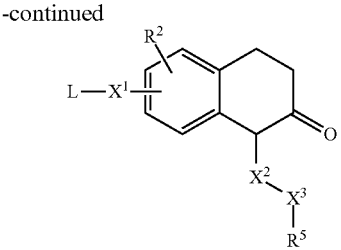

As shown in scheme 30, the compound of general formula 1 readily undergoes enamine alkylation to give the compound of general formula 3.

In scheme 30, the variables $X^1$, $X^2$, $X^3$, $R^2$, $R^5$ are as defined herein and L is a suitable protecting group (e.g. L=Me). The process depicted in scheme 30 is also useful for obtaining tetralines, wherein $X^1$ is optionally substituted alkylene or oxygen. In this case, L is a group that represents, or can be converted into, the desired side chain $R^1$—W-$A^1$-Q-Y-$A^2$—

Alternatively, compounds of formula 3 can be prepared as described in scheme 31.

Scheme 31a:

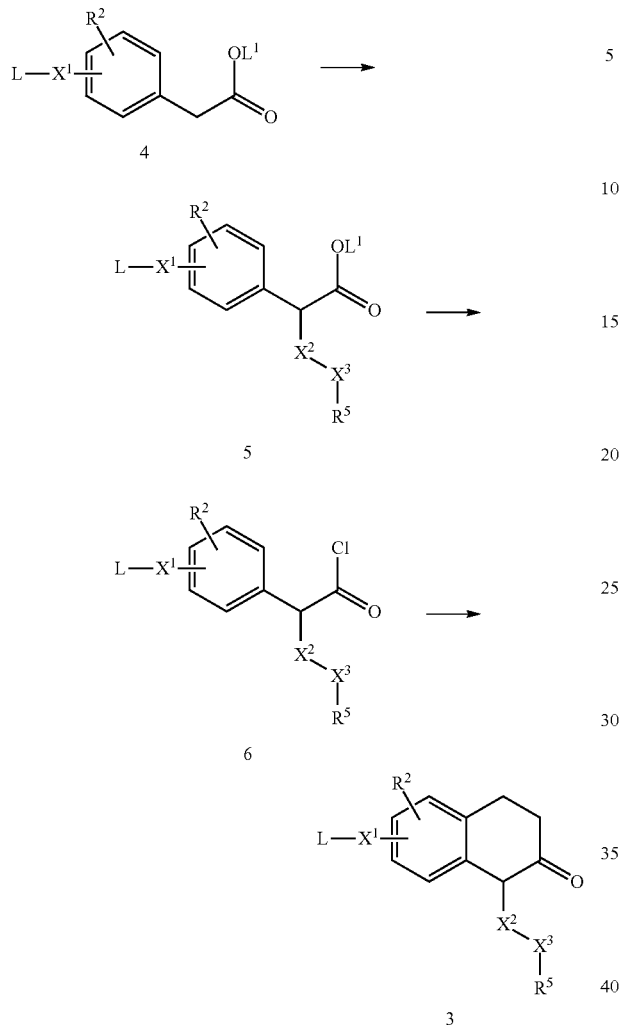

Scheme 31b:

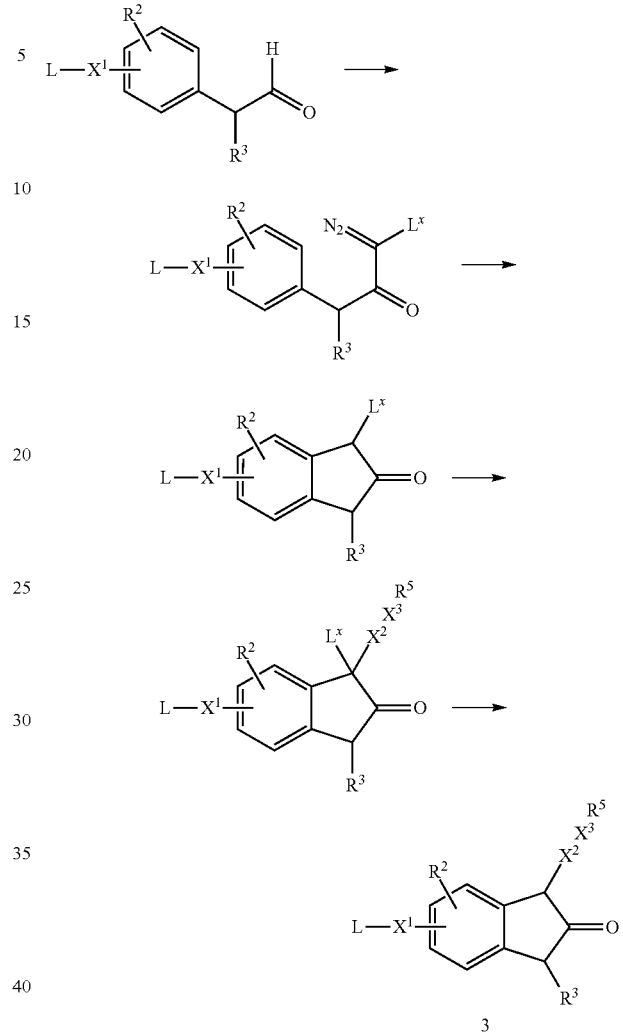

As shown in scheme 31a, the compound of general formula 4 readily undergoes alkylation to give the compound of general formula 5. Conversion to the acid chloride and subsequent ring closure with ethylene in the presence of a Lewis acid (e.g. AlCl$_3$) affords compound 3 (e.g. J. Het. Chem., 23 (2), 343, 1986 and Bioorg. Med. Chem. Lett., 17 (22), 6160, 2007).

In scheme 31a, the variables $X^1$, $X^2$, $X^3$, $R^2$, $R^5$ are as defined herein and L, $L^1$ are suitable protecting groups (e.g. L, $L^1$=Me). Compounds 3 can be further converted to compounds of the general formula (I).

Scheme 31b depicts the general synthesis of indanones 3 using transition metal-catalyzed C,C-bond formation to synthesize the indanone from a diazoprecursor (cf. Tetrahedron Letters (2009), 50, 3568). $L^x$ is an ester moiety. The side chain containing $X^2$, $X^3$ and $R^5$ could be introduced by an alkylation of the 1,3-dicarboyl intermediate. Saponification of the ester moiety and decarboxylation could yield indanone 3.

In scheme 31b, the variables $X^1$, $X^2$, $X^3$, $R^2$, $R^3$, $R^5$ are as defined herein and Lisa suitable protecting group (e.g. L=Me). Compounds 3 can be further converted to compounds of the general formula (I).

Scheme 31c:

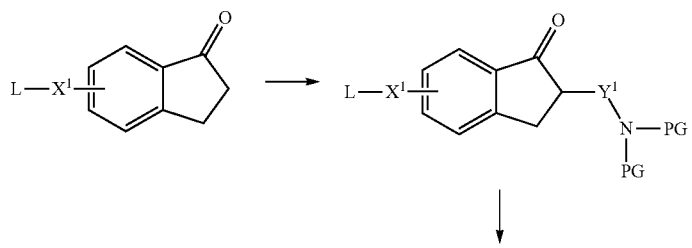

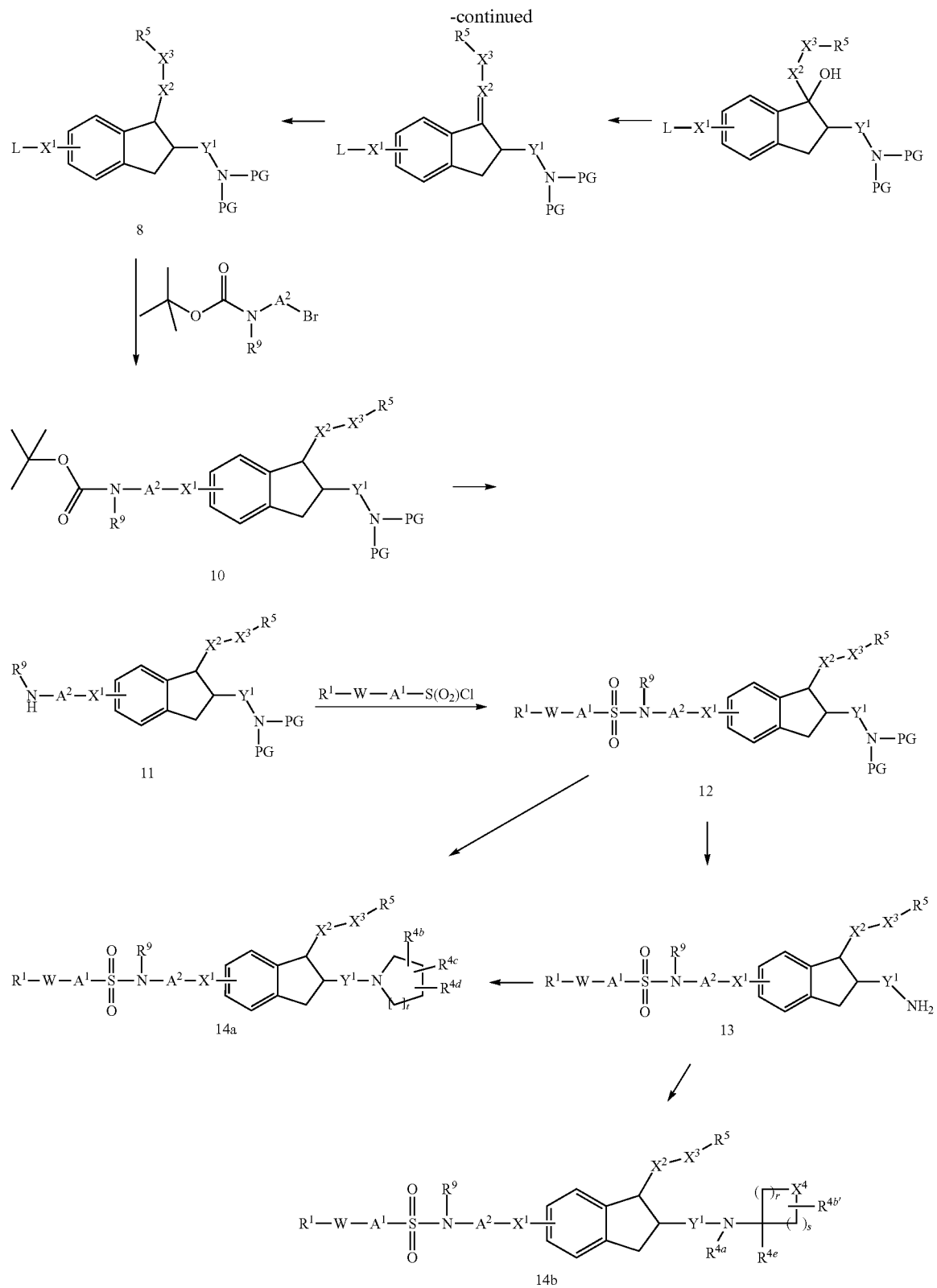

In scheme 31c, an alternative route to compounds 14 is depicted. A substituted 1-indanone can be functionalized in the 2-position after deprotonation next to the carbonyl followed by alkylation with an electrophile bearing a protected nitrogen (PG=protective group; this includes $N(PG)_2$ being nitro or the adjacent carbon in $Y^1$ and $N(PG)_2$ being nitrile). Addition of a functionalized nucleophile (e.g. Li-organyl or Grignard reagent) to the carbonyl of the 1-indanone followed by elimination and hydrogenation can yield compound 8. Standard protective group chemistry followed by alkylation, deprotection of the amine attached to $A^2$ and reaction with a substituted sulfonyl chloride can yield intermediate 12.

The nitrogen attached to $Y^1$ in compound 12 can be deprotected and substituted to yield compound 14.

In scheme 31c, the variables W, $Y^1$, $A^1$, $A^2$, $R^1$, $R^{4a}$, $R^{4b}$, $R^{4b'}$, $R^{4c}$, $R^{4d}$, $R^{4e}$, $R^5$, $R^9$, $X^1$, $X^2$, $X^3$, $X^4$, r, s, t are as defined herein and PG, L are suitable protecting groups (e.g. L=Me).

The process depicted in scheme 32 is useful for obtaining tetralines and indanes, wherein $X^1$ is —O— or —S—, $A^2$ is optionally substituted alkylene, Y is —$NR^9$—, and Q is —$S(O)_2$. $Y^1$ is optionally substituted methylene or ethylene.

Scheme 32:

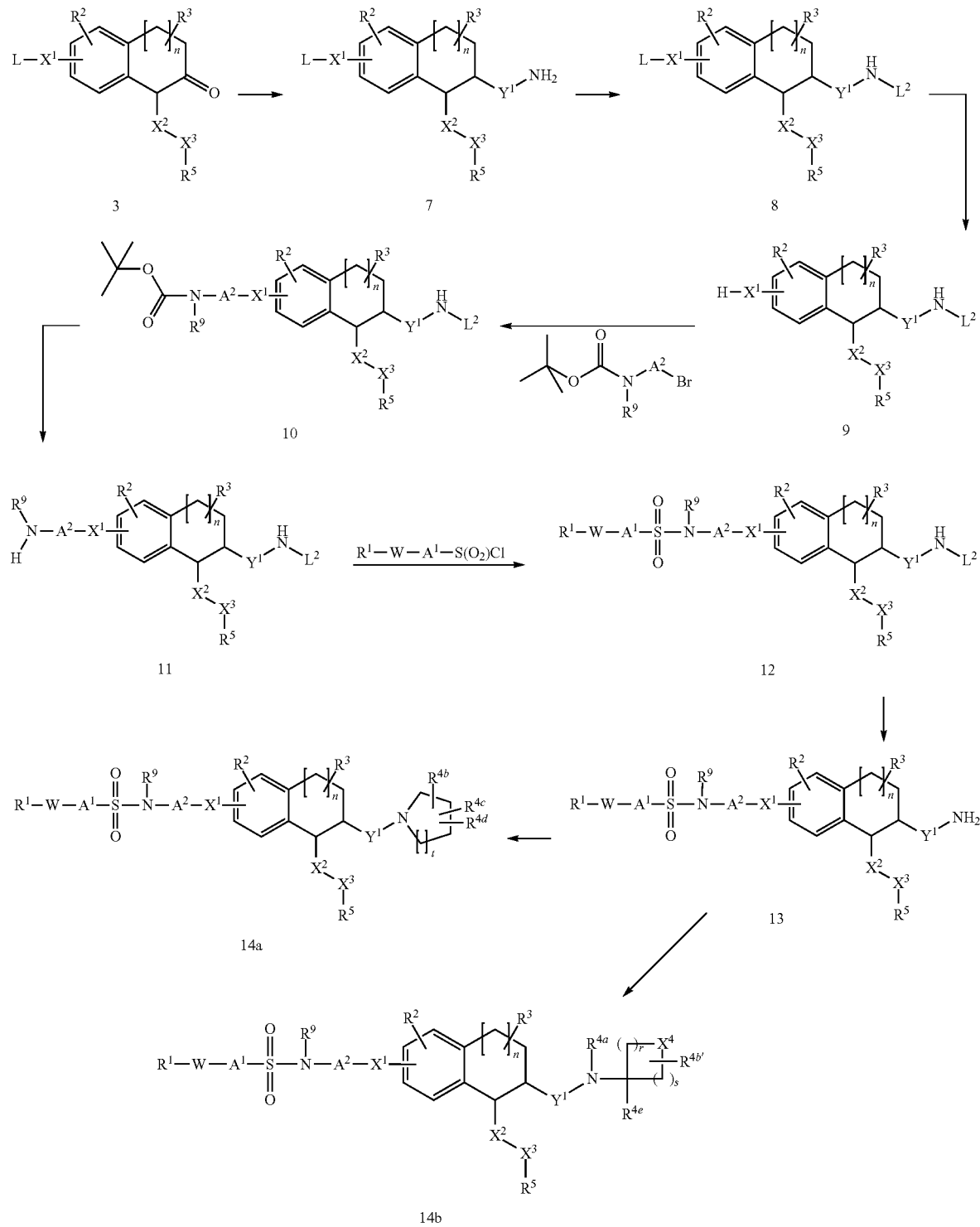

In scheme 32, the variables W, A$^1$, R$^1$, R$^2$, R$^3$, R$^{4a}$, R$^{4b}$, R$^{4b'}$, R$^{4c}$, R$^{4d}$, R$^{4e}$, R$^5$, R$^9$, X$^2$, X$^3$, X$^4$, r, s, t and n are as defined herein and L, L$^2$ are suitable protecting groups (e.g. L$^2$=COOEt).

Compounds 7 in which Y$^1$ is ethylene can be obtained from compounds 3 in analogy to the protocol described in Helv. Chim. Acta (1989), 72, 1463-70 or J. Med. Chem. (2000), 43, 4051-62 followed by reduction of the corresponding nitrile (e.g. with lithium aluminum hydride or borane tetrahydrofuran complex in tetrahydrofuran).

Compounds 7 in which Y$^1$ is methylene can be obtained from compounds 3 by Henry reaction in analogy to the protocol described in DE3901814 followed by reduction of the corresponding nitro group (e.g. catalytic hydrogenation with palladium on charcoal). Alternatively compounds 7 in which Y$^1$ is methylene can be obtained from compounds 3 in analogy to the protocol described in J. Med. Chem. (2000), 43, 4051-62 followed by Curtius rearrangement of the corresponding carboxylic acid to the amine 7.

Side chains containing R$^1$, W, A$^1$, A$^2$, X$^1$ and R$^9$ and R$^5$, X$^2$ and X$^3$ as well as the substituents R$^2$, R$^3$, R$^{4a}$ and R$^{4b}$ can be introduced analogously to the protocols described in WO2009121872.

The process depicted in scheme 32a is useful for obtaining tetralines, wherein X$^1$ is —O— or —S—, and Y is a bond.

Scheme 32a:

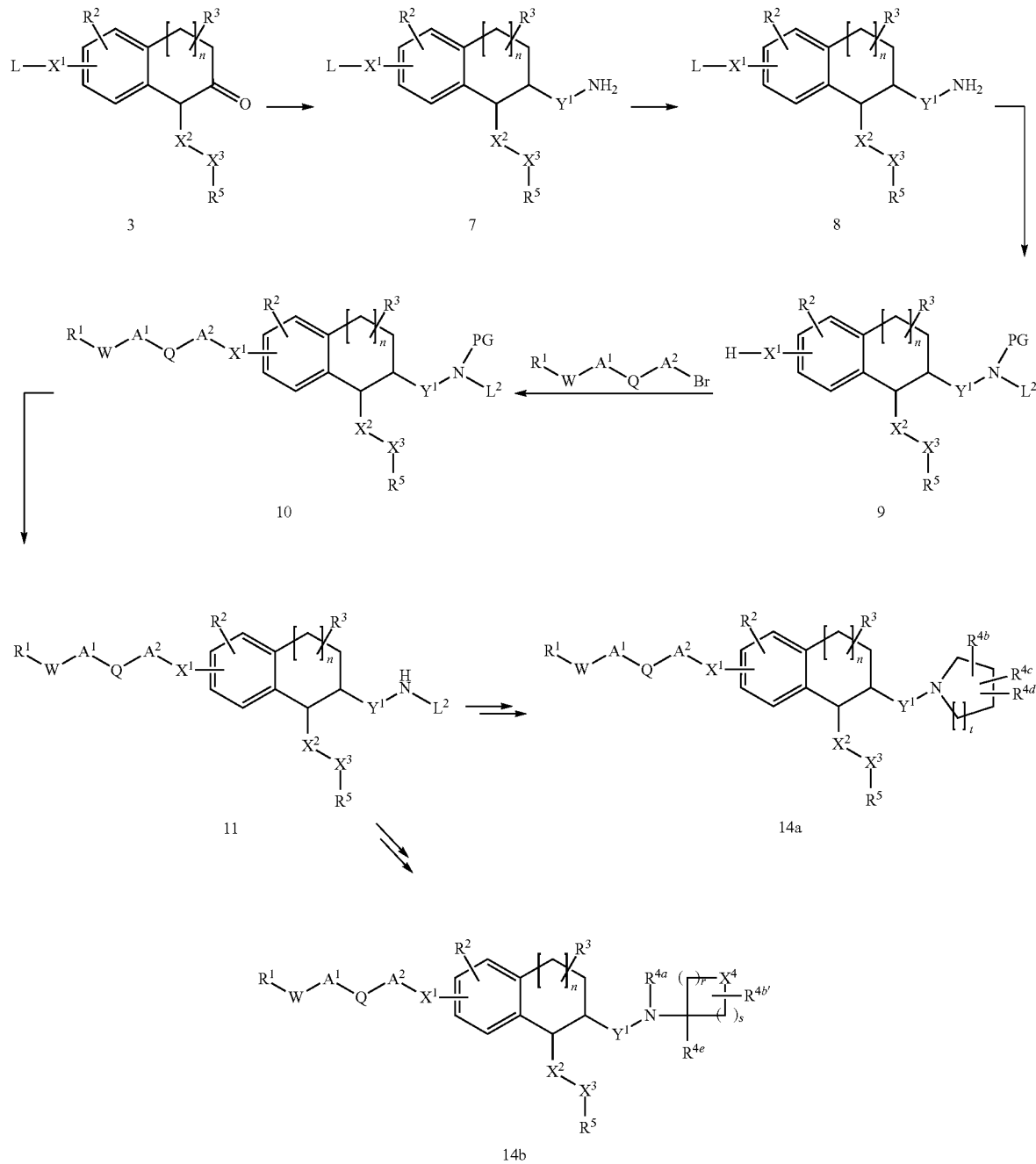

In scheme 32a, the variables W, Q, $Y^1$, $A^1$, $A^2$, $R^1$, $R^2$, $R^3$, $R^{4a}$, $R^{4b}$, $R^{4b'}$, $R^{4c}$, $R^{4d}$, $R^{4e}$, $R^5$, $X^2$, $X^3$, $X^4$, r, s, t and n are as defined herein and PG, L, $L^2$ are suitable protecting groups (e.g. $L^2$=COOEt). One example for compound $R^1$—W-$A^1$-Q-$A^2$-Br could be $CH_3$—$SO_2$—$CH_2$—$CH_2$—Br.

Further protocols for the synthesis of compounds in which Y is a bond and W is $NR^8$ are described in WO 2009/121872.

Scheme 32b:

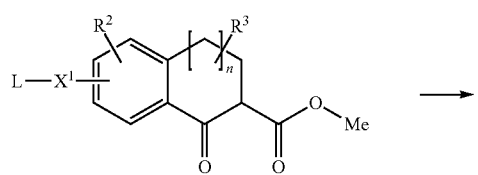

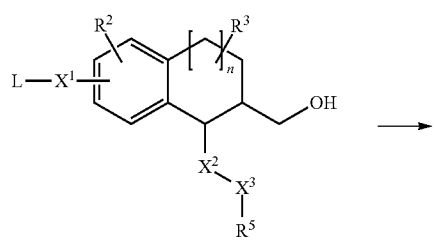

hydroxymethyl intermediate

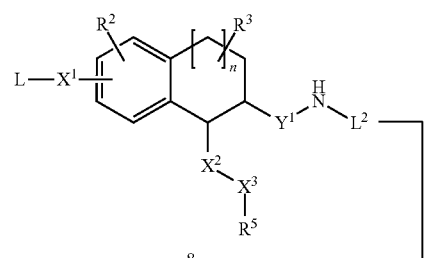

8

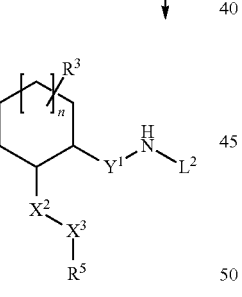

9

(e.g. hydrogenation) of the above nitriles or nitro compounds followed by protection of the corresponding amine can give the compounds 9.

In scheme 32b, $R^2$, $R^3$, $R^5$, $X^1$, $X^2$, $X^3$, n are as defined herein and L, $L^2$ are suitable protecting groups (e.g. $L^2$=COOEt).

Scheme 32c:

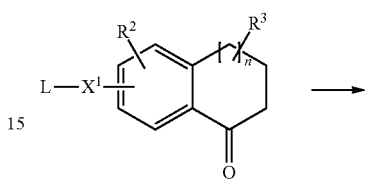

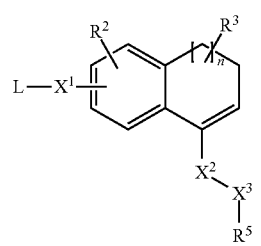

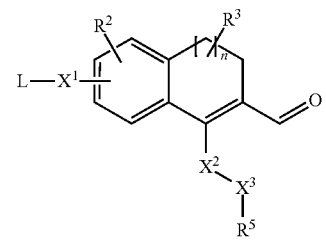

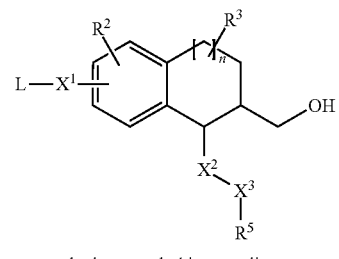

hydroxymethyl intermediate

In scheme 32b, an alternative route to compound 9 is depicted. Starting from a functionalized beta-keto ester the hydroxymethyl intermediate can be obtained in analogy to the protocols described in Bioorg. Med. Chem. Lett. 2005, 15, 1375. Compound 8 wherein $Y^1$ is a linker containing one carbon atom can be obtained in analogy to the protocols described in Bioorg. Med. Chem. Lett. 2005, 15, 1375. To obtain longer linkers $Y^1$ with two or three carbon atoms the hydroxyl group in the hydroxymethyl intermediate can either be converted to a leaving group which then can be substituted by a cyanide or the hydroxymethyl intermediate can be oxidized to an aldehyde which can be converted in a Henry reaction to the corresponding nitro compound. Reduction In scheme 32c, an alternative route to the hydroxymethyl intermediate described above is depicted. Analogously to the protocols described in Journal of Organic Chemistry (1981), 46(26), 5371, U.S. Pat. No. 4,927,838 or http://www3.interscience.wiley.com/cgibin/mrwhome/107610747/HOME the aldehyde can be obtained which upon reduction (e.g. hydrogenation) can yield the hydroxymethyl intermediate.

In scheme 32c, $R^2$, $R^3$, $R^5$, $X^1$, $X^2$, $X^3$, n are as defined herein and L is a suitable protecting group.

The process depicted in scheme 33 is useful for obtaining tetralines and indanes, wherein $X^1$ is methylene, $A^2$ is a bond, Y is —$NR^9$—, and Q is —S(O)$_2$.

Scheme 33:
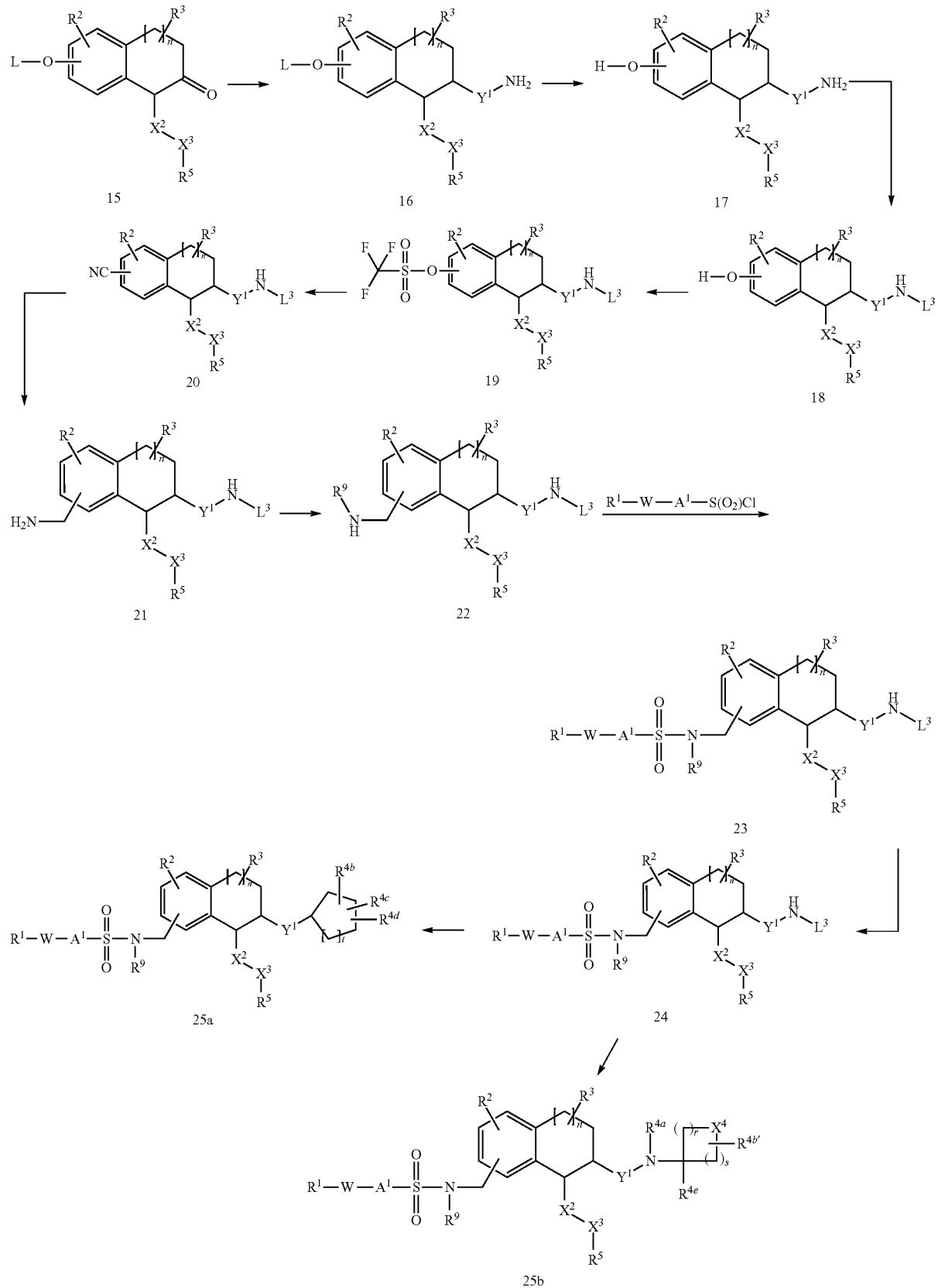

Alternatively to triflate 19, the corresponding bromide or iodide can be used to prepare compound 20.

In scheme 33, the variables W, $A^1$, $R^1$, $R^2$, $R^3$, $R^{4a}$, $R^{4b}$, $R^{4b'}$, $R^{4c}$, $R^{4d}$, $R^{4e}$, $R^5$, $R^9$, $X^2$, $X^3$, $X^4$, r, s, t and n are as defined herein, and L, $L^3$ are suitable protecting groups (e.g. $L^3$=COO$^t$Bu). $Y^1$ is optionally substituted methylene or ethylene.

Compounds 16 with $Y^1$ being methylene or ethylene can be obtained from compound 15 in a similar fashion as compounds 7 from compounds 3.

Side chains containing $R^1$, W, $A^1$, $X^1$ and $R^9$ and $R^5$, $X^2$ and $X^3$ as well as the substituents $R^2$, $R^3$, $R^{4a}$ and $R^{4b}$ can be introduced in analogy to the protocols described in WO2009/121872.

The process depicted in scheme 34 is useful for obtaining tetralines and indanes, wherein $X^1$ is optionally substituted alkylene, $A^2$ is optionally substituted alkylene or a bond, Y is —$NR^9$—, and Q is —$S(O)_2$.

Scheme 34:
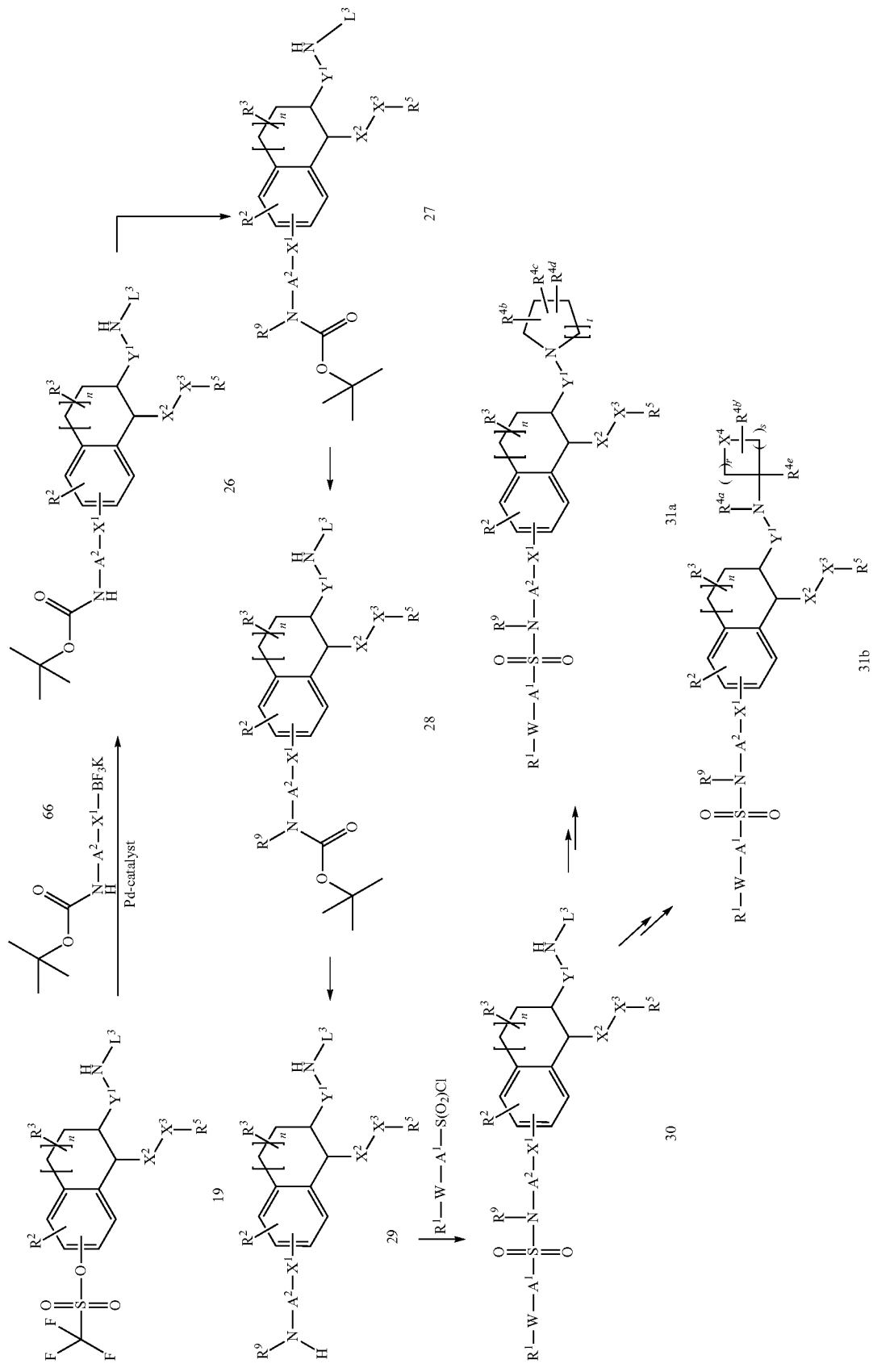

Instead of the trifluoroborate 66, the corresponding 9-borabicyclo[3.3.1]non-9-yl derivative can be used to prepare compound 26.

In scheme 34, the variables W, $A^1$, $R^1$, $R^2$, $R^3$, $R^{4a}$, $R^{4b}$, $R^{4b'}$, $R^{4c}$, $R^{4d}$, $R^{4e}$, $R^5$, $R^9$, $X^2$, $X^3$, $X^4$, r, s, t and n are as defined herein, and $L^3$ is a suitable protecting group (e.g. $L^3$=COOEt). $Y^1$ is optionally substituted methylene or ethylene.

The process depicted in scheme 35 is useful for obtaining tetralines and indanes, wherein $X^1$ is —$NR^{11}$—, $A^2$ is optionally substituted alkylene, Y is —$NR^9$—, and Q is —$S(O)_2$. $Y^1$ is optionally substituted methylene or ethylene.

Scheme 35:

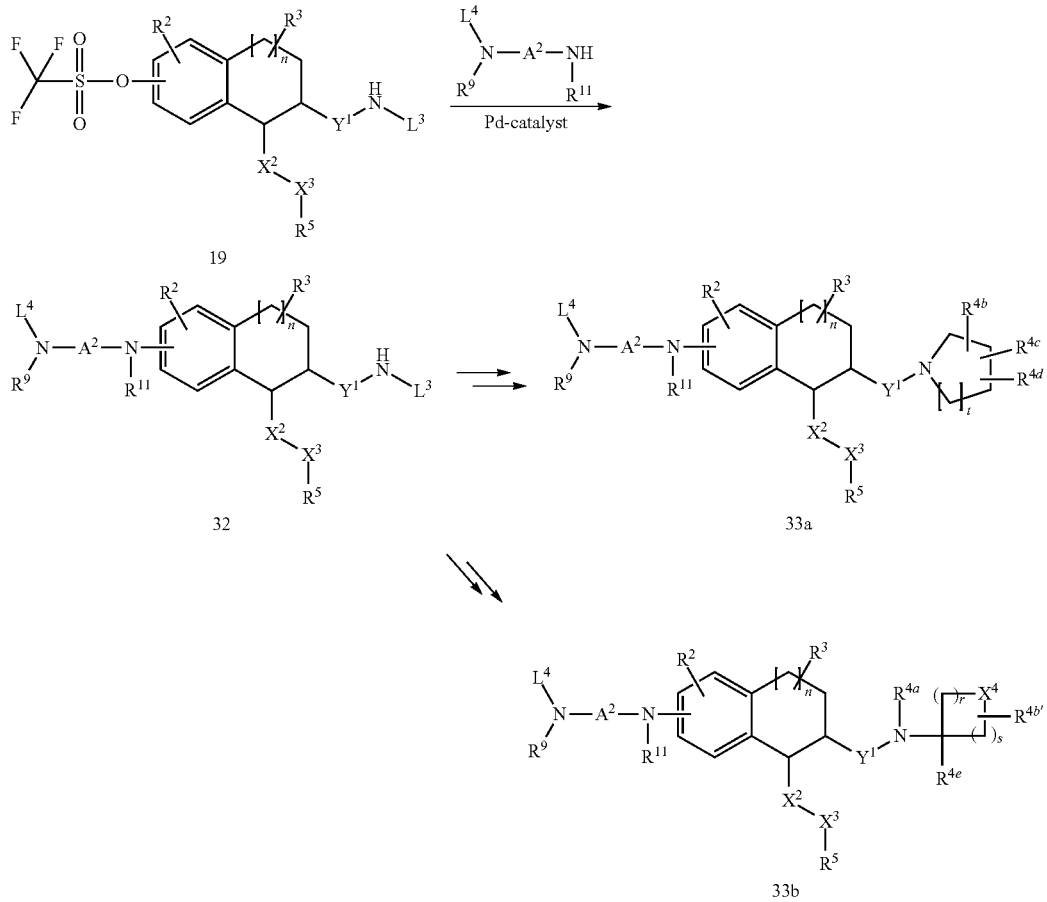

In scheme 35, the variables $R^1$, $R^2$, $R^3$, $R^{4a}$, $R^{4b}$, $R^{4b'}$, $R^{4c}$, $R^{4d}$, $R^{4e}$, $R^5$, $R^9$, $R^{11}$, $X^2$, $X^3$, $X^4$, r, s, t and n are as defined herein, and $L^3$, $L^4$ are suitable protecting groups. Scheme 35a depicts alternative routes for the synthesis of compounds 14.

Scheme 35a:

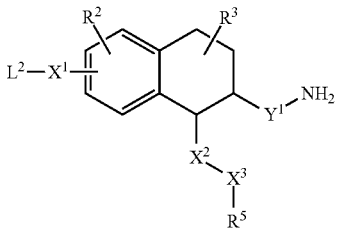

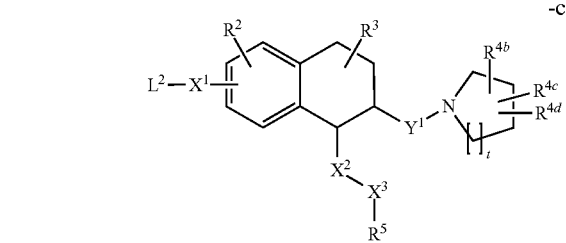
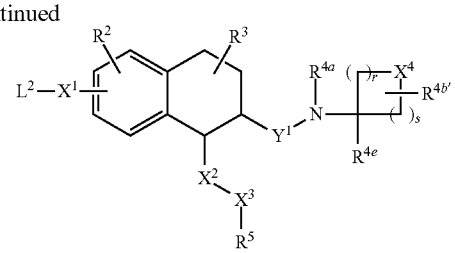
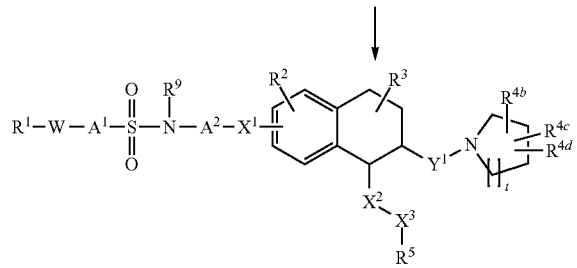
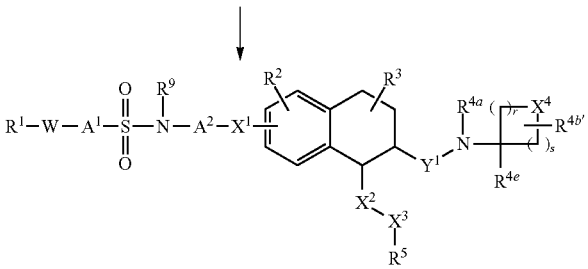
14a  14b
In scheme 35a, the variables $R^1$, W, $A^1$, $A^2$, $R^2$, $R^3$, $R^{4a}$, $R^{4b}$, $R^{4b'}$, $R^{4c}$, $R^{4d}$, $R^{4e}$, $R^5$, $R^9$, $R^{11}$, $X^2$, $X^3$, $X^4$, r, s, t and n are as defined herein, and $L^2$ is a suitable protecting group. $Y^1$ is optionally a bond, substituted methylene or ethylene.
Scheme 35b depicts alternative routes for the synthesis of compounds 14.
Scheme 35b:
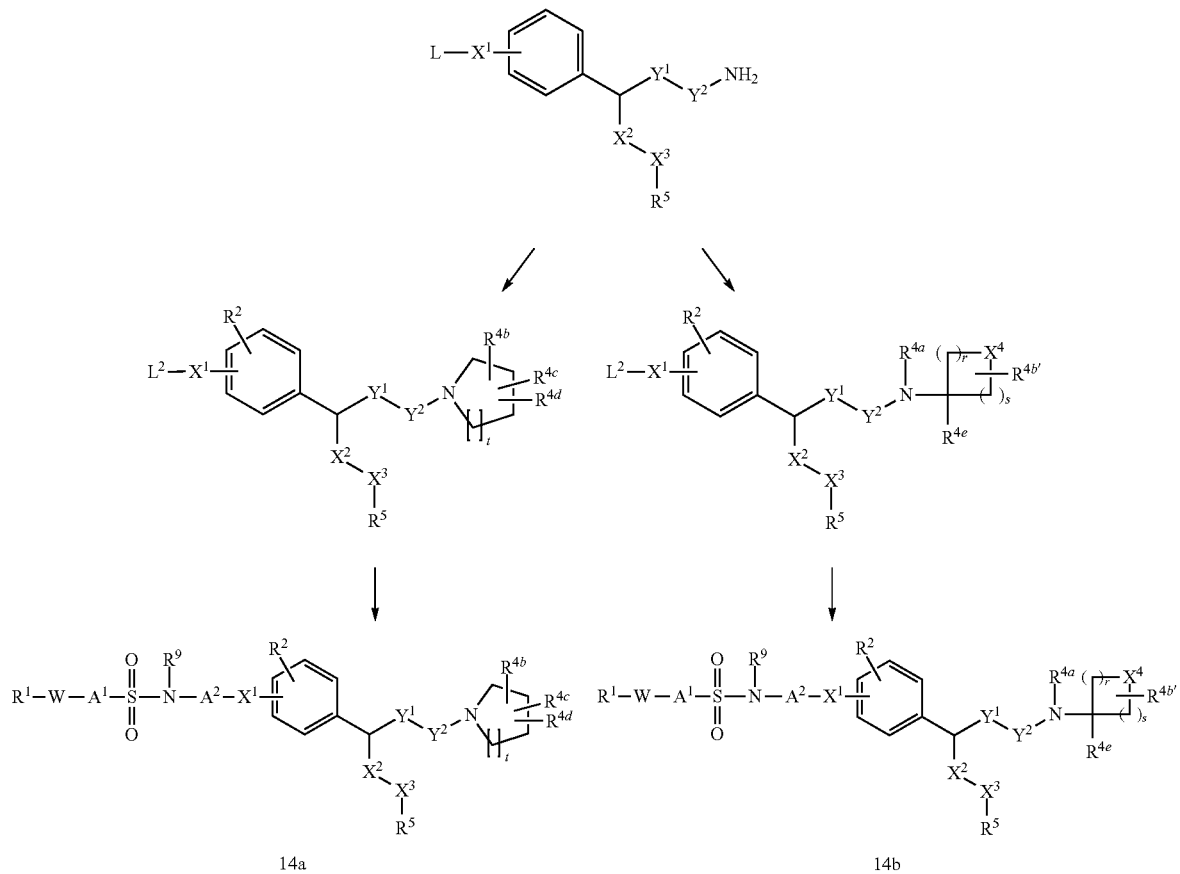
14a  14b In scheme 35b, the variables $R^1$, W, $A^1$, $A^2$, $R^2$, $R^{4a}$, $R^{4b}$, $R^{4b'}$, $R^{4c}$, $R^{4d}$, $R^{4e}$, $R^5$, $R^9$, $R^{11}$, $X^1$, $X^2$, $X^3$, $X^4$, r, s, t and n are as defined herein, and $L^2$ is a suitable protecting group. $Y^1$ is optionally a bond, substituted methylene or ethylene and $Y^2$ is a bond or substituted methylene.

The following schemes 36-40 illustrate further methods for preparing compounds of this invention.

Scheme 36:

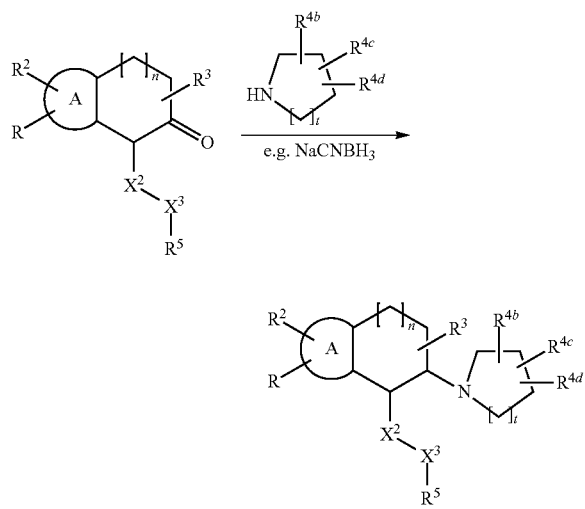

A synthetic approach to the aminotetralines is described in patent applications WO 2010092180 and WO 2009121872.

In scheme 36, the variables A, R, $R^2$, $R^3$, $R^{4b}$, $R^{4c}$, $R^{4d}$, $R^5$, $X^2$, $X^3$, t and n are as defined herein.

Scheme 37:

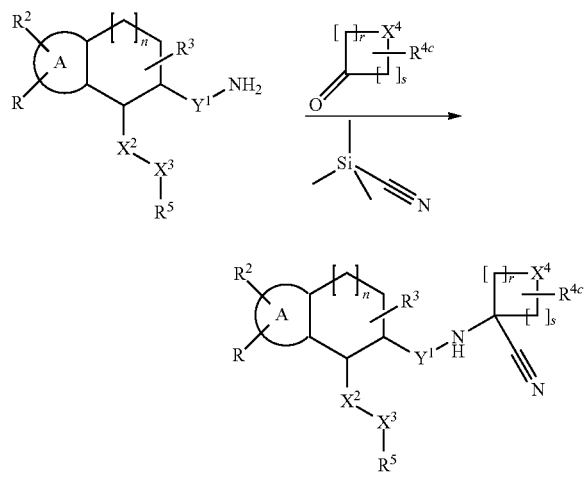

Mai, K.; Patil, G. *Synthetic Communications* 1985, 15(2), 157-163; Kolczewski, S.; Narquizian, R, Pinard, E., WO2010020548.

In scheme 37, the variables A, R, $R^2$, $R^3$, $R^{4c}$, $R^5$, $X^2$, $X^3$, $X^4$, $Y^1$, r, s and n are as defined herein.

Scheme 38:

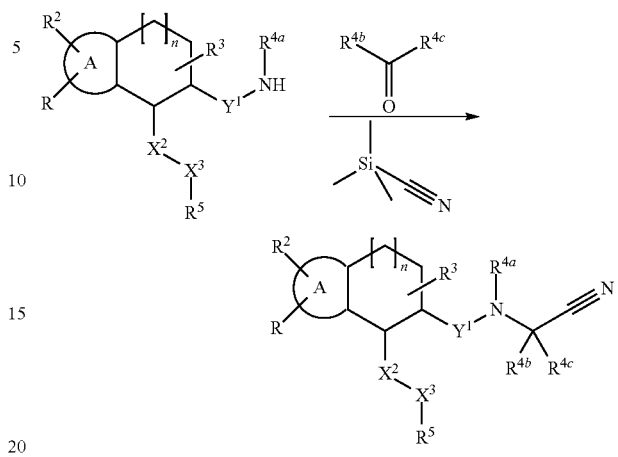

Mai, K.; Patil, G. *Synthetic communications* 1985, 15(2), 157-163; Kolczewski, S.; Narquizian, R, Pinard, E., WO2010020548.

In scheme 38, the variables A, R, $R^2$, $R^3$, $R^{4a}$, $R^{4b}$, $R^{4c}$, $R^5$, $X^2$, $X^3$, $Y^1$ and n are as defined herein.

Scheme 39:

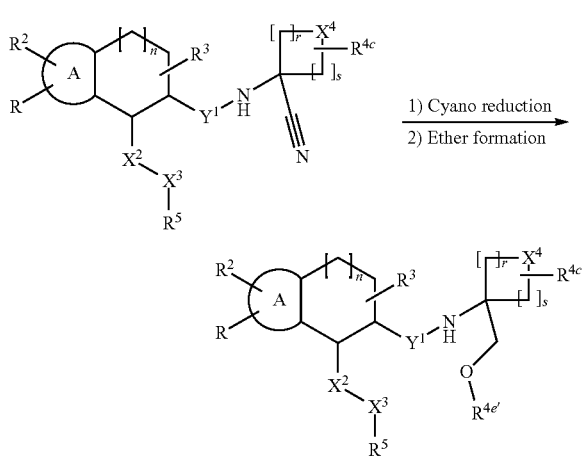

Thompson, H. W.; Rashid, S. Y. *Journal of Organic Chemistry* 2002, 67(9), 2813-2825.

In scheme 39, the variables A, R, $R^2$, $R^3$, $R^{4c}$, $R^{4e'}$, $R^5$, $X^2$, $X^3$, $X^4$, $Y^1$, r, s and n are as defined herein.

Scheme 40:

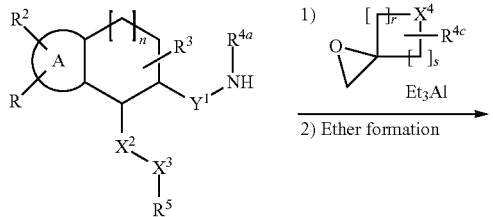

-continued

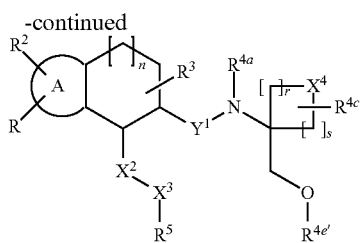

Reddy, K. S.; Solà, L I., Moyano, A.; Pericás, M. A.; Riera, A. *Synthesis* 2000, (1), 165-176.

In scheme 40, the variables A, R, $R^2$, $R^3$, $R^{4a}$, $R^{4c}$, $R^{4e'}$, $R^5$, $X^2$, $X^3$, $X^4$, $Y^1$, r, s and n are as defined herein.

The compounds of formula (V) and (VI)

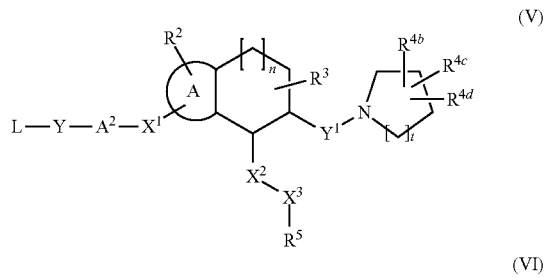
(V)

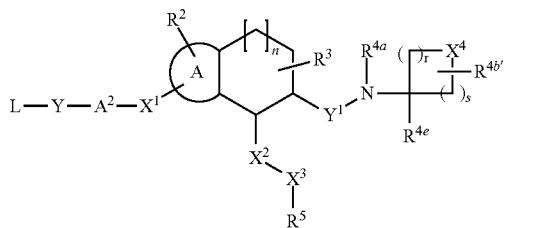
(VI)

wherein L is an amino-protecting group, Y is —$NR^9$—, and A, $A^2$, $X^1$, $R^2$, $R^3$, $Y^1$, r, s, t, $R^{4a}$, $R^{4b}$, $R^{4b'}$, $R^{4c}$, $R^{4d}$, $R^{4e}$, $X^2$, $X^3$, $X^4$, $R^5$, n, $R^9$ are defined as herein are useful as intermediates in the preparation of GlyT1 inhibitors, in particular those of formula (I).

Suitable amino-protecting groups are well known in the art such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991.

According to a particular embodiment, L is optionally substituted alkylcarbonyl (e.g., tert-butylcarbonyl), optionally substituted arylcarbonyl, optionally substituted arylalkycarbonyl (e.g., benzylcarbonyl), optionally substituted alkoxycarbonyl (e.g., methoxycarbonyl or tert-butyloxycarbonyl), optionally substituted aryloxycarbonyl (e.g. phenoxycarbonyl) or optionally substituted arylalkoxycarbonyl.

The compounds of the formula (I), (II), (III) or (IV) are capable of inhibiting the activity of glycine transporter, in particular glycine transporter 1 (GlyT1).

The utility of the compounds in accordance with the present invention as inhibiting the glycine transporter activity, in particular GlyT1 activity, may be demonstrated by methodology known in the art. For instance, human GlyT1c expressing recombinant hGlyT1c_5_CHO cells can be used for measuring glycine uptake and its inhibition ($IC_{50}$) by a compound of formula (I), (II), (III) or (IV).

Amongst the compounds of the formula (I), (II), (III) or (IV) those are preferred which achieve effective inhibition at low concentrations. In particular, compounds of the formula (I), (II), (III) or (IV) are preferred which inhibit glycine transporter 1 (GlyT1) at a level of $IC_{50}$<1 µMol, more preferably at a level of $IC_{50}$<0.5 µMol, particularly preferably at a level of $IC_{50}$<0.2 µMol and most preferably at a level of $IC_{50}$<0.1 µMol.

The compounds of formula (I), (II), (III) or (IV) may exhibit favorable efflux properties which may lead to enhanced oral bioavailability and/or increased brain availability.

The efflux properties of a compound can be measured in well-known assays (e.g. Caco-2, MDCK assay).

The compounds of the formula (I), (II), (III) or (IV) according to the present invention are thus useful as pharmaceuticals.

The present invention therefore also relates to pharmaceutical compositions which comprise an inert carrier and a compound of the formula (I), (II), (III) or (IV).

The present invention also relates to the use of the compounds of the formula (I), (II), (III) or (IV) in the manufacture of a medicament for inhibiting the glycine transporter GlyT1, and to corresponding methods of inhibiting the glycine transporter GlyT1.

The NMDA receptor is central to a wide range of CNS processes, and its role in a variety of diseases in humans or other species has been described. GlyT1 inhibitors slow the removal of glycine from the synapse, causing the level of synaptic glycine to rise. This in turn increases the occupancy of the glycine binding site on the NMDA receptor, which increases activation of the NMDA receptor following glutamate release from the presynaptic terminal. Glycine transport inhibitors and in particular inhibitors of the glycine transporter GlyT1 are thus known to be useful in treating a variety of neurologic and psychiatric disorders. Further, glycine A receptors play a role in a variety of diseases in humans or other species. Increasing extracellular glycine concentrations by inhibiting glycine transport may enhance the activity of glycine A receptors. Glycine transport inhibitors and in particular inhibitors of the glycine transporter GlyT1 are thus useful in treating a variety of neurologic and psychiatric disorders.

The present invention thus further relates to the use of the compounds of the formula (I), (II), (III) or (IV) for the manufacture of a medicament for treating a neurologic or psychiatric disorder, and to corresponding methods of treating said disorders.

According to a particular embodiment, the disorder is associated with glycinergic or glutamatergic neurotransmission dysfunction.

According to a further particular embodiment, the disorder is one or more of the following conditions or diseases: schizophrenia or a psychotic disorder including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder, including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or cognitive impairment including age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention deficit disorders including attention-deficit hyperactivity disorder (ADHD) and conduct disorder; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

According to a further particular embodiment, the disorder is pain, in particular chronic pain and especially neuropathic pain.

Pain can be classified as acute and chronic pain. Acute pain and chronic pain differ in their etiology, pathophysiology, diagnosis and treatment.

Acute pain, which occurs following tissue injury, is self-limiting, serves as an alert to ongoing tissue damage and following tissue repair it will usually subside. There are minimal psychological symptoms associated with acute pain apart from mild anxiety. Acute pain is nociceptive in nature and occurs following chemical, mechanical and thermal stimulation of A-delta and C-polymodal pain receptors.

Chronic pain, on the other hand, serves no protective biological function. Rather than being the symptom of tissue damage it is a disease in its own right. Chronic pain is unrelenting and not self-limiting and can persist for years, perhaps decades after the initial injury. Chronic pain can be refractory to multiple treatment regimes. Psychological symptoms associated with chronic pain include chronic anxiety, fear, depression, sleeplessness and impairment of social interaction. Chronic non-malignant pain is predominantly neuropathic in nature and involves damage to either the peripheral or central nervous systems.

Acute pain and chronic pain are caused by different neurophysiological processes and therefore tend to respond to different types of treatments. Acute pain can be somatic or visceral in nature. Somatic pain tends to be a well localised, constant pain and is described as sharp, aching, throbbing or gnawing. Visceral pain, on the other hand, tends to be vague in distribution, paroxysmal in nature and is usually described as deep, aching, squeezing or colicky in nature. Examples of acute pain include post-operative pain, pain associated with trauma and the pain of arthritis. Acute pain usually responds to treatment with opioids or non-steroidal anti-inflammatory drugs.

Chronic pain, in contrast to acute pain, is described as burning, electric, tingling and shooting in nature. It can be continuous or paroxysmal in presentation. The hallmarks of chronic pain are chronic allodynia and hyperalgesia. Allodynia is pain resulting from a stimulus that normally does not ellicit a painful response, such as a light touch. Hyperalgesia is an increased sensitivity to normally painful stimuli. Primary hyperalgesia occurs immediately within the area of the injury. Secondary hyperalgesia occurs in the undamaged area surrounding the injury. Examples of chronic pain include complex regional pain syndrome, pain arising from peripheral neuropathies, post-operative pain, chronic fatigue syndrome pain, tension-type headache, pain arising from mechanical nerve injury and severe pain associated with diseases such as cancer, metabolic disease, neurotropic viral disease, neurotoxicity, inflammation, multiple sclerosis or any pain arising as a consequence of or associated with stress or depressive illness.

Although opioids are cheap and effective, serious and potentially life-threatening side effects occur with their use, most notably respiratory depression and muscle rigidity. In addition the doses of opioids which can be administered are limited by nausea, emesis, constipation, pruritis and urinary retention, often resulting in patients electing to receive suboptimal pain control rather than suffer these distressing side-effects. Furthermore, these side-effects often result in patients requiring extended hospitalisation. Opioids are highly addictive and are scheduled drugs in many territories.

The compounds of formula (I) are particularly useful in the treatment of schizophrenia, bipolar disorder, depression including unipolar depression, seasonal depression and post-partum depression, premenstrual syndrome (PMS) and premenstrual dysphoric disorder (PDD), learning disorders, pervasive developmental disorder including autistic disorder, attention deficit disorders including Attention-Deficit/Hyperactivity Disorder, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

Particular cognitive disorders are dementia, delirium, amnestic disorders and cognitive impartment including age-related cognitive decline.

Particular anxiety disorders are generalized anxiety disorder, obsessive-compulsive disorder and panic attack.

Particular schizophrenia or psychosis pathologies are paranoid, disorganized, catatonic or undifferentiated schizophrenia and substance-induced psychotic disorder.

Particular neurologic disorders that can be treated with the compounds of the formula (I), (II), (III) or (IV) include in particular a cognitive disorder such as dementia, cognitive impairment, attention deficit hyperactivity disorder.

Particular psychiatric disorders that can be treated with the compounds of the formula (I), (II), (III) or (IV) include in particular an anxiety disorder, a mood disorder such as depression or a bipolar disorder, schizophrenia, a psychotic disorder.

Within the context of the treatment, the use according to the invention of the compounds of the formula (I), (II), (III) or (IV) involves a method. In this method, an effective quantity of one or more compounds or the formula (I), (II), (III) or (IV), as a rule formulated in accordance with pharmaceutical and veterinary practice, is administered to the individual to be treated, preferably a mammal, in particular a human being. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other drugs or drug-containing preparations.

The invention also relates to the manufacture of pharmaceutical compositions for treating an individual, preferably a mammal, in particular a human being. Thus, the compounds of the formula (I), (II), (III) or (IV) are customarily administered in the form of pharmaceutical compositions which comprise an inert carrier (e.g. a pharmaceutically acceptable excipient) together with at least one compound according to the invention and, where appropriate, other drugs. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more carriers (excipients). Carriers (excipients) can be solid, semisolid or liquid materials which serve as vehicles, carriers or medium for the active compound.

Suitable carriers (excipients) are listed in the specialist medicinal monographs. In addition, the formulations can comprise pharmaceutically acceptable auxiliary substances, such as wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], $4^{th}$ edition, Aulendorf: ECV-Editio-Cantor-Verlag, 1996.

The compounds of formula (I), (II), (III) or (IV) may also be suitable for combination with other therapeutic agents.

Thus, the present invention also provides:

i) a combination comprising a compound of formula (I), (II), (III) or (IV) with one or more further therapeutic agents;

ii) a pharmaceutical composition comprising a combination product as defined in i) above and at least one carrier, diluent or excipient;

iii) the use of a combination as defined in i) above in the manufacture of a medicament for treating or preventing a disorder, disease or condition as defined herein;

iv) a combination as defined in i) above for use in treating or preventing a disorder, disease or condition as defined herein;

v) a kit-of-parts for use in the treatment of a disorder, disease or condition as defined herein, comprising a first dosage form comprising a compound of formula (I) and one or more further dosage forms each comprising one or more further therapeutic agents for simultaneous therapeutic administration, vi) a combination as defined in i) above for use in therapy;

vii) a method of treatment or prevention of a disorder, disease or condition as defined herein comprising administering an effective amount of a combination as defined in i) above;

viii) a combination as defined in i) above for treating or preventing a disorder, disease or condition as defined herein.

The combination therapies of the invention may be administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of formula (I), (II), (III) or (IV) and at least one further therapeutic agent are within the scope of the current invention. In one embodiment of adjunctive therapeutic administration as described herein, a patient is typically stabilised on a therapeutic administration of one or more of the components for a period of time and then receives administration of another component.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

In a further aspect, the invention provides a method of treatment of a psychotic disorder by adjunctive therapeutic administration of compounds of formula (I), (II), (III) or (IV) to a patient receiving therapeutic administration of at least one antipsychotic agent. In a further aspect, the invention provides the use of compounds of formula (I), (II), (III) or (IV) in the manufacture of a medicament for adjunctive therapeutic administration for the treatment of a psychotic disorder in a patient receiving therapeutic administration of at least one antipsychotic agent. The invention further provides compounds of formula (I), (II), (III) or (IV) for use for adjunctive therapeutic administration for the treatment of a psychotic disorder in a patient receiving therapeutic administration of at least one antipsychotic agent.

In a further aspect, the invention provides a method of treatment of a psychotic disorder by adjunctive therapeutic administration of at least one antipsychotic agent to a patient receiving therapeutic administration of compounds of formula (I), (II), (III) or (IV). In a further aspect, the invention provides the use of at least one antipsychotic agent in the manufacture of a medicament for adjunctive therapeutic administration for the treatment of a psychotic disorder in a patient receiving therapeutic administration of compounds of formula (I). The invention further provides at least one antipsychotic agent for adjunctive therapeutic administration for the treatment of a psychotic disorder in a patient receiving therapeutic administration of compounds of formula (I), (II), (III) or (IV).

In a further aspect, the invention provides a method of treatment of a psychotic disorder by simultaneous therapeutic administration of compounds of formula (I), (II), (III) or (IV) in combination with at least one antipsychotic agent. The invention further provides the use of a combination of compounds of formula (I), (II), (III) or (IV) and at least one antipsychotic agent in the manufacture of a medicament for simultaneous therapeutic administration in the treatment of a psychotic disorder. The invention further provides a combination of compounds of formula (I), (II), (III) or (IV) and at least one antipsychotic agent for simultaneous therapeutic administration in the treatment of a psychotic disorder. The invention further provides the use of compounds of formula (I), (II), (III) or (IV) in the manufacture of a medicament for simultaneous therapeutic administration with at least one antipsychotic agent in the treatment of a psychotic disorder. The invention further provides compounds of formula (I), (II), (III) or (IV) for use for simultaneous therapeutic administration with at least one antipsychotic agent in the treatment of a psychotic disorder. The invention further provides the use of at least one antipsychotic agent in the manufacture of a medicament for simultaneous therapeutic administration with compounds of formula (I), (II), (III) or (IV) in the treatment of a psychotic disorder. The invention further provides at least one antipsychotic agent for simultaneous therapeutic administration with compounds of formula (I), (II), (III) or (IV) in the treatment of a psychotic disorder.

In further aspects, the invention provides a method of treatment of a psychotic disorder by simultaneous therapeutic administration of a pharmaceutical composition comprising compounds of formula (I), (II), (III) or (IV) and at least one mood stabilising or antimanic agent, a pharmaceutical composition comprising compounds of formula (I), (II), (III) or (IV) and at least one mood stabilising or antimanic agent, the use of a pharmaceutical composition comprising compounds of formula (I), (II), (III) or (IV) and at least one mood stabilising or antimanic agent in the manufacture of a medicament for the treatment of a psychotic disorder, and a pharmaceutical composition comprising compounds of formula (I), (II), (III) or (IV) and at least one mood stabilising or antimanic agent for use in the treatment of a psychotic disorder.

Antipsychotic agents include both typical and atypical antipsychotic drugs. Examples of antipsychotic drugs that are useful in the present invention include, but are not limited to: butyrophenones, such as haloperidol, pimozide, and droperidol; phenothiazines, such as chlorpromazine, thioridazine, mesoridazine, trifluoperazine, perphenazine, fluphenazine, thiflupromazine, prochlorperazine, and acetophenazine; thioxanthenes, such as thiothixene and chlorprothixene; thienobenzodiazepines; dibenzodiazepines; benzisoxazoles; dibenzothiazepines; imidazolidinones; benziso-thiazolyl-piperazines; triazine such as lamotrigine; dibenzoxazepines, such as loxapine; dihydroindolones, such as molindone; aripiprazole; and derivatives thereof that have antipsychotic activity.

Examples of tradenames and suppliers of selected antipsychotic drugs are as follows: clozapine (available under the tradename CLOZARIL®, from Mylan, Zenith Goldline, UDL, Novartis); olanzapine (available under the tradename ZYPREX®, from Lilly); ziprasidone (available under the tradename GEODON®, from Pfizer); risperidone (available under the tradename RISPERDAL®, from Janssen); quetiapine fumarate (available under the tradename SEROQUEL®, from AstraZeneca); haloperidol (available under the tradename HALDOL®, from Ortho-McNeil); chlorpromazine (available under the tradename THORAZINE®, from SmithKline Beecham (GSK)); fluphenazine (available under the tradename PROLIXIN®, from Apothecon, Copley, Schering, Teva, and American Pharmaceutical Partners, Pasadena); thiothixene (available under the tradename NAVANE®, from Pfizer); trifluoperazine (10-[3-(4-methyl-1-piperazinyl)propyl]-2-(trifluoromethyl)phenothiazine dihydrochloride, available under the tradename STELAZINE®, from Smith Klein Beckman); perphenazine (available under the tradename TRILAFON®; from Schering); thioridazine (available under the tradename MELLARIL®; from Novartis, Roxane, HiTech, Teva, and Alpharma); molindone (available under the tradename MOBAN®, from Endo); and loxapine (available under the tradename LOXITANE (D; from Watson). Furthermore, benperidol (Glianimon®), perazine (Taxilan®) or melperone (Eunerpan®) may be used. Other antipsychotic drugs include promazine (available under the tradename SPARINE®), triflurpromazine (available under the tradename VESPRI N®), chlorprothixene (available under the tradename TARACTAN®), droperidol (available under the tradename INAPSINE®), acetophenazine (available under the tradename TINDAL®), prochlorperazine (available under the tradename COMPAZINE®), methotrimeprazine (available under the tradename NOZINAN®), pipotiazine (available under the tradename PIPOTRIL®), ziprasidone, and hoperidone.

In a further aspect, the invention provides a method of treatment of a neurodegenerative disorder such as Alzheimer Disease by adjunctive therapeutic administration of compounds of formula (I), (II), (III) or (IV) to a patient receiving therapeutic administration of at least one agent suitable for the treatment of a neurodegenerative disorder such as Alzheimer Disease. In a further aspect, the invention provides the use of compounds of formula (I), (II), (III) or (IV) in the manufacture of a medicament for adjunctive therapeutic administration for the treatment of a neurodegenerative disorder such as Alzheimer Disease in a patient receiving therapeutic administration of at least one agent suitable for the treatment of a neurodegenerative disorder such as Alzheimer Disease. The invention further provides compounds of formula (I), (II), (III) or (IV) for use for adjunctive therapeutic administration for the treatment of a neurodegenerative disorder such as Alzheimer Disease in a patient receiving therapeutic administration of at least one agent suitable for the treatment of a neurodegenerative disorder such as Alzheimer Disease.

In a further aspect, the invention provides a method of treatment of a neurodegenerative disorder such as Alzheimer Disease by adjunctive therapeutic administration of at least one agent suitable for the treatment of a neurodegenerative disorder such as Alzheimer Disease to a patient receiving therapeutic administration of compounds of formula (I), (II), (III) or (IV). In a further aspect, the invention provides the use of at least one agent suitable for the treatment of a neurodegenerative disorder such as Alzheimer Disease in the manufacture of a medicament for adjunctive therapeutic administration for the treatment of a neurodegenerative disorder such as Alzheimer Disease in a patient receiving therapeutic administration of compounds of formula (I), (II), (III) or (IV). The invention further provides at least one agent suitable for the treatment of a neurodegenerative disorder such as Alzheimer Disease for adjunctive therapeutic administration for the treatment of a neurodegenerative disorder such as Alzheimer Disease in a patient receiving therapeutic administration of compounds of formula (I), (II), (III) or (IV).

In a further aspect, the invention provides a method of treatment of a neurodegenerative disorder such as Alzheimer Disease by simultaneous therapeutic administration of compounds of formula (I), (II), (III) or (IV) in combination with at least one agent suitable for the treatment of a neurodegenerative disorder such as Alzheimer Disease. The invention further provides the use of a combination of compounds of formula (I), (II), (III) or (IV) and at least one agent suitable for the treatment of a neurodegenerative disorder such as Alzheimer Disease in the manufacture of a medicament for simultaneous therapeutic administration in the treatment of a neurodegenerative disorder such as Alzheimer Disease. The invention further provides a combination of compounds of formula (I), (II), (III) or (IV) and at least one agent suitable for the treatment of a neurodegenerative disorder such as Alzheimer Disease for simultaneous therapeutic administration in the treatment of a neurodegenerative disorder such as Alzheimer Disease. The invention further provides the use of compounds of formula (I), (II), (III) or (IV) in the manufacture of a medicament for simultaneous therapeutic administration with at least one agent suitable for the treatment of a neurodegenerative disorder such as Alzheimer Disease in the treatment of a neurodegenerative disorder such as Alzheimer Disease. The invention further provides compounds of formula (I), (II), (III) or (IV) for use for simultaneous therapeutic administration with at least one agent suitable for the treatment of a neurodegenerative disorder such as Alzheimer Disease in the treatment of a neurodegenerative disorder such as Alzheimer Disease. The invention further provides the use of at least one agent suitable for the treatment of a neurodegenerative disorder such as Alzheimer Disease in the manufacture of a medicament for simultaneous therapeutic administration with compounds of formula (I), (II), (III) or (IV) in the treatment of a neurodegenerative disorder such as Alzheimer Disease. The invention further provides at least one agent suitable for the treatment of a neurodegenerative disorder such as Alzheimer Disease for simultaneous therapeutic administration with compounds of formula (I), (II), (III) or (IV) in the treatment of a neurodegenerative disorder such as Alzheimer Disease.

Examples of agents suitable for the treatment of a neurodegenerative disorder such as Alzheimer Disease that are useful in the present invention include, but are not limited to: cholinesterase inhibitors, agents targeting nicotinic or muscarinic acetylcholine receptors, NMDA receptors, amyloid formation, mitochondrial dysfunctions, disease associated calpain activity, neuroinflamation, tumor necrosis factor receptors, NF-kappaB, peroxisome proliferator activator receptor gamma, Apolipoprotein E variant 4 (ApoE4), disease-associated increase of the HPA axis, epileptic discharges, vascular dysfunction, vascular risk factors, and oxidative stress.

Suitable cholinesterase inhibitors which may be used in combination with the compounds of the inventions include for example tacrine, donepezil, galantamine and rivastigmine.

Suitable NMDA receptors targeting agents which may be used in combination with the compounds of the inventions include for example memantine.

Suitable agents affecting increased HPA axis activity which may be used in combination with the compounds of the inventions include for example CRF1 antagonists or V1b antagonists.

In a further aspect therefore, the invention provides a method of treatment of pain by adjunctive therapeutic administration of compounds of formula (I), (II), (III) or (IV) to a patient receiving therapeutic administration of at least one agent suitable for the treatment of pain. In a further aspect, the invention provides the use of compounds of formula (I), (II), (III) or (IV) in the manufacture of a medicament for adjunctive therapeutic administration for the treatment of pain in a patient receiving therapeutic administration of at least one agent suitable for the treatment of pain. The invention further provides compounds of formula (I), (II), (III) or (IV) for use for adjunctive therapeutic administration for the treatment of pain in a patient receiving therapeutic administration of at least one agent suitable for the treatment of pain.

In a further aspect, the invention provides a method of treatment of pain by adjunctive therapeutic administration of at least one agent suitable for the treatment of pain to a patient receiving therapeutic administration of compounds of formula (I), (II), (III) or (IV). In a further aspect, the invention provides the use of at least one agent suitable for the treatment of pain in the manufacture of a medicament for adjunctive therapeutic administration for the treatment of pain in a patient receiving therapeutic administration of compounds of formula (I) or (II). The invention further provides at least one agent suitable for the treatment of pain for adjunctive therapeutic administration for the treatment of pain in a patient receiving therapeutic administration of compounds of formula (I), (II), (III) or (IV).

In a further aspect, the invention provides a method of treatment of pain by simultaneous therapeutic administration of compounds of formula (I), (II), (III) or (IV) in combination with at least one agent suitable for the treatment of pain. The invention further provides the use of a combination of compounds of formula (I), (II), (III) or (IV) and at least one agent suitable for the treatment of pain in the manufacture of a medicament for simultaneous therapeutic administration in the treatment of pain. The invention further provides a combination of compounds of formula (I), (II), (III) or (IV) and at least one agent suitable for the treatment of pain for simultaneous therapeutic administration in the treatment of pain. The invention further provides the use of compounds of formula (I), (II), (III) or (IV) in the manufacture of a medicament for simultaneous therapeutic administration with at least one agent suitable for the treatment of pain in the treatment of pain. The invention further provides compounds of formula (I) for use for simultaneous therapeutic administration with at least one agent suitable for the treatment of pain in the treatment of pain. The invention further provides the use of at least one agent suitable for the treatment of pain in the manufacture of a medicament for simultaneous therapeutic administration with compounds of formula (I), (II), (III) or (IV) in the treatment of pain. The invention further provides at least one agent suitable for the treatment of pain for simultaneous therapeutic administration with compounds of formula (I), (II), (III) or (IV) in the treatment of pain.

Examples of agents suitable for the treatment of pain that are useful in the present invention include, but are not limited to: NSAIDs (Nonsteroidal Antiinflammatory Drugs), anticonvulsant drugs such as carbamazepine and gabapentin, sodium channel blockers, anti-depressant drugs, cannabinoids and local anaesthetics.

Suitable agents used in combination with the compounds of the inventions include for example celecoxib, etoricoxib, lumiracoxib, paracetamol, tramadol, methadone, venlafaxine, imipramine, duloxetine, bupropion, gabapentin, pregabalin, lamotrigine, fentanyl, parecoxib, nefopam, remifentanil, pethidine, diclofenac, rofecoxib, nalbuphine, sufentanil, pethidine, diamorphine and butorphanol.

It will be appreciated by those skilled in the art that the compounds according to the invention may advantageously be used in conjunction with one or more other therapeutic agents, for instance, antidepressant agents such as 5HT3 antagonists, serotonin agonists, NK-1 antagonists, selective serotonin reuptake inhibitors (SSRI), noradrenaline re-uptake inhibitors (SNRI), tricyclic antidepressants, dopaminergic antidepressants, H3 antagonists, 5HT1A antagonists, 5HT1 B antagonists, 5HT1 D antagonists, D1 agonists, M1 agonists and/or anticonvulsant agents, as well as cognitive enhancers.

Suitable 5HT3 antagonists which may be used in combination of the compounds of the inventions include for example ondansetron, granisetron, metoclopramide.

Suitable serotonin agonists which may be used in combination with the compounds of the invention include sumatriptan, rauwolscine, yohimbine, metoclopramide.

Suitable SSRIs which may be used in combination with the compounds of the invention include fluoxetine, citalopram, femoxetine, fluvoxamine, paroxetine, indalpine, sertraline, zimeldine.

Suitable SNRIs which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and amineptine.

Suitable anticonvulsant agents which may be used in combination of the compounds of the invention include for example divalproex, carbamazepine and diazepam.

The following examples serve to explain the invention without limiting it.

The compounds were characterized by mass spectrometry, generally recorded via HPLC-MS in a fast gradient on C18-material (electrospray-ionisation (ESI) mode).

PREPARATION EXAMPLES

Example 1 cis-N-({7-[3-Azabicyclo[3.1.0]hex-3-yl]-8-benzyl-5,6,7,8-tetrahydronaphthalen-2-yl}methyl)-1-methyl-1H-imidazole-4-sulfonamide(2E)-but-2-enedioate

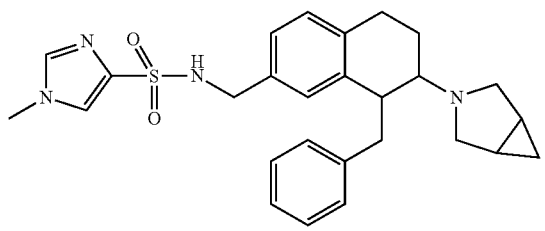

-continued

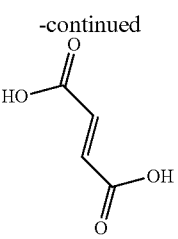

1.1 cis-2-{[1-Benzyl-7-({[(1-methyl-1H-imidazol-4-yl)sulfonyl]amino}methyl)-1,2,3,4-tetrahydronaphthalen-2-yl]carbamoyl}cyclopropanecarboxylic acid

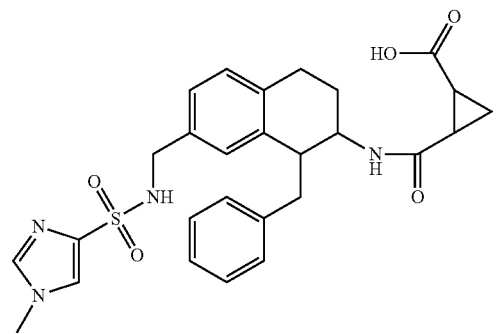 [SMILES: Cn1cnc(S(=O)(=O)NCc2ccc3c(c2)C(Cc2ccccc2)C(NC(=O)C2CC2C(=O)O)CC3)c1]

cis-N-[(7-Amino-8-benzyl-5,6,7,8-tetrahydronaphthalen-2-ylmethyl]-1-methyl-1H-imidazole-4-sulfonamide (300 mg, 0.731 mmol; cf. WO2010092180) was dissolved in toluene (6 mL) and 3-oxabicyclo[3.1.0]hexane-2,4-dione (82 mg, 0.731 mmol) was added in small portions. The reaction mixture was heated under reflux for 1.5 h. The solvent was evaporated in vacuo. Water was added and the aqueous phase was extracted with dichloromethane several times. The combined organic extracts were dried (sodium sulfate) and the solvent was evaporated in vacuo. The crude product was used for the next step without further purification. Yield: 382 mg (colorless solid).

1.2 N-({8-Benzyl-7-[2,4-dioxo-3-azabicyclo[3.1.0]hex-3-yl]-5,6,7,8-tetrahydronaphthalen-2-yl}methyl)-1-methyl-1H-imidazole-4-sulfonamide

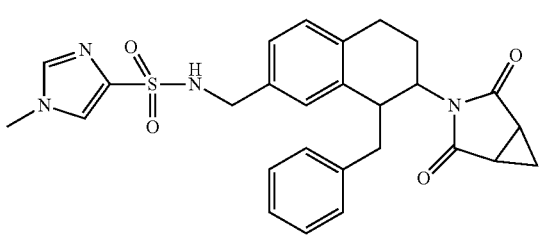 [SMILES: Cn1cnc(S(=O)(=O)NCc2ccc3c(c2)C(Cc2ccccc2)C(N2C(=O)C4CC4C2=O)CC3)c1]

cis-2-{[1-Benzyl-7-({[(1-methyl-1H-imidazol-4-yl)sulfonyl]amino}methyl)-1,2,3,4-tetrahydronaphthalen-2-yl]carbamoyl}cyclopropanecarboxylic acid (382 mg, 0.731 mmol) was dissolved in tetrahydrofuran (10 mL) and acetyl chloride (5 mL, 88 mmol) was added. The reaction mixture was heated under reflux for 2 h. The reaction mixture was diluted with water and extracted with dichloromethane. The combined organic extracts were washed with aqueous sodium bicarbonate solution, dried (sodium sulfate) and concentrated in vacuo. The crude product was used for the next step without further purificiation. Yield: 377 mg (light orange oil).

1.3 cis-N-({7-[3-Azabicyclo[3.1.0]hex-3-yl]-8-benzyl-5,6,7,8-tetrahydronaphthalen-2-yl}methyl)-1-methyl-1H-imidazole-4-sulfonamide(2E)-but-2-enedioate

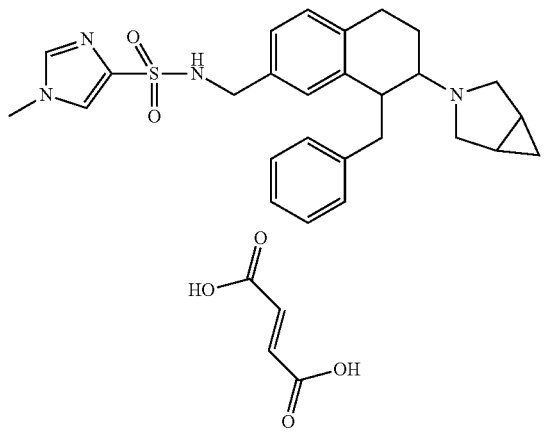

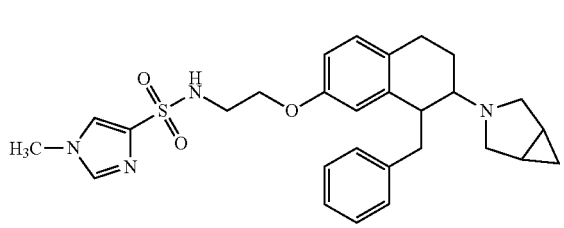

N-({8-Benzyl-7-[2,4-dioxo-3-azabicyclo[3.1.0]hex-3-yl]-5,6,7,8-tetrahydronaphthalen-2-yl}methyl)-1-methyl-1H-imidazole-4-sulfonamide (377 mg, 0.747 mmol) was dissolved in dry tetrahydrofuran (2 mL) and added to a solution of borane in tetrahydrofuran (1 M, 2.241 mL, 2.241 mmol) and the reaction mixture was heated under reflux in an inert atmosphere for 16 h. The reaction mixture was diluted with methanol and stirred for 15 min. Saturated aqueous sodium chloride solution was added. The mixture was extracted several times with dichloromethane. The combined extracts were dried (sodium sulfate) and concentrated in vacuo. The crude product was purified by flash chromatography (12 g silica, dichloromethane/methanol). The purified product was recrystallized from isopropanol and then converted into the fumarate. Yield: 209 mg (0.437 mmol, 59%, colorless solid).

ESI-MS [M+H$^+$]=477 Calculated for $C_{27}H_{32}N_4O_2S$=476.

Example 2

N-[2-({7-[3-Azabicyclo[3.1.0]hex-3-yl]-8-benzyl-5,6,7,8-tetrahydronaphthalen-2-yl}oxy)ethyl]-1-methyl-1H-imidazole-4-sulfonamide(2E)-but-2-enedioate

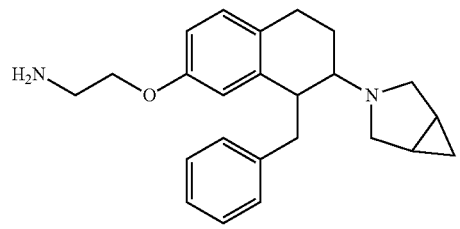

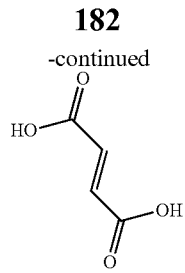

2.1 2-[(1-Benzyl-7-hydroxy-1,2,3,4-tetrahydronaphthalen-2-yl)carbamoyl]cyclopropanecarboxylic acid

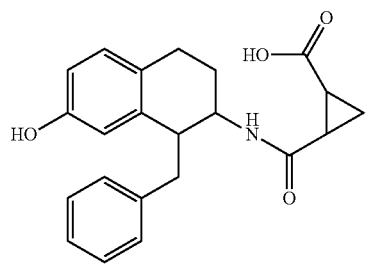 [SMILES: O=C(O)C1CC1C(=O)NC1CCc2ccc(O)cc2C1Cc1ccccc1]

2-[(1-Benzyl-7-hydroxy-1,2,3,4-tetrahydronaphthalen-2-yl)carbamoyl]cyclopropanecarboxylic acid was prepared from cis-7-amino-8-benzyl-5,6,7,8-tetrahydronaphthalene-2-ol analogously to the protocol in example 5.

2.2 cis-7-(3-Azabicyclo[3.1.0]hex-3-yl)-8-benzyl-5,6,7,8-tetrahydronaphthalen-2-ol

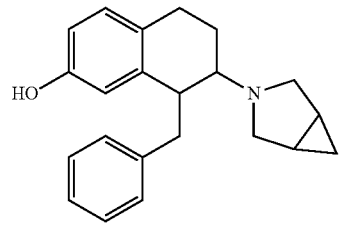 [SMILES: Oc1ccc2c(c1)C(Cc1ccccc1)C(N1CC3CC3C1)CC2]

cis-7-(3-Azabicyclo[3.1.0]hex-3-yl)-8-benzyl-5,6,7,8-tetrahydronaphthalen-2-ol was prepared from cis-2-[(1-benzyl-7-hydroxy-1,2,3,4-tetrahydronaphthalen-2-yl)carbamoyl]cyclopropanecarboxylic acid analogously to the protocol in example 5.

2.3 cis-2-{[7-(3-azabicyclo[3.1.0]hex-3-yl)-8-benzyl-5,6,7,8-tetrahydronaphthalen-2-yl]oxy}ethanamine cis-2-{[7-(3-Azabicyclo[3.1.0]hex-3-yl)-8-benzyl-5,6,7,8-tetrahydronaphthalen-2-yl]oxy}ethanamine was prepared from cis-7-(3-azabicyclo[3.1.0]hex-3-yl)-8-benzyl-5,6,7,8-tetrahydronaphthalen-2-ol analogously to the protocols in WO/2010092180.

2.4 N-[2-({7-[3-Azabicyclo[3.1.0]hex-3-yl]-8-benzyl-5,6,7,8-tetrahydronaphthalen-2-yl}oxy)ethyl]-1-methyl-1H-imidazole-4-sulfonamide(2E)-but-2-enedioate

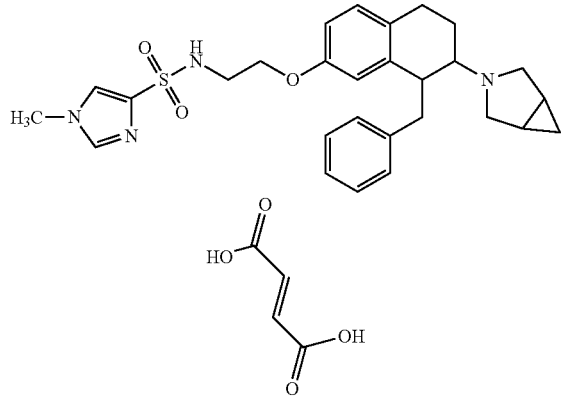

cis-2-{[7-(3-Azabicyclo[3.1.0]hex-3-yl)-8-benzyl-5,6,7,8-tetrahydronaphthalen-2-yl]oxy}ethanamine was converted analogously to protocols in WO/2010092180 to N-[2-({7-[3-azabicyclo[3.1.0]hex-3-yl]-8-benzyl-5,6,7,8-tetrahydronaphthalen-2-yl}oxy)ethyl]-1-methyl-1H-imidazole-4-sulfonamide(2E)-but-2-enedioate.

ESI-MS [M+H$^+$]=507 Calculated for $C_{28}H_{34}N_4O_3S$=506.

Example 3

N-[2-({7-[3-Azabicyclo[3.1.0]hex-3-yl]-8-benzyl-5,6,7,8-tetrahydronaphthalen-2-yl}oxy)ethyl]-1-methyl-1H-pyrazole-4-sulfonamide(2E)-but-2-enedioate

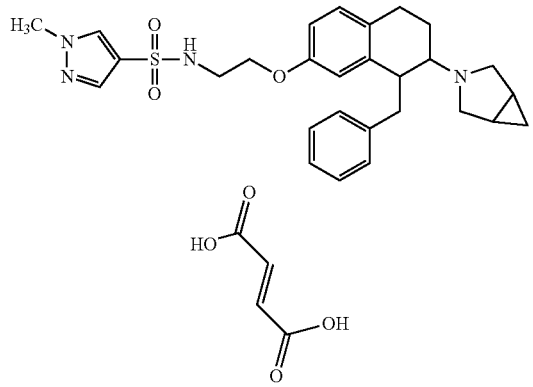

N-[2-({7-[3-Azabicyclo[3.1.0]hex-3-yl]-8-benzyl-5,6,7,8-tetrahydronaphthalen-2-yl}oxy)ethyl]-1-methyl-1H-pyrazole-4-sulfonamide(2E)-but-2-enedioate was prepared analogously to example 2.

ESI-MS [M+H$^+$]=507 Calculated for $C_{28}H_{34}N_4O_3S$=506.

Example 5

N-(2-{[7-[3-Azabicyclo[3.1.0]hex-3-yl]-8-(2-fluorobenzyl)-5,6,7,8-tetrahydronaphthalen-2-yl]oxy}ethyl)-1-methyl-1H-imidazole-4-sulfonamide

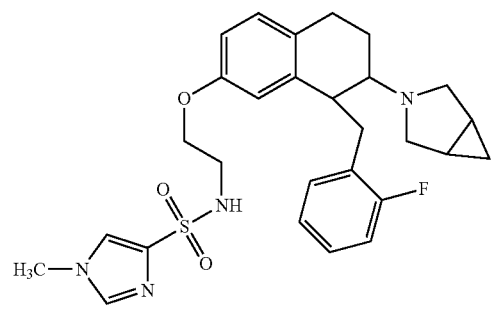 [SMILES: Cn1cnc(S(=O)(=O)NCCOc2ccc3c(c2)C(Cc2ccccc2F)C(N2CC4CC4C2)CC3)c1]

5.1 cis-N-(2-{[7-Amino-8-(2-fluorobenzyl)-5,6,7,8-tetrahydronaphthalen-2-yl]oxy}ethyl)-1-methyl-1H-imidazole-4-sulfonamide

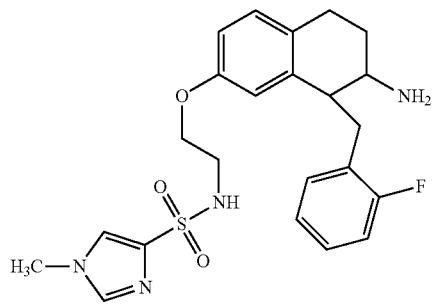 [SMILES: Cn1cnc(S(=O)(=O)NCCOc2ccc3c(c2)C(Cc2ccccc2F)C(N)CC3)c1]

cis-N-(2-{[7-Amino-8-(2-fluorobenzyl)-5,6,7,8-tetrahydronaphthalen-2-yl]oxy}ethyl)-1-methyl-1H-imidazole-4-sulfonamide can be prepared analogously to protocols described in WO/2010092180.

5.2 cis-2-{[1-(2-Fluorobenzyl)-7-(2-{[(1-methyl-1H-imidazol-4-yl)sulfonyl]amino}ethoxy)-1,2,3,4-tetrahydronaphthalen-2-yl]carbamoyl}cyclopropanecarboxylic acid

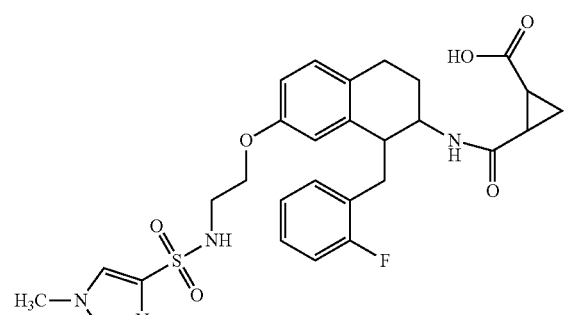

cis-N-(2-{[7-Amino-8-(2-fluorobenzyl)-5,6,7,8-tetrahydronaphthalen-2-yl]oxy}ethyl)-1-methyl-1H-imidazole-4- sulfonamide (50 mg, 0.109 mmol) was dissolved in dimethylformamide (2 mL), 3-oxabicyclo[3.1.0]hexane-2,4-dione (13.4 mg 0.12 mmol) was added and the reaction mixture was heated to 110° C. for 2 h. The solvent was removed in vacuo and the crude product was taken up in dichloromethane and washed successively with water (2×) and saturated sodium chloride solution (1×) and dried (magnesium sulfate). The solvent was evaporated in vacuo and the crude product was used for the next step without further purification. Yield: 63 mg (colorless foam).

5.3 cis-N-(2-{[7-(2,4-Dioxo-3-azabicyclo[3.1.0]hex-3-yl)-8-(2-fluorobenzyl)-5,6,7,8-tetrahydronaphthalen-2-yl]oxy}ethyl)-1-methyl-1H-imidazole-4-sulfonamide

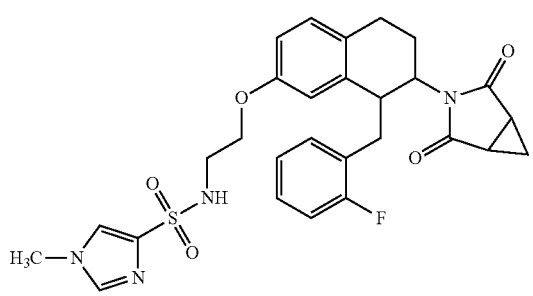 [SMILES: Cn1cnc(S(=O)(=O)NCCOc2ccc3c(c2)C(Cc2ccccc2F)C(N2C(=O)C4CC4C2=O)CC3)c1]

cis-N-(2-{[7-Amino-8-(2-fluorobenzyl)-5,6,7,8-tetrahydronaphthalen-2-yl]oxy}ethyl)-1-methyl-1H-imidazole-4-sulfonamide (60 mg, 0.105 mmol) in acetyl chloride (2 mL, 28.1 mmol) was heated under reflux for 30 min. The acetyl chloride was evaporated in vacuo. The crude product dissolved in dichloromethane and washed successively with saturated sodium bicarbonate and saturated sodium chloride and dried (magnesium sulfate). The crude product was used for next step without further purification. Yield: 38 mg (colorless foam).

5.4 cis-N-(2-{[7-[3-Azabicyclo[3.1.0]hex-3-yl]-8-(2-fluorobenzyl)-5,6,7,8-tetrahydronaphthalen-2-yl]oxy}ethyl)-1-methyl-1H-imidazole-4-sulfonamide

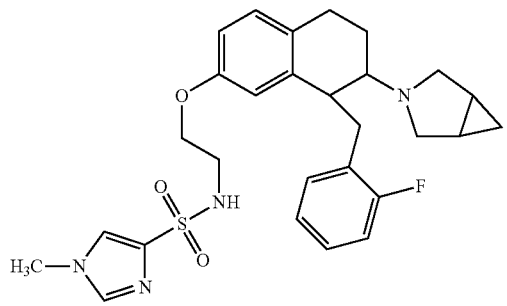 [SMILES: Cn1cnc(S(=O)(=O)NCCOc2ccc3c(c2)C(Cc2ccccc2F)C(N2CC4CC4C2)CC3)c1]

cis-N-(2-{[7-(2,4-Dioxo-3-azabicyclo[3.1.0]hex-3-yl)-8-(2-fluorobenzyl)-5,6,7,8-tetrahydronaphthalen-2-yl]oxy}ethyl)-1-methyl-1H-imidazole-4-sulfonamide (38 mg, 0.069 mmol) was dissolved in tetrahydrofuran (2 mL) and borane tetrahydrofuran complex was added (1 N, 0.4 mL, 0.4 mmol). The reaction mixture was heated to 50° C. for 3.5 h. After cooling to room temperature methanol (0.2 mL) was added dropwise and stirring was continued for 30 min. The reaction mixture was diluted with dichloromethane, washed with saturated sodium chloride solution and dried (magnesium sulfate). The solvent was evaporated in vacuo and the crude product was purified by flash chromatography (silica, dichloromethane/methanol). Yield: 4 mg (7.6 μmol, 11%, colorless oil).

ESI-MS [M+H$^+$]=525 Calculated for $C_{28}H_{33}FN_4O_3S$=524.

Synthesis of Intermediates 5.5
1-Benzyl-7-methoxy-3,4-dihydronaphthalen-2(1H)-one

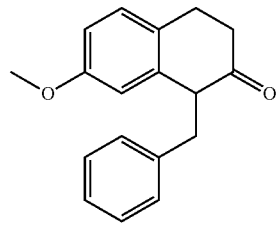 [SMILES: COc1ccc2c(c1)C(Cc1ccccc1)C(=O)CC2]

7-methoxy-3,4-dihydronaphthalen-2(1H)-one (41 g, 233 mmol) was dissolved in MeOH (250 mL). Then pyrrolidine (18.2 g, 256 mmol) was added dropwise. The mixture was stirred for 2 h. The solvent was removed under reduced pressure and the residue was dissolved in acetonitrile (500 mL). The solution was cooled to −5° C. and benzyl bromide (43.8 g, 256 mmol) was added. The solution was stirred overnight at room temperature. The solvent was reduced under reduced pressure. The residue was dissolved in 480 mL of a mixture of MeOH/CH$_2$Cl$_2$/H$_2$O (1:1:1) and 30 mL of glacial acetic acid were added. The mixture was stirred overnight. The reaction mixture was put on ice water and extracted with CH$_2$Cl$_2$. The combined organic layers were washed with a NaHCO$_3$ solution and with brine. The organic phase was dried on MgSO$_4$ and the solvent was evaporated. The residue (80 g) was purified by flash-chromatography on silica gel (100% dichloromethane). 58.8 g (221 mmol, 95%) of the product were obtained.

ESI-MS [M+H$^+$]=267.1 Calculated for $C_{18}H_{18}O_2$=266.1.

5.6 1-Benzyl-7-methoxy-1,2,3,4-tetrahydronaphthalen-2-amine hydrochloride {10483663-0349}

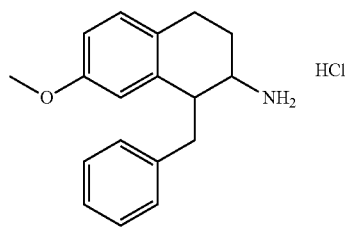 [SMILES: COc1ccc2c(c1)C(Cc1ccccc1)C(N)CC2 ; Cl]

To a solution of 1-benzyl-7-methoxy-3,4-dihydronaphthalen-2(1H)-one (45.65 g, 171 mmol) ammonium acetate (132 g, 1714 mmol) was added. The resulting suspension was stirred for 20 minutes under Argon at room temperature. Sodium cyanoborohydride (16.16 g, 257 mmol) was added portionwise with gas evolution. The mixture was stirred at room temperature overnight. The mixture was evaporated under reduced pressure and the residue was partitioned between 1 M NaOH and ethyl acetate. The combined organic layers were dried on MgSO4 and the solvent was evaporated. The residue (39.0 g) was purified by flash-chromatography on silica gel (100% dichloromethane then gradient to 25% MeOH in dichloromethane in 25 minutes). The purified product was dissolved in isopropanol (500 mL) and 6 M HCl in isopropanol was added carefully keeping the mixture under continuous stirring in an ice-bath. Cis isomer hydrochloride precipitated as a white solid. The solid was collected (×1, 18.478 g) and the mother liquors were concentrated and recrystallized to a white solid (×2: 5.032 g). Yield: 45.2%

ESI-MS [M+H$^+$]=268.1 Calculated for $C_{18}H_{21}NO$=267.4.

5.7
7-Amino-8-benzyl-5,6,7,8-tetrahydronaphthalen-2-ol

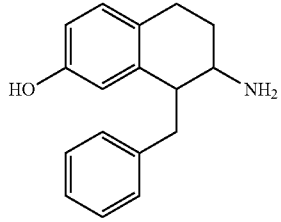 [SMILES: NC1CCc2ccc(O)cc2C1Cc1ccccc1]

To a solution of 1-benzyl-7-methoxy-1,2,3,4-tetrahydronaphthalen-2-amine (2.56 g, 9.57 mmol) in dry dichloromethane (47.4 mL) under Argon at 0° C. 1M BBr$_3$ in dichloromethane (23.93 mL, 23.93 mmol) was added. The cooling bath was removed and the reaction was allowed to reach room temperature overnight. The reaction was quenched with water, and 1 M NaOH was added to alkalinity. The organic layer was separated and the aqueous phase was extracted with dichloromethane (4×50 mL). The collected organic extracts were concentrated until the product precipitated as a green solid. The solid was collected via filtration and washed with cold dichloromethane (ca. 10 mL). The solid obtained was dried to a gray-greenish powder (2.233 g, 8.81 mmol, 92%).

ESI-MS [M+H$^+$]=254.2 Calculated for $C_{21}H_{23}ClN_2O_3$=253.3.

5.8 tert-Butyl 1-benzyl-7-hydroxy-1,2,3,4-tetrahydronaphthalen-2-ylcarbamate

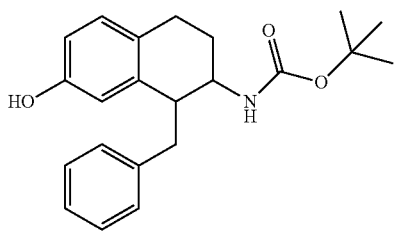 [SMILES: CC(C)(C)OC(=O)NC1CCc2ccc(O)cc2C1Cc1ccccc1]

7-amino-8-benzyl-5,6,7,8-tetrahydronaphthalen-2-ol (2.231 g, 8.81 mmol) was dissolved in DMF (8 mL) at room temperature and di-t-butyl dicarbonate (1.922 g, 8.81 mmol) and triethylamine (3.68 mL, 26.4 mmol) were added. After 3 hours the volatiles were evaporated under reduced pressure and the residue was dissolved in ethyl acetate and washed with brine (5×40 mL). The organic layer was dried on MgSO$_4$ and the volatiles were evaporated under reduced pressure. The solid residue was crystallized from dichloromethane/n-heptane, yielding a light yellow powder (2.512 g). The mother liquors were evaporated yielding a yellow oil (780 mg) that was purified via chromatography (silica 80 g, 20 mL/min, 100% n-heptane 5 min then gradient in 40 mins to 40% ethyl acetate). Product was isolated as a white foam (469.3 mg) and used with the crystallized product in the next step. Yield: 96%

ESI-MS [M+Na$^+$]=376.2 Calculated for $C_{22}H_{27}NO_3$=353.45.

5.9 8-Benzyl-7-(tert-butoxycarbonylamino)-5,6,7,8-tetrahydronaphthalen-2-yl trifluoromethanesulfonate

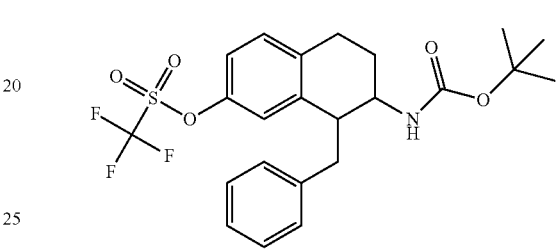

tert-Butyl 1-benzyl-7-hydroxy-1,2,3,4-tetrahydronaphthalen-2-ylcarbamate (2.981 g, 8.43 mmol) was dissolved in dichloromethane (61.6 mL) at 0° C. under argon and triethylamine (2.94 mL, 21.09 mmol) and N-phenyl bis(trifluoromethanesulfonimide) (3.01 g, 8.43 mmol) were added. The cooling bath was removed and the reaction was stirred at room temperature. The volatiles were removed under reduced pressure and the residue was dissolved in ethyl acetate (250 mL) and washed with 5% citric acid (2×50 mL), 1M NaOH (4×70 mL) and brine (2×50 mL). The organic phase was dried on MgSO$_4$ and the volatiles were evaporated under reduced pressure, yielding a yellow solid. The residue was purified by flash-chromatography on silica gel (10% ethyl acetate in n-heptane 5 mins, then 30% ethyl acetate in n-heptane in 40 minutes). 4.100 g (8.44 mmol, 100%) of product were obtained.

ESI-MS [M+Na$^+$]=508.1 Calculated for $C_{23}H_{26}F_3NO_5S$=485.5.

5.10 tert-Butyl 1-benzyl-7-cyano-1,2,3,4-tetrahydronaphthalen-2-ylcarbamate

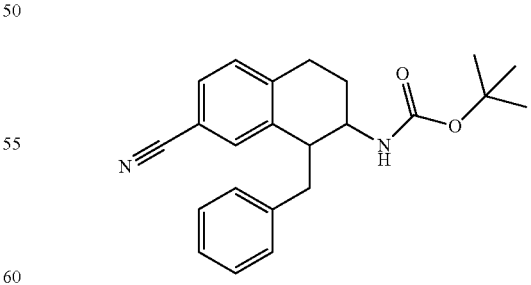

1,1'-Bis(diphenylphosphino)ferrocene (1.917 g, 3.46 mmol) and tris(dibenzylideneacetone)dipalladium (0) (0.792 g, 0.864 mmol) were loaded into a flame-dried Schlenk tube, the tube was evacuated and filled with argon. Previously degassed, ultradry DMF (10.8 mL) was added and the resulting dark brown solution was stirred at room temperature for 20 minutes. 8-Benzyl-7-(tert-butoxycarbonylamino)-5,6,7,8-tetrahydronaphthalen-2-yl trifluoromethanesulfonate (4.197 g, 8.64 mmol) was added and the solution was heated to 90° C. Zinc cyanide (1.218 g, 10.37 mmol) was added in one portion and the reaction was stirred at 90° C. under argon atmosphere. After 2 hours the DMF was evaporated under reduced pressure, the residue was dissolved in ethyl acetate and washed with 1 M NaOH (2×50 mL) and brine (6×50 mL). The organic extract was dried on MgSO$_4$ and evaporated under reduced pressure, yielding 6.521 g crude as a brown solid. The residue was purified by flash-chromatography on silica gel (gradient from 100% dichloromethane to 30% MeOH in dichloromethane). Product was obtained as green powder (1.577 g, 4.35 mmol, 50.3%).

ESI-MS [M+Na$^+$]=385.1 Calculated for C$_{23}$H$_{26}$N$_2$O$_2$=362.5.

5.11 tert-Butyl 7-(aminomethyl)-1-benzyl-1,2,3,4-tetrahydronaphthalen-2-ylcarbamate

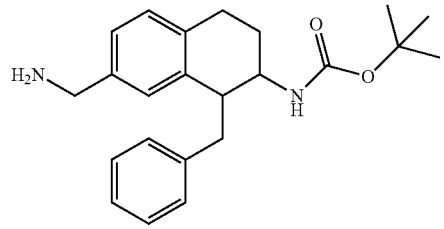 [SMILES: CC(C)(C)OC(=O)NC1CCc2ccc(CN)cc2C1Cc1ccccc1]

tert-Butyl 1-benzyl-7-cyano-1,2,3,4-tetrahydronaphthalen-2-ylcarbamate (1.787 g, 4.93 mmol) was dissolved in THF (40 mL) and 7 N methanolic ammonia (40 mL). Raney nickel (0.422 g, 4.93 mmol) was added. The vessel was evacuated and filled with Hydrogen at atmospheric pressure. The mixture was stirred overnight at room temperature. The catalyst was filtered off on a celite pad and washed with 500 mL MeOH. Product was obtained as a crimson powder (1.813 g, 4.95 mmol, 100%) after evaporating the solvent.

ESI-MS [M+H$^+$]=367.2 Calculated for C$_{23}$H$_{30}$N$_2$O$_2$=366.5.

5.12 tert-Butyl 1-benzyl-7-(ethylsulfonamidomethyl)-1,2,3,4-tetrahydronaphthalen-2-ylcarbamate {10483663-0430}

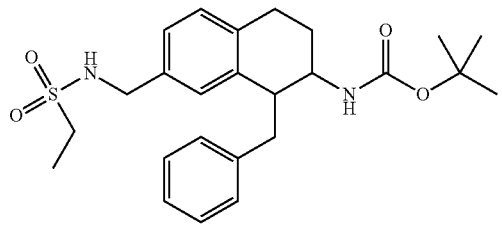 [SMILES: CCS(=O)(=O)NCc1ccc2c(c1)C(Cc1ccccc1)C(NC(=O)OC(C)(C)C)CC2]

tert-Butyl 7-(aminomethyl)-1-benzyl-1,2,3,4-tetrahydronaphthalen-2-ylcarbamate (0.600 g, 1.637 mmol) was suspended in dichloromethane (5 mL) and triethylamine (0.228 mL, 1.637 mmol) and cooled to 0° C. Ethanesulfonyl chloride (0.155 mL, 1.64 mmol) was added and the solid gradually dissolved. After 30 minutes the reaction was stopped by washing it with brine (1×50 mL). The organic phase was collected and dried on MgSO$_4$, evaporated. The residue was purified by flash-chromatography on silica gel (100% DCM). Product was obtained as yellow solid (0.653 g, 1.42 mmol, 87%).

ESI-MS [M+Na$^+$]=481.2 Calculated for C$_{25}$H$_{34}$N$_2$O$_4$S=458.6.

5.13 tert-Butyl 1-benzyl-7-(propylsulfonamidomethyl)-1,2,3,4-tetrahydronaphthalen-2-ylcarbamate

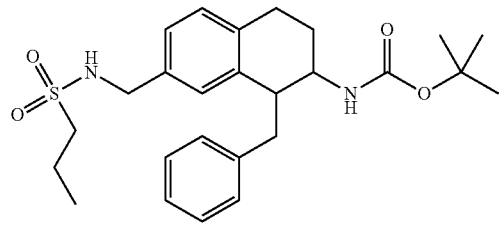 [SMILES: CCCS(=O)(=O)NCc1ccc2c(c1)C(Cc1ccccc1)C(NC(=O)OC(C)(C)C)CC2]

tert-Butyl 7-(aminomethyl)-1-benzyl-1,2,3,4-tetrahydronaphthalen-2-ylcarbamate (0.600 g, 1.637 mmol) was suspended in dichloromethane (5 mL) and triethylamine (0.228 mL, 1.637 mmol) and cooled to 0° C. 1-Propanesulfonyl chloride (0.184 mL, 1.64 mmol) was added. The solid immediately dissolved. The mixture was stirred 35 minutes, and then it was diluted with dichloromethane and washed with brine (1×50 mL). The organic phase was collected, dried on MgSO$_4$ and the volatiles were evaporated under reduced pressure, yielding the product as a pale yellow solid (628.3 mg, 1.33 mmol, 81%).

ESI-MS [M+Na$^+$]=495.2 Calculated for C$_{26}$H$_{36}$N$_2$O$_4$S=472.6.

5.14 tert-butyl 1-benzyl-7-(cyclobutanesulfonamidomethyl)-1,2,3,4-tetrahydronaphthalen-2-ylcarbamate

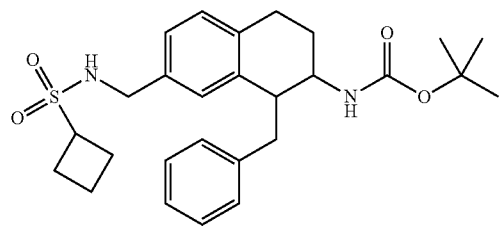 [SMILES: CC(C)(C)OC(=O)NC1CCc2ccc(CNS(=O)(=O)C3CCC3)cc2C1Cc1ccccc1]

tert-Butyl 7-(aminomethyl)-1-benzyl-1,2,3,4-tetrahydronaphthalen-2-ylcarbamate (0.600 g, 1.637 mmol) was suspended in dichloromethane (5 mL) and triethylamine (0.228 mL, 1.637 mmol) and cooled to 0° C. Cyclobutanesulfonyl chloride (0.253 g, 1.637 mmol) was added. The solid immediately dissolved. The mixture was stirred overnight, then it was diluted with DCM and washed with brine (1×50 mL). The organic phase was collected, dried on MgSO$_4$ and the volatiles were evaporated under reduced pressure, yielding the product as a pale yellow solid (731.7 mg, 1.51 mmol, 92%).

ESI-MS [M+Na$^+$]=507.2 Calculated for C$_{27}$H$_{36}$N$_2$O$_4$S=484.6.

5.15 tert-Butyl 1-benzyl-7-((cyclopropylmethylsulfonamido)methyl)-1,2,3,4-tetrahydronaphthalen-2-ylcarbamate

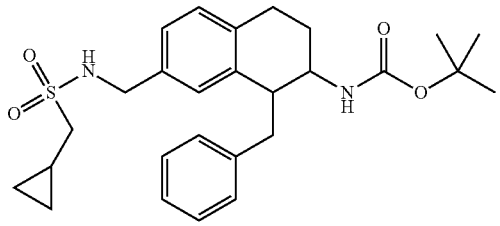 [SMILES: CC(C)(C)OC(=O)NC1CCc2ccc(CNS(=O)(=O)CC3CC3)cc2C1Cc1ccccc1]

tert-Butyl 7-(aminomethyl)-1-benzyl-1,2,3,4-tetrahydronaphthalen-2-ylcarbamate (0.600 g, 1.637 mmol) was suspended in dichloromethane (5 mL) and triethylamine (0.228 mL, 1.637 mmol) and cooled to 0° C. Cyclopropylmethanesulfonyl chloride (0.253 g, 1.637 mmol) was added. The solid immediately dissolved. The mixture was stirred overnight and then diluted with dichloromethane and washed with brine (3×50 mL). The organic extract was collected dried on $MgSO_4$ and evaporated under reduced pressure. The residue was purified by flash-chromatography on silica gel (100% dichloromethane 5 minutes then gradient to 1% MeOH in dichloromethane). Product was isolated as white powder (601.9 mg, 1.24 mmol, 76%).

ESI-MS $[M+Na^+]$=507.2 Calculated for $C_{27}H_{36}N_2O_4S$=484.6.

5.16 N-((7-amino-8-benzyl-5,6,7,8-tetrahydronaphthalen-2-yl)methyl)ethanesulfonamide

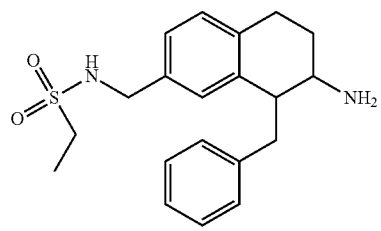 [SMILES: CCS(=O)(=O)NCc1ccc2c(c1)C(Cc1ccccc1)C(N)CC2]

tert-Butyl 1-benzyl-7-(ethylsulfonamidomethyl)-1,2,3,4-tetrahydronaphthalen-2-ylcarbamate (0.652 g, 1.422 mmol) was dissolved in dichloromethane (5 mL) and trifluoroacetic acid (0.5 mL, 6.49 mmol) and stirred overnight at room temperature. The solution was evaporated and partitioned between saturated aqueous $NaHCO_3$ and ethyl acetate. Water was extracted with ethyl acetate (2×30 mL). The collected organic extracts were dried on $MgSO_4$ and evaporated under reduced pressure to give a brown oil.

The residue was purified by flash-chromatography on silica gel (100% dichloromethane to 15% MeOH in dichloromethane in 15 minutes). Product was isolated as a white solid (400 mg, 1.12 mmol, 78%).

ESI-MS $[M+H^+]$=359.2 Calculated for $C_{20}H_{26}N_2O_2S$=358.5.

5.17 N-((7-Amino-8-benzyl-5,6,7,8-tetrahydronaphthalen-2-yl)methyl)propane-1-sulfonamide

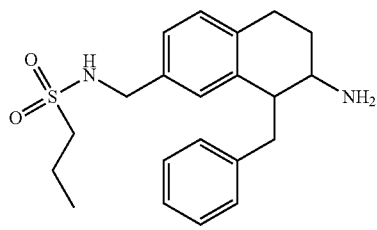 [SMILES: CCCS(=O)(=O)NCc1ccc2c(c1)C(Cc1ccccc1)C(N)CC2]

tert-Butyl 1-benzyl-7-(propylsulfonamidomethyl)-1,2,3,4-tetrahydronaphthalen-2-ylcarbamate (0.628 g, 1.33 mmol) was dissolved in dichloromethane (5 mL) and trifluoroacetic acid (0.5 mL, 6.49 mmol) and stirred overnight at room temperature. The solution was evaporated and partitioned between saturated aqueous $NaHCO_3$ and ethyl acetate. Water was extracted with ethyl acetate (2×30 mL). The collected organic extracts were dried on $MgSO_4$ and evaporated under reduced pressure to give a brown oil. Product was obtained as a brown oil (0.487 g, 1.31, 98%)

ESI-MS $[M+H^+]$=373.2 Calculated for $C_{21}H_{28}N_2O_2S$=372.5.

5.18 N-((7-Amino-8-benzyl-5,6,7,8-tetrahydronaphthalen-2-yl)methyl)cyclobutanesulfonamide

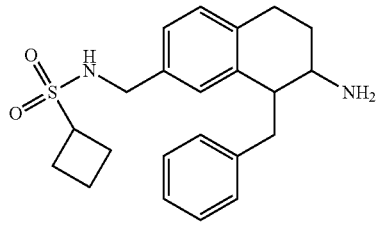 [SMILES: NC1CCc2ccc(CNS(=O)(=O)C3CCC3)cc2C1Cc1ccccc1]

tert-Butyl 1-benzyl-7-(cyclobutanesulfonamidomethyl)-1,2,3,4-tetrahydronaphthalen-2-ylcarbamate (0.732 g, 1.51 mmol) was dissolved in dichloromethane (5 mL) and trifluoroacetic acid (0.5 mL, 6.49 mmol) and stirred overnight at room temperature. The solution was evaporated and partitioned between saturated aqueous $NaHCO_3$ and ethyl acetate. Water was extracted with ethyl acetate (2×30 mL). The collected organic extracts were dried on $MgSO_4$ and evaporated under reduced pressure to give a brown oil. Product was obtained as a brown oil (0.487 g, 1.31, 98%).

ESI-MS $[M+H^+]$=385.2 Calculated for $C_{22}H_{28}N_2O_2S$=384.5.

5.19 N-((7-Amino-8-benzyl-5,6,7,8-tetrahydronaph-
thalen-2-yl)methyl)cyclobutanesulfonamide

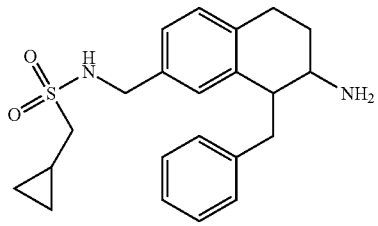 [SMILES: NC1CCc2ccc(CNS(=O)(=O)CC3CC3)cc2C1Cc1ccccc1]

tert-Butyl 1-benzyl-7-((cyclopropylmethylsulfonamido)methyl)-1,2,3,4-tetrahydronaphthalen-2-ylcarbamate (0.602 g, 1.242 mmol) was dissolved in dichloromethane (5 mL) and trifluoroacetic acid (0.5 mL, 6.49 mmol) and stirred overnight at room temperature. The solution was evaporated and partitioned between saturated aqueous NaHCO$_3$ and ethyl acetate. Water was extracted with ethyl acetate (2×30 mL). The collected organic extracts were dried on MgSO$_4$ and evaporated under reduced pressure to give a brown oil. Product was obtained as a brown oil (0.470 g, 1.22, 98%).

ESI-MS [M+H$^+$]=385.2 Calculated for C$_{22}$H$_{28}$N$_2$O$_2$S=384.5.

Example 6

N-((8-Benzyl-7-(3-cyanooxetan-3-ylamino)-5,6,7,8-tetrahydronaphthalen-2-yl)methyl)ethanesulfonamide

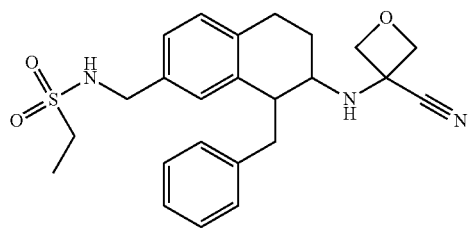 [SMILES: CCS(=O)(=O)NCc1ccc2c(c1)C(Cc1ccccc1)C(NC1(C#N)COC1)CC2]

N-((7-Amino-8-benzyl-5,6,7,8-tetrahydronaphthalen-2-yl)methyl)ethanesulfonamide (0.243 g, 0.678 mmol) and 3-oxetanone (0.098 g, 1.356 mmol) were sealed in a vial and heated at 210° C. for 2 minutes. Trimethylsilyl cyanide (0.181 mL, 1.356 mmol) was added, the vial was resealed and the mixture was heated again at 210° C. for 2 minutes. The mixture was diluted with ethyl acetate (40 mL) and washed with 1 N NaOH (1×20 mL) and brine (1×20 mL). The organic extract was collected, dried on MgSO$_4$ and evaporated under reduced pressure to give a brown oil. The residue was purified by preparative HPLC. Product was obtained as a colourless oil (7.2 mg, 0.016 mmol, 2.4%).

ESI-MS [M+H$^+$]=440.2 Calculated for C$_{24}$H$_{29}$N$_3$O$_3$S=439.5.

Example 7

N-((8-Benzyl-7-(3-cyanooxetan-3-ylamino)-5,6,7,8-tetrahydronaphthalen-2-yl)methyl)propane-1-sulfonamide

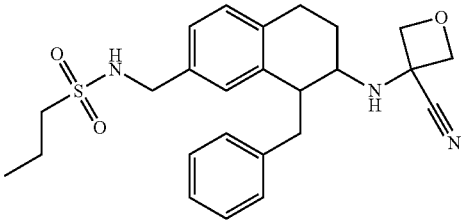 [SMILES: CCCS(=O)(=O)NCc1ccc2c(c1)C(Cc1ccccc1)C(NC1(C#N)COC1)CC2]

N-((7-Amino-8-benzyl-5,6,7,8-tetrahydronaphthalen-2-yl)methyl)propane-1-sulfonamide (0.104 g, 0.279 mmol) and 3-oxetanone (0.040 g, 0.558 mmol) were sealed in a vial and heated at 210° C. for 2 minutes. Trimethylsilyl cyanide (0.074 mL, 0.558 mmol) was added, the vial was resealed and the mixture was heated again at 210° C. for 2 minutes. The mixture was diluted with ethyl acetate (40 mL) and washed with 1 N NaOH (1×20 mL) and brine (1×20 mL). The organic extract was collected, dried on MgSO$_4$ and evaporated under reduced pressure to give a brown oil. The residue was purified by flash-chromatography on silica gel (100% heptane then gradient to 60% ethyl acetate in n-heptane in 40 mins). (0.054 mg, 0.12 mmol, 43%).

ESI-MS [M+H$^+$]=454.2 Calculated for C$_{25}$H$_{31}$N$_3$O$_3$S=453.6.

Example 8

N-((8-Benzyl-7-(3-cyanooxetan-3-ylamino)-5,6,7,8-tetrahydronaphthalen-2-yl)methyl)cyclobutanesulfonamide

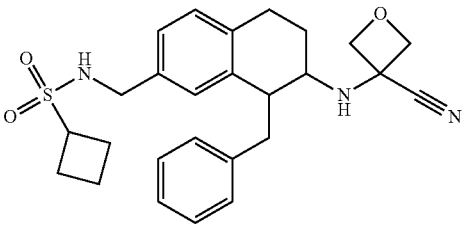 [SMILES: N#CC1(NC2CCc3ccc(CNS(=O)(=O)C4CCC4)cc3C2Cc2ccccc2)COC1]

N-((7-amino-8-benzyl-5,6,7,8-tetrahydronaphthalen-2-yl)methyl)cyclobutanesulfonamide (0.100 g, 0.260 mmol) and 3-oxetanone (0.037 g, 0.520 mmol) were sealed in a vial and heated at 200° C. for 2 minutes. Trimethylsilyl cyanide (0.69 mL, 0.520 mmol) was added, the vial was resealed and the mixture was heated again at 200° C. for 2 minutes. The mixture was diluted with ethyl acetate (40 mL) and washed with 1 N NaOH (1×20 mL) and brine (1×20 mL). The organic extract was collected, dried on MgSO$_4$ and evaporated under reduced pressure to give a brown oil. The residue was purified by preparative HPLC. Product was obtained as a colourless oil (13.2 mg, 0.028 mmol, 11%).

ESI-MS [M+H$^+$]=466.2 Calculated for C$_{26}$H$_{31}$N$_3$O$_3$S=465.6.

Example 9

N-((8-Benzyl-7-(3-cyanooxetan-3-ylamino)-5,6,7,8-tetrahydronaphthalen-2-yl)methyl)-1-cyclopropyl-methanesulfonamide

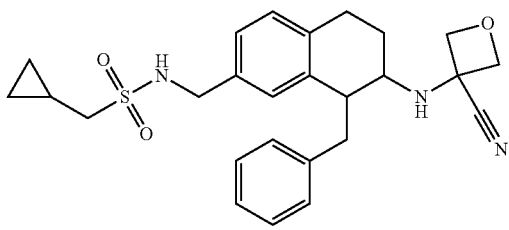 [SMILES: N#CC1(NC2CCc3ccc(CNS(=O)(=O)CC4CC4)cc3C2Cc2ccccc2)COC1]

N-((7-Amino-8-benzyl-5,6,7,8-tetrahydronaphthalen-2-yl)methyl)-1-cyclopropylmethanesulfonamide (0.083 g, 0.216 mmol) and 3-oxetanone (0.031 g, 0.432 mmol) were sealed in a vial and heated at 200° C. for 2 minutes. Trimethylsilyl cyanide (0.58 mL, 0.432 mmol) was added, the vial was resealed and the mixture was heated again at 200° C. for 2 minutes. The mixture was diluted with ethyl acetate (40 mL) and washed with 1N NaOH (1×20 mL) and brine (1×20 mL). The organic extract was collected, dried on $MgSO_4$ and evaporated under reduced pressure to give a brown oil. The residue was purified by flash-chromatography on silica gel (100% heptane then up to 60% ethyl acetate in n-heptane). (24.9 mg, 0.048 mmol, 22.3%).

ESI-MS [M+H$^+$]=466.2 Calculated for $C_{26}H_{31}N_3O_3S$=465.6.

Example 10

N-[2-({7-[3-Azabicyclo[3.1.0]hex-3-yl]-8-benzyl-3-cyano-5,6,7,8-tetrahydronaphthalen-2-yl}oxy)ethyl]-1-methyl-1H-imidazole-4-sulfonamide(2E)-but-2-enedioate

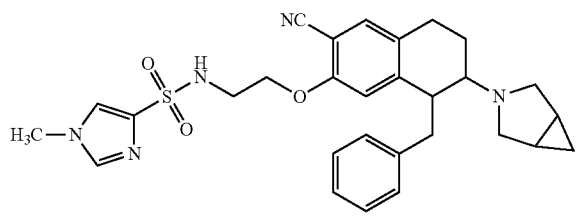

ESI-MS [M + H$^+$] = 532

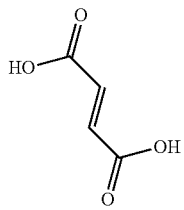

Calculated for $C_{33}H_{37}N_5O_7S$ = 531

Biological Testing

1. [$^3$H]-Glycine Uptake into Recombinant CHO Cells Expressing Human GlyT1:

Human GlyT1c expressing recombinant hGlyT1c_5_CHO cells were plated at 20,000 cells per well in 96 well Cytostar-T scintillation microplates (Amersham Biosciences) and cultured to sub-confluency for 24 h. For glycine uptake assays the culture medium was aspirated and the cells were washed once with 100 µl HBSS (Gibco BRL, #14025-050) with 5 mM L-Alanine (Merck #1007). 80 µl HBSS buffer were added, followed by 10 µl inhibitor or vehicle (10% DMSO) and 10 µl [$^3$H]-glycine (TRK71, Amersham Biosciences) to a final concentration of 200 nM for initiation of glycine uptake. The plates were placed in a Wallac Microbeta (PerkinElmer) and continuously counted by solid phase scintillation spectrometry during up to 3 hours. Nonspecific uptake was determined in the presence of 10 µM Org24598. $IC_{50}$ calculations were made by four-parametric logistic non-linear regression analysis (GraphPad Prism) using determinations within the range of linear increase of [$^3$H]-glycine incorporation between 60 and 120 min.

2. Radioligand Binding Assays Using Recombinant CHO Cell Membranes Expressing Human GlyT1:

Radioligand binding to human GlyT1c transporter-expressing membranes was determined as described in Mezler et al., Molecular Pharmacology 74:1705-1715, 2008.

The following results were obtained with the compounds disclosed in the examples:

| Example | radioligand binding $K_{iapp}$ [nM] |
|---|---|
| 1 | <10 |
| 2 | <10 |
| 3 | <10 |
| 5 | <1000 |
| 6 | <1000 |
| 7 | <1000 |
| 8 | <1000 |
| 9 | <100 |
| 10 | <1000 |

3. Determination of Efflux Ratio Using Madin-Darby Canine Kidney Type II Cells

Bidirectional transport experiments were performed on Madin-Darby Canine Kidney Type II cells over-expressing multidrug resistance protein 1 (MDR1-MDCK) to evaluate the compounds as potential P-gp substrates.

Compounds were added at 1 µM in HBSS-pH 7.4 (hanks balanced salt solution) to either the apical or basolateral side of MDR1-MDCK cell monolayers grown on Millicell 96-Cell polycarbonate filters. Samples were collected from both apical and basolateral sides at time 0 and after 1 h incubation at 37 C, compounds concentrations were measured by HPLC/MS/MS and permeability coefficients were then determined in both transport directions. The efflux ratio was subsequently calculated from the permeability coefficient.

TABLE 2

| Example | Efflux ratio |
| --- | --- |
| 1 | 3.2 |
| 9 | 3.5 |

We claim:
1. A compound of formula (I)

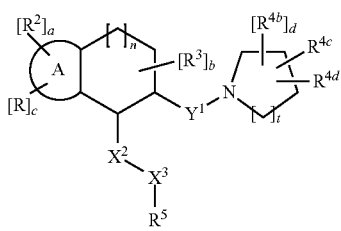

wherein
A is a benzene ring or a ring selected from the group consisting of the following 5- or 6-membered heterocyclic rings:

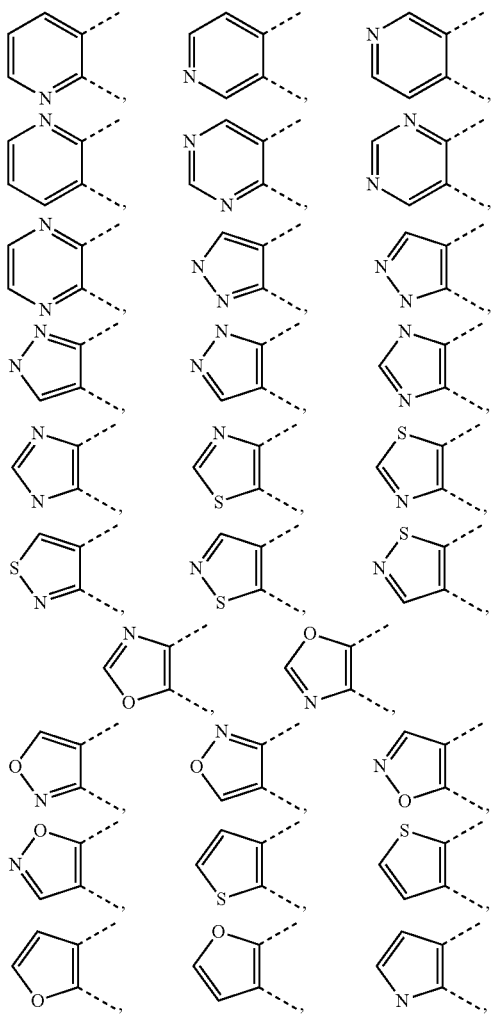

-continued

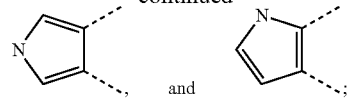

R is $R^1$—W-$A^1$-Q-Y-$A^2$-$X^1$—;
$R^1$ is hydrogen, $C_1$-$C_6$-alkyl, $C_3$-$C_{12}$-cycloalkyl-$C_1$-$C_4$-alkyl, halogenated $C_1$-$C_6$-alkyl, tri-($C_1$-$C_4$-alkyl)-silyl-$C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkylcarbonylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $C_3$-$C_{12}$-heterocyclyl-$C_1$-$C_4$-alkyl, $C_3$-$C_{12}$-cycloalkyl, $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $C_3$-$C_{12}$-heterocyclylsulfonylamino-$C_1$-$C_4$-alkoxy, $C_3$-$C_{12}$-heterocyclyl-$C_1$-$C_4$-alkoxy, $C_6$-$C_{12}$-aryloxy, $C_3$-$C_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $C_3$-$C_{12}$-heterocyclyl;
W is —$NR^8$— or a bond;
$A^1$ is optionally substituted $C_1$-$C_4$-alkylene or a bond;
Q is —$S(O)_2$— or —C(O)—;
Y is —$NR^9$— or a bond;
$A^2$ is optionally substituted $C_1$-$C_4$-alkylene, $C_1$-$C_4$-alkylene-CO—, —CO—$C_1$-$C_4$-alkylene, $C_1$-$C_4$-alkylene-O—$C_1$-$C_4$-alkylene, $C_1$-$C_4$-alkylene-$NR^{10}$-$C_1$-$C_4$-alkylene, optionally substituted $C_2$-$C_4$-alkenylene, optionally substituted $C_2$-$C_4$-alkynylene, optionally substituted $C_6$-$C_{12}$-arylene, optionally substituted $C_6$-$C_{12}$-heteroarylene or a bond;
$X^1$ is —O—, —$NR^{11}$, —S—, optionally substituted $C_1$-$C_4$-alkylene, optionally substituted $C_2$-$C_4$-alkenylene or optionally substituted $C_2$-$C_4$-alkynylene;
$R^2$ is hydrogen, halogen, $C_1$-$C_6$-alkyl, halogenated $C_1$-$C_4$-alkyl, hydroxy-$C_1$-$C_4$-alkyl, —CN, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-alkoxycarbonyl, $C_2$-$C_6$-alkenyloxy, $C_6$-$C_{12}$-aryl- $C_1$-$C_4$-alkoxy, $C_1$-$C_6$-alkylcarbonyloxy, $C_1$-$C_6$-alkylthio, $C_1$-$C_6$-alkylsulfinyl, $C_1$-$C_6$-alkylsulfonyl, aminosulfonyl, amino, $C_1$-$C_6$-alkylamino, $C_2$-$C_6$-alkenylamino, nitro or optionally substituted $C_3$-$C_{12}$-heterocyclyl, or two radicals $R^2$ together with the ring atoms to which they are bound form a 5- or 6 membered ring;

$R^3$ is hydrogen, halogen, $C_1$-$C_6$-alkyl or $C_1$-$C_6$-alkoxy, or two radicals $R^3$ together with the carbon atom to which they are attached form a carbonyl group;

$Y^1$ is a bond or optionally substituted $C_1$-$C_4$-alkylene;

t is 0, 1, 2 or 3;

$R^{4b}$ is hydrogen, halogen, $C_1$-$C_6$-alkyl, $C_3$-$C_{12}$-cycloalkyl-$C_1$-$C_4$-alkyl, halogenated $C_1$-$C_6$-alkyl, tri-($C_1$-$C_4$-alkyl)-silyl-$C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkylcarbonylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $C_3$-$C_{12}$-heterocyclyl-$C_1$-$C_4$-alkyl, $C_3$-$C_{12}$-cycloalkyl, $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl, $C_2$-$C_6$-alkynyl, optionally substituted $C_6$-$C_{12}$-aryl, cyano, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $C_3$-$C_{12}$-heterocyclylsulfonylamino-$C_1$-$C_4$-alkoxy, $C_3$-$C_{12}$-heterocyclyl-$C_1$-$C_4$-alkoxy, $C_6$-$C_{12}$-aryloxy, $C_3$-$C_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $C_3$-$C_{12}$-heterocyclyl;

$R^{4c}$, $R^{4d}$ together are $C_1$-$C_5$-alkylene optionally substituted with 1, 2 or 3 substituents $R^{4f}$, wherein one —$CH_2$— of $C_1$-$C_5$-alkylene may be replaced by an oxygen atom or —$NR^{20}$—;

$R^{4f}$ is hydrogen, halogen, $C_1$-$C_6$-alkyl, $C_3$-$C_{12}$-cycloalkyl-$C_1$-$C_4$-alkyl, halogenated $C_1$-$C_6$-alkyl, tri-($C_1$-$C_4$-alkyl)-silyl-$C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkylcarbonylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $C_3$-$C_{12}$-heterocyclyl-$C_1$-$C_4$-alkyl, $C_3$-$C_{12}$-cycloalkyl, $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl, $C_2$-$C_6$-alkynyl, optionally substituted $C_6$-$C_{12}$-aryl, cyano, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $C_3$-$C_{12}$-heterocyclylsulfonylamino-$C_1$-$C_4$-alkoxy, $C_3$-$C_{12}$-heterocyclyl-$C_1$-$C_4$-alkoxy, $C_6$-$C_{12}$-aryloxy, $C_3$-$C_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $C_3$-$C_{12}$-heterocyclyl;

$X^2$ is —O—, —$NR^6$—, —S—, >$CR^{12a}R^{12b}$ or a bond;

$X^3$ is —O—, —$NR^7$—, —S—, >$CR^{13a}R^{13b}$ or a bond;

$R^5$ is optionally substituted $C_6$-$C_{12}$-aryl, optionally substituted $C_3$-$C_{12}$-cycloalkyl or optionally substituted $C_3$-$C_{12}$-heterocyclyl;

n is 1;

$R^6$ is hydrogen, $C_1$-$C_6$-alkyl or $C_3$-$C_{12}$-cycloalkyl;

$R^7$ is hydrogen, $C_1$-$C_6$-alkyl or $C_3$-$C_{12}$-cycloalkyl;

$R^8$ is hydrogen, $C_1$-$C_6$-alkyl or $C_3$-$C_{12}$-cycloalkyl;

$R^9$ is hydrogen, $C_1$-$C_6$-alkyl, $C_3$-$C_{12}$-cycloalkyl, amino-$C_1$-$C_6$-alkyl, optionally substituted $C_6$-$C_{12}$-aryl-$C_1$-$C_4$-alkyl or $C_3$-$C_{12}$-heterocyclyl; or $R^9$, $R^1$ together are $C_1$-$C_4$-alkylene; or $R^9$ is $C_1$-$C_4$-alkylene that is bound to a carbon atom in $A^2$ and $A^2$ is $C_1$-$C_4$-alkylene or to a carbon atom in $X^1$ and $X^1$ is $C_1$-$C_4$-alkylene;

$R^{10}$ is hydrogen, $C_1$-$C_6$-alkyl, $C_3$-$C_{12}$-cycloalkyl or $C_1$-$C_6$-alkylsulfonyl;

$R^{11}$ is hydrogen, $C_1$-$C_6$-alkyl or $C_3$-$C_{12}$-cycloalkyl, or $R^9$, $R^{11}$ together are $C_1$-$C_4$-alkylene, $R^{12a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy;

$R^{12b}$ is hydrogen or $C_1$-$C_6$-alkyl, or $R^{12a}$, $R^{12b}$ together are carbonyl or optionally substituted $C_1$-$C_4$-alkylene, wherein one —$CH_2$— of $C_1$-$C_4$-alkylene may be replaced by an oxygen atom or —$NR^{16}$—;

$R^{13a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy;

$R^{13b}$ is hydrogen or $C_1$-$C_6$-alkyl, or $R^{13a}$, $R^{13b}$
together are carbonyl or optionally substituted $C_1$-$C_4$-alkylene, wherein one —$CH_2$— of $C_1$-$C_4$-alkylene may be replaced by an oxygen atom or —$NR^{17}$—;

$R^{16}$ is hydrogen, $C_1$-$C_6$-alkyl or $C_3$-$C_{12}$-cycloalkyl;
$R^{17}$ is hydrogen, $C_1$-$C_6$-alkyl or $C_3$-$C_{12}$-cycloalkyl;
$R^{20}$ is hydrogen, $C_1$-$C_6$-alkyl or $C_3$-$C_{12}$-cycloalkyl;
a is 1, 2 or 3;
b is 1, 2, 3, 4, 5 or 6;
c is 1; and
d is 1, 2 or 3,
or a physiologically tolerated salt thereof.

2. Compound of claim 1, wherein the main chain of —Y-$A^2$-$X^1$— is at least 2 atoms long.

3. Compound of claim 1, wherein $R^1$ is $C_1$-$C_6$-alkyl, $C_3$-$C_{12}$-cycloalkyl-$C_1$-$C_4$-alkyl, halogenated $C_1$-$C_6$-alkyl, $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, $C_6$-$C_{12}$-aryl-$C_1$-$C_4$-alkyl, $C_3$-$C_{12}$-cycloalkyl, $C_2$-$C_6$-alkenyl, optionally substituted $C_6$-$C_{12}$-aryl, hydroxy, $C_1$-$C_6$-alkylamino, (halogenated $C_1$-$C_6$-alkyl)amino, di-$C_1$-$C_6$-alkylamino or optionally substituted $C_3$-$C_{12}$-heterocyclyl.

4. Compound of claim 1, wherein $A^1$ is a bond, W is a bond and Y is —$NR^9$—.

5. Compound of claim 1, wherein $X^1$ is —O— and $A^2$ is $C_1$-$C_4$-alkylene, or $X^1$ is $C_1$-$C_4$-alkylene and $A^2$ is a bond.

6. Compound of claim 1, wherein $R^1$—W-$A^1$-Q-Y-$A^2$-$X^1$— is $R^1$—$S(O)_2$—$NR^9$-$A^2$-$X^1$— or $R^1$—$S(O)_2$—$X^1$—.

7. Compound of claim 1, wherein $R^2$ is hydrogen, —CN or halogen.

8. Compound of claim 1, having one of the formulae

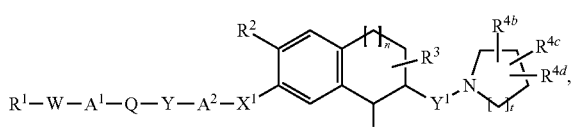

or

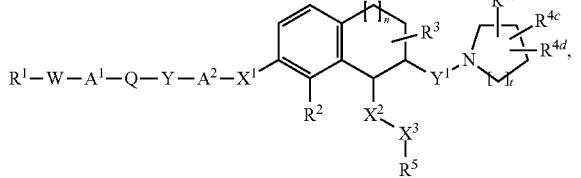

wherein $R^1$, W, $A^1$, Q, Y, $A^2$, $X^1$, $R^2$, $R^3$, $Y^1$, t, $R^{4b}$, $R^{4c}$, $R^{4d}$, $X^2$, $X^3$, $R^5$ and n are as defined in claim 1.

9. Compound of claim 1, wherein $R^3$ is hydrogen.

10. Compound of claim 1, wherein t is 1 and $R^{4c}$, $R^{4d}$ together are optionally substituted $C_1$-$C_5$-alkylene.

11. Compound of claim 1, wherein $R^{4b}$ is hydrogen, halogen, $C_1$-$C_6$-alkyl, $C_3$-$C_{12}$-cycloalkyl-$C_1$-$C_4$-alkyl, halogenated $C_1$-$C_6$-alkyl, hydroxy-$C_1$-$C_4$-alkyl, $C_1$-$C_6$-alkoxy-$C_1$-$C_4$-alkyl, optionally substituted $C_6$-$C_{12}$-aryl-$C_1$-$C_4$-alkyl, $C_2$-$C_6$-alkenyl, $C_2$-$C_6$-alkynyl, optionally substituted $C_6$-$C_{12}$-aryl, cyano, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, $C_6$-$C_{12}$-aryl-$C_1$-$C_4$-alkoxy, $C_3$-$C_{12}$-heterocyclyloxy or optionally substituted $C_3$-$C_{12}$-heterocyclyl.

12. Compound of claim 1, wherein $X^2$ is $CR^{12a}R^{12b}$.

13. Compound of claim 1, having the formula

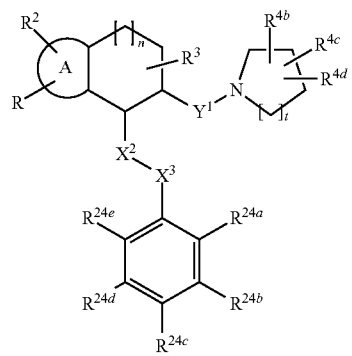

wherein A, R, $R^2$, $R^3$, $Y^1$, t, $R^{4b}$, $R^{4c}$, $R^{4d}$, $X^2$, $X^3$, and n are as defined in claims 1; and $R^{24a}$, $R^{24b}$, $R^{24c}$, $R^{24d}$, and $R^{24e}$
independently are hydrogen, halogen, or halogenated $C_1$-$C_6$-alkyl.

14. Compound as claimed in claim 1, wherein
A is a benzene ring;
R is $R^1$—W-$A^1$-Q-Y-$A^2$-$X^1$—;
is $C_1$-$C_6$-alkyl, $C_3$-$C_{12}$-cycloalkyl-$C_1$-$C_4$-alkyl, $C_3$-$C_{12}$-cycloalkyl, or optionally substituted $C_3$-$C_{12}$-heterocyclyl;
W is a bond;
$A^1$ is a bond;
Q is —$S(O)_2$—;
Y is —$NR^9$— or a bond;
$A^2$ is $C_1$-$C_4$-alkylene or a bond;
$X^1$ is —O— or optionally substituted $C_1$-$C_4$-alkylene;
$R^2$ is hydrogen or cyano;
$R^3$ is hydrogen;
$Y^1$ is a bond;
t is 1;
$R^{4b}$ is hydrogen;
$R^{4c}$, $R^{4d}$
together are $C_1$-$C_5$-alkylene;
$X^2$ is $CR^{12a}R^{12b}$;
$X^3$ is a bond;
$R^5$ is optionally substituted phenyl;
n is 1;
$R^9$ is hydrogen;
$R^{12a}$ is hydrogen; and
$R^{12b}$ is hydrogen.

15. The compound as claimed in claim 1, which is:
cis-N-({7-[3-Azabicyclo[3.1.0]hex-3-yl]-8-benzyl-5,6,7,8-tetrahydronaphthalen-2-yl}methyl)-1-methyl-1H-imidazole-4-sulfonamide;

N-[2-({7-[3-Azabicyclo[3.1.0]hex-3-yl]-8-benzyl-5,6,7,8-tetrahydronaphthalen-2-yl}oxy)ethyl]-1-methyl-1H-imidazole-4-sulfonamide;

N-[2-({7-[3-Azabicyclo[3.1.0]hex-3-yl]-8-benzyl-5,6,7,8-tetrahydronaphthalen-2-yl}oxy)ethyl]-1-methyl-1H-pyrazole-4-sulfonamide(2E)-but-2-enedioate;

N-(2-{[7-[3-Azabicyclo[3.1.0]hex-3-yl]-8-(2-fluorobenzyl)-5,6,7,8-tetrahydronaphthalen-2-yl]oxy}ethyl)-1-methyl-1H-imidazole-4-sulfonamide; or N-[2-({7-[3-Azabicyclo[3.1.0]hex-3-yl]-8-benzyl-3-cyano-5,6,7,8-tetrahydronaphthalen-2-yl}oxy)ethyl]-1-methyl-1H-imidazole-4-sulfonamide, or a physiologically tolerated salt thereof.

16. Pharmaceutical composition which comprises a carrier and a compound of claim 1.

17. A method for treating a neurological or psychiatric disorder or pain in a mammalian patient in need thereof, wherein treatment of the disorder or pain is effected by inhibiting GlyT1 activity, which method comprises administering to the patient a therapeutically effective amount of a compound of claim 1.

18. A compound of formula (V)

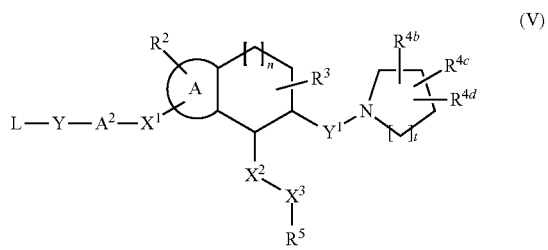

wherein L is an amino-protecting group, Y is $NR^9$, and A, $A^2$, $X^1$, $R^2$, $R^3$, $Y^1$, t, $R^{4b}$, $R^{4c}$, $R^{4d}$, $X^2$, $X^3$, $R^5$, n and $R^9$ are defined as in claim 1; wherein L is selected from the group consisting of optionally substituted alkylcarbonyl, optionally substituted arylcarbonyl, optionally substituted arylalkycarbonyl, optionally substituted alkoxycarbonyl, optionally substituted aryloxycarbonyl and optionally substituted arylalkoxycarbonyl.

19. A pharmaceutical composition which comprises a carrier and a compound of claim 15.

* * * * *